United States Patent
Nilsson et al.

(10) Patent No.: US 12,404,253 B2
(45) Date of Patent: *Sep. 2, 2025

(54) 2,4,6-TRISUBSTITUTED 1,3,5-TRIAZINES AS MODULATORS OF CX3CR1

(71) Applicant: ASTRAZENECA AB, Sodertalje (SE)

(72) Inventors: Karolina Nilsson, Sodertalje (SE); Martin Bauer, Sodertalje (SE); Maria Olwegard Halvarsson, Sodertalje (SE); Mikael Brink, Sodertalje (SE); Fredrik Bergström, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/783,231

(22) Filed: Jul. 24, 2024

(65) Prior Publication Data

US 2024/0383866 A1    Nov. 21, 2024

Related U.S. Application Data

(63) Continuation of application No. 18/489,184, filed on Oct. 18, 2023.

(60) Provisional application No. 63/417,472, filed on Oct. 19, 2022.

(51) Int. Cl.
| | |
|---|---|
| C07D 251/18 | (2006.01) |
| C07D 401/06 | (2006.01) |
| C07D 403/06 | (2006.01) |
| C07D 405/10 | (2006.01) |
| C07D 413/06 | (2006.01) |
| C07D 471/04 | (2006.01) |
| C07D 498/04 | (2006.01) |

(52) U.S. Cl.
CPC ......... *C07D 251/18* (2013.01); *C07D 401/06* (2013.01); *C07D 403/06* (2013.01); *C07D 405/10* (2013.01); *C07D 413/06* (2013.01); *C07D 471/04* (2013.01); *C07D 498/04* (2013.01)

(58) Field of Classification Search
CPC .................................................. C07D 251/18
See application file for complete search history.

(56) References Cited

U.S. PATENT DOCUMENTS

| | | | |
|---|---|---|---|
| 7,067,657 B2 | 6/2006 | Hanson et al. | |
| 7,947,693 B2 | 5/2011 | Nordvall et al. | |
| 7,960,395 B2 | 6/2011 | Johansson et al. | |
| 8,088,780 B2 | 1/2012 | Nordvall et al. | |
| 8,158,785 B2 | 4/2012 | Johansson et al. | |
| 2001/0011063 A1* | 8/2001 | Giencke | C07D 251/18 544/212 |
| 2007/0142386 A1 | 6/2007 | Nordvall et al. | |
| 2009/0192134 A1 | 7/2009 | Meghani et al. | |
| 2009/0247555 A1 | 10/2009 | Dahlstrom et al. | |
| 2024/0199558 A1* | 6/2024 | Nilsson | C07D 405/08 |

FOREIGN PATENT DOCUMENTS

| | | |
|---|---|---|
| WO | 2005070903 A2 | 8/2005 |
| WO | 2013039057 A1 | 3/2013 |

OTHER PUBLICATIONS

Austin R.P., et al., "Discovery and Evaluation of a Novel Monocyclic Series of CXCR2 Antagonists", Bioorganic Medicinal Chemistry Letters, vol. 25, 2015, pp. 1616-1620.
Cederblad L., et al., "AZD8797 is an Allosteric Non-Competitive Modulator of the Human CX3CR1 Receptor", Biochemical Journal, vol. 473, 2016, pp. 641-649.
International Search Report and Written Opinion for International Application No. PCT/EP2023/079035, mailed Feb. 5, 2024, 11 Pages.
Karlström S., et al., "Substituted 7-Amino-5-thio-thiazolo[4,5-d]pyrimidines as Potent and Selective Antagonists of the Fractalkine Receptor (CX3CR1)", Journal of Medicinal Chemistry, vol. 56, No. 8, 2013, pp. 3177-3190.
Suresh P., et al., "Modulation of Microglia Activation and Alzheimer's Disease: CX3 Chemokine Ligand 1/CX3CR and P2X7R Signaling", Tzu Chi Medical Journal, vol. 33, No. 1, 2021, pp. 1-6.
White G.E., et al., "Fractalkine Has Anti-apoptotic and Proliferative Effects on Human Vascular Smooth Muscle Cells via Epidermal Growth Factor Receptor Signalling", Cardiovascular Research, vol. 85, 2010, pp. 825-835.

* cited by examiner

*Primary Examiner* — Jeffrey T. Palenik
*Assistant Examiner* — Gillian A Hutter

(57) ABSTRACT

There are disclosed certain 2,4,6-trisubstituted 1,3,5-triazine compounds of Formula (I),

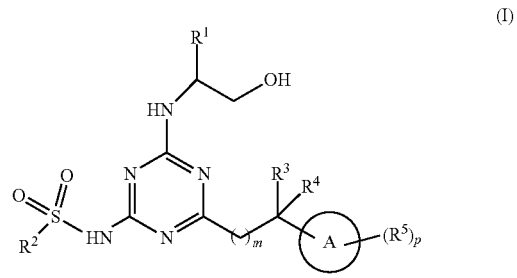

and pharmaceutically acceptable salts thereof, together with compositions containing them and their use in therapy. The compounds are modulators of $CX_3CR1$ and are thereby particularly useful in the treatment or prophylaxis of cardiovascular disorders such as non-ischemic dilated cardiomyopathy and heart failure.

30 Claims, No Drawings

2,4,6-TRISUBSTITUTED 1,3,5-TRIAZINES AS MODULATORS OF CX3CR1

RELATED APPLICATIONS

This application is a continuation of U.S. patent application Ser. No. 18/489,184, filed Oct. 18, 2023, which claims benefit of U.S. Provisional Application No. 63/417,472, filed Oct. 19, 2022, each of which are incorporated by reference herein in its entirety for all purposes.

BACKGROUND

Chemokines play an important role in immune and inflammatory responses in various diseases and disorders, including cardiovascular and respiratory diseases such as asthma, atherosclerosis and allergic diseases, as well as autoimmune pathologies such as rheumatoid arthritis, multiple sclerosis, systemic sclerosis, systemic lupus erythematosus, lupus nephritis and inflammatory myopathy. These small, secreted molecules are a growing superfamily of 8-14 kDa proteins characterized by a conserved cysteine motif. At the present time, the chemokine superfamily comprises four groups exhibiting characteristic structural motifs; the C-X-C, C-C and C-X$_3$-C and XC families. The C-X-C and C-C families have sequence similarity and are distinguished from one another on the basis of a single amino acid insertion between the NH-proximal pair of cysteine residues. The C-X$_3$-C family is distinguished from the other two families on the basis of having a triple amino acid insertion between the NH-proximal pair of cysteine residues. In contrast, members of the XC family lack one of the first two cysteine residues.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes, lymphocytes and neutrophils.

The C-X$_3$-C chemokine (also known as fractalkine, FKN, or CX3CL1) is a potent chemoattractant and activator of microglia in the central nervous system (CNS) as well as of monocytes, T cells, NK cells and mast cells. It also functions as an adhesion molecule on immune active cells, such as monocytes and others for infiltration of cells from the blood to the tissue. Blocking the interaction has been proven to reduce atherosclerosis progression and plaque growth (Poupel et al., Arterioscler. Thromb. Vasc. Biol., 2013, 33, 2297-2305). In humans, CX$_3$CR1 and fractalkine is expressed in early and late atherosclerosis (Stolla et al. PLOS one 2012 (https://doi.org/10.1371/journal.pone.0043572) and Pucci et al. BioMed Res Int 2013 (http://dx.doi.org/10.1155/2013/451349).

Fractalkine neutralisation improves cardiac function in mouse myocardial infarction (MI) models by enhanced systolic function, ventricular remodeling and decreased infarct size (Xuan et al 2011, Cardiovascular Research 92, 385) and also LVEF and survival rate 2 weeks post treatment after an induced MI in mouse (Gu et al 2015, Exp Physiol 100, 805).

Additionally, fractalkine cause cardio-depressive actions with impaired contractility observed in mouse cardiomyocytes (Taube et al 2013, PLOS ONE 8(7) (https://doi.org/10.1371/journal.pone.0069832)). Human serum soluble FKN (sFKN) levels are associated with NYHA heart failure functional score where in patients with HF have an increased level of soluble fractalkine (Husberg et al. J. of Mol. and Cellular Cardiology, 2008, 45(2), 261). sFKN concentration has a prognostic value in patients with acute myocardial infarction treated with primary percutaneous coronary intervention (Xu Bing et al Cytokine 2019 113 (365-370). Elevated sFKN plasma levels predictor of mortality in subjects with advanced systolic HF (Richter et al 2012, Thrombosis & Haemostasis 108, 1220).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and CX3CR1 for the C-X3-C family. These receptors represent good targets for drug development since agents that modulate these receptors would be useful in the treatment of disorders and diseases such as those mentioned above.

WO2005/070903 discloses certain triazine derivatives for use in the treatment of chemokine mediated diseases and disorders.

WO2006/107258 discloses certain 5-substituted 7-amino-[1,3]thiazolo[4,5-d]pyrimidine derivatives as antagonists of the CX3CR1 receptor.

WO2006/107257 and WO2009/120140 disclose certain 5,7-disubstituted [1,3]thiazolo[4,5-d]pyrimidin-2(3H)one derivatives as antagonists of the CX$_3$CR1 receptor.

WO2013039057 discloses certain pyrrolidine-3-ylacetic acid derivatives having an inhibitory pathway in the fractalkine-CX$_3$CR1 pathway.

Linkage of CX$_3$CR1 activity to diseases has thus been implicated in cardiovascular diseases (CVD) including heart failure, cardiomyopathy, acute coronary syndrome, myocardial infarction, stable coronary artery disease and atherosclerosis related conditions.

There is a need for an orally active modulator of CX$_3$CR1 for the treatment cardiovascular diseases (CVD) e.g. heart failure, cardiac muscle diseases and coronary artery disease related conditions.

DETAILED DESCRIPTION

Definitions

The term "alkoxy" refers to an alkyl group attached to the rest of the molecule via an oxygen atom. Representative alkoxy groups include, but are not limited to, methoxy, ethoxy, propoxy, tert-butoxy and the like.

The term "alkyl" or "alkane" is a straight chained or branched non-aromatic hydrocarbon which is completely saturated. Examples of straight chained and branched alkyl groups include methyl, ethyl, n-propyl, iso-propyl, n-butyl, sec-butyl, tert-butyl, pentyl, hexyl, pentyl and octyl.

The term "alkoxyalkyl" refers to an alkyl group attached to an alkoxy group, where in the group is attached to the rest of the molecule via a carbon on the alkyl group, i.e. a group having a structure of —R—O—R' wherein R and R' are the same or different alkyl groups.

The term "aryl" refers to an aromatic hydrocarbon. The term aryl includes monocyclic aryls, with a single ring, such as phenyl, as well as polycyclic aryls, including "bicyclic aryls" having two or more cyclic rings, in which two or more atoms are common to two adjoining rings wherein at least one of the rings is aromatic, for example, the other cyclic ring is cycloalkyl, cycloalkenyl, cycloalkynyl and/or aryl. Examples of polycyclic aryl rings include naphthalene and tetrahydronaphthalene.

The term "cycloalkyl" refers to a partially or completely saturated monocyclic, bicyclic, polycyclic or bridged hydrocarbon ring system.

The term "halo" means fluoro, chloro, bromo, and iodo. In an embodiment, halo is fluoro or chloro. In another embodiment, halo is fluoro. In yet another embodiment, halo is chloro.

The term "haloalkoxy" means an alkoxy in which one or more hydrogens has been substituted with a halo.

The term "haloalkyl" means an alkyl group in which one or more hydrogens has been substituted with a halo.

The term "heteroaryl" and "heteroarylene" as used herein, refers to substituted or unsubstituted aromatic ring structures whose ring structures include at least one heteroatom selected from nitrogen, oxygen, and sulphur. Heteroaryl and heteroarylene groups can be attached to the rest of the molecule via a carbon or nitrogen ring-member atom. Heteroaryl/heteroarylene groups include monocyclic heteroaryls as well as polycyclic heteroaryls such as bicyclic heteroaryls, having two or more cyclic rings in which two or more atoms are common to two adjoining rings wherein at least one of the rings is aromatic and at least one of the rings includes at least one heteroatom selected from nitrogen, oxygen, and sulphur. Examples of monocyclic heteroaryls or heteroarylenes include, but are not limited to, pyrrole, pyridine, pyrazine, pyridazine, pyrimidine, furan, triazole, thiophene, imidazole, isoxazole, oxazole, oxadiazole, thiazole and pyrazole. Examples of bicyclic heteroaryls, include, but are not limited to purine, indole, indazole, quinoline, quinazoline, benzofuran, benzoxazole, benzodioxole, benzodioxin, pyrrolopyridine, indazole, 2H-indazole, isoquinoline, tetrahydroisoquinoline, dihydroquinazoline, 1H-pyrrolo[2,3-b]pyridine, 2,3-dihydrobenzo[d]oxazole, 3,4-dihydroquinazoline, 3,4-dihydro-2H-pyrido[3,2-b][1,4]oxazine, 2,3-dihydro-1,4-benzodioxin and 2,3-dihydro-1-benzofuran. Additional polycyclic heteroaryls or heteroarylenes include, but are not limited to, carbazole and dibenzazepine The term "monocyclic N-heteroaryl" refers to a monocyclic heteroaryl whose ring structures include at least one nitrogen. Examples of monocyclic N-heteroaryls include, but are not limited to imidazole, pyrrole, triazole, pyridine, pyrazine, pyridazine, pyrimidine, and triazine.

The term "heterocycle" "heterocyclic" or "heterocyclyl" refers to a partially or completely saturated hydrocarbon ring system wherein at least one of the ring carbon atoms is replaced with a heteroatom independently selected from nitrogen, oxygen and sulphur. Heterocyclic groups can be attached to the rest of the molecule via a carbon or nitrogen ring-member atoms. Heterocycles include monocyclic heterocycles as well as polycyclic heterocycles such as bicyclic heterocycles. Examples of monocyclic heterocycles include, but are not limited to, tetrahydropyran, tetrahydrofuran, morpholine, piperidine, piperazine, oxetane, and isoxazolidine.

The term "hydroxy" refers to an —OH group.

The term "hydroxyalkyl" means an alkyl group in which one or more hydrogens has been substituted with a hydroxy.

The term "oxo" refers to an "=O" group, i.e., a substituent oxygen atom connected to another atom by a double bond.

In this specification the prefix $C_{x-y}$ as used in terms such as "$C_{x-y}$ alkyl" and the like where x and y are integers, indicates the numerical range of carbon atoms that are present in the group. Examples of suitable $C_{1-3}$ alkyl groups include, but are not limited to, methyl, ethyl, n-propyl, and i-propyl. Examples of suitable $C_{1-4}$ alkyl groups include, but are not limited to, methyl, ethyl, n-propyl, and i-propyl, n-butyl, i-butyl, s-butyl and t-butyl. In some cases, a group will have two instances of $C_{x-y}$ in which case the prefix indicates the numerical range of carbons in each part of the group, e.g., $C_{1-3}$ alkoxy-$C_{1-4}$ alkyl, refers to an alkoxyalkyl group wherein the alkyl group has 1 to 3 carbons and the alkoxy group has 1-4 carbons.

Compounds

One embodiment disclosed herein provides a compound of formula (I)

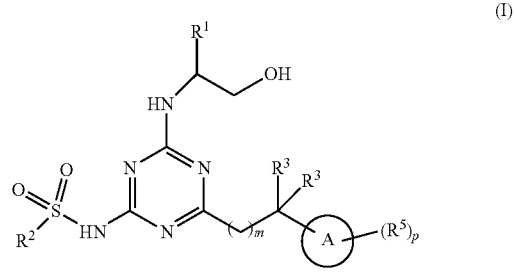

wherein $R^1$ is a $C_{3-6}$ branched alkyl or $C_{3-6}$ branched haloalkyl;

$R^2$ is a $C_{1-3}$ alkyl or $C_{1-3}$ haloalkyl;

m is 1 or 2;

$R^3$ and $R^4$ are, independently, selected from H, halo, $C_{1-3}$ alkyl, and $C_{1-3}$ haloalkyl;

A is phenyl, monocyclic heteroaryl, bicyclic aryl, or bicyclic heteroaryl;

p is 0, 1, 2, 3, or 4;

each $R^5$ is independently selected from halo, hydroxy, oxo, $C_{1-3}$ alkyl, $C_{1-3}$ haloalkyl, $C_{1-4}$ alkoxy, $C_{1-4}$ haloalkoxy, $C_{1-4}$ alkoxy-$C_{1-3}$ alkyl, $C_{1-3}$ hydroxyalkyl, —CN, —(CH$_2$)$_q$CN, —C(O)NR$^6$R$^7$, —NS(O)R$^6$R$^7$, —(CH$_2$)$_q$R$^8$, —C(O)R', —C(O)OR$^9$, —OC(O)R$^9$, —NR$^6$C(O)R$^7$, —NR$^6$R$^7$, $C_{3-6}$ cycloalkyl, 4-6 member heteroaryl, 4-6 member heterocyclyl, and phenyl, wherein the $C_{3-6}$ cycloalkyl or 4-6 member heterocyclyl can be optionally substituted with 1 to 3 substituents selected from hydroxy, oxy, halo, and —C(O)OR$^9$, the 4-6 member heteroaryl can be optionally substituted with 1 to 3 halo substituents, the $C_{1-4}$ alkoxy can be optionally substituted with a 4-6 member heterocyclyl, each $R^6$ and $R^7$ are, independently, selected from H and $C_{1-3}$ alkyl, each q is, independently, 1, 2, or 3, each $R^8$ is, independently a 4-6 member heterocyclyl, wherein the heterocyclyl is optionally substituted with a oxy, and each $R^9$ is, independently, a $C_{1-5}$ alkyl;

or a stereoisomer, pharmaceutically acceptable salt, or tautomer thereof.

Another embodiment disclosed herein provides a compound having the structure:

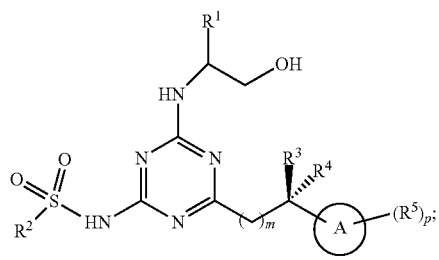
(Ia)

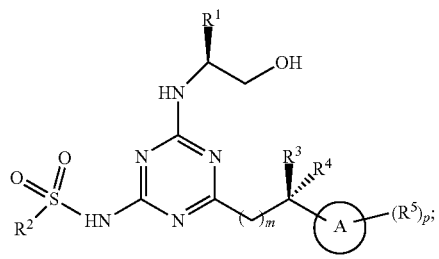
(Ib)

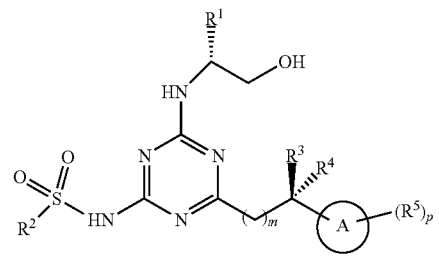
(Ic)

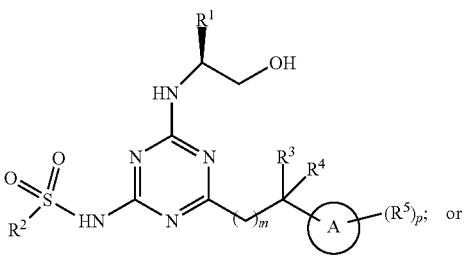
(Id)

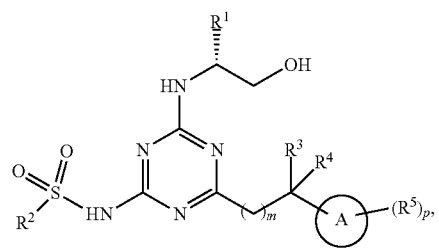
(Ie)

wherein $R^1$, $R^2$, $R^3$, $R^4$, $R^5$, m, p and A are defined as above for formula (I).

Another embodiment disclosed herein provides a compound having the structure:

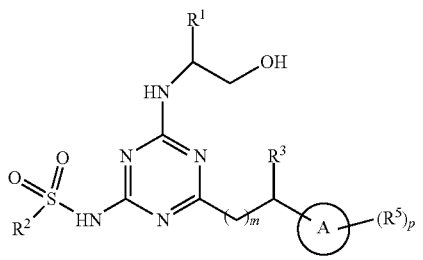
(If)

wherein $R_1$, $R^2$, $R^3$, $R^5$, m, p and A are defined as above for formula (I).

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein A is phenyl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein A is a monocyclic heteroaryl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein A is a monocyclic N-heteroaryl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein A is a 6-member monocyclic heteroaryl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein A is pyridyl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein A is pyrimidine.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein A is pyrazine.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein A is a phenyl or a 6-member monocyclic heteroaryl, wherein p is at least 1 and an $R^5$ is para to the ring atom attached to the compound, (e.g, $R^5$ is para to the ring atom bound to the $R^3$-$R^4$-substituted carbon).

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein A is a phenyl or a 6-member monocyclic heteroaryl, wherein p is at least 1 and an $R^5$ is ortho to the ring atom attached to the compound (e.g, $R^5$ is ortho to the ring atom bound to the $R^3$-$R^4$-substituted carbon).

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein A is a phenyl or a 6-member monocyclic heteroaryl, wherein p is at least 1 and an $R^5$ is meta to the ring atom attached to the compound (e.g, $R^5$ is meta to the ring atom bound to the $R^3$-$R^4$— substituted carbon).

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least one $R^5$ is halo.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least one $R^5$ is F.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least two $R^5$s are F.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least three $R^5$s are F.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least one $R^5$ is Cl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least two $R^5$s are Cl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least one $R^5$ is a $C_{1-4}$ alkoxy.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least one $R^5$ is —$OCH_3$.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least one $R^5$ is —$OCH_2CH_3$.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least one $R^5$ is a $C_{1-4}$ haloalkoxy.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least one $R^5$ is a $C_1$-$C_3$ alkyl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least one $R^5$ is methyl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein at least one $R^5$ is a hydroxy or a $C_1$-$C_3$ hydroxyalkyl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein one of $R^3$ or $R^4$ is $C_{1-3}$ alkyl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein one of $R^3$ or $R^4$ is methyl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein one of $R^3$ or $R^4$ is ethyl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein one of $R^3$ or $R^4$ is H.

Some embodiments disclosed herein provide a compound of formulae (I), (Ia), (Ib), (Ic), (Id), or (Ie) as defined above, or a stereoisomer, pharmaceutically acceptable salt, or tautomer thereof, wherein $R^4$ is H.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein one of $R^3$ or $R^4$ is halo.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein $R_1$ is a $C_{3-6}$ branched alkyl Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein $R_1$ is a C4 branched alkyl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein $R_1$ is —$CH_2CH(CH_3)_2$.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein $R^2$ is a $C_{1-3}$ alkyl Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein $R^2$ is methyl.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein p is 1, 2, or 3.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein p is 1.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein p is 2.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein p is 3.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein m is 1.

Some embodiments disclosed herein provide a compound of formulae (I), (Ia), (Ib), (Ic), (Id), (Ie), or (If) as defined above, or a stereoisomer, pharmaceutically acceptable salt, or tautomer thereof, wherein m is 2.

Some embodiments disclosed herein provide a compound selected from:
N-(4-((R)-2-(3,4-Dichlorophenyl)propyl)-6-(((R)-1-hydroxy-4-methylpentan-2-yl)amino)-1,3,5-triazin-2-yl) methanesulfonamide,
N-(4-((S)-2-(3,4-Dichlorophenyl)propyl)-6-(((R)-1-hydroxy-4-methylpentan-2-yl)amino)-1,3,5-triazin-2-yl) methanesulfonamide, N-(4-((R)-2-(3-Chloro-2-fluorophenyl)propyl)-6-(((R)-1-hydroxy-4-methylpentan-2-yl)amino)-1,3,5-triazin-2-yl)methanesulfonamide, N-(4-((S)-2-(3-Chloro-2-fluorophenyl)propyl)-6-(((R)-1-hydroxy-4-methylpentan-2-yl)amino)-1,3,5-triazin-2-yl)methanesulfonamide, N-(4-((R)-2-(2,4-Difluorophenyl)propyl)-6-(((R)-1-hydroxy-4-methylpentan-2-yl)amino)-1,3,5-triazin-2-yl)methanesulfonamide, N-(4-((S)-2-(2,4-Difluorophenyl)propyl)-6-(((R)-1-hydroxy-4-methylpentan-2-yl)amino)-1,3,5-triazin-2-yl)methanesulfonamide, N-(4-((R)-2-(5-Fluoro-6-methoxypyridin-3-yl)propyl)-6-(((R)-1-hydroxy-4-methylpentan-2-yl)amino)-1,3,5-triazin-2-yl)methanesulfonamide, N-(4-((S)-2-(5-Fluoro-6-methoxypyridin-3-yl)propyl)-6-(((R)-1-hydroxy-4-methylpentan-2-yl)amino)-1,3,5-triazin-2-yl)methanesulfonamide, N-(4-((R)-2-(5-Chloro-6-methoxypyridin-3-yl)propyl)-6-(((R)-1-hydroxy-4-methylpentan-2-yl)amino)-1,3,5-triazin-2-yl)methanesulfonamide, N-(4-((S)-2-(5-Chloro-6-methoxypyridin-3-yl)propyl)-6-(((R)-1-hydroxy-4-methylpentan-2-yl)amino)-1,3,5-triazin-2-yl)methanesulfonamide, N-(4-((R)-2-(2-Cyclopropylpyrimidin-5-yl)propyl)-6-(((R)-1-hydroxy-4-methylpentan-2-yl)amino)-1,3,5-triazin-2-yl)methanesulfonamide, N-(4-((S)-2-(2-Cyclopropylpyrimidin-5-yl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-((R)-2-(6-methoxy-4-methylpyridin-3-yl)propyl)-1,3,5-triazin-2-yl)methanesulfonamide, N-(4-(((R)-1-Hydroxy-4-methylpentan-2-yl)amino)-6-((S)-2-(6-methoxy-4-methylpyridin-3-yl)propyl)-1,3,5-triazin-2-yl)methanesulfonamide, N-(4-(((R)-1-Hydroxy-4-methylpentan-2-yl)amino)-6-((R)-2-(6-methoxy-5-methylpyridin-3-yl)propyl)-1,3,5-triazin-2-yl)methanesulfonamide, N-(4-(((R)-1-Hydroxy-4-methylpentan-2-yl)amino)-6-((S)-2-(6-methoxy-5-methylpyridin-3-yl)propyl)-1,3,5-triazin-2-yl)methanesulfonamide, N-(4-(((R)-1-Hydroxy-4-methylpentan-2-yl)amino)-6-((R)-2-(2-methoxypyridin-3-yl)propyl)-1,3,5-triazin-2-yl)methanesulfonamide, N-(4-(((R)-1-Hydroxy-4-methylpentan-2-yl)amino)-6-((S)-2-(2-methoxypyridin-3-yl)propyl)-1,3,5-triazin-2-yl)methanesulfonamide, N-(4-((R)-2-(3-Fluoro-4-methoxyphenyl)propyl)-6-(((R)-1-hydroxy-4-methylpentan-2-yl)amino)-1,3,5-triazin-2-yl)methanesulfonamide, N-(4-((S)-2-(3-Fluoro-4-methoxyphenyl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-((R)-2-(3,4,5-trifluorophenyl)propyl)-1,3,5-triazin-2-yl)methanesulfonamide, N-(4-(((R)-1-Hydroxy-4-methylpentan-2-yl)amino)-6-((S)-2-(3,4,5-trifluorophenyl)propyl)-1,3,5-triazin-2-yl)methanesulfonamide, N-(4-((R)-2-(2,5-Difluorophenyl)propyl)-6-(((R)-1-hydroxy-4-methylpentan-2-yl)amino)-1,3,5-triazin-2-yl)methanesulfonamide, N-(4-((S)-2-(2,5-Difluorophenyl)propyl)-6-(((R)-1-hydroxy-4-methylpentan-2-yl)amino)-1,3,5-triazin-2-yl)methanesulfonamide, N-(4-((R)-2-(2-Chloropyridin-4-yl)propyl)-6-(((R)-1-hydroxy-4-methylpentan-2-yl)amino)-1,3,5-triazin-2-yl)methanesulfonamide, N-(4-((S)-2-(2-Chloropyridin-4-yl)propyl)-6-(((R)-1-hydroxy-4-methylpentan-2-yl)amino)-1,3,5-triazin-2-yl)methanesulfonamide, N-(4-((R)-2-(6-Ethoxypyridin-3-yl)propyl)-6-(((R)-1-hydroxy-4-methylpentan-2-yl)amino)-1,3,5-triazin-2-yl)methanesulfonamide, N-(4-((S)-2-(6-Ethoxypyridin-3-yl)propyl)-6-(((R)-1-hydroxy-4-methylpentan-2-yl)amino)-1,3,5-triazin-2-yl)methanesulfonamide, N-(4-((R)-2-(5-Chloro-2-fluorophenyl)propyl)-6-(((R)-1-hydroxy-4-methylpentan-2-yl)amino)-1,3,5-triazin-2-yl)methanesulfonamide, N-(4-((S)-2-(5-Chloro-2-fluorophenyl)propyl)-6-(((R)-1-hydroxy-4-methylpentan-2-yl)amino)-1,3,5-triazin-2-yl)methanesulfonamide, N-(4-((R)-2-(4-Chloro-3,5-difluorophenyl)propyl)-6-(((R)-1-hydroxy-4-methylpentan-2-yl)amino)-1,3,5-triazin-2-yl)methanesulfonamide, N-(4-((S)-2-(4-Chloro-3,5-difluorophenyl)propyl)-6-(((R)-1-hydroxy-4-methylpentan-2-yl)amino)-1,3,5-triazin-2-yl)methanesulfonamide, N-(4-((R)-2-(4-Chloro-2,3-difluorophenyl)propyl)-6-(((R)-1-hydroxy-4-methylpentan-2-yl)amino)-1,3,5-triazin-2-yl)methanesulfonamide, N-(4-((S)-2-(4-Chloro-2,3-difluorophenyl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-((R)-2-(2,4,5-trifluorophenyl)propyl)-1,3,5-triazin-2-yl)methanesulfonamide, N-(4-(((R)-1-Hydroxy-4-methylpentan-2-yl)amino)-6-((S)-2-(2,4,5-trifluorophenyl)propyl)-1,3,5-triazin-2-yl)methanesulfonamide, N-(4-((R)-2-(4-Chloro-2,5-difluorophenyl)propyl)-6-(((R)-1-hydroxy-4-methylpentan-2-yl)amino)-1,3,5-triazin-2-yl)methanesulfonamide, N-(4-((S)-2-(4-Chloro-2,5-difluorophenyl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-((R)-2-(2,4,6-trifluorophenyl)propyl)-1,3,5-triazin-2-yl)methanesulfonamide, N-(4-(((R)-1-Hydroxy-4-methylpentan-2-yl)amino)-6-((S)-2-(2,4,6-trifluorophenyl)propyl)-1,3,5-triazin-2-yl)methanesulfonamide, N-(4-(((R)-1-Hydroxy-4-methylpentan-2-yl)amino)-6-((R)-2-(2,3,6-trifluorophenyl)propyl)-1,3,5-triazin-2-yl)methanesulfonamide, N-(4-(((R)-1-Hydroxy-4-methylpentan-2-yl)amino)-6-((S)-2-(2,3,6-trifluorophenyl)propyl)-1,3,5-triazin-2-yl)methanesulfonamide, N-(4-((R)-2-(4-Chloro-2,6-difluorophenyl)propyl)-6-(((R)-1-hydroxy-4-methylpentan-2-yl)amino)-1,3,5-triazin-2-yl)methanesulfonamide, N-(4-((S)-2-(4-Chloro-2,6-difluorophenyl)propyl)-6-(((R)-1-hydroxy-4-methylpentan-2-yl)amino)-1,3,5-triazin-2-yl)methanesulfonamide, N-(4-((R)-2-(4-Fluoro-6-methoxypyridin-3-yl)propyl)-6-(((R)-1-hydroxy-4-methylpentan-2-yl)amino)-1,3,5-triazin-2-yl)methanesulfonamide, N-(4-((S)-2-(4-Fluoro-6-methoxypyridin-3-yl)propyl)-6-(((R)-1-hydroxy-4-methylpentan-2-yl)amino)-1,3,5-triazin-2-yl)methanesulfonamide, N-(4-((R)-2-(2,3-Difluorophenyl)butyl)-6-(((R)-1-hydroxy-4-methylpentan-2-yl)amino)-1,3,5-triazin-2-yl)methanesulfonamide, N-(4-((S)-2-(2,3-Difluorophenyl)butyl)-6-(((R)-1-hydroxy-4-methylpentan-2-yl)amino)-1,3,5-triazin-2-yl)methanesulfonamide, N-(4-(2-(4-Fluoro-6-methoxypyridin-3-yl)butyl)-6-(((R)-1-hydroxy-4-methylpentan-2-yl)amino)-1,3,5-triazin-2-yl)methanesulfonamide, N-(4-((R)-2-(6-Aminopyridin-3-yl)propyl)-6-(((R)-1-hydroxy-4-methylpentan-2-yl)amino)-1,3,5-triazin-2-yl)methanesulfonamide, N-(4-((S)-2-(6-Aminopyridin-3-yl)propyl)-6-(((R)-1-hydroxy-4-methylpentan-2-yl)amino)-1,3,5-triazin-2-yl)methanesulfonamide, N-(4-((R)-2-(2,6-Dimethoxypyridin-3-yl)propyl)-6-(((R)-1-hydroxy-4-methylpentan-2-yl)amino)-1,3,5-triazin-2-yl)methanesulfonamide, N-(4-((S)-2-(2,6-Dimethoxypyridin-3-yl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(4-(piperazin-1-yl)phenyl)propyl)-1,3,5-triazin-2-yl)methanesulfonamide, N-(4-(2-(4-(Cyanomethyl)phenyl)propyl)-6-(((R)-1-hydroxy-4-methylpentan-2-yl)amino)-1,3,5-triazin-2-yl)methanesulfonamide, N-(4-(2-(3-Fluoro-4-methylphenyl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(4-(oxetan-3-yl)phenyl)propyl)-1,3,5-triazin-2-yl)methanesulfonamide, N-(4-(2-(3-Fluorophenyl)propyl)-6-(((R)-1-hydroxy-4-methylpentan-2-yl)amino)-1,3,5-triazin-2-yl)methanesulfonamide, N-(4-(1-(4-(((R)-1-Hydroxy-4-methylpentan-2-yl)amino)-6-(methylsulfonamido)-1,3,5-triazin-2-yl)propan-2-yl)phenyl)acetamide, N-(4-(2-(1H-Indol-5-yl)propyl)-6-(((R)-1-hydroxy-4-methylpentan-2-yl)amino)-1,3,5-triazin-2-yl)methanesulfonamide, N-(4-(2-(Benzo[d]oxazol-6-yl)propyl)-6-(((R)-1-hydroxy-4-methylpentan-2-yl)amino)-1,3,5-triazin-2-yl)methanesulfonamide, N-(4-(2-(Benzo[d]oxazol-5-yl)propyl)-6-(((R)-1-hydroxy-4-methylpentan-2-yl)amino)-1,3,5-triazin-2-yl)methanesulfonamide, N-(4-(2-(4-((Dimethyl(oxo)-$\lambda^6$-sulfaneylidene)amino)phenyl)propyl)-6-(((R)-1-hydroxy-4-methylpentan-2-yl)amino)-1,3,5-triazin-2-yl)methanesulfonamide, N-(4-(2-(4-(1H-1,2,3-Triazol-1-yl)phenyl)propyl)-6-(((R)-1-hydroxy-4-methylpentan-2-yl)amino)-1,3,5-triazin-2-yl)methanesulfonamide, N-(4-((R)-2-(3-Chloro-4-fluorophenyl)propyl)-6-(((R)-1-hydroxy-4-methylpentan-2-yl)amino)-1,3,5-triazin-2-yl)methanesulfonamide, N-(4-((S)-2-(3-Chloro-4-fluorophenyl)propyl)-6-(((R)-1-hydroxy-4-methylpentan-2-yl)amino)-1,3,5-triazin-2-yl)methanesulfonamide, N-(4-(2-(2-Ethoxypyridin-4-yl)propyl)-6-(((R)-1-hydroxy-4-methylpentan-2-yl)amino)-1,3,5-triazin-2-yl)methanesulfonamide, N-(4-(2-(4-Cyanophenyl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(4-(methoxymethyl)phenyl)propyl)-1,3,5-triazin-2-yl)methanesulfonamide, N-(4-(2-(3,4-Dimethylphenyl)propyl)-6-(((R)-1-hydroxy-4-methylpentan-2-yl)amino)-1,3,5-triazin-2-yl)methanesulfonamide, N-(4-(2-(4-(1,1-Difluoroethyl)phenyl)propyl)-6-(((R)-1-hydroxy-4-methylpentan-2-yl)amino)-1,3,5-triazin-2-yl)methanesulfonamide, N-(4-(2-(3-Chlorophenyl)propyl)-6-(((R)-1-hydroxy-4-methylpentan-2-yl)amino)-1,3,5-triazin-2-yl)methanesulfonamide, N-(4-(1-(4-(((R)-1-Hydroxy-4-methylpentan-2-yl)amino)-6-(methylsulfonamido)-1,3,5-triazin-2-yl)propan-2-yl)phenyl)-N-methylacetamide, N-(4-(((R)-1-Hydroxy-4-methylpentan-2-yl)amino)-6-(2-(4-(trifluoromethyl)phenyl)propyl)-1,3,5-triazin-2-yl)methanesulfonamide, N-(4-(((R)-1-Hydroxy-4-methylpentan-2-yl)amino)-6-((R)-2-(6-methoxypyridin-3-yl)propyl)-1,3,5-triazin-2-yl)methanesulfonamide, N-(4-(((R)-1-Hydroxy-4-methylpentan-2-yl)amino)-6-((S)-2-(6-methoxypyridin-3-yl)propyl)-1,3,5-triazin-2-yl)methanesulfonamide, N-(4-((R)-2-(2,6-Difluorophenyl)propyl)-6-(((R)-1-hydroxy-4-methylpentan-2-yl)amino)-1,3,5-triazin-2-yl)methanesulfonamide, N-(4-((S)-2-(2,6-Difluorophenyl)propyl)-6-(((R)-1-hydroxy-4-methylpentan-2-yl)amino)-1,3,5-triazin-2-yl)methanesulfonamide, N-(4-((R)-2-(4-Fluorophenyl)propyl)-6-(((R)-1-hydroxy-4-methylpentan-2-yl)amino)-1,3,5-triazin-2-yl)methanesulfonamide, N-(4-((S)-2-(4-Fluorophenyl)propyl)-6-(((R)-1-hydroxy-4-methylpentan-2-yl)amino)-1,3,5-triazin-2-yl)methanesulfonamide, N-(4-((R)-2-(2-Fluoro-4-methoxyphenyl)propyl)-6-(((R)-1-hydroxy-4-methylpentan-2-yl)amino)-1,3,5-triazin-2-yl)methanesulfonamide, N-(4-((S)-2-(2-Fluoro-4-methoxyphenyl)propyl)-6-(((R)-1-hydroxy-4-methylpentan-2-yl)amino)-1,3,5-triazin-2-yl)methanesulfonamide, N-(4-((R)-2-(4-Chloro-2-fluorophenyl)propyl)-6-(((R)-1-hydroxy-4-methylpentan-2-yl)amino)-1,3,5-triazin-2-yl)methanesulfonamide, N-(4-((S)-2-(4-Chloro-2-fluorophenyl)propyl)-6-(((R)-1-hydroxy-4-methylpentan-2-yl)amino)-1,3,5-triazin-2-yl)methanesulfonamide, N-(4-((R)-2-(2-Fluoro-6-methoxypyridin-3-yl)propyl)-6-(((R)-1-hydroxy-4-methylpentan-2-yl)amino)-1,3,5-triazin-2-yl)methanesulfonamide, N-(4-((S)-2-(2-Fluoro-6-methoxypyridin-3-yl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-((R)-2-(2,3,4-trifluorophenyl)propyl)-1,3,5-triazin-2-yl)methanesulfonamide, N-(4-(((R)-1-Hydroxy-4-methylpentan-2-yl)amino)-6-((S)-2-(2,3,4-trifluorophenyl)propyl)-1,3,5-triazin-2-yl)methanesulfonamide, N-(4-(2-(2-Fluorophenyl)butyl)-6-(((R)-1-hydroxy-4-methylpentan-2-yl)amino)-1,3,5-triazin-2-yl)methanesulfonamide, N-(4-((R)-2-(2-Fluoropyridin-4-yl)propyl)-6-(((R)-1-hydroxy-4-methylpentan-2-yl)amino)-1,3,5-triazin-2-yl)methanesulfonamide, N-(4-((S)-2-(2-Fluoropyridin-4-yl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(3-methoxyphenyl)propyl)-1,3,5-triazin-2-yl)methanesulfonamide, N-(4-(2-(1H-Pyrrolo[2,3-b]pyridin-3-yl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(2-methylpyridin-4-yl)propyl)-1,3,5-triazin-2-yl)methanesulfonamide, N-(4-(((R)-1-Hydroxy-4-methylpentan-2-yl)amino)-6-(2-(4-(morpholinomethyl)phenyl)propyl)-1,3,5-triazin-2-yl)methanesulfonamide, N-(4-(2-(3,4-Dimethoxyphenyl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(8-methoxyquinolin-5-yl)propyl)-1,3,5-triazin-2-yl)methanesulfonamide, N-(4-(2-(3-Chloro-4-ethoxyphenyl)propyl)-6-(((R)-1-hydroxy-4-methylpentan-2-yl)amino)-1,3,5-triazin-2-yl)methanesulfonamide, N-(4-(2-(2-Fluoro-3-methoxyphenyl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(3-methyl-2-oxo-2,3-dihydrobenzo[d]oxazol-6-yl)propyl)-1,3,5-triazin-2-yl)methanesulfonamide, N-(4-(((R)-1-Hydroxy-4-methylpentan-2-yl)amino)-6-(2-(3-((3-oxoisoxazolidin-2-yl)methyl)phenyl)propyl)-1,3,5-triazin-2-yl)methanesulfonamide, N-(4-(((R)-1-Hydroxy-4-methylpentan-2-yl)amino)-6-(2-(4-(tetrahydro-2H-pyran-4-yl)phenyl)propyl)-1,3,5-triazin-2-yl)methanesulfonamide, N-(4-(((R)-1-Hydroxy-4-methylpentan-2-yl)amino)-6-(2-(quinolin-8-yl)propyl)-1,3,5-triazin-2-yl)methanesulfonamide, N-(4-(((R)-1-Hydroxy-4-methylpentan-2-yl)amino)-6-(2-(4-hydroxy-5,6,7,8-tetrahydronaphthalen-2-yl)propyl)-1,3,5-triazin-2-yl)methanesulfonamide, N-(4-(((R)-1-Hydroxy-4-methylpentan-2-yl)amino)-6-(2-(3-(oxetan-3-yl)phenyl)propyl)-1,3,5-triazin-2-yl)methanesulfonamide, N-(4-(2-(2,3-Dimethyl-2H-indazol-6-yl)propyl)-6-(((R)-1-hydroxy-4-methylpentan-2-yl)amino)-1,3,5-triazin-2-yl)methanesulfonamide, N-(4-(2-(5-Chloro-2-hydroxyphenyl)propyl)-6-(((R)-1-hydroxy-4-methylpentan-2-yl)amino)-1,3,5-triazin-2-yl)methanesulfonamide, N-(4-(2-(Benzo[d][1,3]dioxol-5-yl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(3-methyl-4-oxo-3,4-dihydroquinazolin-8-yl)propyl)-1,3,5-triazin-2-yl)methanesulfonamide, N-(4-(2-(3,5-Difluoro-4-(hydroxymethyl)phenyl)propyl)-6-(((R)-1-hydroxy-4-methylpentan-2-yl)amino)-1,3,5-triazin-2-yl)methanesulfonamide, N-(4-(2-(4-Fluoro-3-methylphenyl)propyl)-6-(((R)-1-hydroxy-4-methylpentan-2-yl)amino)-1,3,5-triazin-2-yl)methanesulfonamide, N-(4-(2-(4-Aminophenyl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(4-methoxyphenyl)propyl)-1,3,5-triazin-2-yl)methanesulfonamide, N-(4-(2-(3-Amino-4-methylphenyl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(4-(2-morpholinoethoxy)phenyl)propyl)-1,3,5-triazin-2-yl)methanesulfonamide, 2-Fluoro-4-(1-(4-(((R)-1-hydroxy-4-methylpentan-2-yl)amino)-6-(methylsulfonamido)-1,3,5-triazin-2-yl)propan-2-yl)-N,N-dimethylbenzamide, N-(4-(((R)-1-Hydroxy-4-methylpentan-2-yl)amino)-6-(2-(1-methyl-1H-pyrrolo[2,3-b]pyridin-5-yl)propyl)-1,3,5-triazin-2-yl)methanesulfonamide, N-(4-(((R)-1-Hydroxy-4-methylpentan-2-yl)amino)-6-(2-(4-(3-oxomorpholino)phenyl)propyl)-1,3,5-triazin-2-yl)methanesulfonamide, N-(4-(2-(4-Ethoxy-3-fluorophenyl)propyl)-6-(((R)-1-hydroxy-4-methylpentan-2-yl)amino)-1,3,5-triazin-2-yl)methanesulfonamide, 2-Fluoro-4-(1-(4-(((R)-1-hydroxy-4-methylpentan-2-yl)amino)-6-(methylsulfonamido)-1,3,5-triazin-2-yl)propan-2-yl)-N-methylbenzamide, N-(4-(2-(3-Aminophenyl)propyl)-6-(((R)-1-hydroxy-4-methylpentan-2-yl)amino)-1,3,5-triazin-2-yl)methanesulfonamide, N-(4-(2-(4-Fluoro-3-(hydroxymethyl)phenyl)propyl)-6-(((R)-1-hydroxy-4-methylpentan-2-yl)amino)-1,3,5-triazin-2-yl)methanesulfonamide, N-(4-(2-(4-Ethoxyphenyl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(3-methyl-4-oxo-3,4-dihydroquinazolin-6-yl)propyl)-1,3,5-triazin-2-yl)methanesulfonamide, N-(4-(((R)-1-Hydroxy-4-methylpentan-2-yl)amino)-6-(2-(4-methyl-3-oxo-3,4-dihydro-2H-pyrido[3,2-b][1,4]oxazin-7-yl)propyl)-1,3,5-triazin-2-yl)methanesulfonamide, N-(4-(((R)-1-Hydroxy-4-methylpentan-2-yl)amino)-6-(2-(3-methyl-4-oxo-3,4-dihydroquinazolin-7-yl)propyl)-1,3,5-triazin-2-yl)methanesulfonamide, N-(4-(2-(6-(Difluoromethoxy)pyridin-3-yl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(2-methyl-3-oxo-1,2,3,4-tetrahydroisoquinolin-6-yl)propyl)-1,3,5-triazin-2-yl)methanesulfonamide, N-(4-(((R)-1-Hydroxy-4-methylpentan-2-yl)amino)-6-(2-(4-methyl-3-oxo-3,4-dihydro-2H-benzo[b][1,4]oxazin-7-yl)propyl)-1,3,5-triazin-2-yl)methanesulfonamide, N-(4-(((R)-1-Hydroxy-4-methylpentan-2-yl)amino)-6-(2-(2-methyl-3-oxo-1,2,3,4-tetrahydroisoquinolin-7-yl)propyl)-1,3,5-triazin-2-yl)methanesulfonamide, N-(4-(2-(5-Amino-6-methylpyridin-3-yl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(6-(2-hydroxyethyl)pyridin-3-yl)propyl)-1,3,5-triazin-2-yl)methanesulfonamide, N-(4-(2-(3-Fluoro-4-(hydroxymethyl)phenyl)propyl)-6-(((R)-1-hydroxy-4-methylpentan-2-yl)amino)-1,3,5-triazin-2-yl)methanesulfonamide, N-(4-(((R)-1-Hydroxy-4-methylpentan-2-yl)amino)-6-(2-(quinolin-3-yl)propyl)-1,3,5-triazin-2-yl)methanesulfonamide, N-(4-(2-(3-Fluoro-2-hydroxyphenyl)propyl)-6-(((R)-1-hydroxy-4-methylpentan-2-yl)amino)-1,3,5-triazin-2-yl)methanesulfonamide,
N-(4-(2-(4-Amino-3-fluorophenyl)propyl)-6-(((R)-1-hydroxy-4-methylpentan-2-yl)amino)-1,3,5-triazin-2-yl)methanesulfonamide,
N-(4-(2-(3-Chloro-2-hydroxyphenyl)propyl)-6-(((R)-1-hydroxy-4-methylpentan-2-yl)amino)-1,3,5-triazin-2-yl)methanesulfonamide,
N-(4-(((R)-1-Hydroxy-4-methylpentan-2-yl)amino)-6-(2-(4-(2-morpholinoethyl)phenyl)propyl)-1,3,5-triazin-2-yl)methanesulfonamide,
N-(4-(2-(2-Hydroxy-3-methoxyphenyl)propyl)-6-(((R)-1-hydroxy-4-methylpentan-2-yl)amino)-1,3,5-triazin-2-yl)methanesulfonamide,
N-(4-(2-(3-Fluoro-4-isopropoxyphenyl)propyl)-6-(((R)-1-hydroxy-4-methylpentan-2-yl)amino)-1,3,5-triazin-2-yl)methanesulfonamide,
N-(4-(2-(4-Cyano-3-fluorophenyl)propyl)-6-(((R)-1-hydroxy-4-methylpentan-2-yl)amino)-1,3,5-triazin-2-yl)methanesulfonamide,
N-(4-(2-(4-Fluoro-2-hydroxyphenyl)propyl)-6-(((R)-1-hydroxy-4-methylpentan-2-yl)amino)-1,3,5-triazin-2-yl)methanesulfonamide,
N-(4-((R)-2-(2,3-Difluorophenyl)propyl)-6-(((R)-1-hydroxy-4-methylpentan-2-yl)amino)-1,3,5-triazin-2-yl)methanesulfonamide,
N-(4-((S)-2-(2,3-Difluorophenyl)propyl)-6-(((R)-1-hydroxy-4-methylpentan-2-yl)amino)-1,3,5-triazin-2-yl)methanesulfonamide,
N-(4-((R)-2-(2-Fluorophenyl)propyl)-6-(((R)-1-hydroxy-4-methylpentan-2-yl)amino)-1,3,5-triazin-2-yl)methanesulfonamide,
N-(4-((S)-2-(2-Fluorophenyl)propyl)-6-(((R)-1-hydroxy-4-methylpentan-2-yl)amino)-1,3,5-triazin-2-yl)methanesulfonamide
N-(4-(((R)-1-Hydroxy-4-methylpentan-2-yl)amino)-6-((R)-2-phenylpropyl)-1,3,5-triazin-2-yl)methanesulfonamide,
N-(4-(((R)-1-Hydroxy-4-methylpentan-2-yl)amino)-6-((S)-2-phenylpropyl)-1,3,5-triazin-2-yl)methanesulfonamide,
N-(4-((R)-2-(5-Chloropyridin-2-yl)propyl)-6-(((R)-1-hydroxy-4-methylpentan-2-yl)amino)-1,3,5-triazin-2-yl)methanesulfonamide,
N-(4-((S)-2-(5-Chloropyridin-2-yl)propyl)-6-(((R)-1-hydroxy-4-methylpentan-2-yl)amino)-1,3,5-triazin-2-yl)methanesulfonamide,
N-(4-(((R)-1-Hydroxy-4-methylpentan-2-yl)amino)-6-(3,3,3-trifluoro-2-phenylpropyl)-1,3,5-triazin-2-yl)methanesulfonamide, and pharmaceutically acceptable salts and tautomers thereof.

Some embodiments disclosed herein provide a compound selected from:
(R)—N-(4-((1-Hydroxy-4-methylpentan-2-yl)amino)-6-(2-methyl-2-phenylpropyl)-1,3,5-triazin-2-yl)methanesulfonamide,
(R)—N-(4-(3-(4-Chlorophenyl)-3,3-difluoropropyl)-6-((1-hydroxy-4-methylpentan-2-yl)amino)-1,3,5-triazin-2-yl)methanesulfonamide,
(R)—N-(4-(3,3-Difluoro-3-(4-fluorophenyl)propyl)-6-((1-hydroxy-4-methylpentan-2-yl)amino)-1,3,5-triazin-2-yl)methanesulfonamide,
N-(4-(2-(3-Fluoro-6-methylpyridin-2-yl)propyl)-6-(((R)-1-hydroxy-4-methylpentan-2-yl)amino)-1,3,5-triazin-2-yl)methanesulfonamide,
N-(4-(((R)-1-Hydroxy-4-methylpentan-2-yl)amino)-6-(2-(4-(morpholine-4-carbonyl)phenyl)propyl)-1,3,5-triazin-2-yl)methanesulfonamide,
N-(4-(2-([1,1'-Biphenyl]-3-yl)propyl)-6-(((R)-1-hydroxy-4-methylpentan-2-yl)amino)-1,3,5-triazin-2-yl)methanesulfonamide,
N-(4-(((R)-1-Hydroxy-4-methylpentan-2-yl)amino)-6-(2-(3-(1-hydroxycyclopropyl)phenyl)propyl)-1,3,5-triazin-2-yl)methanesulfonamide,
N-(4-(((R)-1-Hydroxy-4-methylpentan-2-yl)amino)-6-(2-(6-isopropoxypyridin-3-yl)propyl)-1,3,5-triazin-2-yl)methanesulfonamide,
N-(4-(2-(3-Fluoro-2-methoxyphenyl)propyl)-6-(((R)-1-hydroxy-4-methylpentan-2-yl)amino)-1,3,5-triazin-2-yl)methanesulfonamide,
N-(4-(2-(3-Cyano-4-fluorophenyl)propyl)-6-(((R)-1-hydroxy-4-methylpentan-2-yl)amino)-1,3,5-triazin-2-yl)methanesulfonamide,
N-(4-(2-(4-Fluoro-2-methoxyphenyl)propyl)-6-(((R)-1-hydroxy-4-methylpentan-2-yl)amino)-1,3,5-triazin-2-yl)methanesulfonamide,
N-(4-(((R)-1-Hydroxy-4-methylpentan-2-yl)amino)-6-(2-(2-oxoindolin-7-yl)propyl)-1,3,5-triazin-2-yl)methanesulfonamide,
N-(4-((R)-2-(4-Cyanophenyl)propyl)-6-(((R)-1-hydroxy-4-methylpentan-2-yl)amino)-1,3,5-triazin-2-yl)methanesulfonamide,
N-(4-((S)-2-(4-Cyanophenyl)propyl)-6-(((R)-1-hydroxy-4-methylpentan-2-yl)amino)-1,3,5-triazin-2-yl)methanesulfonamide,
N-(4-(((R)-1-Hydroxy-4-methylpentan-2-yl)amino)-6-(2-(6-methoxypyridin-2-yl)propyl)-1,3,5-triazin-2-yl)methanesulfonamide,
N-(4-(2-(6-Ethoxypyridin-3-yl)propyl)-6-(((R)-1-hydroxy-4-methylpentan-2-yl)amino)-1,3,5-triazin-2-yl)methanesulfonamide,
N-(4-(2-([1,1'-Biphenyl]-4-yl)propyl)-6-(((R)-1-hydroxy-4-methylpentan-2-yl)amino)-1,3,5-triazin-2-yl)methanesulfonamide,
N-(4-(2-(3-Chloro-4-cyanophenyl)propyl)-6-(((R)-1-hydroxy-4-methylpentan-2-yl)amino)-1,3,5-triazin-2-yl)methanesulfonamide,
N-(4-((R)-2-(4-Chlorophenyl)propyl)-6-(((R)-1-hydroxy-4-methylpentan-2-yl)amino)-1,3,5-triazin-2-yl)methanesulfonamide,
N-(4-((S)-2-(4-Chlorophenyl)propyl)-6-(((R)-1-hydroxy-4-methylpentan-2-yl)amino)-1,3,5-triazin-2-yl)methanesulfonamide, and pharmaceutically acceptable salts and tautomers thereof.

Some embodiments disclosed herein provide a compound selected from:
N-(4-(2-(3,4-dichlorophenyl)propyl)-6-(((R)-1-hydroxy-4-methylpentan-2-yl)amino)-1,3,5-triazin-2-yl)methanesulfonamide,
N-(4-(2-(3-chloro-2-fluorophenyl)propyl)-6-(((R)-1-hydroxy-4-methylpentan-2-yl)amino)-1,3,5-triazin-2-yl)methanesulfonamide,
N-(4-(2-(2,4-difluorophenyl)propyl)-6-(((R)-1-hydroxy-4-methylpentan-2-yl)amino)-1,3,5-triazin-2-yl)methanesulfonamide,
N-(4-(2-(5-fluoro-6-methoxypyridin-3-yl)propyl)-6-(((R)-1-hydroxy-4-methylpentan-2-yl)amino)-1,3,5-triazin-2-yl)methanesulfonamide,
N-(4-(2-(5-chloro-6-methoxypyridin-3-yl)propyl)-6-(((R)-1-hydroxy-4-methylpentan-2-yl)amino)-1,3,5-triazin-2-yl)methanesulfonamide,
N-(4-(2-(2-cyclopropylpyrimidin-5-yl)propyl)-6-(((R)-1-hydroxy-4-methylpentan-2-yl)amino)-1,3,5-triazin-2-yl)methanesulfonamide, N-(4-(((R)-1-hydroxy-4-methylpentan-2-yl)amino)-6-(2-(6-methoxy-4-methylpyridin-3-yl)propyl)-1,3,5-triazin-2-yl)methanesulfonamide, N-(4-(((R)-1-hydroxy-4-methylpentan-2-yl)amino)-6-(2-(6-methoxy-5-methylpyridin-3-yl)propyl)-1,3,5-triazin-2-yl)methanesulfonamide, N-(4-(((R)-1-hydroxy-4-methylpentan-2-yl)amino)-6-(2-(2-methoxypyridin-3-yl)propyl)-1,3,5-triazin-2-yl)methanesulfonamide, N-(4-(2-(3-fluoro-4-methoxyphenyl)propyl)-6-(((R)-1-hydroxy-4-methylpentan-2-yl)amino)-1,3,5-triazin-2-yl)methanesulfonamide, N-(4-(((R)-1-hydroxy-4-methylpentan-2-yl)amino)-6-(2-(3,4,5-trifluorophenyl)propyl)-1,3,5-triazin-2-yl)methanesulfonamide, N-(4-(2-(2,5-difluorophenyl)propyl)-6-(((R)-1-hydroxy-4-methylpentan-2-yl)amino)-1,3,5-triazin-2-yl)methanesulfonamide, N-(4-(2-(2-chloropyridin-4-yl)propyl)-6-(((R)-1-hydroxy-4-methylpentan-2-yl)amino)-1,3,5-triazin-2-yl)methanesulfonamide, N-(4-(2-(6-ethoxypyridin-3-yl)propyl)-6-(((R)-1-hydroxy-4-methylpentan-2-yl)amino)-1,3,5-triazin-2-yl)methanesulfonamide, N-(4-(2-(5-chloro-2-fluorophenyl)propyl)-6-(((R)-1-hydroxy-4-methylpentan-2-yl)amino)-1,3,5-triazin-2-yl)methanesulfonamide, N-(4-(2-(4-chloro-3,5-difluorophenyl)propyl)-6-(((R)-1-hydroxy-4-methylpentan-2-yl)amino)-1,3,5-triazin-2-yl)methanesulfonamide, N-(4-(2-(4-chloro-2,3-difluorophenyl)propyl)-6-(((R)-1-hydroxy-4-methylpentan-2-yl)amino)-1,3,5-triazin-2-yl)methanesulfonamide, N-(4-(((R)-1-hydroxy-4-methylpentan-2-yl)amino)-6-(2-(2,4,5-trifluorophenyl)propyl)-1,3,5-triazin-2-yl)methanesulfonamide, N-(4-(2-(4-chloro-2,5-difluorophenyl)propyl)-6-(((R)-1-hydroxy-4-methylpentan-2-yl)amino)-1,3,5-triazin-2-yl)methanesulfonamide, N-(4-(((R)-1-hydroxy-4-methylpentan-2-yl)amino)-6-(2-(2,4,6-trifluorophenyl)propyl)-1,3,5-triazin-2-yl)methanesulfonamide, N-(4-(((R)-1-hydroxy-4-methylpentan-2-yl)amino)-6-(2-(2,3,6-trifluorophenyl)propyl)-1,3,5-triazin-2-yl)methanesulfonamide, N-(4-(2-(4-chloro-2,6-difluorophenyl)propyl)-6-(((R)-1-hydroxy-4-methylpentan-2-yl)amino)-1,3,5-triazin-2-yl)methanesulfonamide, N-(4-(2-(4-fluoro-6-methoxypyridin-3-yl)propyl)-6-(((R)-1-hydroxy-4-methylpentan-2-yl)amino)-1,3,5-triazin-2-yl)methanesulfonamide, N-(4-(2-(2,3-difluorophenyl)butyl)-6-(((R)-1-hydroxy-4-methylpentan-2-yl)amino)-1,3,5-triazin-2-yl)methanesulfonamide, N-(4-(2-(6-aminopyridin-3-yl)propyl)-6-(((R)-1-hydroxy-4-methylpentan-2-yl)amino)-1,3,5-triazin-2-yl)methanesulfonamide, N-(4-(2-(2,6-dimethoxypyridin-3-yl)propyl)-6-(((R)-1-hydroxy-4-methylpentan-2-yl)amino)-1,3,5-triazin-2-yl)methanesulfonamide, N-(4-(2-(3-chloro-4-fluorophenyl)propyl)-6-(((R)-1-hydroxy-4-methylpentan-2-yl)amino)-1,3,5-triazin-2-yl)methanesulfonamide, N-(4-(((R)-1-hydroxy-4-methylpentan-2-yl)amino)-6-(2-(6-methoxypyridin-3-yl)propyl)-1,3,5-triazin-2-yl)methanesulfonamide, N-(4-(2-(2,6-difluorophenyl)propyl)-6-(((R)-1-hydroxy-4-methylpentan-2-yl)amino)-1,3,5-triazin-2-yl)methanesulfonamide, N-(4-(2-(4-fluorophenyl)propyl)-6-(((R)-1-hydroxy-4-methylpentan-2-yl)amino)-1,3,5-triazin-2-yl)methanesulfonamide, N-(4-(2-(2-fluoro-4-methoxyphenyl)propyl)-6-(((R)-1-hydroxy-4-methylpentan-2-yl)amino)-1,3,5-triazin-2-yl)methanesulfonamide, N-(4-(2-(4-chloro-2-fluorophenyl)propyl)-6-(((R)-1-hydroxy-4-methylpentan-2-yl)amino)-1,3,5-triazin-2-yl)methanesulfonamide, N-(4-(2-(2-fluoro-6-methoxypyridin-3-yl)propyl)-6-(((R)-1-hydroxy-4-methylpentan-2-yl)amino)-1,3,5-triazin-2-yl)methanesulfonamide, N-(4-(((R)-1-hydroxy-4-methylpentan-2-yl)amino)-6-(2-(2,3,4-trifluorophenyl)propyl)-1,3,5-triazin-2-yl)methanesulfonamide, N-(4-(2-(2-fluoropyridin-4-yl)propyl)-6-(((R)-1-hydroxy-4-methylpentan-2-yl)amino)-1,3,5-triazin-2-yl)methanesulfonamide, N-(4-(2-(2,3-difluorophenyl)propyl)-6-(((R)-1-hydroxy-4-methylpentan-2-yl)amino)-1,3,5-triazin-2-yl)methanesulfonamide, N-(4-(2-(2-fluorophenyl)propyl)-6-(((R)-1-hydroxy-4-methylpentan-2-yl)amino)-1,3,5-triazin-2-yl)methanesulfonamide, N-(4-(((R)-1-hydroxy-4-methylpentan-2-yl)amino)-6-(2-phenylpropyl)-1,3,5-triazin-2-yl)methanesulfonamide, N-(4-(2-(5-chloropyridin-2-yl)propyl)-6-(((R)-1-hydroxy-4-methylpentan-2-yl)amino)-1,3,5-triazin-2-yl)methanesulfonamide, and pharmaceutically acceptable salts and tautomers thereof.

Some embodiments disclosed herein provide a compound selected from:

N-(4-(-2-(4-Cyanophenyl)propyl)-6-(((R)-1-hydroxy-4-methylpentan-2-yl)amino)-1,3,5-triazin-2-yl)methanesulfonamide, N-(4-(2-(4-chlorophenyl)propyl)-6-(((R)-1-hydroxy-4-methylpentan-2-yl)amino)-1,3,5-triazin-2-yl)methanesulfonamide, and pharmaceutically acceptable salts and tautomers thereof.

Some embodiments disclosed herein provide a pharmaceutical composition comprising a compound of formulae (I), (Ia), (Ib), (Ic), (Id), (Ie), or (If), a compound disclosed herein, or a pharmaceutically acceptable salt or tautomer thereof.

For the avoidance of doubt it is to be understood that where in this specification a group is qualified by "defined above" the said group encompasses the first occurring and broadest definition as well as each and all of the other definitions for that group. It is to be understood that any of definitions, claims, aspects or embodiments of the variable groups of the formulae disclosed herein, may be combined with any other definitions, claims, aspects or embodiments herein (unless the context does not permit) to provide further embodiments of the specification.

It shall be noted that any one of these specific compounds may be disclaimed from any of the herein mentioned embodiments.

In one embodiment there is provided a process for the preparation of compounds of formulae (I), (Ia), (Ib), (Ic), (Id), (Ie), or (If), or a compound disclosed herein, or a pharmaceutically acceptable salt thereof, and the intermediates used in the preparation thereof.

Another embodiment is a product obtainable by any of the processes or examples disclosed herein.

Medical and Pharmaceutical Use

The compounds of formulae (I), (Ia), (Ib), (Ic), (Id), (Ie), or (If), or a compound disclosed herein, or a pharmaceutically acceptable salt thereof, may be useful in the prevention or treatment of cardiovascular disease in a mammal, particularly a human. Cardiovascular disease includes, but is not limited to, conditions associated with cardiac dysfunction and/or microvascular dysfunction and/or macrovascular pathology, such as atherosclerosis, arteriosclerosis, coronary artery disease including stable and high risk coronary artery disease (defined as recent acute coronary syndrome (ACS) or by biomarkers of microvascular and cardiac dysfunction), ischemic heart disease, myocardial infarction, restenosis following revascularization procedures, heart failure, abdominal aortic aneurysm (AAA), peripheral artery disease (PAD) including erectile dysfunction due to vascular disease, stroke, cardiomyopathy, including non-ischemic dilated cardiomyopathy, transient ischemic attack (TIA) and reversible ischemic neurologic disease (RIND), multi-infarct dementia, renovascular disease, and renal arterial disease.

The compounds of formulae (I), (Ia), (Ib), (Ic), (Id), (Ie), or (If), or a compound disclosed herein, or a pharmaceutically acceptable salt thereof, may be useful in the prevention or treatment of non-ischemic dilated cardiomyopathy.

The compounds of formulae (I), (Ia), (Ib), (Ic), (Id), (Ie), or (If), or a compound disclosed herein, or a pharmaceutically acceptable salt thereof, may be useful in the prevention or treatment of cardiovascular disease in a patient having co-morbidities such as renal dysfunction.

The compounds of formulae (I), (Ia), (Ib), (Ic), (Id), (Ie), or (If), or a compound disclosed herein, or a pharmaceutically acceptable salt thereof, may be useful in the prevention or treatment of cardiovascular disease associated with chronic inflammatory diseases, e.g., rheumatoid arthritis, systemic lupus erythematosus (SLE), polymyositis, dermatomyositis, Still's disease, and inflammatory arthropathies/multisystem diseases such as psoriatic arthropathy.

The compounds of formulae (I), (Ia), (Ib), (Ic), (Id), (Ie), or (If), or a compound disclosed herein, or a pharmaceutically acceptable salt thereof, may be useful in the prevention or treatment of cardiovascular disease associated with autoimmune conditions, e.g., rheumatoid arthritis, systemic lupus erythematosus (SLE), polymyositis, dermatomyositis, Still's disease, and inflammatory arthropathies/multisystem diseases such as psoriatic arthropathy.

The compounds of formulae (I), (Ia), (Ib), (Ic), (Id), (Ie), or (If), or a compound disclosed herein, or a pharmaceutically acceptable salt thereof, may be useful in the prevention or treatment of heart failure, including heart failure with reduced ejection fraction, heart failure with mildly reduced ejection fraction, and heart failure with preserved ejection fraction.

The compounds of formulae (I), (Ia), (Ib), (Ic), (Id), (Ie), or (If), or a compound disclosed herein, or a pharmaceutically acceptable salt thereof, may be useful in the prevention or treatment of inflammatory bowel disease.

The compounds of formulae (I), (Ia), (Ib), (Ic), (Id), (Ie), or (If), or a compound disclosed herein, or a pharmaceutically acceptable salt thereof, may be useful in the prevention or treatment of lupus nephritis.

The compounds of formulae (I), (Ia), (Ib), (Ic), (Id), (Ie), or (If), or a compound disclosed herein, or a pharmaceutically acceptable salt thereof, may be useful in the prevention or treatment of patients with remaining risk for a cardiovascular event despite standard of care (SoC) treatment, such as, but not limited to, lipid lowering statins, antiplatelets, ACE inhibitors, mineralocorticoid receptor antagonists, and beta blockers.

The compounds of formulae (I), (Ia), (Ib), (Ic), (Id), (Ie), or (If), or a compound disclosed herein, or a pharmaceutically acceptable salt thereof, may be useful in the prevention or treatment of chronic kidney disease.

The compounds of formulae (I), (Ia), (Ib), (Ic), (Id), (Ie), or (If), or a compound disclosed herein, or a pharmaceutically acceptable salt thereof, may be useful in the prevention or treatment of type II diabetes mellitus and complications of type II diabetes mellitus in a mammal, particularly a human. This includes and is not restricted to, diabetic micro and macrovascular pathology, neuropathy and nephropathy.

The compounds of formulae (I), (Ia), (Ib), (Ic), (Id), (Ie), or (If), or a compound disclosed herein, or a pharmaceutically acceptable salt thereof, may be useful in the prevention or treatment of renal inflammatory and vascular diseases and complications associated with renal disease in a mammal, particularly a human. Renal inflammatory and vascular disease includes, but is not limited to chronic kidney disease, drug and toxin induced nephrotoxicity, lupus nephritis, glomerulonephritis, nephrotic syndrome, IgA nephritis, reflux nephropathy, focal segmental glomerulosclerosis, Henoch-Schonleins purpura, and diabetic nephropathy.

The compounds of formulae (I), (Ia), (Ib), (Ic), (Id), (Ie), or (If), or a compound disclosed herein, or a pharmaceutically acceptable salt thereof, may be useful in the prevention or treatment of autoimmune diseases, such as, but not limited to, dermatomyositis, polymyositis, and systemic lupus erythematosus (SLE).

The compounds of formulae (I), (Ia), (Ib), (Ic), (Id), (Ie), or (If), or a compound disclosed herein, or a pharmaceutically acceptable salt thereof, may be useful in the prevention or treatment of non-alcoholic fatty liver disease (NAFLD), non-alcoholic steatohepatitis (NASH), and ASH (alcoholic steatohepatitis).

Treatment with the compounds of formulae (I), (Ia), (Ib), (Ic), (Id), (Ie), or (If), or a compound disclosed herein, or a pharmaceutically acceptable salt thereof, may lower the cardiovascular and/or cerebrovascular and/or renal and/or peripheral arterial disease morbidity and mortality associated with cardiac dysfunction and/or atherosclerosis, and/or renal dysfunction and/or microvascular dysfunction and/or macrovascular pathology due to their anti-inflammatory properties and influence on vasoactive mechanisms.

The compounds of formulae (I), (Ia), (Ib), (Ic), (Id), (Ie), or (If), or a compound disclosed herein, or a pharmaceutically acceptable salt thereof, may serve to prevent or reduce the risk of developing cardiac dysfunction and/or renal dysfunction and/or microvascular dysfunction and/or macrovascular pathology, as well as for halting or slowing the progression and/or promoting the regression of atherosclerotic cardiovascular disease once it has become clinically evident, comprising the administration of a prophylactically or therapeutically effective amount, as appropriate, of a compound of formulae (I), (Ia), (Ib), (Ic), (Id), (Ie), or (If), or a compound disclosed herein, or a pharmaceutically acceptable salt thereof, to a mammal, including a human, who is at risk of developing atherosclerosis or who already has atherosclerotic cardiovascular disease.

Compounds of formulae (I), (Ia), (Ib), (Ic), (Id), (Ie), or (If), or a compound disclosed herein, or a pharmaceutically acceptable salt thereof, may be useful in preventing or reducing the incidence or severity of acute events related to atherosclerotic plaque rupture or erosion, including, but not limited to, myocardial infarction, unstable angina and stroke.

Compounds of formulae (I), (Ia), (Ib), (Ic), (Id), (Ie), or (If), or a compound disclosed herein, or a pharmaceutically acceptable salt thereof, may be useful in preventing or reducing the incidence or severity of acute events by improving microvascular function, macrovascular pathology and/or cardiac function.

Compounds of formulae (I), (Ia), (Ib), (Ic), (Id), (Ie), or (If), or a compound disclosed herein, or a pharmaceutically acceptable salt thereof, may be useful in preventing or reducing the progression of abdominal aortic aneurysms (AAA) and incidence of rupture.

The compounds of formulae (I), (Ia), (Ib), (Ic), (Id), (Ie), or (If), or a compound disclosed herein, or a pharmaceutically acceptable salt thereof, may be useful in the prevention or treatment of respiratory inflammatory disease and complications associated with respiratory inflammatory disease in a mammal, particularly a human. Respiratory inflammatory disease includes, but is not limited to asthma, chronic obstructive pulmonary disease, emphysema, interstitial lung disease associated with connective tissue diseases, and rhinitis.

Some embodiments disclosed herein provide a method of treating or preventing one or more of the diseases or conditions discussed herein, wherein the method comprises administering to a person suffering from, or at risk of, said disease or condition, a therapeutically effective amount of a compound of formulae (I), (Ia), (Ib), (Ic), (Id), (Ie), or (If), a compound disclosed herein, or a pharmaceutically acceptable salt thereof.

Some embodiments disclosed herein provide a method of treating or preventing non-ischemic dilated cardiomyopathy, wherein the method comprises administering to a person in need thereof, a therapeutically effective amount of a compound of formulae (I), (Ia), (Ib), (Ic), (Id), (Ie), or (If), a compound disclosed herein, or a pharmaceutically acceptable salt thereof.

Some embodiments disclosed herein provide a method of treating or preventing cardiovascular disease in a patient having co-morbidities such as renal dysfunction, wherein the method comprises administering to a person in need of thereof, a therapeutically effective amount of a compound of formulae (I), (Ia), (Ib), (Ic), (Id), (Ie), or (If), a compound disclosed herein, or a pharmaceutically acceptable salt thereof.

Some embodiments disclosed herein provide a method of treating or preventing cardiovascular disease associated with chronic inflammatory diseases, e.g., rheumatoid arthritis, systemic lupus erythematosus (SLE), polymyositis, dermatomyositis, Still's disease, and inflammatory arthropathies/multisystem diseases such as psoriatic arthropathy, wherein the method comprises administering to a person in need of thereof, a therapeutically effective amount of a compound of formulae (I), (Ia), (Ib), (Ic), (Id), (Ie), or (If), a compound disclosed herein, or a pharmaceutically acceptable salt thereof.

Some embodiments disclosed herein provide a method of treating or preventing heart failure wherein the method comprises administering to a person in need of thereof, a therapeutically effective amount of a compound of formulae (I), (Ia), (Ib), (Ic), (Id), (Ie), or (If), a compound disclosed herein, or a pharmaceutically acceptable salt thereof. In further embodiments the heart failure is heart failure with reduced ejection fraction, heart failure with mildly reduced ejection fraction, or heart failure with preserved ejection fraction Some embodiments disclosed herein provide a method of treating or preventing inflammatory bowel disease, wherein the method comprises administering to a person in need of thereof, a therapeutically effective amount of a compound of formulae (I), (Ia), (Ib), (Ic), (Id), (Ie), or (If), a compound disclosed herein, or a pharmaceutically acceptable salt thereof.

Some embodiments disclosed herein provide a method of treating or preventing lupus nephritis, wherein the method comprises administering to a person in need of thereof, a therapeutically effective amount of a compound of formulae (I), (Ia), (Ib), (Ic), (Id), (Ie), or (If), a compound disclosed herein, or a pharmaceutically acceptable salt thereof.

Some embodiments disclosed herein provide a method of treating or preventing respiratory inflammatory disease and complications associated with respiratory inflammatory disease, wherein the method comprises administering to a person in need of thereof, a therapeutically effective amount of a compound of formulae (I), (Ia), (Ib), (Ic), (Id), (Ie), or (If), a compound disclosed herein, or a pharmaceutically acceptable salt thereof. In further embodiments, the respiratory inflammatory disease is asthma, chronic obstructive pulmonary disease, emphysema, interstitial lung disease associated with connective tissue diseases, and/or rhinitis.

The terms "preventing", "prevention", and "prevent" are readily understood by an ordinarily skilled physician and, with respect to treatment of a particular condition, can include is intended to have its normal meaning and includes primary prophylaxis to prevent the development of the condition and secondary prophylaxis whereby the condition has already developed and the patient is temporarily or permanently protected against exacerbation or worsening of the disease or the development of new symptoms associated with the condition.

The terms "treating", "treatment", and "treat" are readily understood by an ordinarily skilled physician and, with respect to treatment of a particular condition, can include (1) diminishing the extent or cause of the condition being treated, and/or (2) alleviating or ameliorating one or more symptoms associated with that condition. Treatment of cardiovascular disease, for example, can include stabilizing (i.e., not worsening), delaying, or slowing the spread or progression of the cardiovascular disease; prolonging survival as compared to expected survival if not receiving treatment; and/or otherwise ameliorating or palliating the severity of the cardiovascular disease, in whole or in part.

The compounds disclosed herein may have the advantage that they may be more efficacious, be less toxic, be more selective, be more potent, produce fewer side effects, be more easily absorbed, and/or have a better pharmacokinetic profile (e.g. higher oral bioavailability and/or lower clearance), than compounds known in the prior art.

These and other embodiments are described in greater detail herein below, where further aspects will be apparent to one skilled in the art from reading this specification.

Pharmacological Properties

The compounds of formulae (I), (Ia), (Ib), (Ic), (Id), (Ie), or (If), or a compound disclosed herein, or a pharmaceutically acceptable salt thereof, or pharmaceutically acceptable salts thereof are believed to be useful in the prevention or treatment of cardiovascular conditions, including but not limited to coronary artery disease, acute coronary syndrome, cardiomyopathy, non-ischemic dilated cardiomyopathy, heart failure, heart failure with reduced ejection fraction, heart failure with mildly reduced ejection fraction, and heart failure with preserved ejection fraction in a mammal, particularly a human.

When a compound or salt described herein is administered as therapy for treating a disorder, a "therapeutically effective amount" is an amount sufficient to reduce or completely alleviate symptoms or other detrimental effects of the disorder, cure the disorder, reverse, completely stop, or slow the progress of the disorder or reduce the risk of the disorder getting worse.

The compounds described herein are thus indicated both in the therapeutic and/or prophylactic treatment of these conditions.

Pharmaceutical Compositions

There is provided a method of treatment of a condition where modulation of $CX_3CR1$ is required, which method comprises administration of a therapeutically effective amount of a compound of formulae (I), (Ia), (Ib), (Ic), (Id), (Ie), or (If), or a compound disclosed herein, or a pharmaceutically acceptable salt thereof, to a person suffering from, or susceptible to, such a condition.

The compounds of formulae (I), (Ia), (Ib), (Ic), (Id), (Ie), or (If), or a compound disclosed herein, or a pharmaceutically acceptable salt thereof, will normally be administered via the oral, topical, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt thereof, in a pharmaceutically acceptable dosage form. Depending upon the disorder and patient to be treated and the route of administration, the compositions may be administered at varying doses. Conventional procedures for the selection and preparation of suitable pharmaceutical formulations are described in, for example, *Pharmaceuticals—The Science of Dosage Form Designs*, M. E. Aulton, Churchill Livingstone, 2$^{nd}$ Ed. 2002.

The optimum dosage and frequency of administration will depend on the particular condition being treated and its severity; the species of the patient; the age, sex, size and weight, diet, and general physical condition of the particular patient; brain/body weight ratio; other medication the patient may be taking; the route of administration; the formulation; and various other factors known to physicians and others skilled in the art.

According to a further aspect there is thus provided a pharmaceutical formulation comprising a compound of formulae (I), (Ia), (Ib), (Ic), (Id), (Ie), or (If), or a compound disclosed herein, or a pharmaceutically acceptable salt thereof, or pharmaceutically acceptable derivatives thereof, in admixture with a pharmaceutically acceptable adjuvant, diluent and/or carrier.

The compounds of formulae (I), (Ia), (Ib), (Ic), (Id), (Ie), or (If), or a compound disclosed herein, or a pharmaceutically acceptable salt thereof, may be present in the pharmaceutical formulation in a concentration from 0.1 to 99.5%, such as from 0.5 to 95%, by weight of the total formulation. A further embodiment encompasses pharmaceutically acceptable salts of the compounds of formulae (I), (Ia), (Ib), (Ic), (Id), (Ie), or (If), or a compound disclosed herein.

A salt of a compound of formulae (I), (Ia), (Ib), (Ic), (Id), (Ie), or (If), or a compound disclosed herein, may be advantageous due to one or more of its chemical or physical properties, such as stability in differing temperatures and humidities, or a desirable solubility in $H_2O$, oil, or other solvent. In some instances, a salt may be used to aid in the isolation or purification of the compound. In some embodiments (particularly where the salt is intended for administration to an animal, e.g. a human, or is a reagent for use in making a compound or salt intended for administration to an animal), the salt is pharmaceutically acceptable.

The term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

Where the compound is sufficiently basic, pharmaceutically acceptable salts include, but are not limited to, inorganic or organic acid addition salts. Where the compound is sufficiently acidic, pharmaceutically acceptable salts include, but are not limited to, inorganic or organic base addition salts.

For reviews on suitable salts, see Berge et al., *J. Pharm. Sci.*, 1977, 66, 1-19 or *Handbook of Pharmaceutical Salts: Properties, selection and use*, P. H. Stahl, P. G. Vermuth, IUPAC, Wiley-VCH, 2002.

It is also to be understood that certain compounds of formulae (I), (Ia), (Ib), (Ic), (Id), (Ie), or (If), or a compound disclosed herein, may exist in solvated form, e.g. hydrates, including solvates of a pharmaceutically acceptable salt of a compound of formula (I).

It is also to be understood that certain compounds of formulae (I), (Ia), (Ib), (Ic), (Id), (Ie), or (If), or a compound disclosed herein, or a pharmaceutically acceptable salt thereof, may exist as a mixture of tautomers. "Tautomers" are structural isomers that exist in equilibrium resulting from the migration of a hydrogen atom, e.g., amide-imidic acid tautomerism. The disclosure herein includes all tautomers of compounds of formulae (I), (Ia), (Ib), (Ic), (Id), (Ie), or (If), or a compound disclosed herein, or a pharmaceutically acceptable salt thereof.

In particular embodiments, certain compounds of formulae (I), (Ia), (Ib), (Ic), (Id), (Ie), or (If), or a compound disclosed herein, or a pharmaceutically acceptable salt thereof, may exist as racemates and racemic mixtures, single enantiomers, individual diastereomers and diastereomeric mixtures. Certain compounds of formulae (I), (Ia), (Ib), (Ic), (Id), (Ie), or (If), or a compound disclosed herein, or a pharmaceutically acceptable salt thereof, may also contain linkages (e.g. carbon-carbon bonds, carbon-nitrogen bonds such as amide bonds) wherein bond rotation is restricted about that particular linkage, e.g. restriction resulting from the presence of a ring bond or double bond. Stereoisomers may be separated using conventional techniques, e.g. chromatography or fractional crystallization, or the stereoisomers may be made by stereoselective synthesis.

The compounds of formula (I) as below contain one stereogenic center if $R^3$ and $R^4$ are identical or two stereogenic centers, provided $R^3$ and $R^4$ are not identical, and may thus exist in the following stereoisomeric forms as shown in formulae (Ib), (Ic), (Id), or (Ie).

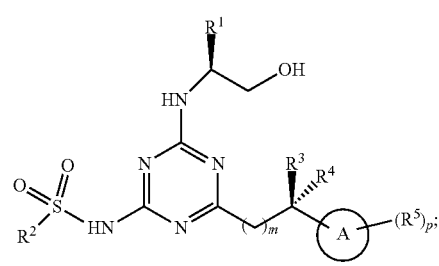

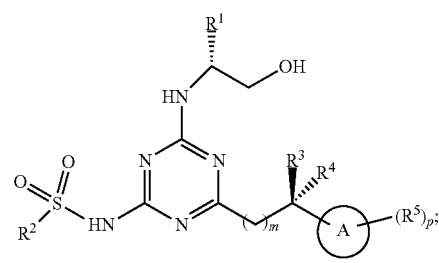

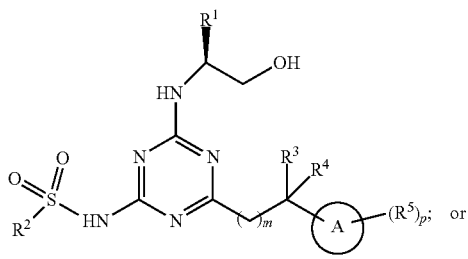

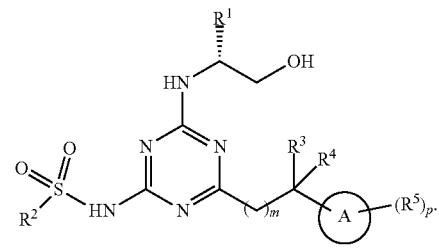

Intermediate compounds may also exist in enantiomeric forms and may be used as purified enantiomers, diastereomers, racemates or mixtures.

In a further embodiment, the compounds of formulae (I), (Ia), (Ib), (Ic), (Id), (Ie), or (If), or a compound disclosed herein, or a pharmaceutically acceptable salt thereof, encompass any isotopically-labelled (or "radio-labelled") derivatives of a compound of formulae (I), (Ia), (Ib), (Ic), (Id), (Ie), or (If), or a compound disclosed herein, or a pharmaceutically acceptable salt thereof. Such a derivative is a derivative of a compound of formulae (I), (Ia), (Ib), (Ic), (Id), (Ie), or (If), or a compound disclosed herein, or a pharmaceutically acceptable salt thereof, wherein one or more atoms are replaced by an atom having an atomic mass or mass number different from the atomic mass or mass number typically found in nature. Examples of isotopes that can be incorporated into compounds of formulae (I), (Ia), (Ib), (Ic), (Id), (Ie), or (If), or a compound disclosed herein, or a pharmaceutically acceptable salt thereof, include, but are not limited to, isotopes of hydrogen, carbon, nitrogen, oxygen, phosphorous, sulfur, fluorine, chlorine and iodine, such as $^2H$, $^3H$, $^{11}C$, $^{13}C$, $^{14}C$, $^{15}N$, $^{35}S$, $^{36}Cl$ and $^{125}I$. Isotopically labelled compounds disclosed herein can generally be prepared by conventional techniques known to those skilled in the art or by processes analogous to those described in the accompanying Examples using appropriate isotopically labelled reagents in place of the non-labelled reagents previously employed.

In a further embodiment, the compounds of formulae (I), (Ia), (Ib), (Ic), (Id), (Ie), or (If), or a compound disclosed herein, or a pharmaceutically acceptable salt thereof, may be administered in the form of a prodrug which is broken down in the human or animal body to give a compound of the formulae (I), (Ia), (Ib), (Ic), (Id), (Ie), or (If), or a compound disclosed herein, or a pharmaceutically acceptable salt thereof.

Various forms of prodrugs are known in the art. For examples of prodrug derivatives, see: *Nature Reviews Drug Discovery* 2008, 7, 255 and references cited therein.

Intermediate compounds may also exist in enantiomeric forms and may be used as purified enantiomers, diastereomers, racemates or mixtures.

EXAMPLES

The following examples are non-limiting examples.
Synthetic Methods
General conditions (i) operations were carried out at room temperature (rt), i.e. in the range 17 to 28° C. and where needed under an atmosphere of an inert gas such as $N_2$; optionally reactions were carried out using a MBRAUN UNILab Plus ECO or a MBRAUN UNILab SP Eco glovebox workstation, in which case it is indicated;

(ii) where reactions refer to being degassed or purged, this can be performed for example by purging the reaction solvent with a constant flow of nitrogen for a suitable period of time (for example 5 to 10 min) or by repeatedly evacuating the vessel and backfill with appropriate inert atmosphere (for example nitrogen (g) or argon (g));

(iii) where reactions refer to the use of a microwave reactor, one of the following microwave reactors were used: Biotage Initiator, Personal Chemistry Emrys Optimizer, Personal Chemistry Smith Creator or CEM Explorer;

(iv) in general, the course of reactions was followed by thin layer chromatography (TLC) and/or analytical high performance liquid chromatography (HPLC or UPLC) which was usually coupled to a mass spectrometer (LCMS).

(v) when necessary, organic solutions were dried over anhydrous $MgSO_4$ or $Na_2SO_4$, or by using ISOLUTE® Phase Separator, and workup procedures were carried out using traditional phase separating techniques. When a drying agent such as e.g. $MgSO_4$ or $Na_2SO_4$ is used for drying an organic layer, it is understood that said organic layer is filtered before concentration of said layer.

(vi), evaporations were carried out either by rotary evaporation in vacuo or in a Genevac HT-4/EZ-2 or Biotage V10;

(vii) unless otherwise stated, flash column chromatography was performed on straight phase silica, using either Merck Silica Gel (Art. 9385) or prep-packed cartridges such as Biotage® SNAP cartridges (40-63 m silica, 4-330 g), Biotage® Sfar Silica HC D cartridges (20 μm, 10-100 g), Interchim puriFlash™ cartridges (25 μm, 4-120 g), Interchim puriFlash™ cartridges (50 μm, 25-330 g), Grace™ GraceResolv™ Silica Flash Cartridges (4-120 g) or Agela Flash Colum Silica-CS cartridges (80-330 g), or on reversed phase silica using Agela Technologies C-18, spherical cartridges (20-35 µm, 100A, 80-330 g), manually or automated using a Grace Reveleris® x2 Flash system or similar system;

(viii) preparative reverse phase HPLC and preparative reverse phase SFC were performed using standard HPLC and SFC instruments, respectively, equipped with either a MS and/or UV triggered fraction collecting instrument, using either isocratic or a gradient of the mobile phase as described in the experimental section and using one of the following methods: PrepMethod A: The compound was purified by preparative HPLC on a Kromasil C8 column (10 µm, 250×50 mm ID) using a gradient of MeCN in $H_2O$/MeCN/FA (95/5/0.2) as mobile phase; PrepMethod B: The compound was purified by preparative HPLC on a Kromasil C8 column (10 µm, 250×20 mm ID) using a gradient of MeCN in $H_2O$/MeCN/FA (95/5/0.2) as mobile phase; PrepMethod C: The compound was purified by preparative HPLC on an unspecified column using a gradient of MeCN in $H_2O$/MeCN/FA (95/5/0.2) as mobile phase; PrepMethod D: The compound was purified by preparative HPLC on a XBridge™ C18 column (10 m, 250×19 mm ID) using a gradient of MeCN in $H_2O$/MeCN/NH3 (95/5/0.2) as mobile phase; PrepMethod E: The compound was purified by preparative HPLC on a Xbridge™ C18 ODB column (5 µm, 150×30 mm ID) using a gradient of MeCN in a $H_2O$/$NH_3$ (0.2%, pH 10) buffer system as mobile phase; PrepMethod F: The compound was purified by preparative HPLC on a XBridge™ C18 ODB column (5 µm, 150×19 mm ID) using a gradient of MeCN in $H_2O$/$NH_3$ (0.2%, pH 10) buffer system as mobile phase; PrepMethod G: The compound was purified by preparative HPLC on a Phenomenex Luna Hilic column (5 µm, 250×30) using MeOH/$NH_3$ 20 mM as mobile phase; PrepMethod H: The compound was purified by preparative HPLC on a Waters *Viridis* 2-EP column (5 µm, 250×30) using MeOH/$NH_3$ 20 mM as mobile phase; PrepMethod I: The compound was purified by preparative HPLC on a Xbridge™ C18 ODB column (5 µm, 100×10 mm ID) using a gradient of MeCN in a $H_2O$/$NH_3$ (0.2%, pH 10) buffer system as mobile phase; PrepMethod J: The compound was purified by preparative HPLC on a Acquity™ UPC2 BEH column (3.5 µm, 100×3 mm ID) using MeOH/$H_2O$/$NH_3$ (97/3/50 mM) buffer system as mobile phase; PrepMethod K: The compound was purified by preparative HPLC on a Virdis™ BEH OBD column (5 µm, 250×30 mm ID) using MeOH/$H_2O$/$NH_3$ (97/3/50 mM) buffer system as mobile phase; PrepMethod L: The compound was purified by preparative HPLC on a Virdis™ BEH column (5 µm, 250×30 mm ID) using EtOH/FA 20 mM buffer system as mobile phase; PrepMethod M: The compound was purified by preparative HPLC on a Sunfire™ C18 ODB column (5 µm, 150×30 mm ID) using a gradient of MeCN in FA (0.1 M aq) buffer system as mobile phase; PrepMethod N: The compound was purified by preparative HPLC on a Sunfire™ C18 ODB column (5 µm, 100×10 mm ID) using a gradient of MeCN in FA (0.1 M aq) buffer system as mobile phase; PrepMethod O: The compound was purified by preparative HPLC on an XSelect CSH Prep C18 OBD column (5 µm, 250×19 mm ID) using a gradient of MeCN in FA (0.1 M aq) buffer system as mobile phase; PrepMethod P: The compound was purified by preparative HPLC on an XSelect CSH Prep C18 OBD column (5 µm, 150×30 mm ID) using a gradient of MeCN in FA (0.1 M aq) buffer system as mobile phase; PrepMethod Q: The compound was purified by preparative SFC on a Waters™ BEH (5 µm, 30×250 mm ID) using EtOH/FA (20 mM) in CO2 as mobile phase;

relevant fractions were collected, combined and freeze-dried or evaporated to give the purified compound or relevant fractions were collected, combined and concentrated at reduced pressure, the aqueous layer was extracted with DCM or EtOAc, and the organic layer was dried, either over $Na_2SO_4$ or by using a phase-separator, and then concentrated at reduced pressure and when needed dried in vacuo, to give the purified compound;

(ix) chiral preparative chromatography was carried out using HPLC or SFC on a standard HPLC or SFC instruments, respectively, and using either isocratic or gradient run with mobile phase as described in the experimental section;

(x) yields, where present, are not necessarily the maximum attainable, and when necessary, reactions were repeated if a larger amount of the reaction product was required;

(xi) where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;

(xii) in general, the structures of the end-products of the Formula (I) were confirmed by nuclear magnetic resonance (NMR) and/or mass spectral techniques; proton NMR chemical shift values were measured on the delta scale using Bruker Avance III 300, 400, 500 and 600 spectrometers, operating at $^1$H frequencies of 300, 400, 500 and 600 MHz, respectively. The experiments were typically recorded at 25° C. Chemical shifts are given in ppm with the solvent as internal standard. Protons on heteroatoms such as NH and OH protons are only reported when detected in NMR and can therefore be missing. In certain instances, protons can be masked or partially masked by solvent peaks and will therefore either be missing and not reported or reported as multiplets overlapping with solvent. The following abbreviations have been used (and derivatives thereof, e.g. dd, doublet of doublets, etc.): s, singlet; d, doublet; t, triplet; q, quartet; m, multiplet; br, broad; qn, quintet; p, pentet. It is understood, where the NMR spectra contains residual impurities and/or residual solvent(s), this is not reported unless it partially coincides with peaks of Intermediates and/or Structures of Formula (I), in which case said peaks of Intermediates and/or Structures of Formula (I) are reported as multiplets partially overlapping with said solvent or impurity, and the Integral is omitted. In some cases, the structures of the end-products of the Formula (I) might appear as rotamers in the NMR-spectrum, in which instances only peaks of the major rotamer are reported. In some cases, the structures of the end-products of Formula (I) might appear as rotamers in a more equal relationship, in such instances the peaks of such rotamers are either reported as multiplets, if the signals of said rotamers are partially overlapping, or as individual peaks, if the signals of said rotamers are well separated;

electrospray mass spectral data were obtained using a Waters Acquity UPLC coupled to a Waters single quadrupole mass spectrometer or similar equipment, acquiring both positive and negative ion data, and generally, only ions relating to the parent structure are reported; high resolution electrospray mass spectral data were obtained using a Waters XEVO qToF mass spectrometer or similar equipment, coupled to a Waters Acquity UPLC, acquiring either positive and negative ion data, and generally, only ions relating to the parent structure are reported;

(xiii) intermediates were not necessarily fully purified but their structures and purity were assessed by TLC, analytical HPLC/UPLC, and/or NMR analysis and/or mass spectrometry;

(xiv) unless stated otherwise compounds containing an asymmetric carbon and/or sulfur atom were not resolved;

(xv) in general Examples and Intermediate compounds are named using ChemDraw Professional version 20.1.1.125 or version 21.0.0 from PerkinElmer. ChemDraw Professional version 20.1.1.125 or version 21.0.0 generates the names of chemical structures using the Cahn-Ingold-Prelog (CIP) rules for stereochemistry and follows IUPAC rules as closely as possible when generating chemical names. Stereoisomers are differentiated from each other by stereodescriptors cited in names and assigned in accordance with the CIP rules.

ChemDraw is optionally using labels in the graphical representation of stereocenters such as '&' and 'or' to describe the configuration of the stereochemical centers present in the structure. A number following the '&' and 'or' flag is assigned to each stereocenter present in the structure. The numbers are incremented automatically to indicate that stereocenters may vary independently to each other.

In general, for chemical structures of Examples and Intermediates where more than one stereocenter is present and said stereocenters have a fixed relative configuration, the same number is used after the label '&' and 'or' to indicate that said stereocenters forms a group. A third stereocenter present in the same chemical structure, that varies independently to the former stereocenters, is designated with a unique new number following the label '&' and 'or'.

In general chemical structures of Examples and Intermediates containing the label '&' at a stereocenter, means the configuration of such Example or Intermediate at that stereocenter is a mixture of both (R) and (S); and a label 'or' means the configuration of such Example or Intermediate at that stereocenter is either (S) or (R). Absolute, unspecified, '&', and 'or' stereocenters can all be present in a single structure.

In general for structures of Examples and Intermediates where all of the stereocenters are designated as '&', the structure is named with a "rac-" prefix.

The descriptors (RS) and (SR) are used to denote general '&' centers for chemical structures with multiple chiral centers where only some are designated as'&'.

In general, for structures of Examples and Intermediates where all of the stereocenters are designated as 'or', the structure is named with a "rel-" prefix.

The descriptors (R*) and (S*) are used to denote the general 'or' centers for chemical structures with multiple chiral centers where only some are designated as 'or'. It is to be understood that an Example or Intermediate with a stereocenter labled (R*) or (S*) has an absolute configuration at said stereocenter and while said stereocenter in the compound has been designated as (R*) or (S*), the actual stereochemistry of that particular isomer could be the opposite of the label. For example, while Example 1, the first eluting isomer from the chiral separation of N-(4-(2-(3,4-dichlorophenyl)propyl)-6-(((R)-1-hydroxy-4-methylpentan-2-yl)amino)-1,3,5-triazin-2-yl)methanesulfonamide (Intermediate 6) is named "N-(4-((R*)-2-(3,4-Dichlorophenyl)propyl)-6-(((R)-1-hydroxy-4-methylpentan-2-yl)amino)-1,3,5-triazin-2-yl)methanesulfonamide" it could be N-(4-((R)-2-(3,4-Dichlorophenyl)propyl)-6-(((R)-1-hydroxy-4-methylpentan-2-yl)amino)-1,3,5-triazin-2-yl)methanesulfonamide orN-(4-((S)-2-(3,4-Dichlorophenyl)propyl)-6-(((R)-1-hydroxy-4-methylpentan-2-yl)amino)-1,3,5-triazin-2-yl)methanesulfonamide. Similarly Example 2, the second eluting isomer from the chiral separation of N-(4-(2-(3,4-dichlorophenyl)propyl)-6-(((R)-1-hydroxy-4-methylpentan-2-yl)amino)-1,3,5-triazin-2-yl)methanesulfonamide (Intermediate 6) is named "N-(4-((S*)-2-(3,4-Dichlorophenyl)propyl)-6-(((R)-1-hydroxy-4-methylpentan-2-yl)amino)-1,3,5-triazin-2-yl)methanesulfonamide" it could be N-(4-((S)-2-(3,4-Dichlorophenyl)propyl)-6-(((R)-1-hydroxy-4-methylpentan-2-yl)amino)-1,3,5-triazin-2-yl)methanesulfonamide orN-(4-((R)-2-(3,4-Dichlorophenyl)propyl)-6-(((R)-1-hydroxy-4-methylpentan-2-yl)amino)-1,3,5-triazin-2-yl)methanesulfonamide. It is to be further understood that while Example 1 is illustrated as Isomer 1

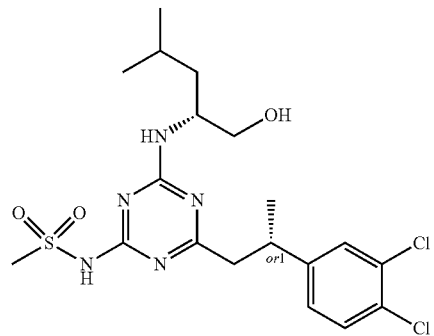

the actual structure of Example 1, (i.e., the first eluting isomer) could be

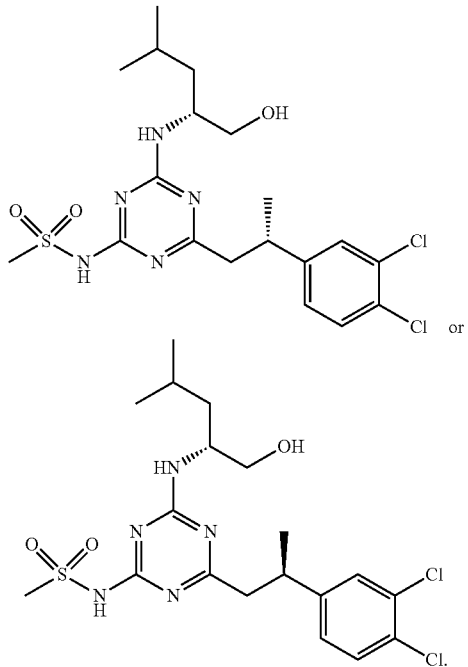

In general, for chemical structures of Examples and Intermediates where a stereocenter present is racemic, no flag is designated to the stereocenter and the bond to said stereocenter is drawn with a straight bond.

In general the label "Isomer 1" corresponds to the first eluted isomer, and "Isomer 2" corresponds to the second eluted isomer, on a given chiral HPLC column and eluent, and are used to distinguish two isomers containing one or more stereocenters with absolute unknown configuration;

(xvi) in addition to the ones mentioned above, the following abbreviations and units have been used:
Abs Absolute
AcOH Acetic acid
Aq Aqueous
9-BBN 9-borabicyclo[3.3.1]nonane
B2pin$_2$ 4,4,4',4',5,5,5',5'-octamethyl-2,2'-bi(1,3,2-dioxaborolane)
tBu tert-Butyl
n-BuLi 1-Butyllithium
t-BuOH tert-Butanol
KOtBu Potassium tert-butoxide
Brine Saturated aqueous sodium chloride solution
Calcd Calculated
DCM Dichloromethane
DEA Diethylamine
DIPE Diisopropyl ether
DIPEA N-ethyl-N-isopropyl-propan-2-amine
DMA N,N-dimethylacetamide
DMF N,N-dimethylformamide
DMSO Dimethyl sulfoxide
DPEphos (oxybis(2,1-phenylene))bis(diphenylphosphane)
e.g. for example
ESI Electrospray ionization
Et$_2$O Diethyl ether
EtOAc Ethyl acetate
EtOH Ethanol
eq equivalent
FA Formic acid
HPLC High performance liquid chromatography
IPA 2-propyl alcohol
HOAc Acetic acid
HRMS High resolution mass spectrometry
KOAc potassium acetate
LCMS Liquid chromatography Mass spectrometry
MeCN Acetonitrile
MeMgBr Methylmagnesium bromide
MeOH Methanol
MS Mass spectrometry
MTBE Methyl tert-butyl ether
2-MeTHF 2-Methyltetrahydrofuran
m/z mass spectrometry peak(s)
NaOtBu Sodium tert-butoxide
NMR Nuclear magnetic resonance
OAc O(CO)CH$_3$
OTf triflate
PE petroleum ether
Pd/C Palladium on charcoal
Pd(dtbpf)Cl$_2$ [1,1'-Bis(di-tert-butylphosphino)ferrocene]dichloropalladium(II)
Pd$_2$dba$_3$ Tris(dibenzylideneacetone)dipalladium(0)
Pd(dppf)Cl$_2$ [1,1'-Bis(diphenylphosphino)ferrocene]dichloropalladium(II)
Pd(dppf)Cl$_2$·DCM [1,1'-Bis(diphenylphosphino)ferrocene]dichloropalladium(II) CH$_2$Cl$_2$ (1:1)
pTsOH para-toluenesulfonic acid
[Rh(COD)Cl]$_2$ Bis(1,5-cyclooctadiene)dirhodium(I) dichloride
Rt Room temperature
sat Saturated
TBDMS tert-butyldimehylsilyl
TBDMSCl tert-butylchlorodimethylsilane
TBTU 2-(1H-benzo[d][1,2,3]triazol-1-yl)-1,1,3,3-tetramethyluronium tetrafluoroborate
TEA Triethylamine
THF Tetrahydrofuran
TLC Thin layer chromatography
UV ultraviolet
X-Phos dicyclohexyl(2',4',6'-triisopropyl-[1,1'-biphenyl]-2-yl)phosphane
Xantphos 4,5-Bis(diphenylphosphino)-9,9-dimethylxanthene, (9,9-dimethyl-9H-xanthene-4,5-diyl)bis(diphenylphosphine)
Units
C Celcius
g gram
h hour(s)
L litre
M mole per liter
mg milligram
MHz megaherz
min minute(s)
mL milliliter
mm millimeter
mol mole
mmol millimole(s)
μm micrometer
pmol micromole(s)
μL microlitre
nm nanometer
ppm parts per million General Synthesis Schemes The compounds of formula (I) may be formed by reacting a compound of formula (II), in which $R^1$ and $R^2$ are as defined in formula (I), and $LG_1$ is a suitable leaving group such as halo or OTf, e.g., chloro,

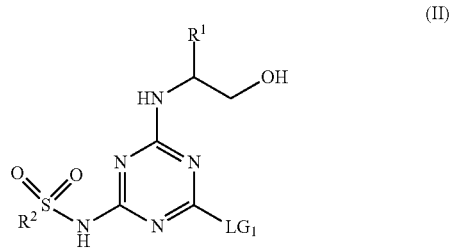

with a coupling partner of formula (III), in which A, $R^3$, $R^5$ and p are as defined in formula (I).

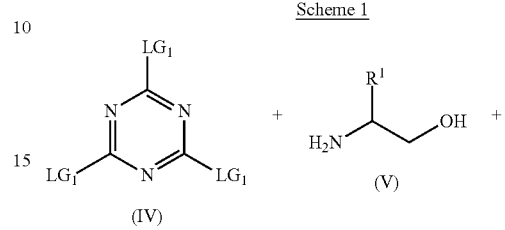

Compounds of formula (II) can also be protected at the hydroxyl moiety with a suitable protecting group, for instance a silyl group such as TBDMS and suitable methods are known to a person skilled in the art (for introduction and removal of such groups see "Protective Groups in Organic Synthesis", 4th edition, T. W. Greene & P. G. M Wutz, Wiley-Interscience (2007)).

The compounds of formula (III) may be pre-mixed with an organoboron reagent, e.g., 9-BBN dimer or a solution of 9-BBN in an organic solvent, e.g., THF, at rt for 1-24 h or at elevated temperatures, e.g., 35° C. to reflux, for 1-2 h, and then a compound of formula (II) as defined above is added together with an inorganic salt e.g. $K_3PO_4$ or CsOH, and a catalytic amount of a palladium source e.g. Pd(dppf) $Cl_2 \cdot DCM$. The resulting reaction mixture is stirred at temperatures ranging from 35° C. to reflux for a prolonged time, e.g., 2-48 h until the reaction is complete, to give the compound of formula (I).

The compounds of formula (II) may be prepared by sequentially reacting a compound of formula (V), in which $R^1$ is as defined in formula (I), and a compound of formula (VI), in which $R^2$ is as defined in formula (I), with a compound of formula (IV), in which $LG_1$ is as defined in formula (II), as illustrated in Scheme 1.

Scheme 1

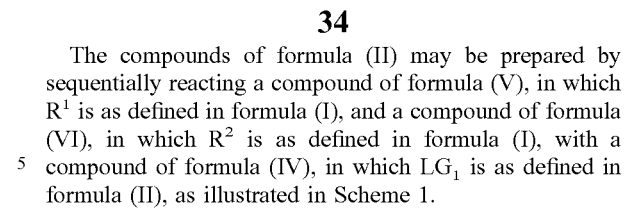

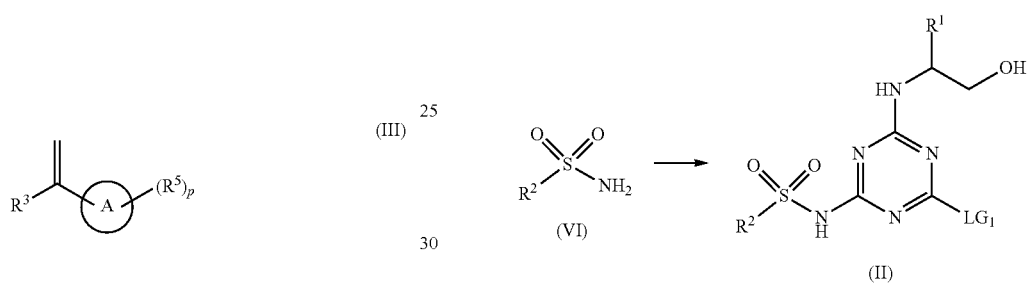

A solution of a compound of formula (V) in a suitable organic solvent, such as 2-MeTHF, is added to a solution of (IV) in an organic solvent, such as 2-MeTHF, at −35° C. to −10° C. and then an organic base such as DIPEA dissolved in an organic solvent, e.g., 2-MeTHF is added to the reaction mixture at −35° C. to 0° C. and the reaction mixture is stirred until finished before any solids are filtered. The filtrate is added to a compound of formula (VI) in an organic solvent, such as DMA, and an inorganic base, e.g., $K_2CO_3$, and the reaction mixture is stirred at an elevated temperature, e.g., 70° C. to 80° C. for a prolonged time, e.g., 48 h until the reaction is complete, to give the compound of formula (II).

Compounds of formula (IV), (V) and (VI) are commercially available or can be prepared in a conventional manner by a person skilled in the art.

Compounds of formula (III) may be prepared from compounds of formula (VII) or (VIII) and (IX), in which A, $R^3$, $R^5$ and p are as defined in formula (I), according to Methods illustrated in Scheme 2.

Scheme 2

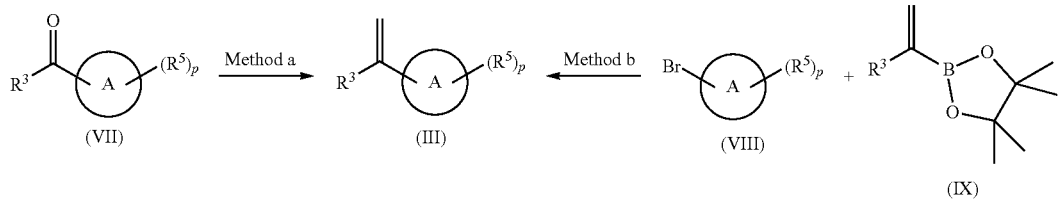

Method a: A compound of formula (III) may be prepared by a Wittig reaction between a compound of formula (VII) and a suitable phosphonium salt, such as methyl triphenylphosphonium bromide, with an appropriate base, such as KOtBu or n-BuLi, in an inert solvent such as Et$_2$O or THF. The base and phosphonium salt may be premixed in the solvent at −10° C. to 40° C. for 30 min to 1 h before a compound of formula (VII) is added and the reaction is kept at temperatures ranging from rt to 50° C. for reaction times between 1 h and 24 h, until the reaction is complete, to give the compound of formula (III).

Method b: A compound of formula (VIII) may be reacted with a compound of formula (IX) to give a compound of formula (III). The reaction may be performed using a catalytic amount of a palladium source e.g. Pd(dppf)Cl$_2$·DCM or Pd(dtbpf), in the presence of a base, e.g., an inorganic base, such as K$_2$CO$_3$, Cs$_2$CO$_3$ or CsOH, using an organic solvent such as THF or 1,4-dioxane together with water, and at elevated temperatures e.g., ranging from 50° C. to 95° C. for a prolonged time, e.g. 2 h to 24 h, until the reaction is finished, to give the compound of formula (III).

Compounds of formula (VII) may be prepared in a two-step sequence from compounds of formula (X) in which A, R$^5$ and p are as defined in formula (I), as illustrated in Scheme 3.

Scheme 3

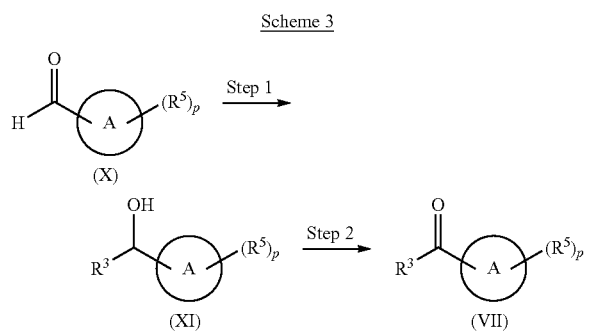

Step 1: A compound of formula (X) may be reacted with a nucleophilic reagent containing a suitable R$^3$-group, where R$^3$ is as defined in formula (I), e.g., a Grignard reagent, in an inert solvent, e.g. Et$_2$O to give an alcohol of formula (XI).

Step 2: A compound of formula (XI), in which A, R$^3$, R$^5$ and p are as defined in formula (I), may be reacted with an appropriate oxidizing reagent, e.g., Dess-Martin periodinane, in an inert solvent to give a compound of formula (VII).

Compounds of formula (VII) may also be prepared in a two-step sequence from compounds of formula (XII) in which A, R$^5$ and p are as defined in formula (I), as illustrated in Scheme 4.

Scheme 4

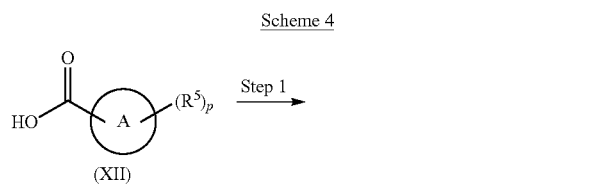

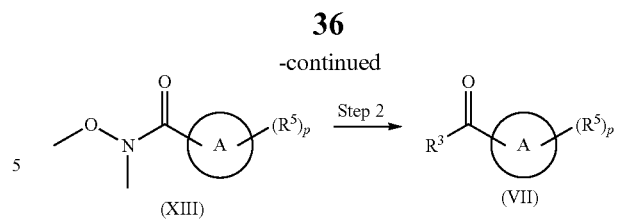

Step 1: A compound of formula (XII) may be reacted with N,O-dimethylhydroxylamine hydrochloride using a suitable coupling reagent e.g. TBTU, in the presence of an organic base such as DIPEA, using a solvent such as DCM, to give the corresponding Weinreb amide of formula (XIII).

Step 2: A compound of formula (XIII), in which A, R$^5$ and p are as defined in formula (I), may be reacted with a nucleophilic reagent containing a suitable R$^3$-group, where R$^3$ is as defined in formula (I), e.g., a Grignard reagent, in an inert solvent, e.g. THF to give a compound of formula (VII).

Certain compounds of formula (VII), (VIII), (IX), (X), (XI), (XII) and (XIII) are commercially available or can be prepared in a conventional manner by a person skilled in the art.

A compound of formula (I) may be formed by reacting a compound of formula (XIV), in which A, R$^1$, R$^3$, R$^5$, and p are as defined in formula (I), and LG$_1$ is a suitable leaving group such as halo or OTf, such as chloro,

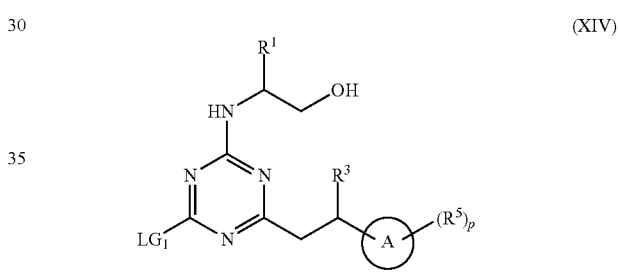

with a coupling partner of formula (VI), as defined above.

A compound of formula (I) may be formed by reacting a compound of formula (XIV-a), in which A, R$^1$, R$^3$, R$^4$, R$^5$, and p are as defined in formula (I), and LG$_1$ is a suitable leaving group such as halo or OTf, such as chloro,

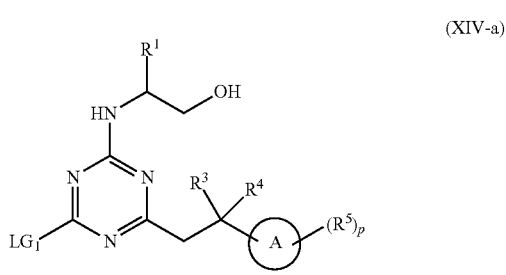

with a coupling partner of formula (VI), as defined above.

Catalytic amounts of a phosphine ligand, e.g., X-Phos, and a palladium source, e.g., Pd$_2$dba$_3$, are premixed under inert atmosphere in a suitable solvent such as THf, and then a compound of formula (XIV) or a compound of formula (XIV-a) and a compound of formula (VI) are added together with a base, such as K$_2$CO$_3$, and the reaction is run under inert atmosphere at an elevated temperature, e.g., 70° C., for a prolonged time, such as overnight, until the reaction is finished, to give the compound of formula (I).

A compound of formula (XIV) may be prepared by reacting a compound of formula (XV), which can be a cis- or trans-isomer or a mix of both, and in which $R^1$ and $R^3$ are as defined in formula (I), and $LG_1$ is a suitable leaving group such as halo or OTf, e.g., chloro, and a compound of formula (XVI), in which A, $R^5$ and p are as defined in formula (I), and B is a boron species, e.g., a boronic acid or a boronate ester, as illustrated in Scheme 5.

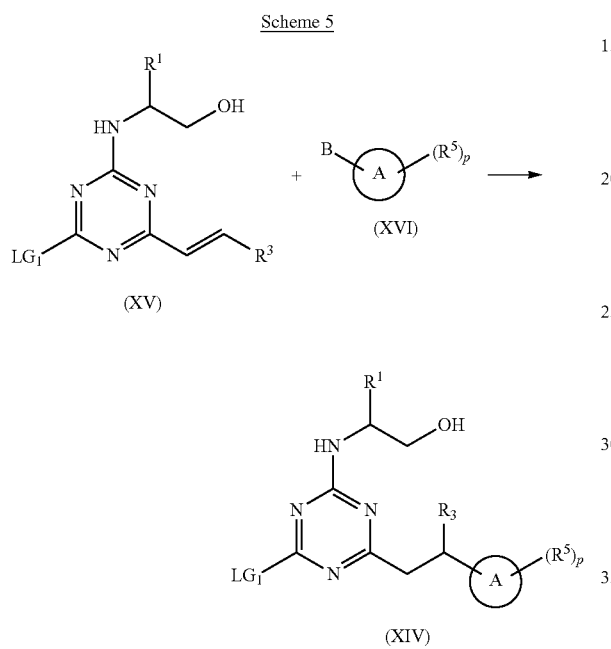

Catalytic amounts of a suitable organometallic catalyst, such as [Rh(COD)Cl]$_2$, is mixed with a compound of formula (XV), a compound of formula (XVI) together with a base, such as KOH, using an organic solvent such as 1,4-dioxane, together with water, at elevated temperatures, e.g., from 50° C. to 95° C. for a prolonged time, e.g. 2 h to 24 h, until the reaction is finished, to give the compound of formula (XIV).

The compounds of formula (XV), which can be a cis- or trans-isomer or a mix of both, may be prepared by sequentially reacting a compound of formula (XVII), in which $R^3$ is as defined in formula (I) and M is metal or a halo metal, usually MgBr, and a compound of formula (V), as defined above, with a compound of formula (IV), as defined above, as illustrated in Scheme 6.

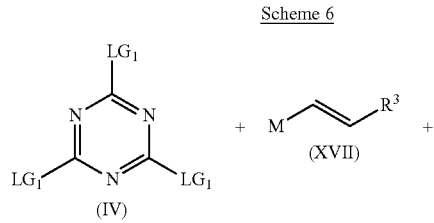

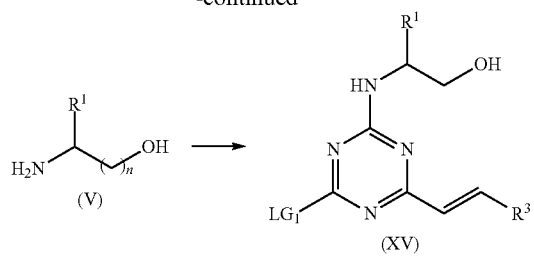

A solution of a compound of formula (XVII) in a suitable organic solvent, e.g., THF, is added to a cold solution of (IV) in an organic solvent, e.g., THF, and the mixture is allowed to reach rt during a short period of time, usually 30 min, and then cooled and a solution of a compound of formula (V) in a suitable organic solvent, e.g., THF and an organic base, such as DIPEA, are added and the reaction mixture is allowed to reach rt during a prolonged time until finished, to give the compound of formula (XV).

Compounds of formula (XVI) and (XVII) are commercially available or can be prepared in a conventional manner by a person skilled in the art.

A compound of formula (I) may be prepared by reacting a compound of formula (XVIII), in which $R^1$, $R^2$ and $R^3$ are as defined in formula (I),

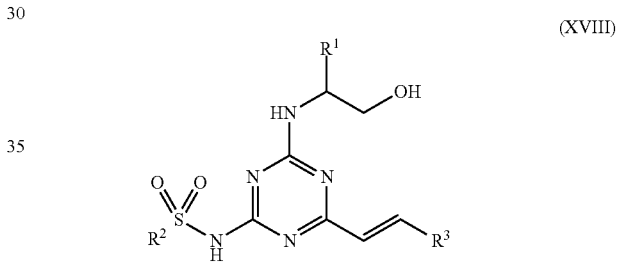

with a coupling partner of formula (XVI) as defined above. The reaction may be performed in a similar manner as the preparation of formula (XIV).

A compound of formula (XIV) may also be prepared by reacting a compound of formula (XIX), in which A, $R^3$, $R^5$ and p are as defined in formula (I), and $LG_1$ is a suitable leaving group such as halo or OTf, e.g., chloro,

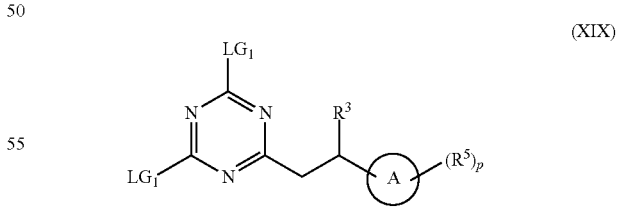

with a compound of formula (V), as defined above, in a suitable solvent, e.g. THF or MeCN, and base, e.g., $K_2CO_3$ for a prolonged time, e.g., 2 h to 24 h at rt, until the reaction is finished to give the compound of formula (XIV).

Compounds of formula (XIX) may be prepared in a two-step sequence from compounds of formula (XX) in which A, $R^3$, $R^5$ and p are as defined in formula (I), as illustrated in Scheme 7.

Scheme 7

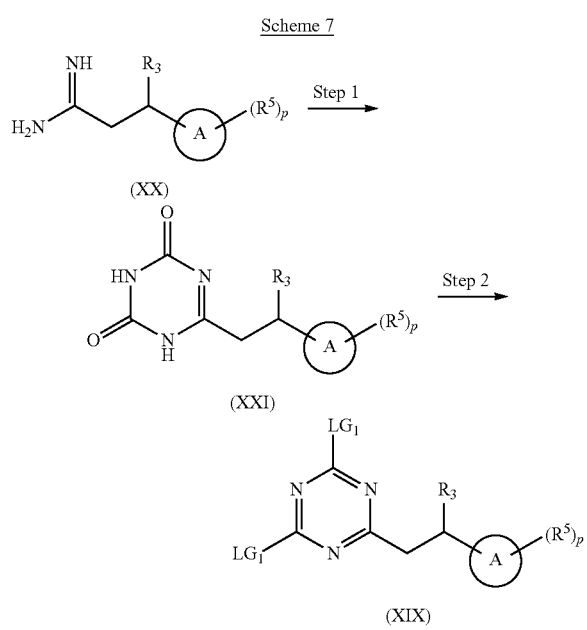

Step 1: A compound of formula (XX) may be reacted with diphenyl iminodicarboxylate in a suitable solvent, e.g., MeCN, in the presence of a base, such as $K_2CO_3$, at temperatures ranging from rt to 70° C. for a prolonged time, e.g. 2 h to 24 h, until the reaction is finished, to give a compound of formula (XXI).

Step 2: A compound of formula (XXI), in which A, $R^3$, $R^5$ and p are as defined in formula (I), may be reacted with a suitable reagent, e.g., POCl3 in excess, with or without an amine base such as N,N-diethyl aniline as an additive, at elevated temperatures ranging from 70° C. to reflux for a prolonged reaction time, e.g., 1.5 h to 15 h, until the reaction is finished, to give a compound of formula (XIX).

A compound of formula (XX), as defined above, may be prepared from a compound of formula (XXII), in which A, $R^3$, $R^5$ and p are as defined in formula (I), according to Methods illustrated in Scheme 8.

Scheme 8

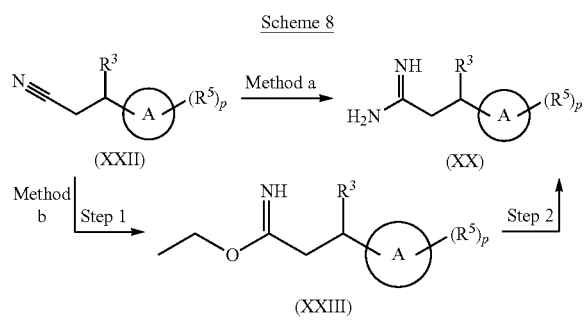

Method a: A compound of formula (XX) may be prepared by adding a compound of formula (XXII) to a mixture of $AlMe_3$ and $NH_4Cl$ in an inert solvent, e.g., toluene, at temperatures ranging from 70° C. to 90° C. for prolonged reaction times until the reaction is complete, to give the compound of formula (XX).

Method b:

Step 1: A compound of formula (XXIII), in which A, $R^3$, $R^5$ and p are as defined in formula (I), may be prepared by adding AcCl to a cold solution of a compound of formula (XXII) in a suitable solvent, e.g., EtOH, and allowing the temperature to reach rt during a prolonged time, e.g., 15 h to 24 h.

Step 2: A compound of formula (XX) may be prepared by adding a cold solution of $NH_3$ in a solvent such as MeOH, to a compound of formula (XXIII) and allowing the temperature to reach rt during a prolonged time, e.g., 22 h.

A compound of formula (XXII) may be prepared in a two-step sequence from a compound of formula (VII), as defined above, as illustrated in Scheme 9.

Scheme 9

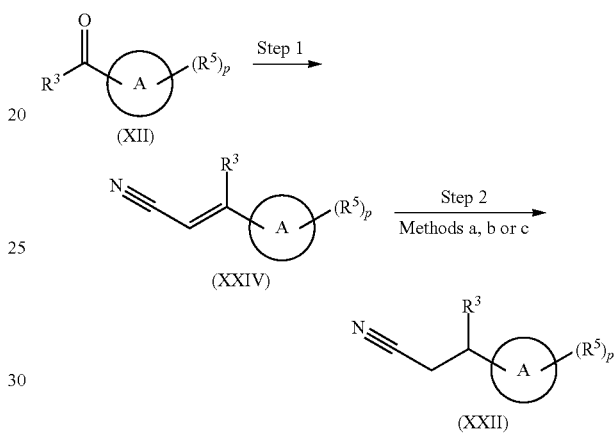

Step 1: A compound of formula (VII), as defined above, may be reacted with a suitable phosphonate, such as diethyl cyanomethyl phosphonate, with an appropriate base, such as NaOtBu or NaH, using a solvent such as abs EtOH or THF. The base and phosphonate may be premixed in the solvent for a short period of time before a compound of formula (VII) is added and the reaction is kept at rt for reaction times between 2 h and 24 h, until the reaction is complete, to give a compound of formula (XXIV).

Step 2: A compound of formula (XXIV), in which A, $R^3$, $R^5$ and p are as defined in formula (I), may be reduced by either of the methods described below;

Method a: A compound of formula (XXII) may be prepared by reacting a compound of formula (XXIV) with Pd/C under hydrogen atmosphere, in an inert solvent such as EtOAc, at rt for a prolonged time, until the reaction is complete.

Method b: A compound of formula (XXII) may be prepared by reacting a compound of formula (XXIV) with $NaBH_4$, in a suitable solvent, such as MeOH at rt for a prolonged time, until the reaction is complete.

Method c: A compound of formula (XXII) may be prepared by adding a compound of formula (XXIV) to a premixed slurry of diphenylsilane, $Cu(OAc)_2$ and DPEphos in a suitable solvent such as toluene at rt, and kept at rt for a prolonged time, until the reaction is complete.

A compound of formula (XIV-a) may be prepared by reacting a compound of formula (XIX-a), in which A, $R^3$, $R^4$, $R^5$ and p are as defined in formula (I), and $LG_1$ is a suitable leaving group such as halo or OTf, e.g., chloro, as illustrated in Scheme 10.

Scheme 10

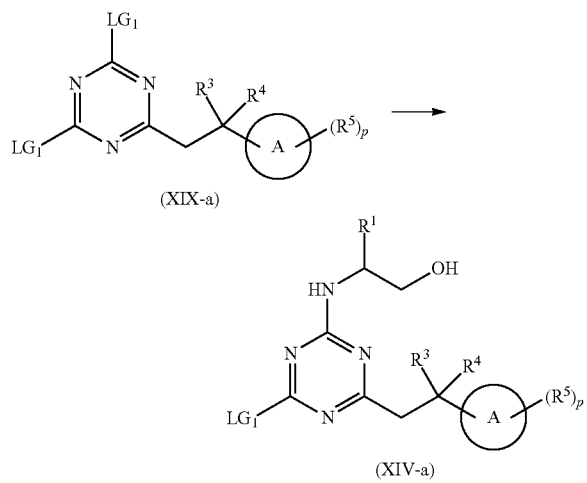

with a compound of formula (V), as defined above, in a suitable solvent, e.g. THF or MeCN, and base, e.g., K$_2$CO$_3$ for a prolonged time, e.g., 2 h to 24 h at rt, until the reaction is finished to give the compound of formula (XIV-a).

Compounds of formula (XIX-a) may be prepared in a two-step sequence from compounds of formula (XX-a) in which A, R$^3$, R$^4$, R$^5$ and p are as defined in formula (I), as illustrated in Scheme 11.

Scheme 11

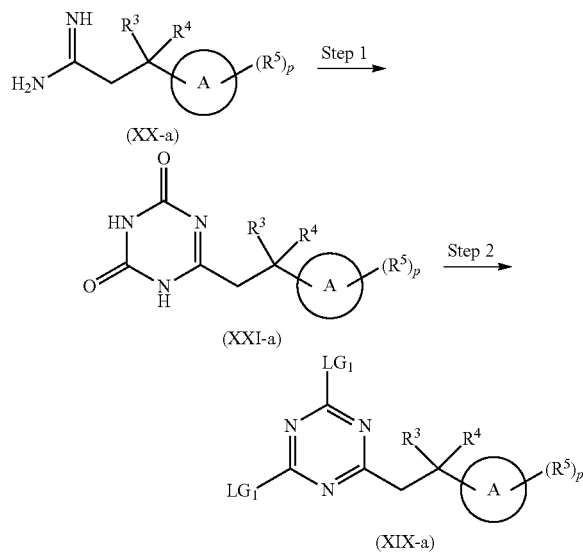

Step 1: A compound of formula (XX-a) may be reacted with diphenyl iminodicarboxylate in a suitable solvent, e.g., MeCN, in the presence of a base, such as K$_2$CO$_3$, at temperatures ranging from rt to 70° C. for a prolonged time, e.g. 2 h to 24 h, until the reaction is finished, to give a compound of formula (XXI-a).

Step 2: A compound of formula (XXI-a), in which A, R$^3$, R$^4$, R$^5$ and p are as defined in formula (I), may be reacted with a suitable reagent, e.g., POCl$_3$ in excess, with or without an amine base such as N,N-diethyl aniline as an additive, at elevated temperatures ranging from 70° C. to reflux for a prolonged reaction time, e.g., 1.5 h to 15 h, until the reaction is finished, to give a compound of formula (XIX-a).

A compound of formula (XX-a), as defined above, may be prepared from a compound of formula (XXII-a), in which A, R$^3$, R$^4$, R$^5$ and p are as defined in formula (I), according to Methods illustrated in Scheme 12.

Scheme 12

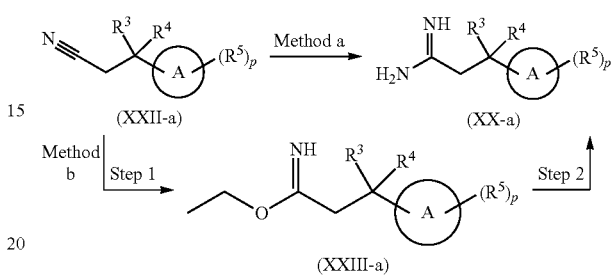

Method a: A compound of formula (XX-a) may be prepared by adding a compound of formula (XXII-a) to a mixture of AlMe$_3$ and NH$_4$Cl in an inert solvent, e.g., toluene, at temperatures ranging from 70° C. to 90° C. for prolonged reaction times until the reaction is complete, to give the compound of formula (XX-a).

Method b:

Step 1: A compound of formula (XXIII-a), in which A, R$^3$, R$^4$, R$^5$ and p are as defined in formula (I), may be prepared by adding AcCl to a cold solution of a compound of formula (XXII-a) in a suitable solvent, e.g., EtOH, and allowing the temperature to reach rt during a prolonged time, e.g., 15 h to 24 h.

Step 2: A compound of formula (XX-a) may be prepared by adding a cold solution of NH$_3$ in a solvent such as MeOH, to a compound of formula (XXIII-a) and allowing the temperature to reach rt during a prolonged time, e.g., 22 h.

Certain compounds of formula (XXII-a) may be prepared in a two-step sequence from compounds of formula (XXVII-a), in which R$^3$, R$^4$, R$^5$, A and p are as defined in formula (I), as illustrated in Scheme 13.

Scheme 13

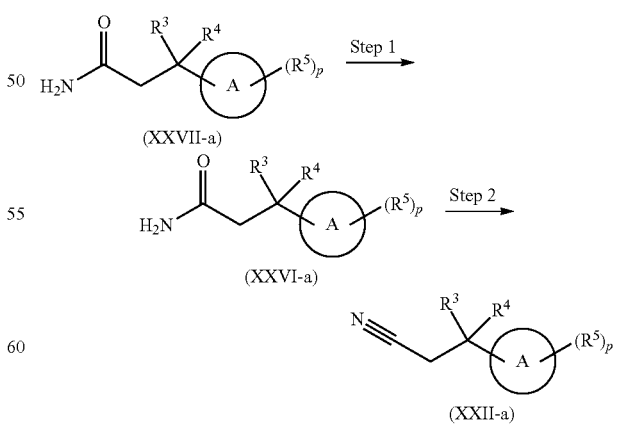

Step 1: A Compound of formula (XXVI-a) may be prepared from a compound of formula (XXVII-a) by reacting with oxalyl chloride and catalytical amounts of DMF in a solvent e.g. DCM at low temperature to rt for 30 min to 12 h. The formed product may after concentration at reduced pressure be reacted with NH₃ in a solvent e.g. THF at low temperature for a period of time, typically 1 h to 24 h.

Step 2: A compound of formula (XXII-a) may be prepared from a compound of formula (XXVI-a) by reacting with a PdCl₂ in a solvent e.g a mixture of MeCN and water at rt for a 12 h to 24 h.

h or at elevated temperatures, e.g., 35° C. to reflux, for 1-2 h, before a compound of formula (II) as defined above is added together with an inorganic salt e.g. K₃PO₄ or CsOH, and a catalytic amount of a palladium source e.g. Pd(dppf)Cl₂·DCM. The resulting reaction mixture is stirred at temperatures ranging from 35° C. to reflux for a prolonged time, e.g., 2-48 h until the reaction is complete, to give the compound of formula (I).

Scheme 15

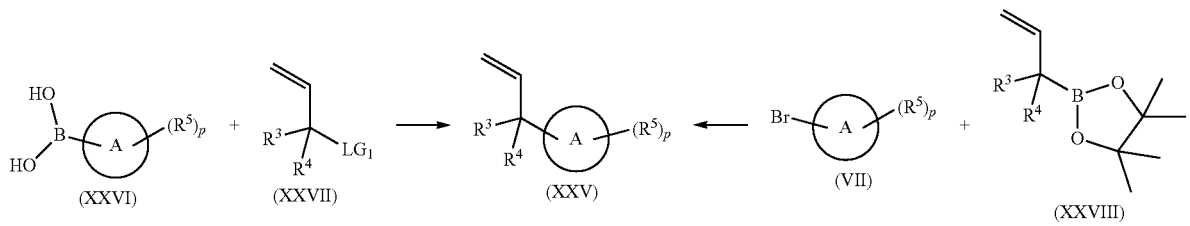

Compounds of formula (XXII-a) and (XXVII-a) are commercially available or can be prepared in a conventional manner by a person skilled in the art (for example, see methods described in; *Liebigs Annalen* 1996, 8, 1289-1294).

A compound of formula (I) in which A, R¹, R², R³, R⁴, R⁵ and p are as defined in formula (I) and m is 2, may be formed by reacting a compound of formula (II), as defined above, with a coupling partner of formula (XXV), in which A, R³, R⁴, R⁵ and p are as defined in formula (I), as illustrated in Scheme 14.

Compounds of formula (XXV) are commercially available or can be prepared as described in Scheme 11 in a conventional manner by a person skilled in the art (for example, see methods described in; *J. Org. Chem.* 1958, 23, 1658; *J. Am. Chem. Soc.* 2012, 134, 17470; *Angew. Chem. Int. Ed.* 2021, 60, 25746).

Intermediate 1

(R)—N-(4-Chloro-6-((1-hydroxy-4-methylpentan-2-yl)amino)-1,3,5-triazin-2-yl)methanesulfonamide Scheme 14

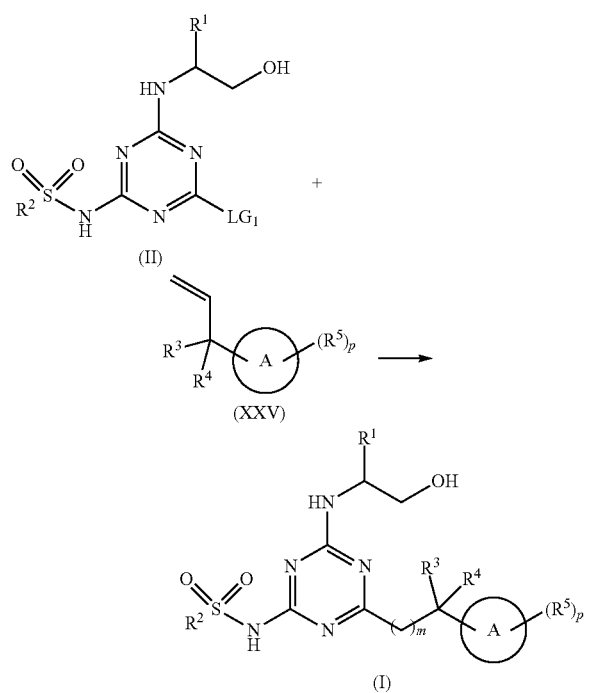

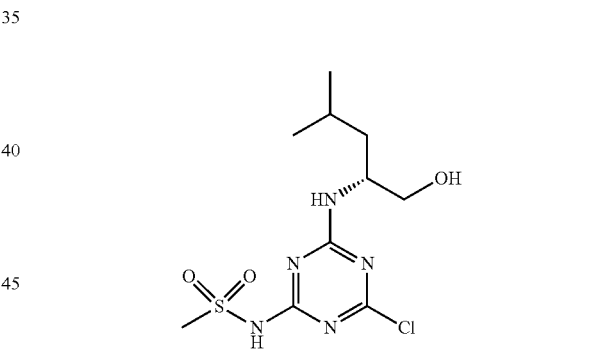

A compound of formula (XXV) can be premixed with an organoboron reagent, e.g., 9-BBN dimer or a solution of 9-BBN in an organic solvent, e.g., THF, at rt for 1 h to 24

2,4,6-Trichloro-1,3,5-triazine (50.0 g, 271.1 mmol) was dissolved in 2-MeTHF (500 mL) under nitrogen atmosphere and the stirred solution was cooled to −30° C. A solution of (R)-2-amino-4-methylpentan-1-ol (31.1 g, 265.7 mmol) in 2-MeTHF (125 mL) was added dropwise during approximately 45 min. A thick slurry was obtained and DIPEA (47.2 mL, 271.1 mmol) in 2-MeTHF (125 mL) was added at −30° C. during 70 min. The reaction mixture was allowed to reach −5° C. during 30 min and then filtered and used directly, without purification, as described below. DMA (875 mL) was added to methanesulfonamide (77.0 g, 813.5 mmol) followed by K₂CO₃ (75.0 g, 542.4 mmol) and the mixture was stirred at 50° C. for 10 min and then the filtered reaction solution above was added during 2 min. The reaction mixture was stirred at 75° C. for 48 h and then allowed to reach rt. Water (1 L) was added and pH was adjusted to approximately 3 with the addition of 6 M HCl. The two phases were separated and the aqueous phase was extracted with 2-MeTHF (2×300 mL). The combined organic extract was washed with sat NH$_4$Cl (aq) (2×500 mL) and concentrated in vacuo. The solid was dissolved in MTBE (250 mL) and the product was extracted with 5% K$_2$CO$_3$ (aq) (3×200 mL). The pH of the aqueous phase was adjusted to approximately 4 by the addition of 6 M HCl and extracted with MTBE (2×250 mL). The organic extract was dried over MgSO$_4$, filtered and evaporated to yield the title compound (57.4 g, 67%) as an off-white solid foam; MS (ESI) m/z [M+H]$^+$ 324.2.

Intermediate 2

(R)—N-(4-((1-(((tert-Butyldimethylsilyl)oxy)-4-methylpentan-2-yl)amino)-6-chloro-1,3,5-triazin-2-yl)methanesulfonamide

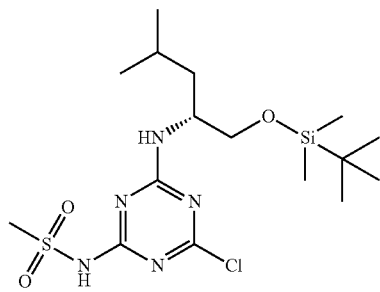 [SMILES: CC(C)C[C@H](CO[Si](C)(C)C(C)(C)C)Nc1nc(Cl)nc(NS(C)(=O)=O)n1]

TBDMSCl (1.4 g, 9.3 mmol) and imidazole (1.26 g, 18.5 mmol) were added to a solution of (R)—N-(4-chloro-6-((1-hydroxy-4-methylpentan-2-yl)amino)-1,3,5-triazin-2-yl) methanesulfonamide Intermediate 1 (1.0 g, 3.1 mmol) in DMF (5 mL). The reaction mixture was stirred at rt for 40 min and then poured into ice water and extracted with EtOAc (×3). The combined organic phase was washed with water and brine, dried over Na$_2$SO$_4$, filtered and evaporated. The residue was purified by straight phase flash chromatography on silica (40-100% EtOAc in heptane) to yield the title compound as a colourless viscous oil (1.04 g, 77%); MS (ESI) m/z [M+H]$^+$ 438.4.

Intermediate 3

(R,E)-2-((4-Chloro-6-(prop-1-en-1-yl)-1,3,5-triazin-2-yl)amino)-4-methylpentan-1-ol

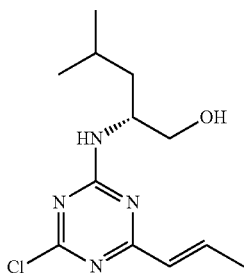 [SMILES: C/C=C/c1nc(Cl)nc(N[C@@H](CO)CC(C)C)n1]

(E)-Prop-1-en-1-ylmagnesium bromide (35.8 mL, 17.9 mmol, 0.5 M in THF) was added to a stirred suspension of 2,4,6-trichloro-1,3,5-triazine (3.0 g, 16.3 mmol) in THF (10 mL) at 0° C. during 10 min. The reaction mixture was allowed to reach rt during 30 min and then cooled again to 0° C. DIPEA (2.98 mL, 17.1 mmol) and a solution of (R)-2-amino-4-methylpentan-1-ol (1.91 g, 16.3 mmol) in THF (5 mL) were added and the reaction mixture was stirred at rt for 2 h. Water and MTBE were added and the two phases were separated. The aqueous phase was acidified by the addition of 1 M HCl and extracted twice with EtOAc. The organic extract was evaporated and the product was used in next step without further purification (2.23 g, 51%); MS (ESI) m/z [M+H]$^+$ 271.3. NMR indicates a mix of E- and Z-isomers.

Intermediate 4

(R,E)-N-(4-((1-Hydroxy-4-methylpentan-2-yl)amino)-6-(prop-1-en-1-yl)-1,3,5-triazin-2-yl)methanesulfonamide

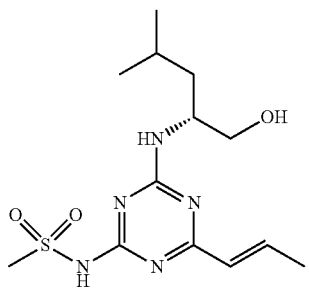 [SMILES: C/C=C/c1nc(N[C@@H](CO)CC(C)C)nc(NS(C)(=O)=O)n1]

THF (20 mL) was added to (R,E)-2-((4-chloro-6-(prop-1-en-1-yl)-1,3,5-triazin-2-yl)amino)-4-methylpentan-1-ol Intermediate 3 (2.0 g, 7.39 mmol), methanesulfonamide (0.738 g, 7.76 mmol), Pd$_2$dba$_3$ (271 mg, 0.30 mmol), X-Phos (0.563 g, 1.18 mmol) and K$_2$CO$_3$ (2.04 g, 14.8 mmol) under nitrogen atmosphere. The reaction mixture was stirred at 55° C. for 23 h and then water and MTBE were added and the two phases were separated. The organic phase was extracted with water and the pH of the combined aqueous extract was adjusted to approximately 6 by the addition of 1 M HCl. EtOAc was added and the aqueous phase was extracted with EtOAc (×2). The combined organic phase was dried over MgSO$_4$, filtered and evaporated and the residue was purified by straight phase flash chromatography on silica (EtOAc as eluent) to yield the title compound (1.55 g, 64%); MS (ESI) m/z [M+H]$^+$ 330.2.

Intermediate 5

1,2-Dichloro-4-(prop-1-en-2-yl)benzene

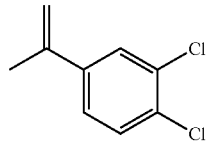

KOtBu (2.37 g, 21.16 mmol) was added to a stirred suspension of methyltriphenylphosphonium bromide (7.56 g, 21.16 mmol) in THF (17 mL). The reaction mixture was stirred at 0° C. for 30 min. A solution of 1-(3,4- dichlorophenyl)ethanone (2.0 g, 10.6 mmol) in THF (10 mL) was added at 0° C., and stirring was continued at rt for 48 h.

The mixture was evaporated to ⅓ volume, diluted with EtOAc/heptane and filtered through a silica pad. The solvent was evaporated to yield the title compound (1.6 g, 81%); $^1$H NMR (500 MHz, CDCl$_3$) 2.12 (3H, dd), 5.14 (1H, p), 5.37 (1H, p), 7.28 (1H, dd), 7.38 (1H, d), 7.52 (1H, d).

Intermediate 6

N-(4-(2-(3,4-Dichlorophenyl)propyl)-6-(((R)-1-hydroxy-4-methylpentan-2-yl)amino)-1,3,5-triazin-2-yl)methanesulfonamide

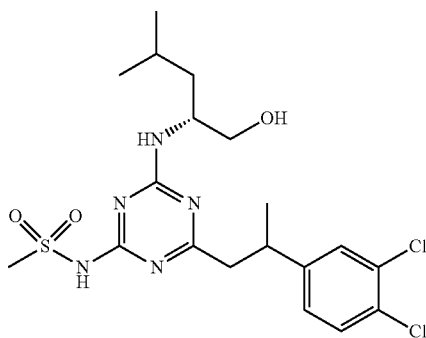

A solution of 0.5 M 9-BBN in THF (1.54 mL, 0.77 mmol) was added to 2-dichloro-4-(prop-1-en-2-yl)benzene Intermediate 5 (75 mg, 0.40 mmol) under nitrogen atmosphere and the reaction mixture was stirred at rt for 1.5 h. A degassed solution of 3 M K$_3$PO$_4$ (aq, 0.62 mL, 1.85 mmol) was added followed by the addition of (R)—N-(4-chloro-6-((1-hydroxy-4-methylpentan-2-yl)amino)-1,3,5-triazin-2-yl)methanesulfonamide Intermediate 1 (100 mg, 0.31 mmol) and Pd(dppf)Cl$_2$·DCM (37.5 mg, 0.05 mmol). The reaction mixture was stirred under nitrogen atmosphere at rt for 1 h and then at 40° C. overnight. DCM and water were added and the aqueous phase was acidified with 3 M HCl and extracted twice with DCM. The combined organic extract was treated with SiliaMetS Thiol, filtrated and evaporated. The residue was dissolved in a small amount of DCM and passed through a pad of silica and SiliaMetS Thiol eluted with MeOH/EtOAc. Solvents were evaporated and the residue was purified by preparative HPLC, PrepMethod C, (gradient: 20-70%) to yield the title compound (70 mg, 48%); MS (ESI) m/z [M+H]$^+$ 476.2.

Intermediate 7

1-Chloro-2-fluoro-3-(prop-1-en-2-yl)benzene

KOtBu (2.60 g, 23.18 mmol) was added at 0° C. to a stirred suspension of methyltriphenylphosphonium bromide (8.28 g, 23.18 mmol) in THF (17 mL) and the reaction mixture was stirred at 0° C. for 30 min. A solution of 1-(3-chloro-2-fluorophenyl)ethan-1-one (2.0 g, 11.6 mmol) in THF (10 mL) was added at 0° C. and stirring was continued at rt for 2 days. The mixture was evaporated to ⅓ volume, diluted with EtOAc/heptane and passed through a silica pad. Fractions with product were evaporated to yield the title compound as a colourless oil (1.0 g, 51%); $^1$H NMR (500 MHz, CDCl$_3$) 2.13-2.15 (3H, m), 5.22-5.24 (1H, m), 5.25-5.28 (1H, m), 7.04 (1H, td), 7.19 (1H, ddd), 7.30 (1H, ddd).

Intermediate 8

N-(4-(2-(3-Chloro-2-fluorophenyl)propyl)-6-(((R)-1-hydroxy-4-methylpentan-2-yl)amino)-1,3,5-triazin-2-yl)methanesulfonamide

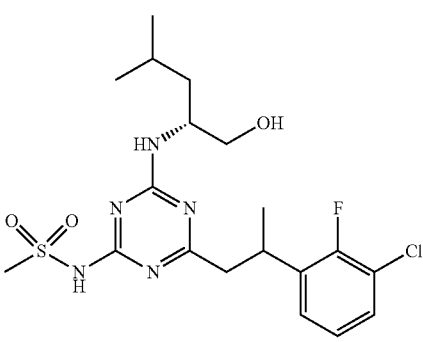 [SMILES: CC(C)C[C@H](CO)Nc1nc(CC(C)c2cccc(Cl)c2F)nc(NS(C)(=O)=O)n1]

A solution of 0.5 M 9-BBN in THF (2.19 mL, 1.10 mmol) was added to 1-chloro-2-fluoro-3-(prop-1-en-2-yl)benzene Intermediate 7 (125 mg, 0.73 mmol) under nitrogen atmosphere. The reaction mixture was stirred at rt for 1 h and then at reflux for 15 min. A degassed solution of 3 M K$_3$PO$_4$ (aq, 0.73 mL, 2.19 mmol) was added, followed by the addition of (R)—N-(4-((1-(((tert-butyldimethylsilyl)oxy)-4-methylpentan-2-yl)amino)-6-chloro-1,3,5-triazin-2-yl)methanesulfonamide Intermediate 2 (160 mg, 0.37 mmol) and Pd(dppf)Cl$_2$·DCM (44.3 mg, 0.05 mmol). The reaction mixture was stirred at 35° C. under nitrogen atmosphere for 42 h. EtOAc and water were added and the two phases were separated. The aqueous phase was acidified by the addition of 3 M HCl and extracted with EtOAc. The organic extract was evaporated and redissolved in a small amount of DCM/EtOAc (1/1) and filtered through a short column of silica (eluted with DCM/EtOAc). The solvent was evaporated and the residue was dissolved in EtOH (2 mL) and HCl (0.4 mL) and the solution was stirred at rt for 30 min. The solvent was evaporated and the residue was dissolved in DMSO and SiliaMetS Thiol was added, stirred for a minute, filtered and purified by preparative HPLC, PrepMethod C, (gradient: 20-75%) to yield the title compound (158 mg, 94%); MS (ESI) m/z [M+H]$^+$ 460.3.

Intermediate 9

2,4-Difluoro-1-(prop-1-en-2-yl)benzene

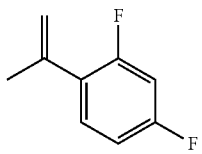

KOtBu (1.44 g, 12.81 mmol) was added at rt to a stirred suspension of methyltriphenylphosphonium bromide (4.58 g, 12.81 mmol) in Et$_2$O (8.0 mL). The reaction mixture was stirred at rt for 30 min and then at 40° C. for 10 min. 1-(2,4-Difluorophenyl)ethan-1-one (1.0 g, 6.4 mmol) was added and stirring was continued at rt for 30 min and then the reaction mixture was filtered and the solid was washed with Et$_2$O. The combined organic extract was carefully evaporated to approximately 4 mL (product is volatile) and then purified by straight phase flash chromatography on silica (Et$_2$O as eluent) to yield the title compound (990 mg, 100%) containing some residual Et20; $^1$H NMR (500 MHz, CDCl$_3$) 2.01-2.03 (3H, m), 5.08-5.10 (1H, m), 5.11-5.13 (1H, m), 6.65-6.76 (2H, m), 7.12-7.19 (1H, m).

Intermediate 10

N-(4-(2-(2,4-Difluorophenyl)propyl)-6-(((R)-1-hydroxy-4-methylpentan-2-yl)amino)-1,3,5-triazin-2-yl)methanesulfonamide

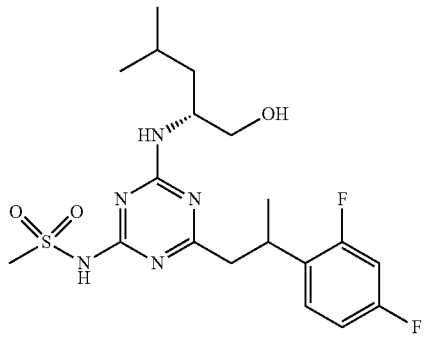 [SMILES: CC(C)C[C@H](CO)Nc1nc(CC(C)c2ccc(F)cc2F)nc(NS(C)(=O)=O)n1]

A solution of 0.5 M 9-BBN in THF (2.19 mL, 1.10 mmol) was added to 2,4-difluoro-1-(prop-1-en-2-yl)benzene Intermediate 9 (113 mg, 0.73 mmol) under nitrogen atmosphere. The reaction mixture was stirred at rt for 30 min and then at 50° C. for 20 min. A degassed solution of 3 M K$_3$PO$_4$ (aq, 0.73 mL, 2.19 mmol) was added followed by the addition of (R)—N-(4-((1-(((tert-butyldimethylsilyl)oxy)-4-methylpentan-2-yl)amino)-6-chloro-1,3,5-triazin-2-yl)methanesulfonamide Intermediate 2 (160 mg, 0.37 mmol) and Pd(dppf)Cl$_2$·DCM (44.3 mg, 0.05 mmol). The reaction mixture was stirred at 35° C. under nitrogen atmosphere for 42 h. EtOAc and water were added and the two phases were separated. The aqueous phase was acidified to pH 4 with 3 M HCl and extracted with EtOAc. The organic extract was evaporated and redissolved in a small amount of DCM and filtered through a short column of silica (eluted with DCM/EtOAc). The solvent was evaporated and the residue was dissolved in EtOH (2 mL) and HCl (0.4 mL) and the solution was stirred at rt for 30 min. The solvent was evaporated and the residue was purified by preparative HPLC, PrepMethod C, to yield the title compound (92 mg, 57%); MS (ESI) m/z [M+H]$^+$ 444.3.

Intermediate 11

3-Fluoro-2-methoxy-5-(prop-1-en-2-yl)pyridine

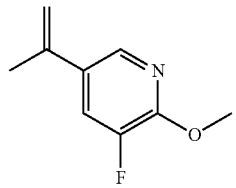

KOtBu (0.663 g, 5.91 mmol) was added to a stirred suspension of methyltriphenylphosphonium bromide (2.11 g, 5.91 mmol) in Et$_2$O (4 mL) at rt and the reaction mixture was stirred at rt for 30 min. A solution of 1-(5-fluoro-6-methoxypyridin-3-yl)ethan-1-one (0.50 g, 2.96 mmol) in THF (1.5 mL) was added and stirring was continued at rt for 30 min. The reaction mixture was filtered, and the solid was washed with Et$_2$O. The combined filtrate was carefully evaporated (product is volatile) and the residue was purified by straight phase flash chromatography on silica (pentane:Et20, 4:1 as eluent) to yield the title compound (530 mg, 107%), containing some residual solvents; $^1$H NMR (500 MHz, CDCl$_3$) 2.11-2.13 (3H, m), 4.03 (3H, s), 5.08-5.10 (1H, m), 5.30-5.32 (1H, m), 7.45 (1H, dd), 8.01 (1H, d).

Intermediate 12

N-(4-(2-(5-Fluoro-6-methoxypyridin-3-yl)propyl)-6-(((R)-1-hydroxy-4-methylpentan-2-yl)amino)-1,3,5-triazin-2-yl)methanesulfonamide

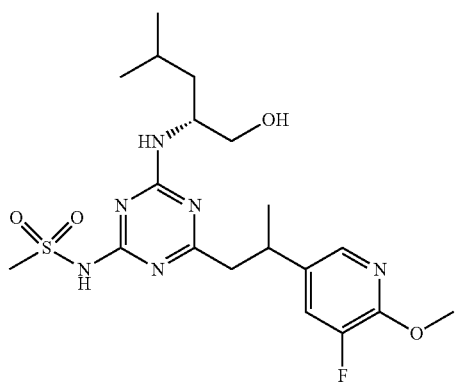

9-BBN dimer (224 mg, 0.93 mmol) was added to a solution of 3-fluoro-2-methoxy-5-(prop-1-en-2-yl)pyridine Intermediate 11 (112 mg, 0.67 mmol) in THF (2 mL) under nitrogen atmosphere and the reaction mixture was stirred at rt for 1 h. A degassed solution of 3 M K$_3$PO$_4$ (aq, 0.74 mL, 2.22 mmol) was added, followed by the addition of (R)—N-(4-chloro-6-((1-hydroxy-4-methylpentan-2-yl)amino)-1,3,5-triazin-2-yl)methanesulfonamide Intermediate 1 (120 mg, 0.37 mmol) and Pd(dppf)Cl₂·DCM (44.9 mg, 0.06 mmol). The reaction mixture was diluted with THF (1 mL) and stirred at 35° C. for 15 h. EtOAc and water were added and the two phases were separated. The aqueous phase was neutralised and extracted several times with EtOAc and the combined organic extract was evaporated. The residue was filtered through silica eluted with DCM, EtOAc and MeOH. The solvents were evaporated and the residue was purified by preparative HPLC, PrepMethod C, (gradient: 15-60%). Repurified by straight phase flash chromatography on silica (gradient: 35-100% EtOAc/MeOH:20/1 in DCM as eluent) to yield the title compound (33 mg, 20%); MS (ESI) m/z [M+H]⁺ 457.3.

Intermediate 13

3-Chloro-2-methoxy-5-(prop-1-en-2-yl)pyridine

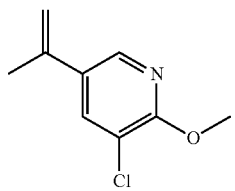

KOtBu (0.605 g, 5.39 mmol) was added to a stirred suspension of methyltriphenylphosphonium bromide (1.92 g, 5.39 mmol) in Et₂O (4 mL) and the reaction mixture was stirred at rt for 30 min. A solution of 1-(5-chloro-6-methoxypyridin-3-yl)ethan-1-one (0.50 g, 2.69 mmol) in THF (1.5 mL) was added and the reaction mixture was stirred at rt for 30 min and then filtered. The solid was washed with Et₂O and the combined organic extract was evaporated. The residue was purified by straight phase flash chromatography on silica (pentane/Et20:4/1 as eluent) to yield the title compound (484 mg, 98%) as a colourless oil; ¹H NMR (500 MHz, CDCl₃) 2.10-2.13 (3H, m), 4.03 (3H, s), 5.07-5.10 (1H, m), 5.30-5.33 (1H, m), 7.74 (1H, d), 8.14 (1H, d).

Intermediate 14

N-(4-(2-(5-Chloro-6-methoxypyridin-3-yl)propyl)-6-(((R)-1-hydroxy-4-methylpentan-2-yl)amino)-1,3,5-triazin-2-yl)methanesulfonamide

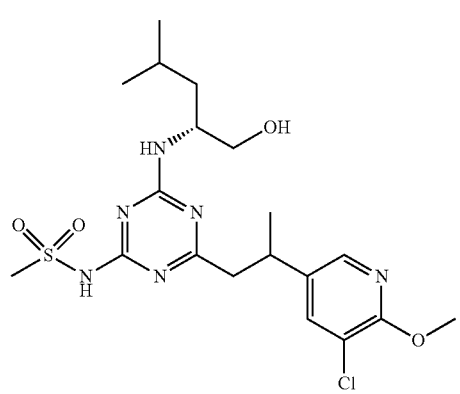

9-BBN dimer (224 mg, 0.93 mmol) was added to a solution of 3-chloro-2-methoxy-5-(prop-1-en-2-yl)pyridine Intermediate 13 (122 mg, 0.67 mmol) in THF (2 mL) under nitrogen atmosphere and the reaction mixture was stirred at rt for 1 h. A degassed solution of 3 M K₃PO₄ (aq, 0.74 mL, 2.22 mmol) was added, followed by the addition of (R)—N-(4-chloro-6-((1-hydroxy-4-methylpentan-2-yl)amino)-1,3,5-triazin-2-yl)methanesulfonamide Intermediate 1 (120 mg, 0.37 mmol) and Pd(dppf)Cl₂·DCM (44.9 mg, 0.06 mmol). The reaction mixture was diluted with THF (1 mL) and stirred at 35° C. for 15 h. Water and EtOAc were added and the aqueous phase was neutralised and extracted several times with EtOAc. The combined organic extract was evaporated and filtered through silica sequentially eluted with EtOAc, MeOH and DCM. Solvents were evaporated and the residue was purified by preparative HPLC, PrepMethod C, (gradient: 15-60%). Repurified by straight phase flash chromatography on silica (gradient: 20-100% EtOAc/MeOH:20/1 in DCM as eluent) to yield the title compound (24 mg, 14%); MS (ESI) m/z [M+H]⁺ 473.2.

Intermediate 15

2-Cyclopropyl-5-(prop-1-en-2-yl)pyrimidine

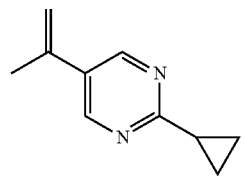

4,4,5,5-Tetramethyl-2-(prop-1-en-2-yl)-1,3,2-dioxaborolane (1.04 mL, 5.53 mmol), a solution of 5-bromo-2-cyclopropylpyrimidine (1.0 g, 5.02 mmol) in THF (7 mL), and Pd(dppf)Cl₂ (44 mg, 0.06 mmol) were added to a degassed solution of K₂CO₃ (2.08 g, 15.07 mmol) in water (2 mL) under nitrogen atmosphere. The reaction mixture was stirred at 95° C. overnight. Water and Et₂O were added, and the two phases were separated. The organic phase was washed with brine and evaporated. The residue was purified by straight phase flash chromatography on silica (gradient: 0-50% EtOAc in heptane) to yield the title compound (0.95 g, 118%); ¹H NMR (500 MHz, CDCl₃) 1.03-1.14 (4H, m), 2.10-2.13 (3H, m), 2.20-2.26 (1H, m), 5.13-5.15 (1H, m), 5.37-5.39 (1H, m), 8.61 (2H, s).

Intermediate 16

N-(4-(2-(2-Cyclopropylpyrimidin-5-yl)propyl)-6-(((R)-1-hydroxy-4-methylpentan-2-yl)amino)-1,3,5-triazin-2-yl)methanesulfonamide

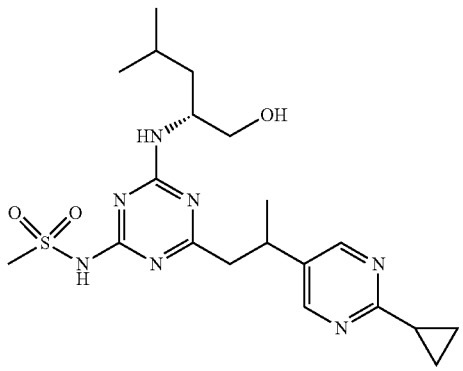 [SMILES: CC(C)C[C@H](CO)Nc1nc(CC(C)c2cnc(C3CC3)nc2)nc(NS(C)(=O)=O)n1]

9-BBN dimer (139 mg, 0.57 mmol) was added to a solution of 2-cyclopropyl-5-(prop-1-en-2-yl)pyrimidine Intermediate 15 (89 mg, 0.56 mmol) in THF (1.5 mL) under nitrogen atmosphere and the reaction mixture was stirred at 35° C. for 1 h. A degassed solution of CsOH monohydrate (187 mg, 1.11 mmol) in water (0.3 mL) was added followed by the addition of (R)—N-(4-chloro-6-((1-hydroxy-4-methylpentan-2-yl)amino)-1,3,5-triazin-2-yl)methanesulfonamide Intermediate 1 (120 mg, 0.37 mmol) and Pd(dppf)Cl$_2$·DCM (24.0 mg, 0.03 mmol). The reaction mixture was stirred at 35° C. for 15 h, water (1 mL) was added and the reaction mixture was neutralized with the addition of HOAc. EtOAc was added and the two phases were separated. The aqueous phase was further acidified with the addition of dilute HCl and extracted with EtOAc. The aqueous phase was neutralised with NaHCO$_3$(aq) and extracted twice with DCM. The combined organic extract was evaporated and the residue was purified by preparative HPLC, PrepMethod C, (gradient: 15-75%) to yield the title compound (32 mg, 19%); MS (ESI) m/z [M+H]$^+$ 450.3.

Intermediate 17

5-Bromo-2-methoxy-4-methylpyridine

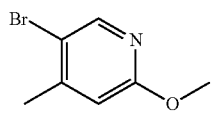

Sodium methoxide (30% in MeOH, 1.61 mL, 8.59 mmol) was added to 2,5-dibromo-4-methylpyridine (0.539 g, 2.15 mmol) in MeOH (3.75 mL) and the reaction mixture was heated at 100° C. for 1 h followed by heating at 140° C. in a single node microwave oven for 15 min. The solvent was evaporated and the residue was dissolved in EtOAc and washed with NH$_4$Cl (aq) and brine, dried over Na$_2$SO$_4$ and evaporated. The residue was purified by straight phase flash chromatography on silica (5% EtOAc in heptane as eluent) to yield the title compound (328 mg, 76%) as a colourless solid; $^1$H NMR (400 MHz, CDCl$_3$) 2.33 (3H, d), 3.89 (3H, s), 6.64 (1H, s), 8.17 (1H, s).

Intermediate 18

2-Methoxy-4-methyl-5-(prop-1-en-2-yl)pyridine

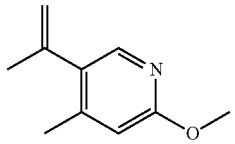

A degassed solution of 5-bromo-2-methoxy-4-methylpyridine Intermediate 17 (300 mg, 1.48 mmol) in THF (3 mL) was added to a degassed solution of Cs$_2$CO$_3$ (1.45 g, 4.45 mmol) in water (0.8 mL) followed by the addition of Pd(dppf)Cl$_2$·DCM (22 mg, 0.03 mmol) and 4,4,5,5-tetramethyl-2-(prop-1-en-2-yl)-1,3,2-dioxaborolane (0.45 mL, 2.38 mmol) and the reaction mixture was stirred under nitrogen atmosphere at 80° C. overnight. EtOAc and water were added. The two phases were separated and the organic phase was washed with CsOH (aq) and water and then evaporated. The residue was purified by straight phase flash chromatography on silica (gradient: 0-25% EtOAc in heptane) to yield the title compound (157 mg, 65%) as a colourless oil; $^1$H NMR (400 MHz, CDCl$_3$) 2.00-2.03 (3H, m), 2.26 (3H, s), 3.91 (3H, s), 4.85-4.89 (1H, m), 5.20-5.24 (1H, m), 6.55 (1H, s), 7.89 (1H, s).

Intermediate 19

N-(4-(((R)-1-Hydroxy-4-methylpentan-2-yl)amino)-6-(2-(6-methoxy-4-methylpyridin-3-yl)propyl)-1,3,5-triazin-2-yl)methanesulfonamide

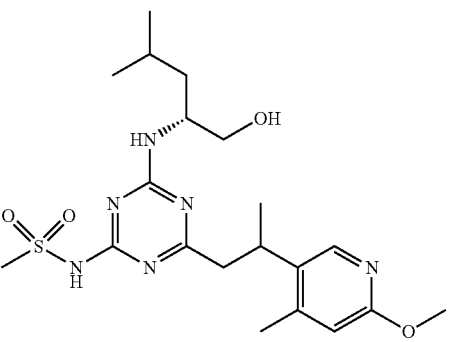

9-BBN dimer (239 mg, 0.99 mmol) was added to a solution of 2-methoxy-4-methyl-5-(prop-1-en-2-yl)pyridine Intermediate 18 (150 mg, 0.92 mmol) in THF (2 mL) under nitrogen atmosphere. The reaction mixture was stirred at rt for 15 min, then at 40° C. for 15 min, and left at rt overnight. A degassed solution of 3 M K$_3$PO$_4$ (aq, 1.03 ml, 3.09 mmol) was added, followed by the addition of (R)—N-(4-chloro-6-((1-hydroxy-4-methylpentan-2-yl)amino)-1,3,5-triazin-2-yl)methanesulfonamide Intermediate 1 (200 mg, 0.62 mmol) and Pd(dppf)Cl$_2$·DCM (74.9 mg, 0.09 mmol). The reaction mixture was stirred under nitrogen atmosphere at 35° C. for 15 h. EtOAc and water were added. The aqueous phase was neutralised and extracted several times with EtOAc. SiliaMetS Thiol was added to the combined organic extract and the mixture was stirred for a few min, filtered through silica, and eluted with EtOAc and MeOH. The filtrate was evaporated and the residue was purified by preparative HPLC, PrepMethod C, (gradient: 15-60%). Repurified by preparative HPLC, PrepMethod C, (gradient: 15-60%) to yield the title compound (42 mg, 15%); MS (ESI) m/z [M+H]$^+$ 453.4.

Intermediate 20

2-Methoxy-3-methyl-5-(prop-1-en-2-yl)pyridine

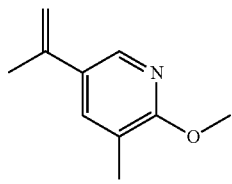

4,4,5,5-Tetramethyl-2-(prop-1-en-2-yl)-1,3,2-dioxaborolane (0.75 mL, 3.96 mmol), a degassed solution of 5-bromo-2-methoxy-3-methylpyridine (0.50 g, 2.47 mmol) in THF (4.2 mL), and Pd(dppf)Cl$_2$·DCM (36 mg, 0.05 mmol) were added to a degassed solution of Cs$_2$CO$_3$ (2.42 g, 7.42 mmol) in water (1.21 mL) under nitrogen atmosphere. The reaction mixture was stirred at 80° C. for 2 h. CsOH monohydrate (208 mg, 1.24 mmol) and Pd(dppf)Cl$_2$·DCM (36 mg, 0.05 mmol) were added and the reaction mixture was stirred at 80° C. overnight. EtOAc and water were added and the two phases were separated. The organic phase was washed with CsOH (aq) and water and then evaporated. The residue was purified by straight phase flash chromatography on silica (gradient: 0-25% EtOAc in heptane) to yield the title compound as a colourless oil (200 mg, 50%); $^1$H NMR (500 MHz, CDCl$_3$) 2.08-2.17 (3H, m), 2.20 (3H, s), 3.96 (3H, s), 4.99-5.04 (1H, m), 5.26-5.31 (1H, m), 7.47-7.54 (1H, m), 8.06-8.12 (1H, m).

Intermediate 21

N-(4-(((R)-1-Hydroxy-4-methylpentan-2-yl)amino)-6-(2-(6-methoxy-5-methylpyridin-3-yl)propyl)-1,3,5-triazin-2-yl)methanesulfonamide

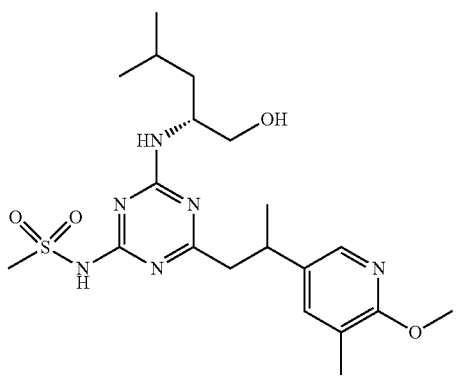

9-BBN dimer (239 mg, 0.99 mmol) was added to a solution of 2-methoxy-3-methyl-5-(prop-1-en-2-yl)pyridine Intermediate 20 (144 mg, 0.88 mmol) in THF (2 mL) under nitrogen atmosphere and the reaction mixture was stirred at rt for 15 min, at 35° C. for 15 min and then left at rt overnight. A degassed solution of 3 M K$_3$PO$_4$ (aq, 1.03 mL, 3.09 mmol) was added followed by the addition of (R)—N-(4-chloro-6-((1-hydroxy-4-methylpentan-2-yl)amino)-1,3,5-triazin-2-yl)methanesulfonamide Intermediate 1 (200 mg, 0.62 mmol) and Pd(dppf)Cl$_2$·DCM (49.9 mg, 0.06 mmol). The reaction mixture was stirred at 35° C. for 35 h. EtOAc and water were added and the aqueous phase was neutralized and the two phases were separated. The aqueous phase was extracted several times with EtOAc and the combined organic extract was partly evaporated. SiliaMetS Thiol was added and the mixture was stirred for a few min. The residue was passed through silica eluted with EtOAc and MeOH. The filtrate was evaporated and the residue was purified by preparative HPLC, PrepMethod C, (gradient: 15-60%) to yield the title compound (55 mg, 20%); MS (ESI) m/z [M+H]$^+$ 453.4.

Intermediate 22

2-Methoxy-3-(prop-1-en-2-yl)pyridine

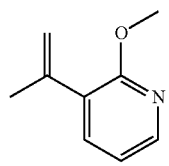

4,4,5,5-Tetramethyl-2-(prop-1-en-2-yl)-1,3,2-dioxaborolane (1.00 g, 5.96 mmol), a degassed solution of 3-bromo-2-methoxypyridine (0.70 g, 3.72 mmol) in THF (7.2 mL), and Pd(dppf)Cl$_2$·DCM (2.72 g, 3.72 mmol) were added to a degassed solution of Cs$_2$CO$_3$ (3.64 g, 11.17 mmol) in water (2.1 mL) under nitrogen atmosphere. The reaction mixture was stirred at 80° C. for 15 h. EtOAc and water were added and the two phases separated. The organic phase was stirred with NaOH (aq), washed with water and then evaporated. The residue was purified by straight phase flash chromatography on silica (gradient: 0-20% EtOAc in heptane). Fractions with product were combined, evaporated and dissolved in Et$_2$O and stirred with CsOH (aq) for 1 h. The two phases were separated and the organic phase was washed with water and brine, dried over MgSO$_4$, filtered and evaporated to give the title compound (165 mg, 30%) as a colourless oil; $^1$H NMR (500 MHz, CDCl$_3$) 2.11 (3H, dd), 3.97 (3H, s), 5.16-5.22 (2H, m), 6.85 (1H, dd), 7.47 (1H, dd), 8.07 (1H, dd).

Intermediate 23

N-(4-(((R)-1-Hydroxy-4-methylpentan-2-yl)amino)-6-(2-(2-methoxypyridin-3-yl)propyl)-1,3,5-triazin-2-yl)methanesulfonamide

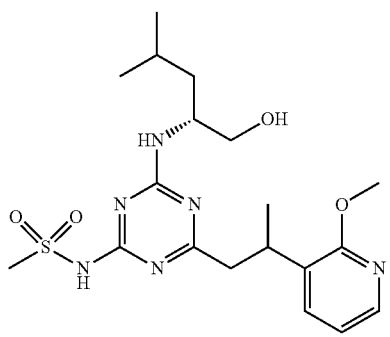

A solution of 0.5 M 9-BBN in THF (3.24 mL, 1.62 mmol) was added to to 2-methoxy-3-(prop-1-en-2-yl)pyridine Intermediate 22 (117 mg, 0.78 mmol) under nitrogen atmosphere. The reaction mixture was stirred at rt overnight and then a degassed solution of 3 M $K_3PO_4$ (aq, 0.93 mL, 2.78 mmol) was added followed by the addition of (R)—N-(4-chloro-6-((1-hydroxy-4-methylpentan-2-yl)amino)-1,3,5-triazin-2-yl)methanesulfonamide Intermediate 1 (150 mg, 0.46 mmol) and Pd(dppf)$Cl_2$·DCM (37.5 mg, 0.05 mmol). The reaction mixture was stirred at 38° C. under nitrogen atmosphere for 20 h. EtOAc and water were added and the two phases were separated. The aqueous phase was acidified with dilute HCl and extracted twice with EtOAc. $MgSO_4$ and SiliaMetS Thiol were added to the combined organic phase and the mixture was stirred for a few min and then filtered. The filtrate was evaporated and the residue was purified by preparative HPLC, PrepMethod A, (gradient: 15-60%) to yield the title compound (176 mg, 87%); MS (ESI) m/z $[M+H]^+$ 439.3.

Intermediate 24

(2R)-2-((4-Chloro-6-(2-(3-fluoro-4-methoxyphenyl)propyl)-1,3,5-triazin-2-yl)amino)-4-methylpentan-1-ol

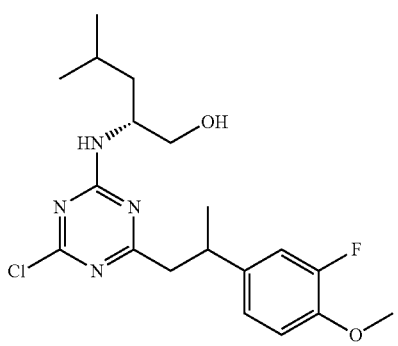 [SMILES: COc1ccc(C(C)Cc2nc(Cl)nc(N[C@@H](CO)CC(C)C)n2)cc1F]

1,4-Dioxane (1.11 mL) and water (0.19 mL) were added to (R,E)-2-((4-chloro-6-(prop-1-en-1-yl)-1,3,5-triazin-2-yl)amino)-4-methylpentan-1-ol Intermediate 3 (70 mg, 0.26 mmol), (3-fluoro-4-methoxyphenyl)boronic acid (132 mg, 0.78 mmol), [Rh(COD)Cl]$_2$ (6.4 mg, 0.01 mmol) and KOH (43.5 mg, 0.78 mmol) under nitrogen atmosphere. The reaction mixture was stirred at 65° C. for 3.5 h. EtOAc and water were added and the two phases were separated. The organic layer was washed with brine and evaporated. The residue was purified by preparative HPLC, PrepMethod A, (gradient: 30-80%) to yield the title compound (70 mg, 68%) as a colourless solid; MS (ESI) m/z $[M+H]^+$ 397.4.

Intermediate 25

N-(4-(2-(3-Fluoro-4-methoxyphenyl)propyl)-6-(((R)-1-hydroxy-4-methylpentan-2-yl)amino)-1,3,5-triazin-2-yl)methanesulfonamide

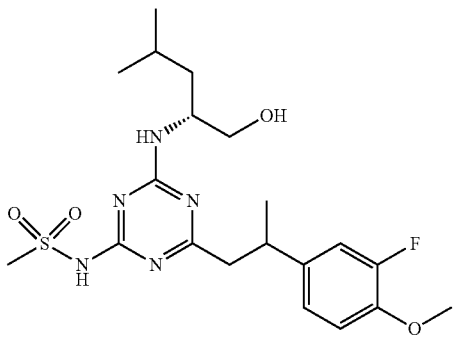

THF (0.25 mL) was added to Pd$_2$dba$_3$ (6.5 mg, 7.1 μmol) and X-Phos (13.5 mg, 0.03 mmol) under nitrogen atmosphere. The mixture was stirred for 10 min and then (2R)-2-((4-chloro-6-(2-(3-fluoro-4-methoxyphenyl)propyl)-1,3,5-triazin-2-yl)amino)-4-methylpentan-1-ol Intermediate 24 (56 mg, 0.14 mmol) in THF (0.75 mL), methanesulfonamide (32 mg, 0.34 mmol) and $K_2CO_3$ (44 mg, 0.32 mmol) were added. The reaction mixture was stirred under nitrogen atmosphere at 70° C. overnight. EtOAc was added and the mixture was washed with dilute HCl and brine. The combined aqueous phase was extracted with EtOAc. The combined organic extract was dried over $MgSO_4$, filtered and evaporated. The residue was purified by preparative HPLC, PrepMethod A, (gradient: 30-80%) to yield the title compound (54 mg, 84%) as a colourless solid; MS (ESI) m/z $[M+H]^+$ 456.4.

Intermediate 26

(2R)-2-((4-Chloro-6-(2-(3,4,5-trifluorophenyl)propyl)-1,3,5-triazin-2-yl)amino)-4-methylpentan-1-ol

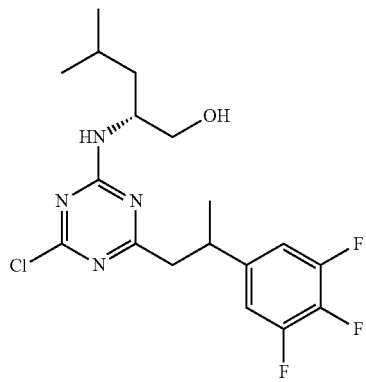 [SMILES: CC(C)C[C@H](CO)Nc1nc(Cl)nc(CC(C)c2cc(F)c(F)c(F)c2)n1]

(3,4,5-Trifluorophenyl)boronic acid (134 mg, 0.76 mmol) was added to a solution of (R,E)-2-((4-chloro-6-(prop-1-en-1-yl)-1,3,5-triazin-2-yl)amino)-4-methylpentan-1-ol Intermediate 3 (69 mg, 0.25 mmol) in 1,4-dioxane (1.1 mL) under nitrogen atmosphere. [Rh(COD)Cl]$_2$ (6.3 mg, 0.01 mmol), KOH (42.9 mg, 0.76 mmol) and water (0.19 mL) were added and the reaction mixture was stirred at 65° C. overnight. EtOAc and water were added and the two phases were separated. The organic extract was washed with brine and evaporated. The residue (combined with two other batches made in a similar manner starting from 138 mg of Intermediate 3 in total) was purified by preparative HPLC, PrepMethod A, (gradient: 30-90%) to yield the title compound (90 mg, 44% in total) as a colourless solid; MS (ESI) m/z [M+H]$^+$ 403.3.

Intermediate 27

N-(4-(((R)-1-Hydroxy-4-methylpentan-2-yl)amino)-6-(2-(3,4,5-trifluorophenyl)propyl)-1,3,5-triazin-2-yl)methanesulfonamide

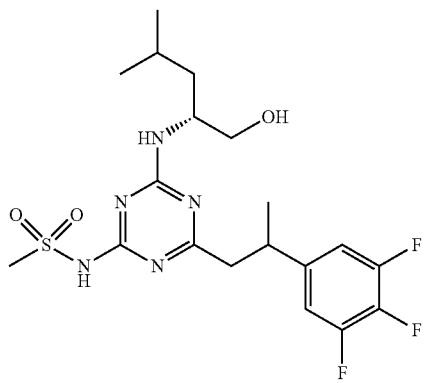 [SMILES: CC(C)C[C@H](CO)Nc1nc(CC(C)c2cc(F)c(F)c(F)c2)nc(NS(C)(=O)=O)n1]

THF (0.25 mL) was added to Pd$_2$dba$_3$ (5.1 mg, 5.6 µmol) and X-Phos (10.6 mg, 0.02 mmol) under nitrogen atmosphere. The mixture was stirred for 10 min and then (2R)-2-((4-chloro-6-(2-(3,4,5-trifluorophenyl)propyl)-1,3,5-triazin-2-yl)amino)-4-methylpentan-1-ol Intermediate 26 (56 mg, 0.14 mmol) in THF (0.75 mL), methanesulfonamide (30 mg, 0.32 mmol) and K$_2$CO$_3$ (39 mg, 0.28 mmol) were added. The reaction mixture was stirred under nitrogen atmosphere at 70° C. overnight. EtOAc was added and the mixture was washed with dilute HCl and brine. The combined aqueous phase was extracted with EtOAc. The combined organic extract was dried over MgSO$_4$, filtered and evaporated. The residue was purified by preparative HPLC, PrepMethod A, (gradient: 30-80%) to yield the title compound (60 mg, 94%) as a colourless solid; MS (ESI) m/z [M+H]$^+$ 462.4.

Intermediate 28

(2R)-2-((4-Chloro-6-(2-(2,5-difluorophenyl)propyl)-1,3,5-triazin-2-yl)amino)-4-methylpentan-1-ol

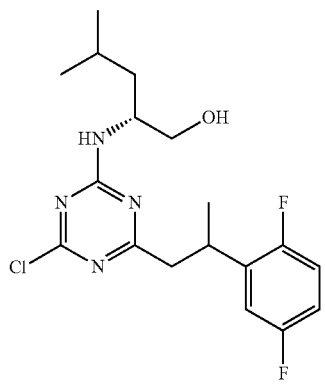 [SMILES: CC(C)C[C@H](CO)Nc1nc(Cl)nc(CC(C)c2cc(F)ccc2F)n1]

1,4-Dioxane (1.11 mL) and water (0.19 mL) were added to (R,E)-2-((4-chloro-6-(prop-1-en-1-yl)-1,3,5-triazin-2-yl)amino)-4-methylpentan-1-ol Intermediate 3 (70 mg, 0.26 mmol), (2,5-difluorophenyl)boronic acid (122 mg, 0.78 mmol), [Rh(COD)Cl]$_2$ (6.4 mg, 0.01 mmol) and KOH (43.5 mg, 0.78 mmol) under nitrogen atmosphere. The reaction mixture was stirred at 50° C. for 3.5 h. EtOAc and dilute HCl were added, the organic phase was washed with water and brine, and evaporated. The residue was purified by preparative HPLC, PrepMethod B, (gradient: 30-80%) to yield the title compound (36 mg, 36%) as a colourless solid; MS (ESI) m/z [M+H]$^+$ 385.3.

Intermediate 29

N-(4-(2-(2,5-Difluorophenyl)propyl)-6-(((R)-1-hydroxy-4-methylpentan-2-yl)amino)-1,3,5-triazin-2-yl)methanesulfonamide

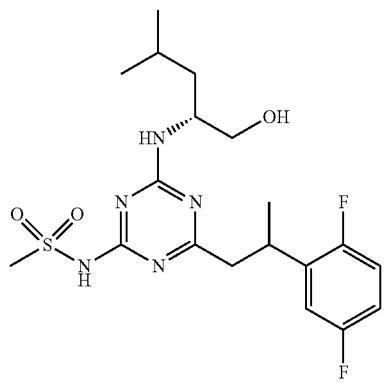 [SMILES: CC(C)C[C@H](CO)Nc1nc(CC(C)c2cc(F)ccc2F)nc(NS(C)(=O)=O)n1]

THF (0.25 mL) was added to Pd$_2$dba$_3$ (3.1 mg, 3.4 μmol) and X-Phos (6.3 mg, 0.01 mmol) under nitrogen atmosphere. The mixture was stirred for 10 min and then (2R)-2-((4-chloro-6-(2-(2,5-difluorophenyl)propyl)-1,3,5-triazin-2-yl)amino)-4-methylpentan-1-ol Intermediate 28 (32 mg, 0.08 mmol) in THF (0.75 mL), methanesulfonamide (17.8 mg, 0.19 mmol) and K$_2$CO$_3$ (23.6 mg, 0.17 mmol) were added. The reaction mixture was stirred under nitrogen atmosphere at 70° C. overnight. EtOAc was added and the mixture was washed with dilute HCl and brine. The combined aqueous phase was extracted with EtOAc. The combined organic extract was dried over MgSO$_4$, filtered and evaporated. The residue was purified by preparative HPLC, PrepMethod A, (gradient: 30-80%) to yield the title compound (29 mg, 79%) as a colourless solid; MS (ESI) m/z [M+H]$^+$ 444.4.

Intermediate 30

2-Chloro-4-(prop-1-en-2-yl)pyridine

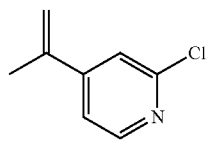

KOtBu (0.620 g, 5.53 mmol) was added to a stirred suspension of methyltriphenylphosphonium bromide (1.98 g, 5.53 mmol) in Et$_2$O (4 mL) and the reaction mixture was stirred at rt for 30 min. A solution of 1-(2-chloropyridin-4-yl)ethan-1-one (0.43 g, 2.76 mmol) in Et$_2$O (1.5 mL) was added, and stirring was continued at rt for 30 min. The reaction mixture was filtered, the solid was washed with Et$_2$O and the combined filtrate was carefully evaporated (product is volatile). The residue was purified by straight phase flash chromatography on silica (pentane/Et20:4/1 as eluent) to yield the title compound (350 mg, 82%) as a colourless oil; $^1$H NMR (400 MHz, CDCl$_3$) 2.11-2.14 (3H, m), 5.29-5.33 (1H, m), 5.56-5.60 (1H, m), 7.25 (1H, dd), 7.35 (1H, dd), 8.32 (1H, dd).

Intermediate 31

N-(4-(2-(2-Chloropyridin-4-yl)propyl)-6-(((R)-1-hydroxy-4-methylpentan-2-yl)amino)-1,3,5-triazin-2-yl)methanesulfonamide

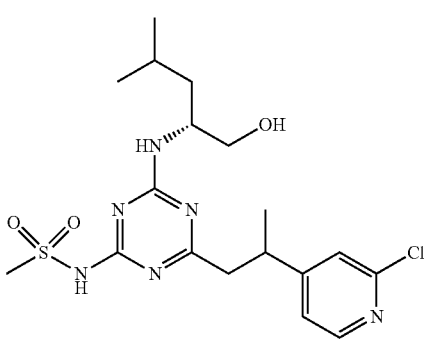 [SMILES: CC(C)C[C@H](CO)Nc1nc(CC(C)c2ccnc(Cl)c2)nc(NS(C)(=O)=O)n1]

A solution of 0.5 M 9-BBN in THF (2.16 mL, 1.08 mmol) was added to 2-chloro-4-(prop-1-en-2-yl)pyridine Intermediate 30 (89 mg, 0.58 mmol) under nitrogen atmosphere. The reaction mixture was stirred at rt overnight and then a degassed solution of 3 M K$_3$PO$_4$ (aq, 0.62 mL, 1.85 mmol) was added followed by the addition of (R)—N-(4-chloro-6-((1-hydroxy-4-methylpentan-2-yl)amino)-1,3,5-triazin-2-yl)methanesulfonamide Intermediate 1 (100 mg, 0.31 mmol) and Pd(dppf)Cl$_2$·DCM (25.0 mg, 0.03 mmol). The reaction mixture was stirred at 35° C. under nitrogen atmosphere for 20 h. EtOAc and water were added and the two phases were separated. The aqueous phase was acidified with dilute HCl and extracted with EtOAc. SiliaMetS Thiolwas added to the organic phase and stirred for a few min, then was filtered. The filtrate was collected and evaporated and the residue was purified by preparative HPLC, PrepMethod A, (gradient: 20-75%). Repurified by preparative HPLC, PrepMethod D, (gradient: 0-50%) to yield the title compound (23 mg, 17%); $^1$H NMR (500 MHz, CDCl$_3$) 0.88-0.98 (6H, m), 1.21-1.77 (8H, m), 2.85-3.06 (2H, m), 3.29-3.46 (4H, m), 3.54-3.85 (2H, m), 4.15-4.30 (1H, m), 7.15 (1H, dd), 7.24-7.27 (m, partially overlapping with solvent), 8.31 (1H, dd).

Intermediate 32

(2R)-2-((4-Chloro-6-(2-(6-ethoxypyridin-3-yl)propyl)-1,3,5-triazin-2-yl)amino)-4-methylpentan-1-ol

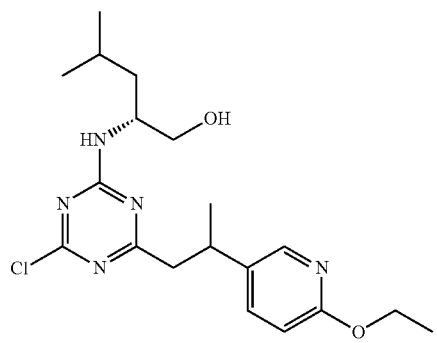 [SMILES: CCOc1ccc(C(C)Cc2nc(Cl)nc(N[C@@H](CO)CC(C)C)n2)cn1]

(6-Ethoxypyridin-3-yl)boronic acid (126 mg, 0.75 mmol) and KOH (62.2 mg, 1.11 mmol) in water (0.27 mL) were added to a solution of (R,E)-2-((4-chloro-6-(prop-1-en-1-yl)-1,3,5-triazin-2-yl)amino)-4-methylpentan-1-ol Intermediate 3 (100 mg, 0.37 mmol) in 1,4-dioxane (1.58 mL) under nitrogen atmosphere. [Rh(COD)Cl]$_2$ (9.1 mg, 0.02 mmol) was added and the reaction mixture was stirred at 70° C. overnight. EtOAc and water were added and the two phases were separated. The organic extract was washed with brine and evaporated. The residue was purified by preparative HPLC, PrepMethod A, (gradient: 40-100%) to yield the title compound (18 mg, 12%) as a colourless solid; MS (ESI) m/z [M+H]$^+$ 394.4.

Intermediate 33

N-(4-(2-(6-Ethoxypyridin-3-yl)propyl)-6-(((R)-1-hydroxy-4-methylpentan-2-yl)amino)-1,3,5-triazin-2-yl)methanesulfonamide

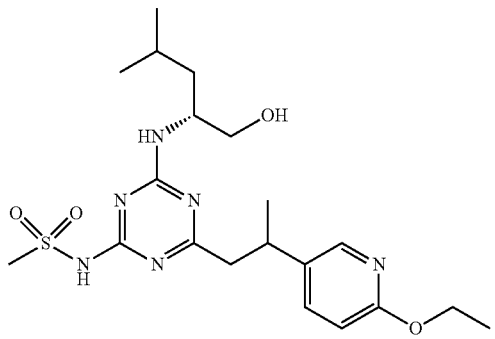 [SMILES: CCOc1ccc(C(C)Cc2nc(N[C@@H](CO)CC(C)C)nc(NS(C)(=O)=O)n2)cn1]

THF (0.15 mL) was added to Pd$_2$dba$_3$ (2.1 mg, 2.3 μmol) and X-Phos (4.5 mg, 9.34 μmol) under nitrogen atmosphere. The mixture was stirred for 10 min and then (2R)-2-((4-chloro-6-(2-(6-ethoxypyridin-3-yl)propyl)-1,3,5-triazin-2-yl)amino)-4-methylpentan-1-ol Intermediate 32 (23 mg, 0.06 mmol) in THF (0.50 mL), methanesulfonamide (12.5 mg, 0.13 mmol) and K$_2$CO$_3$ (16.5 mg, 0.12 mmol) were added. The reaction mixture was stirred under nitrogen atmosphere at 70° C. overnight. EtOAc was added and the mixture was washed with dilute HCl and brine. The combined aqueous phase was extracted with EtOAc. The combined organic extract was dried over MgSO$_4$, filtered and evaporated. The residue was purified by preparative HPLC, PrepMethod B, (gradient: 25-70%) to yield the title compound (24 mg, 89%) as a colourless solid; MS (ESI) m/z [M+H]$^+$ 453.4.

Intermediate 34

(2R)-2-((4-Chloro-6-(2-(5-chloro-2-fluorophenyl)propyl)-1,3,5-triazin-2-yl)amino)-4-methylpentan-1-ol

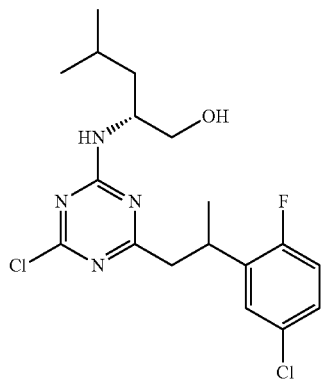 [SMILES: CC(C)C[C@H](CO)Nc1nc(Cl)nc(CC(C)c2cc(Cl)ccc2F)n1]

1,4-Dioxane (1.1 mL) and water (0.12 mL) were added to (R,E)-2-((4-chloro-6-(prop-1-en-1-yl)-1,3,5-triazin-2-yl)amino)-4-methylpentan-1-ol Intermediate 3 (70 mg, 0.26 mmol), (5-chloro-2-fluorophenyl)boronic acid (135 mg, 0.78 mmol), [Rh(COD)Cl]$_2$ (6.4 mg, 0.01 mmol) and KOH (43.5 mg, 0.78 mmol) under nitrogen atmosphere. The reaction mixture was stirred at 65° C. for 3.5 h. EtOAc and dilute HCl were added and the two phases were separated and the organic phase was washed with water and brine. The combined aqueous phase was extracted with EtOAc. The combined organic extract was evaporated and the residue was purified by preparative HPLC, PrepMethod B, (gradient: 30-80%) to yield the title compound (14.6 mg, 14%); MS (ESI) m/z [M+H]$^+$ 401.3.

Intermediate 35

N-(4-(2-(5-Chloro-2-fluorophenyl)propyl)-6-(((R)-1-hydroxy-4-methylpentan-2-yl)amino)-1,3,5-triazin-2-yl)methanesulfonamide

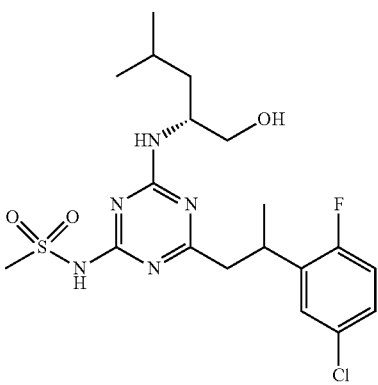 [SMILES: CC(C)C[C@H](CO)Nc1nc(CC(C)c2cc(Cl)ccc2F)nc(NS(C)(=O)=O)n1]

THF (0.15 mL) was added to Pd$_2$dba$_3$ (1.3 mg, 1.4 μmol) and X-Phos (2.7 mg, 5.6 μmol) under nitrogen atmosphere and the reaction mixture was stirred for 10 min. (2R)-2-((4-Chloro-6-(2-(5-chloro-2-fluorophenyl)propyl)-1,3,5-triazin-2-yl)amino)-4-methylpentan-1-ol Intermediate 34 (14.0 mg, 0.03 mmol) in THF (0.50 mL), methanesulfonamide (7.5 mg, 0.08 mmol) and K$_2$CO$_3$ (9.9 mg, 0.07 mmol) were added and the reaction mixture was stirred under nitrogen atmosphere at 70° C. overnight. EtOAc and dilute HCl were added and the two phases were separated. The organic phase was washed with brine. The combined aqueous phase was extracted with EtOAc and the combined organic extract was evaporated. The residue was purified by preparative HPLC, PrepMethod D, (gradient: 25-70%) to yield the title compound (12.6 mg, 79%) as a colourless solid; MS (ESI) m/z [M+H]$^+$ 460.4.

Intermediate 36

(2R)-2-((4-Chloro-6-(2-(4-chloro-3,5-difluorophenyl)propyl)-1,3,5-triazin-2-yl)amino)-4-methylpentan-1-ol

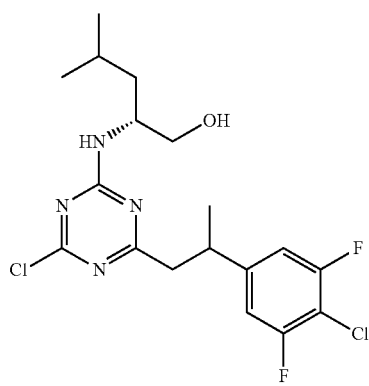 [SMILES: CC(C)C[C@H](CO)Nc1nc(Cl)nc(CC(C)c2cc(F)c(Cl)c(F)c2)n1]

2-(4-Chloro-3,5-difluorophenyl)-4,4,5,5-tetramethyl-1,3,2-dioxaborolane (203 mg, 0.74 mmol) and KOH (62.2 mg, 1.11 mmol) in water (0.26 mL) was added to a solution of (R,E)-2-((4-chloro-6-(prop-1-en-1-yl)-1,3,5-triazin-2-yl)amino)-4-methylpentan-1-ol Intermediate 3 (100 mg, 0.37 mmol) in 1,4-dioxane (1.58 mL) followed by the addition of [Rh(COD)Cl]$_2$ (9.1 mg, 0.02 mmol). The reaction mixture was stirred at 70° C. overnight and then EtOAc and water were added. The two phases were separated and the organic extract was washed with brine and evaporated. The residue was purified by preparative HPLC, PrepMethod A, (gradient: 30-90%) to yield the title compound (20 mg, 13%); $^1$H NMR (400 MHz, CDCl$_3$) 0.86-0.98 (6H, m), 1.21-1.70 (7H, m), 2.76-2.95 (2H, m), 3.31-3.52 (1H, m), 3.52-3.84 (2H, m), 4.10-4.27 (1H, m), 5.56-5.69 (1H, d), 6.81-6.89 (2H, m).

Intermediate 37

N-(4-(2-(4-Chloro-3,5-difluorophenyl)propyl)-6-(((R)-1-hydroxy-4-methylpentan-2-yl)amino)-1,3,5-triazin-2-yl)methanesulfonamide

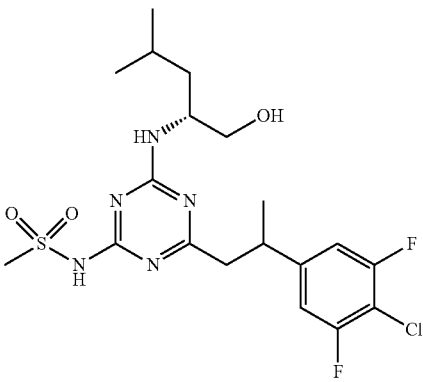 [SMILES: CC(C)C[C@H](CO)Nc1nc(CC(C)c2cc(F)c(Cl)c(F)c2)nc(NS(C)(=O)=O)n1]

THF (0.25 mL) was added to Pd$_2$dba$_3$ (4.3 mg, 4.8 μmol) and X-Phos (9.1 mg, 0.02 mmol) under nitrogen atmosphere. The mixture was stirred for 10 min and then (2R)-2-((4-chloro-6-(2-(4-chloro-3,5-difluorophenyl)propyl)-1,3,5-triazin-2-yl)amino)-4-methylpentan-1-ol Intermediate 36 (50 mg, 0.12 mmol) in THF (0.75 mL), methanesulfonamide (26.1 mg, 0.27 mmol) and K$_2$CO$_3$ (33.8 mg, 0.24 mmol) were added. The reaction mixture was stirred under nitrogen atmosphere at 70° C. overnight. EtOAc and dilute HCl were added and the two phases were separated. The organic phase was washed with brine and the combined aqueous phase was extracted with EtOAc. The combined organic extract was dried over MgSO$_4$, filtered and evaporated. The residue was purified by preparative HPLC, PrepMethod A, (gradient: 30-80%) to yield the title compound (25 mg, 44%) as a colourless solid; MS (ESI) m/z [M+H]$^+$ 478.3.

Intermediate 38

(2R)-2-((4-Chloro-6-(2-(4-chloro-2,3-difluorophenyl)propyl)-1,3,5-triazin-2-yl)amino)-4-methylpentan-1-ol

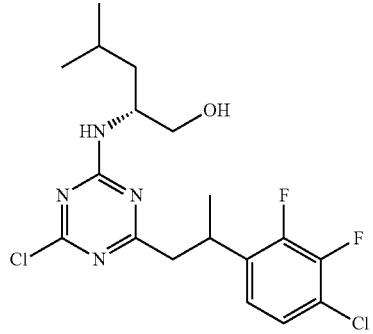 [SMILES: CC(C)C[C@H](CO)Nc1nc(Cl)nc(CC(C)c2ccc(Cl)c(F)c2F)n1]

1,4-Dioxane (3.66 mL) and water (0.41 mL) were added to (R,E)-2-((4-chloro-6-(prop-1-en-1-yl)-1,3,5-triazin-2-yl)amino)-4-methylpentan-1-ol Intermediate 3 (220 mg, 0.81 mmol), (4-chloro-2,3-difluorophenyl)boronic acid (313 mg,

Intermediate 39

N-(4-(2-(4-Chloro-2,3-difluorophenyl)propyl)-6-(((R)-1-hydroxy-4-methylpentan-2-yl)amino)-1,3,5-triazin-2-yl)methanesulfonamide

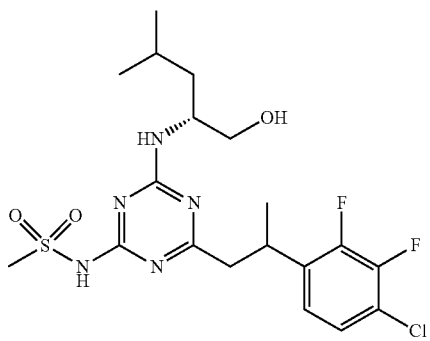 [SMILES: CC(C)C[C@H](CO)Nc1nc(CC(C)c2ccc(Cl)c(F)c2F)nc(NS(C)(=O)=O)n1]

THF (0.25 mL) was added to Pd₂dba₃ (7.6 mg, 8.3 µmol) and X-Phos (15.8 mg, 0.03 mmol) under nitrogen atmosphere. The mixture was stirred for 10 min and then (2R)-2-((4-chloro-6-(2-(4-chloro-2,3-difluorophenyl)propyl)-1,3,5-triazin-2-yl)amino)-4-methylpentan-1-ol Intermediate 38 (87 mg, 0.21 mmol) in THF (0.75 mL), methanesulfonamide (45.4 mg, 0.48 mmol) and K₂CO₃ (58.8 mg, 0.43 mmol) were added. The reaction mixture was stirred under nitrogen atmosphere at 70° C. overnight. EtOAc and dilute HCl were added and the two phases were separated. The organic phase was washed with brine and the combined aqueous phase was extracted with EtOAc. The combined organic extract was dried over MgSO₄, filtered and evaporated. The residue was purified by preparative HPLC, PrepMethod A, (gradient: 30-75%) to yield the title compound (64 mg, 65%) as a colourless solid; MS (ESI) m/z [M+H]⁺ 478.4.

Intermediate 40

1,2,4-Trifluoro-5-(prop-1-en-2-yl)benzene

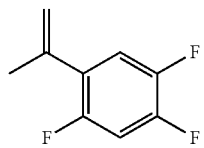

A degassed solution of Cs₂CO₃ (4.63 g, 14.22 mmol) in water (2.38 mL) was added to a degassed solution of 1-bromo-2,4,5-trifluorobenzene (1.0 g, 4.7 mmol) in THF (8.3 mL) followed by the addition of and Pd(dppf)Cl₂·DCM (69 mg, 0.09 mmol) and 4,4,5,5-tetramethyl-2-(prop-1-en-2-yl)-1,3,2-dioxaborolane (1.16 mL, 6.16 mmol). The reaction mixture was stirred at 70° C. for 20 h and then MTBE and water were added. The two phases were separated and the organic extract was washed with water and carefully evaporated (product is volatile). The residue was purified by straight phase flash chromatography on silica (gradient: 0-15% Et₂O in pentane) to yield the title compound (0.64 g, 78%); ¹H NMR (500 MHz, CDCl₃) 2.09-2.12 (3H, m), 5.22-5.24 (1H, m), 5.25-5.28 (1H, m), 6.86-6.94 (1H, m), 7.07-7.14 (1H, m).

Intermediate 41

N-(4-(((R)-1-Hydroxy-4-methylpentan-2-yl)amino)-6-(2-(2,4,5-trifluorophenyl)propyl)-1,3,5-triazin-2-yl)methanesulfonamide

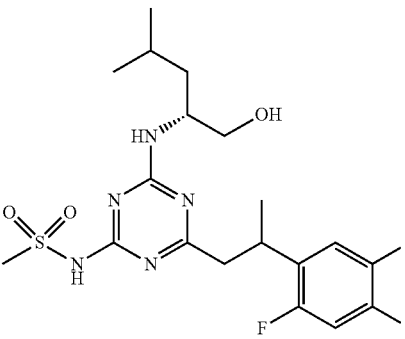

A solution of 0.5 M 9-BBN in THF (2.96 mL, 1.48 mmol) was added to a solution of 1,2,4-trifluoro-5-(prop-1-en-2-yl)benzene Intermediate 40 (170 mg, 0.99 mmol) in THF (0.5 mL) and the reaction mixture was stirred at rt overnight. A degassed solution of 3 M K₃PO₄ (aq, 0.99 mL, 2.96 mmol) was added followed by the addition of (R)—N-(4-chloro-6-((1-hydroxy-4-methylpentan-2-yl)amino)-1,3,5-triazin-2-yl)methanesulfonamide Intermediate 1 (160 mg, 0.49 mmol) and Pd(dppf)Cl₂·DCM (32.3 mg, 0.04 mmol). The reaction mixture was stirred under nitrogen atmosphere at 40° C. overnight and then EtOAc and dilute HCl were added. The two phases were separated and the organic phase was washed with water and brine. The organic extract was treated with SILIAMES THIOL, filtered and dried over MgSO₄, filtered and evaporated. The residue was purified by preparative HPLC, PrepMethod A, (gradient: 30-85%). Repurified by straight phase flash chromatography on silica (eluted with DCM and EtOAc) to yield the title compound (120 mg, 53%); ¹H NMR (400 MHz, CDCl₃) 0.81-0.98 (6H, m), 1.05-1.70 (9H, m), 2.85-3.01 (2H, m), 3.20-3.30 (3H, m), 3.50-4.30 (4H, m), 6.75-7.20 (3H, m).

Intermediate 42

1-Chloro-2,5-difluoro-4-(prop-1-en-2-yl)benzene

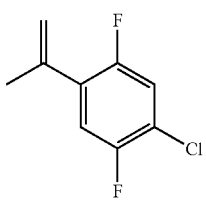

KOtBu (1.18 g, 10.49 mmol) was added to a stirred suspension of methyltriphenylphosphonium bromide (3.75 g, 10.49 mmol) in Et$_2$O (6 mL) at 10° C. followed by the addition of 1-(4-chloro-2,5-difluorophenyl)ethan-1-one (1.0 g, 5.3 mmol) in Et$_2$O (6 mL). The reaction mixture was stirred at rt overnight and then diluted with Et$_2$O and filtered. The filtrate was washed with water, diluted HCl, water and brine, dried over MgSO$_4$, filtered and carefully evaporated (product is volatile). Pentane was added and the solid was filtered and solvents were evaporated. The residue was purified by straight phase flash chromatography on silica (pentane/EtOAc:10/1 as eluent) to yield the title compound (688 mg, 70%); $^1$H NMR (400 MHz, CDCl$_3$) 2.29 (3H, s), 5.47 (2H, s), 7.21-7.35 (2H, m).

Intermediate 43

N-(4-(2-(4-Chloro-2,5-difluorophenyl)propyl)-6-(((R)-1-hydroxy-4-methylpentan-2-yl)amino)-1,3,5-triazin-2-yl)methanesulfonamide

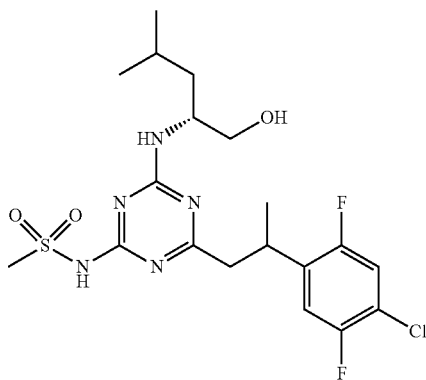 [SMILES: CC(C)C[C@H](CO)Nc1nc(CC(C)c2cc(F)c(Cl)cc2F)nc(NS(C)(=O)=O)n1]

A solution of 0.5 M 9-BBN in THF (2.78 mL, 1.39 mmol) was added to 1-chloro-2,5-difluoro-4-(prop-1-en-2-yl)benzene Intermediate 42 (175 mg, 0.93 mmol) and the reaction mixture was stirred at 70° C. for 1 h under nitrogen. A degassed solution of 3 M K$_3$PO$_4$ (aq, 0.93 mL, 2.78 mmol) was added followed by the addition of (R)—N-(4-chloro-6-((1-hydroxy-4-methylpentan-2-yl)amino)-1,3,5-triazin-2-yl)methanesulfonamide Intermediate 1 (150 mg, 0.46 mmol) and Pd(dppf)Cl$_2$·DCM (56.7 mg, 0.07 mmol). The reaction mixture was stirred under nitrogen atmosphere at 40° C. overnight and then EtOAc and dilute HCl were added and the two phases were separated. The organic extract was treated with SILIAMES THIOL, filtered and evaporated. The residue was purified by preparative HPLC, PrepMethod E, (gradient: 5-95%) to yield the title compound (99 mg, 48%); MS (ESI) m/z [M+H]$^+$ 478.2.

Intermediate 44

2,4,6-Trifluoro-N-methoxy-N-methylbenzamide

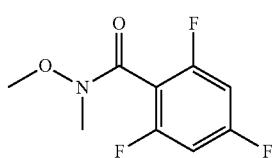

N,O-Dimethylhydroxylamine hydrochloride (1.11 g, 11.36 mmol) followed by TBTU (4.38 g, 13.63 mmol) were added to a solution of 2,4,6-trifluorobenzoic acid (2.0 g, 11.4 mmol) in DIPEA (7.9 mL, 45.4 mmol) and DCM (20.5 mL) and the reaction mixture was stirred at rt overnight. DCM and sat NaHCO$_3$(aq) were added and the two phases were separated. The organic extract was washed with water, dilute HCl, water and brine and evaporated to yield the title compound (2.40 g, 96%); $^1$H NMR (500 MHz, CDCl$_3$) 3.39 (3H, s), 3.54 (3H, s), 6.67-6.76 (2H, m).

Intermediate 45

1-(2,4,6-Trifluorophenyl)ethan-1-one

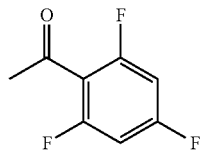

A solution of 3 M MeMgBr in Et$_2$O (11.0 mL, 32.85 mmol) was added dropwise to an ice cold solution of 2,4,6-trifluoro-N-methoxy-N-methylbenzamide Intermediate 44 (2.4 g, 10.95 mmol) in THF (60 mL) and the reaction mixture was stirred at 0° C. for 4 h and at rt overnight. 0.5 M HCl and Et$_2$O were added. The phases were separated and the organic extract was washed with water and brine, dried over MgSO$_4$, filtered and carefully evaporated (product is volatile). The residue was purified by straight phase flash chromatography on silica (gradient: 0-15% Et$_2$O in pentane) to yield the title compound (1.73 g, 91%) as a colourless oil; $^1$H NMR (500 MHz, CDCl$_3$) 2.58 (3H, t), 6.67-6.78 (2H, m).

Intermediate 46

1,3,5-Trifluoro-2-(prop-1-en-2-yl)benzene

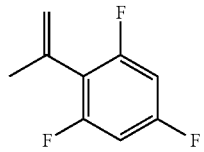

KOtBu (1.29 g, 11.49 mmol) was added to a stirred suspension of methyltriphenylphosphonium bromide (4.10 g, 11.49 mmol) in Et$_2$O (5 mL). THF (1 mL) was added and the reaction mixture was stirred at rt for 30 min. 1-(2,4,6-Trifluorophenyl)ethan-1-one Intermediate 45 (1.0 g, 5.7 mmol) was added and stirring was continued at rt overnight. Pentane was added and the mixture was filtered. The solid was washed with Et$_2$O and the combined filtrate was washed with water and brine and carefully evaporated (product is volatile). The residue was purified by straight phase flash chromatography on silica (gradient: 0-15% Et$_2$O in pentane) to yield the title compound (760 mg, 77%) as a colourless oil; $^1$H NMR (400 MHz, CDCl$_3$) 2.04-2.09 (3H, m), 5.06-5.11 (1H, m), 5.39-5.44 (1H, m), 6.59-6.73 (2H, m).

Intermediate 47

N-(4-(((R)-1-Hydroxy-4-methylpentan-2-yl)amino)-6-(2-(2,4,6-trifluorophenyl)propyl)-1,3,5-triazin-2-yl)methanesulfonamide

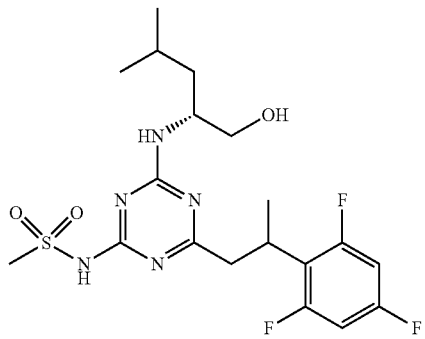 [SMILES: CC(C)C[C@H](CO)Nc1nc(CC(C)c2c(F)cc(F)cc2F)nc(NS(C)(=O)=O)n1]

A solution of 0.5 M 9-BBN in THF (2.96 mL, 1.48 mmol) was added to 1,3,5-trifluoro-2-(prop-1-en-2-yl)benzene Intermediate 46 (170 mg, 0.99 mmol) in THF (0.5 mL) under nitrogen atmosphere and the reaction mixture was stirred at 40° C. for 2 h. Another portion of a solution of of 0.5 M 9-BBN in THF (1.98 mL, 0.99 mmol) was added and the stirring was continued at 40° C. for 1 h. A degassed solution of 3 M $K_3PO_4$ (aq, 1.32 mL, 3.95 mmol) was added followed by the addition of (R)—N-(4-chloro-6-((1-hydroxy-4-methylpentan-2-yl)amino)-1,3,5-triazin-2-yl)methanesulfonamide Intermediate 1 (160 mg, 0.49 mmol) and Pd(dppf)Cl$_2$·DCM (32.3 mg, 0.04 mmol). The reaction mixture was stirred at 40° C. under nitrogen atmosphere overnight. EtOAc and 3.8 M HCl were added and the two phases were separated. The organic extract was washed with water and brine, dried over MgSO$_4$ and SILIAMES THIOL. The mixture was filtered and evaporated. The residue was purified by preparative HPLC, PrepMethod A, (gradient: 35-75%) to yield the title compound (150 mg, 66%); MS (ESI) m/z [M+H]$^+$ 462.4.

Intermediate 48

2,3,6-Trifluoro-N-methoxy-N-methylbenzamide

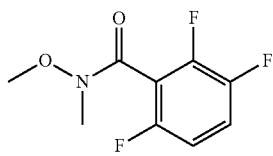

N,O-Dimethylhydroxylamine hydrochloride (1.11 g, 11.36 mmol) was added to a solution of 2,3,6-trifluorobenzoic acid (2.0 g, 11.4 mmol) in DIPEA (7.9 mL, 45.4 mmol) and DCM (20.5 mL) followed by the addition of TBTU (4.38 g, 13.63 mmol). The reaction mixture was stirred at rt overnight and then DCM and sat NaHCO$_3$(aq) was added and the two phases were separated. The organic extract was washed with water, dilute HCl, water and brine, and evaporated to yield the title compound (3.60 g, 140%); $^1$H NMR (500 MHz, CDCl$_3$) 3.40 (3H, s), 3.56 (3H, s), 6.85-6.93 (1H, m), 7.14-7.23 (1H, m).

Intermediate 49

1-(2,3,6-Trifluorophenyl)ethan-1-one

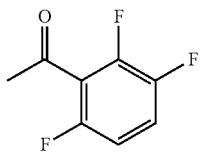

A solution of 3 M MeMgBr in Et$_2$O (11.0 mL, 32.85 mmol) was added dropwise to an ice cold solution of 2,3,6-trifluoro-N-methoxy-N-methylbenzamide Intermediate 48 (2.4 g, 10.95 mmol) in THF (60 mL) and the reaction mixture was stirred at 0° C. for 3 h and at rt overnight. 0.5 M HCl and Et$_2$O were added. The organic extract was washed with water and brine, dried over MgSO$_4$, filtered and carefully evaporated (product is volatile). The residue was purified by straight phase flash chromatography on silica (gradient: 0-15% Et$_2$O in pentane) to yield the title compound (1.78 g, 93%) as a colourless oil; $^1$H NMR (500 MHz, CDCl$_3$) 2.61 (3H, t), 6.87-6.94 (1H, m), 7.19-7.29 (1H, m).

Intermediate 50

1,2,4-Trifluoro-3-(prop-1-en-2-yl)benzene

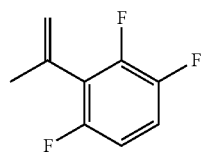

KOtBu (1.29 g, 11.49 mmol) was added to a stirred suspension of methyltriphenylphosphonium bromide (4.10 g, 11.49 mmol) in THF (14.4 mL) and the reaction mixture was stirred at rt for 30 min. 1-(2,3,6-Trifluorophenyl)ethan-1-one Intermediate 49 (1.0 g, 5.7 mmol) was added and stirring was continued at rt overnight. Pentane was added and the mixture was filtered. The solid was washed with pentane and the combined filtrate was washed with water and brine. The organic extract was filtered again and the filtrate was carefully evaporated (product is volatile). The residue was purified by straight phase flash chromatography on silica (gradient: 0-15% Et$_2$O in pentane) to yield the title compound (750 mg, 76%) as a colourless oil; $^1$H NMR (400 MHz, CDCl$_3$) 2.07-2.12 (3H, m), 5.11-5.16 (1H, m), 5.43-5.48 (1H, m), 6.75-6.85 (1H, m), 6.96-7.09 (1H, m).

Intermediate 51

N-(4-(((R)-1-Hydroxy-4-methylpentan-2-yl)amino)-6-(2-(2,3,6-trifluorophenyl)propyl)-1,3,5-triazin-2-yl)methanesulfonamide

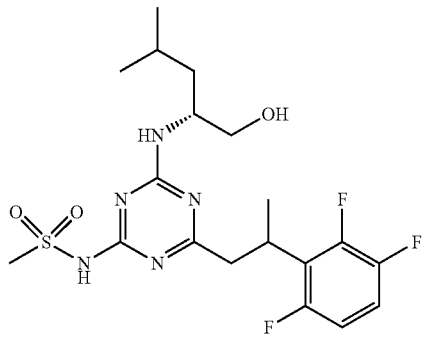 [SMILES: CC(C)C[C@H](CO)Nc1nc(CC(C)c2c(F)ccc(F)c2F)nc(NS(C)(=O)=O)n1]

A solution of 0.5 M 9-BBN in THF (2.96 mL, 1.48 mmol) was added to 1,2,4-trifluoro-3-(prop-1-en-2-yl)benzene Intermediate 50 (170 mg, 0.99 mmol) in THF (0.5 mL) under nitrogen atmosphere and the reaction mixture was stirred at 40° C. for 2 h. Another portion of a solution of 0.5 M 9-BBN in THF (1.98 mL, 0.99 mmol) was added and the stirring was continued at 40° C. for 1 h. A degassed solution of 3 M K$_3$PO$_4$ (aq, 1.32 mL, 3.95 mmol) was added followed by the addition of (R)—N-(4-chloro-6-((1-hydroxy-4-methylpentan-2-yl)amino)-1,3,5-triazin-2-yl)methanesulfonamide Intermediate 1 (160 mg, 0.49 mmol) and Pd(dppf)Cl$_2$·DCM (32.3 mg, 0.04 mmol). The reaction mixture was stirred at 40° C. under nitrogen atmosphere overnight.

EtOAc and 3.8 M HCl were added and the two phases were separated. The organic extract was washed with water and brine and dried over MgSO$_4$. SiliaMetS Thiol and Silica was added and the mixture was filtered and evaporated and the residue was purified by preparative HPLC, PrepMethod A, (gradient: 35-75%). Repurified by preparative HPLC, PrepMethod B, (gradient: 15-65%) to yield the title compound (54 mg, 24%); MS (ESI) m/z [M+H]$^+$ 462.4.

Intermediate 52

1-(4-Chloro-2,6-difluorophenyl)ethan-1-ol

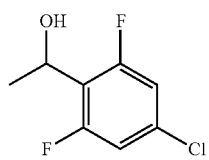

A solution of 3 M MeMgBr in Et$_2$O (5.66 mL, 16.99 mmol) was added dropwise to a stirred ice-cold solution of 4-chloro-2,6-difluorobenzaldehyde (2.0 g, 11.33 mmol) in Et$_2$O (32.1 mL) under nitrogen atmosphere. The reaction mixture was allowed to reach rt during 4 h and then a solution of NH$_4$Cl (aq, 10%) was added. The mixture was acidified by the addition of 3.8 M HCl. The two phases were separated and the organic extract was washed with water and brine, dried over MgSO$_4$, filtered and evaporated to yield the title compound (1.0 g, 46%); $^1$H NMR (400 MHz, CDCl$_3$) 1.61 (3H, d), 2.19 (1H, br s), 5.20 (1H, p), 6.87-6.97 (2H, m).

Intermediate 53

1-(4-Chloro-2,6-difluorophenyl)ethan-1-one

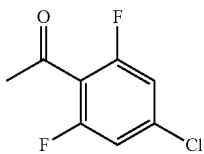

Dess-Martin periodinane (2.42 g, 5.71 mmol) was added to a solution of 1-(4-chloro-2,6-difluorophenyl)ethan-1-ol Intermediate 52 (1.0 g, 5.19 mmol) in DCM (51.9 mL) and the reaction mixture was stirred at rt overnight. NaHCO$_3$(aq, 20 mL) was added and the reaction mixture was stirred vigorously for 2 h and then filtered. The solid was washed with DCM and the two phases were separated. The organic extract was washed with NaHCO$_3$(aq), Na$_2$S$_2$O$_5$ (aq), water and brine. The organic extract was evaporated and the residue was purified by straight phase flash chromatography on silica (heptane/EtOAc:10/1 as eluent) to yield the title compound (0.87 g, 88%); $^1$H NMR (400 MHz, CDCl$_3$) 2.58 (3H, t), 6.95-7.04 (2H, m).

Intermediate 54

5-Chloro-1,3-difluoro-2-(prop-1-en-2-yl)benzene

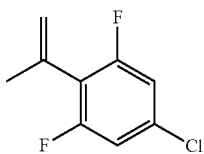

KOtBu (1.03 g, 9.13 mmol) was added to a stirred suspension of methyltriphenylphosphonium bromide (3.26 g, 9.13 mmol) in Et$_2$O (6 mL) at 10° C. followed by the addition of 1-(4-chloro-2,6-difluorophenyl)ethan-1-one Intermediate 53 (1.0 g, 5.3 mmol) in Et$_2$O (6 mL). The reaction mixture was stirred at rt overnight and then diluted with Et$_2$O and filtered. The filtrate was washed with water, dilute HCl, water and brine, dried over MgSO$_4$, filtered and carefully evaporated (product is volatile). Pentane was added, the solid was filtered and the solvents were evaporated. The residue was purified by straight phase flash chromatography on silica (pentane/EtOAc:10/1 as eluent) to yield the title compound (315 mg, 37%); $^1$H NMR (400 MHz, CDCl$_3$) 2.05-2.08 (3H, m), 5.08-5.12 (1H, m), 5.42 (1H, p), 6.87-6.97 (2H, m).

Intermediate 55

N-(4-(2-(4-Chloro-2,6-difluorophenyl)propyl)-6-(((R)-1-hydroxy-4-methylpentan-2-yl)amino)-1,3,5-triazin-2-yl)methanesulfonamide

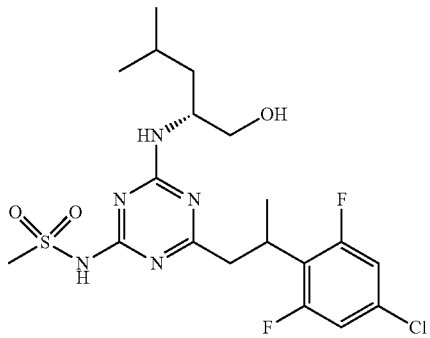 [SMILES: CC(C)C[C@H](CO)Nc1nc(CC(C)c2c(F)cc(Cl)cc2F)nc(NS(C)(=O)=O)n1]

A solution of 0.5 M 9-BBN in THF (2.78 mL, 1.39 mmol) was added to 5-chloro-1,3-difluoro-2-(prop-1-en-2-yl)benzene Intermediate 54 (175 mg, 0.93 mmol) and the reaction mixture was stirred at 70° C. for 1 h under nitrogen atmosphere. A degassed solution of 3 M $K_3PO_4$ (aq, 0.926 mL, 2.78 mmol) was added followed by the addition of (R)—N-(4-chloro-6-((1-hydroxy-4-methylpentan-2-yl)amino)-1,3,5-triazin-2-yl)methanesulfonamide Intermediate 1 (150 mg, 0.46 mmol) and Pd(dppf)Cl$_2$·DCM (56.7 mg, 0.07 mmol) and the reaction mixture was stirred under nitrogen atmosphere at 40° C. overnight. EtOAc and dilute HCl were added and the two phases were separated. The aqueous phase was acidified with 3.8 M HCl and extracted with EtOAc. The combined organic extract was treated with SiliaMetS Thiol and dried over MgSO$_4$. The mixture was filtered, the filtrate was evaporated and the residue was purified by preparative HPLC, PrepMethod E, (gradient: 5-95%) to yield the title compound (59 mg, 27%); MS (ESI) m/z [M+H]$^+$ 478.2.

Intermediate 56

5-Bromo-4-fluoro-2-methoxypyridine

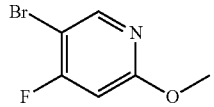

Dibromine (56.6 g, 354.0 mmol) in HOAc (100 mL) was added dropwise during 15 min to a solution of 4-fluoro-2-methoxypyridine (30.0 g, 236.0 mmol) in HOAc (150 mL) and the reaction mixture was stirred at rt overnight. EtOAc and water were added followed by the addition of Na$_2$S$_2$O$_5$ (aq) until bromine colour disappeared, and the two phases were separated. The aqueous phase was extracted twice with EtOAc. The combined organic extract was washed with 2 M NaOH and water, dried over MgSO$_4$, filtered and evaporated. The residue was purified by straight phase flash chromatography on silica (heptane/EtOAc:10/1 as eluent) to yield the title compound as a colourless oil that solidified upon standing (25.6 g, 53%); $^1$H NMR (500 MHz, CDCl$_3$) 3.93 (3H, s), 6.52 (1H, d), 8.23 (1H, d).

Intermediate 57

4-Fluoro-2-methoxy-5-(prop-1-en-2-yl)pyridine

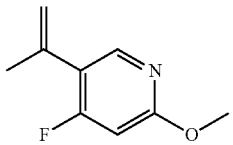

4,4,5,5-Tetramethyl-2-(prop-1-en-2-yl)-1,3,2-dioxaborolane (27.4 ml, 145.6 mmol) was added to a mixture of 5-bromo-4-fluoro-2-methoxypyridine Intermediate 56 (25.0 g, 121.4 mmol), K$_2$CO$_3$ (41.9 g, 303.4 mmol) and Pd(dtbpf)Cl$_2$ (4.75 g, 7.28 mmol) in THF (240 mL) and water (60 mL) under nitrogen atmosphere. The reaction mixture was stirred at 50° C. for 2 h and then it was allowed to reach rt. Water and Et$_2$O were added and the two phases were separated. The aqueous phase was extracted with Et$_2$O and the combined organic extract was washed with water (×2) and brine, dried over MgSO$_4$, filtered and evaporated. The residue was purified by straight phase flash chromatography on silica (heptane/MTBE:20/1 as eluent) to yield the title compound as an oil (17.1 g, 84%); $^1$H NMR (500 MHz, CDCl$_3$) 2.10-2.12 (3H, m), 3.94 (3H, s), 5.19-5.21 (1H, m), 5.22-5.24 (1H, m), 6.42 (1H, d), 8.10 (1H, d).

Intermediate 58

N-(4-(2-(4-Fluoro-6-methoxypyridin-3-yl)propyl)-6-(((R)-1-hydroxy-4-methylpentan-2-yl)amino)-1,3,5-triazin-2-yl)methanesulfonamide

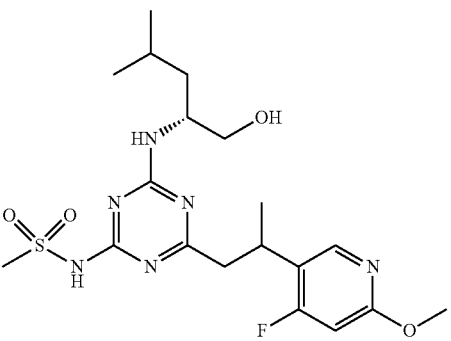

A solution of 0.5 M 9-BBN in THF (7.41 mL, 3.71 mmol) was added to 4-fluoro-2-methoxy-5-(prop-1-en-2-yl)pyridine Intermediate 57 (341 mg, 2.04 mmol) under nitrogen atmosphere and the reaction mixture was stirred at rt for 1 h. The reaction mixture was added to (R)—N-(4-chloro-6-((1-hydroxy-4-methylpentan-2-yl)amino)-1,3,5-triazin-2-yl)methanesulfonamide Intermediate 1 (600 mg, 1.85 mmol), Pd(dppf)Cl$_2$·DCM (151 mg, 0.19 mmol) and K$_3$PO$_4$ (1.57 g, 7.41 mmol) and the reaction mixture was stirred at 50° C. for 1 h under nitrogen atmosphere. Water and EtOAc were added and the two phases were separated. The organic extract was washed with water and brine. The combined aqueous phase was acidified by the addition of 1 M HCl and extracted with EtOAc (×3). The combined organic extract was dried over MgSO₄, filtered and evaporated. The residue was purified by straight phase flash chromatography on silica (EtOAc as eluent) to yield the title compound (498 mg, 59%); MS (ESI) m/z [M+H]⁺ 457.4.

Intermediate 59

1-(But-1-en-2-yl)-2,3-difluorobenzene

KOtBu (523 mg, 4.66 mmol) was added to methyltriphenylphosphonium bromide (1.47 g, 4.10 mmol) in THF (8 mL). The reaction mixture was stirred at rt for 30 min and then it was added to a solution of 1-(2,3-difluorophenyl)propan-1-one (635 mg, 3.73 mmol) in THF (2 mL). The reaction mixture was stirred at rt for 2 h and then water and pentane were added. The two phases were separated and the aqueous phase was extracted with pentane. The combined organic extract was washed with water, dried over MgSO₄, filtered and carefully evaporated (product is volatile). The residue was purified by straight phase flash chromatography on silica (pentane as eluent) to yield the title compound (233 mg, 37%) as a colourless oil; ¹H NMR (500 MHz, CDCl₃) 1.05 (3H, t), 2.44-2.51 (2H, m), 5.15-5.18 (1H, m), 5.24-5.28 (1H, m), 6.96-7.12 (3H, m).

Intermediate 60

N-(4-(2-(2,3-Difluorophenyl)butyl)-6-(((R)-1-hydroxy-4-methylpentan-2-yl)amino)-1,3,5-triazin-2-yl)methanesulfonamide

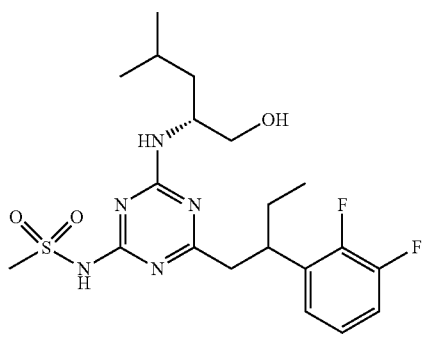 [SMILES: CCC(Cc1nc(N[C@@H](CO)CC(C)C)nc(NS(C)(=O)=O)n1)c1cccc(F)c1F]

A solution of 0.5 M 9-BBN in THF (2.97 mL, 1.48 mmol) was added to 1-(but-1-en-2-yl)-2,3-difluorobenzene Intermediate 59 (125 mg, 0.74 mmol) under nitrogen atmosphere. The reaction mixture was stirred at rt for 1 h and then added to (R)—N-(4-chloro-6-((1-hydroxy-4-methylpentan-2-yl)amino)-1,3,5-triazin-2-yl)methanesulfonamide Intermediate 1 (240 mg, 0.74 mmol), Pd(dppf)Cl₂·DCM (60.5 mg, 0.07 mmol) and K₃PO₄ (629 mg, 2.96 mmol). The reaction mixture was stirred at 50° C. for 2.5 h under nitrogen atmosphere and then water and EtOAc were added. The two phases were separated and the organic extract was washed with water and brine. The combined aqueous phase was acidified by the addition of 1 M HCl and the aqueous phase was extracted with EtOAc (×3). The combined organic extract was dried over MgSO₄, filtered and evaporated. The residue was purified by straight phase flash chromatography on silica (EtOAc as eluent) to yield the title compound (75 mg, 22%); MS (ESI) m/z [M+H]⁺ 458.3.

Intermediate 61

2-(But-1-en-2-yl)-4,4,5,5-tetramethyl-1,3,2-dioxaborolane

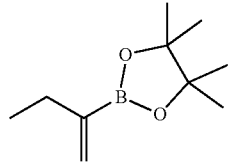

1,4-Dioxane (10 mL) was added to B₂pin₂ (4.51 g, 17.78 mmol), KOAc (4.36 g, 44.44 mmol) and Pd(dppf)Cl₂·DCM (0.968 g, 1.19 mmol) under nitrogen atmosphere. 2-Bromobut-1-ene (2.0 g, 14.81 mmol) in dioxane (5 mL) was added and the reaction mixture was stirred at 60° C. for 18 h. The reaction mixture was allowed to cool and then water and Et₂O were added and the two phases were separated. The organic extract was dried over MgSO₄, filtered and evaporated. The residue was purified by straight phase flash chromatography on silica (pentane/MTBE:20/1 as eluent) to yield the title compound (0.68 g, 25%) as a colourless oil; ¹H NMR (500 MHz, CDCl₃) 1.01 (3H, t), 1.27 (12H, s), 2.13-2.20 (2H, m), 5.60 (1H, s), 5.72-5.77 (1H, m).

Intermediate 62

5-(But-1-en-2-yl)-4-fluoro-2-methoxypyridine

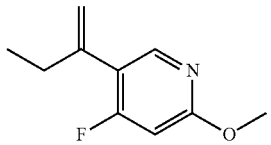

2-(But-1-en-2-yl)-4,4,5,5-tetramethyl-1,3,2-dioxaborolane Intermediate 61 (610 mg, 3.35 mmol) was added to a mixture of 5-bromo-4-fluoro-2-methoxypyridine (575 mg, 2.79 mmol), K₂CO₃ (964 mg, 6.98 mmol) and Pd(dtbpf)Cl₂ (182 mg, 0.28 mmol) in water (1.5 mL) and THF (6 mL) under nitrogen atmosphere. The reaction mixture was stirred at 60° C. for 2 h. The reaction mixture was allowed to reach rt and then water and Et₂O were added and the two phases were separated. The aqueous phase was extracted with Et₂O and the combined organic extract was washed with water, dried over MgSO₄, filtered and evaporated. The residue was purified by straight phase flash chromatography on silica (heptane/MTBE:20/1 as eluent). Fractions with product were combined and repurified by straight phase flash chromatography on silica (heptane/MTBE:25/1 as eluent) to yield the title compound (172 mg, 34%) as a colourless oil; 1H NMR (500 MHz, CDCl$_3$) 1.04 (3H, t), 2.44 (2H, q), 3.94 (3H, s), 5.11-5.15 (1H, m), 5.18-5.21 (1H, m), 6.41 (1H, d), 8.04 (1H, d).

Intermediate 63 tert-Butyl (5-(prop-1-en-2-yl)pyridin-2-yl)carbamate

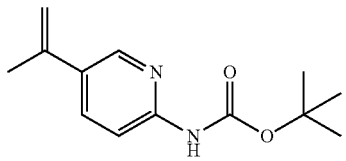 [SMILES: C=C(C)c1ccc(NC(=O)OC(C)(C)C)nc1]

4,4,5,5-Tetramethyl-2-(prop-1-en-2-yl)-1,3,2-dioxaborolane (1.24 mL, 6.59 mmol) was added to a mixture of tert-butyl (5-bromopyridin-2-yl)carbamate (1.50 g, 5.49 mmol), K$_2$CO$_3$ (1.90 g, 13.73 mmol) and Pd(dtbpf)Cl$_2$ (0.358 g, 0.55 mmol) in water (3 mL) and THF (12 mL) under nitrogen atmosphere. The reaction mixture was stirred at 60° C. for 1.5 h and then water and Et$_2$O were added and the two phases were separated. The aqueous phase was extracted with Et$_2$O and the combined organic extract was washed with water, dried over MgSO$_4$, filtered and evaporated. The residue was purified by straight phase flash chromatography on silica (heptane/MTBE:10/1 as eluent) to yield the title compound (514 mg, 40%) as a colourless solid; $^1$H NMR (500 MHz, CDCl$_3$) 1.54 (9H, s), 2.11-2.15 (3H, m), 5.06-5.09 (1H, m), 5.33-5.36 (1H, m), 7.75 (1H, dd), 7.91 (1H, d), 8.12 (1H, br s), 8.37 (1H, d).

Intermediate 64 tert-Butyl (5-(1-(4-(((R)-1-hydroxy-4-methylpentan-2-yl)amino)-6-(methylsulfonamido)-1,3,5-triazin-2-yl)propan-2-yl)pyridin-2-yl)carbamate

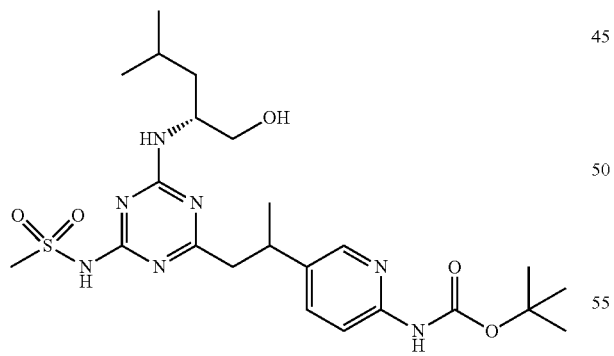

A solution of 0.5 M 9-BBN in THF (2.47 mL, 1.24 mmol) was added to tert-butyl (5-(prop-1-en-2-yl)pyridin-2-yl)carbamate Intermediate 63 (139 mg, 0.59 mmol) under nitrogen atmosphere. The reaction mixture was stirred at rt for 1 h and then it was added to (R)—N-(4-chloro-6-(((1-hydroxy-4-methylpentan-2-yl)amino)-1,3,5-triazin-2-yl)methanesulfonamide Intermediate 1 (160 mg, 0.49 mmol), Pd(dppf)Cl$_2$·DCM (40.4 mg, 0.05 mmol) and K$_3$PO$_4$ (420 mg, 1.98 mmol) under nitrogen atmosphere and the reaction mixture was heated to 50° C. for 2 h. Water and EtOAc were added. The two phases were separated and the organic phase was extracted with water. The combined aqueous extract was acidified with 1 M HCl to pH 5 and then extracted with EtOAc (×3). The combined organic extract was dried over MgSO$_4$, filtered and evaporated.

The residue was purified by straight phase flash chromatography on silica (gradient: 0-10% MeOH in EtOAc) to yield the title compound (125 mg, 48%); MS (ESI) m/z [M+H]$^+$ 524.4.

Intermediate 65

N-(4-(2-(6-Aminopyridin-3-yl)propyl)-6-(((R)-1-hydroxy-4-methylpentan-2-yl)amino)-1,3,5-triazin-2-yl)methanesulfonamide

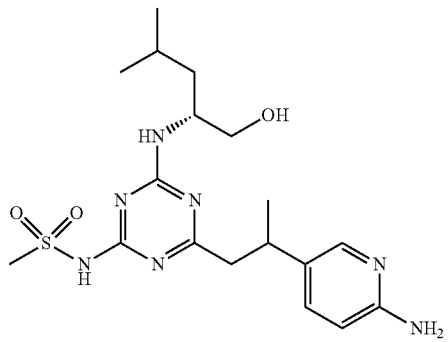 [SMILES: CC(C)C[C@H](CO)Nc1nc(CC(C)c2ccc(N)nc2)nc(NS(C)(=O)=O)n1]

A solution of 4 M HCl in dioxane (2.0 mL, 8.0 mmol) was added to tert-butyl (5-(1-(4-(((R)-1-hydroxy-4-methylpentan-2-yl)amino)-6-(methylsulfonamido)-1,3,5-triazin-2-yl)propan-2-yl)pyridin-2-yl)carbamate Intermediate 64 (105 mg, 0.20 mmol) and the reaction mixture was stirred at 40° C. for 1 h. Et$_2$O was added to precipitate the product and the solvent was decanted. Another portion of Et$_2$O was added to wash the solid. The solid residue was dried under vacuum to yield the title compound as an HCl-salt (107 mg, 100% if 3 HCl); MS (ESI) m/z [M+H]$^+$ 424.3.

Intermediate 66

2,6-Dimethoxy-3-(prop-1-en-2-yl)pyridine

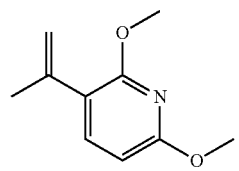

3-Bromo-2,6-dimethoxypyridine (1.0 g, 4.59 mmol), 4,4,5,5-tetramethyl-2-(prop-1-en-2-yl)-1,3,2-dioxaborolane (1.38 mL, 7.34 mmol), K$_2$CO$_3$ (1.90 g, 13.76 mmol) and Pd(dppf)Cl$_2$ (40 mg, 0.06 mmol) were added to 1,4-dioxane (7 mL) and water (2 mL). The reaction mixture was stirred at 100° C. for 2 h under nitrogen atmosphere. Another portion of Pd(dppf)Cl$_2$ (40 mg, 0.06 mmol) was added followed by the addition 4,4,5,5-tetramethyl-2-(prop-1-en-2-yl)-1,3,2-dioxaborolane (0.89 mL, 4.76 mmol) and stirring was continued at 100° C. until complete reaction. Et₂O and water were added and the two phases were separated. The aqueous phase was extracted with Et₂O and the combined organic extract was evaporated. The residue was purified by straight phase flash chromatography on silica (gradient: 1-7% EtOAc in heptane) to yield the title compound (190 mg, 23%) as an oil; ¹H NMR (500 MHz, CDCl₃) 2.08-2.10 (3H, m), 3.92 (3H, s), 3.96 (3H, s), 5.10-5.14 (1H, m), 5.17-5.20 (1H, m), 6.27 (1H, d), 7.44 (1H, d).

Intermediate 67

N-(4-(2-(2,6-Dimethoxypyridin-3-yl)propyl)-6-(((R)-1-hydroxy-4-methylpentan-2-yl)amino)-1,3,5-triazin-2-yl)methanesuiofonamide

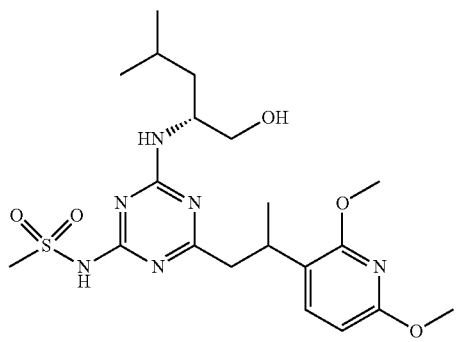

9-BBN dimer (44.8 mg, 0.18 mmol) was added to 2,6-dimethoxy-3-(prop-1-en-2-yl)pyridine (31.4 mg, 0.18 mmol) Intermediate 66 (31.4 mg, 0.18 mmol) dissolved in Et₂O (1 mL) under nitrogen atmosphere and the reaction mixture was stirred at rt for 45 min. A degassed solution of 3 M K₃PO₄ (aq, 0.274 ml, 0.82 mmol) was added followed by the addition of (R)—N-(4-((1-((tert-butyldimethylsilyl) oxy)-4-methylpentan-2-yl)amino)-6-chloro-1,3,5-triazin-2-yl)methanesulfonamide Intermediate 2 (60 mg, 0.14 mmol) and Pd(dppf)Cl₂·DCM (16.6 mg, 0.02 mmol). The reaction mixture was stirred under nitrogen atmosphere at 35° C. overnight and then EtOAc and water were added. The mixture was acidified with dilute HCl and the two phases were separated. The aqueous phase was extracted with EtOAc and the combined organic phase was washed with brine and evaporated. The residue was dissolved in EtOH (2 mL) and conc HCl (0.4 mL) were added and the mixture was stirred at rt for 1 h and then the solvents were evaporated. The residue (combined with two other batches made in a similar manner starting from 176 mg of Intermediate 2 in total) was purified by preparative HPLC, PrepMethod A, (gradient: 20-65%) to yield the title compound (57.0 mg, 30% in total); MS (ESI) m/z [M+H]⁺ 469.4.

Intermediate 68 tert-Butyl 4-(4-(1-(4-chloro-6-(((R)-1-hydroxy-4-methylpentan-2-yl)amino)-1,3,5-triazin-2-yl)propan-2-yl)phenyl)piperazine-1-carboxylate

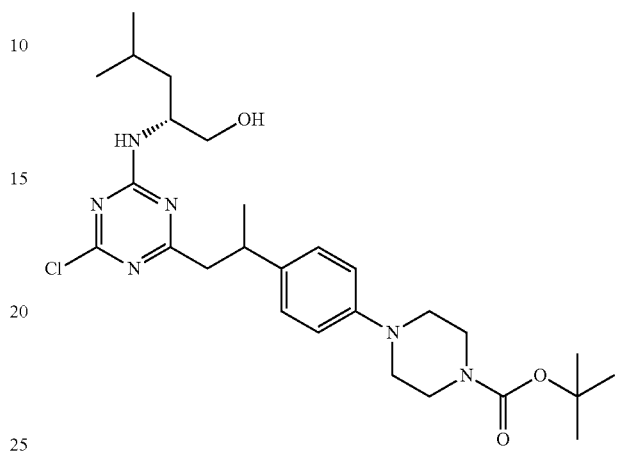

A solution of (R,E)-2-((4-chloro-6-(prop-1-en-1-yl)-1,3,5-triazin-2-yl)amino)-4-methylpentan-1-ol Intermediate 3 (45 mg, 0.17 mmol) in 1,4-dioxane (1.5 mL) and a solution of 4 M KOH (aq, 83 μL, 0.33 mmol), followed by [Rh (COD)Cl]₂ (4.1 mg, 0.01 mmol) were added to (4-(4-(tert-butoxycarbonyl)piperazin-1-yl)phenyl)boronic acid (51 mg, 0.17 mmol) and the reaction mixture was stirred at 50° C. under nitrogen atmosphere for 2 h. DCM and water were added. The aqueous phase was acidified and the phases were separated. The aqueous phase was extracted with EtOAc and the combined organic extract was filtered through a short pad of silica and evaporated to give the crude title compound (yield assumed quantitative) which was used in next step without further purification; MS (ESI) m/z [M+H]⁺ 533.5.

Intermediate 69 tert-Butyl 4-(4-(1-(4-(((R)-1-hydroxy-4-methylpentan-2-yl)amino)-6-(methylsulfonamido)-1,3,5-triazin-2-yl)propan-2-yl)phenyl)piperazine-1-carboxylate

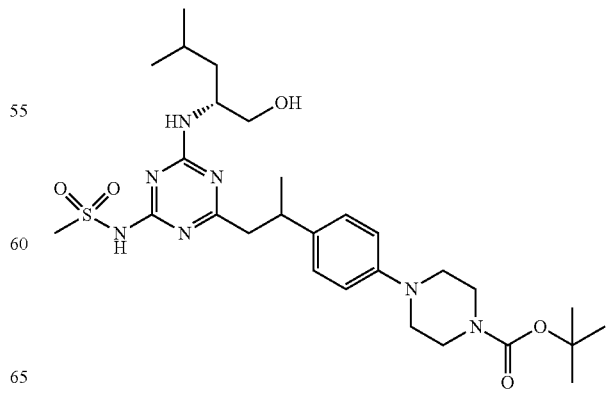

THF (0.3 mL) was added to Pd₂dba₃ (10.6 mg, 0.01 mmol) and X-Phos (22 mg, 0.05 mmol) and the mixture was stirred under nitrogen atmosphere at rt for 10 min. tert-Butyl 4-(4-(1-(4-chloro-6-(((R)-1-hydroxy-4-methylpentan-2-yl)amino)-1,3,5-triazin-2-yl)propan-2-yl)phenyl)piperazine-1-carboxylate Intermediate 68 (90 mg, 0.17 mmol) in THF (1 mL), methanesulfonamide (55 mg, 0.58 mmol) in THF (0.5 mL) and K₂CO₃ (82 mg, 0.59 mmol) were added and the reaction mixture was stirred at 70° C. overnight. EtOAc and water were added. The mixture was acidified with 3.8 M HCl and the two phases were separated. The aqueous phase was extracted with EtOAc and the combined organic extract was dried over MgSO₄, treated with SiliaMetS Thiol for 30 min, filtered and evaporated to give the crude title compound (yield assumed quantitative) which was used in next step without further purification; MS (ESI) m/z [M+H]⁺ 592.6.

Intermediate 70

2-(4-(1-(4-Chloro-6-(((R)-1-hydroxy-4-methylpentan-2-yl)amino)-1,3,5-triazin-2-yl)propan-2-yl)phenyl)acetonitrile

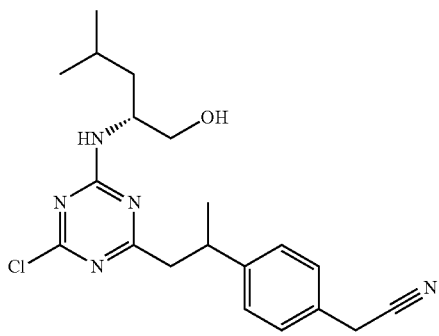 [SMILES: CC(C)C[C@H](CO)Nc1nc(Cl)nc(CC(C)c2ccc(CC#N)cc2)n1]

A solution of (R,E)-2-((4-chloro-6-(prop-1-en-1-yl)-1,3,5-triazin-2-yl)amino)-4-methylpentan-1-ol Intermediate 3 (78 mg, 0.29 mmol) in 1,4-dioxane (1.5 mL) and a solution of 4 M KOH (aq, 0.18 mL, 0.72 mmol) followed by [Rh(COD)Cl]₂ (7.1 mg, 0.01 mmol) were added to (4-(cyanomethyl)phenyl)boronic acid (93 mg, 0.58 mmol) and the reaction mixture was stirred at 50° C. under nitrogen atmosphere for 2 h. EtOAc and water were added. The aqueous phase was acidified and the phases were separated. The organic extract was dried over MgSO₄ and filtered through a short pad of silica. The eluate was evaporated to give the crude title compound (yield assumed quantitative) which was used in next step without further purification; MS (ESI) m/z [M+H]⁺ 388.4.

Intermediate 71

(2R)-2-((4-Chloro-6-(2-(3-fluoro-4-methylphenyl)propyl)-1,3,5-triazin-2-yl)amino)-4-methylpentan-1-ol

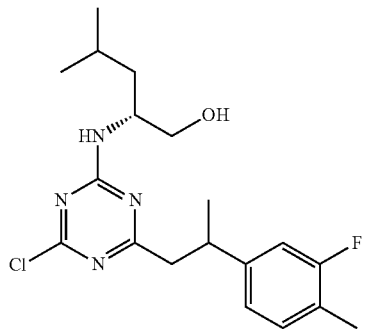 [SMILES: Cc1ccc(C(C)Cc2nc(Cl)nc(N[C@@H](CO)CC(C)C)n2)cc1F]

A solution of (R,E)-2-((4-chloro-6-(prop-1-en-1-yl)-1,3,5-triazin-2-yl)amino)-4-methylpentan-1-ol Intermediate 3 (78 mg, 0.29 mmol) in 1,4-dioxane (1.5 mL) and a solution of 4 M KOH (aq, 0.18 mL, 0.72 mmol) followed by [Rh(COD)Cl]₂ (7.1 mg, 0.01 mmol) were added to (3-fluoro-4-methylphenyl)boronic acid (89 mg, 0.58 mmol) and the reaction mixture was stirred at 50° C. under nitrogen atmosphere for 2 h. EtOAc and water were added. The aqueous phase was acidified and the phases were separated. The organic extract was dried over MgSO₄ and filtered through a short pad of silica. The eluate was evaporated to give the crude title compound (yield assumed quantitative) which was used in next step without further purification; MS (ESI) m/z [M+H]⁺ 381.3.

Intermediate 72

(2R)-2-((4-Chloro-6-(2-(4-(oxetan-3-yl)phenyl)propyl)-1,3,5-triazin-2-yl)amino)-4-methylpentan-1-ol

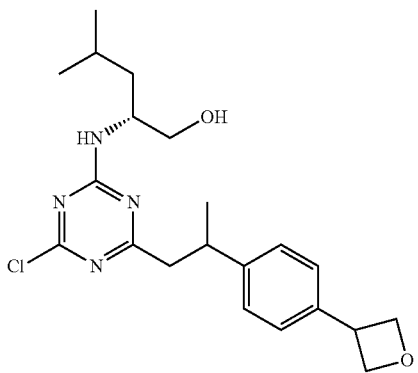 [SMILES: CC(C)C[C@H](CO)Nc1nc(Cl)nc(CC(C)c2ccc(C3COC3)cc2)n1]

A solution of (R,E)-2-((4-chloro-6-(prop-1-en-1-yl)-1,3,5-triazin-2-yl)amino)-4-methylpentan-1-ol Intermediate 3 (78 mg, 0.29 mmol) in 1,4-dioxane (1.5 mL) and a solution of 4 M KOH (aq, 0.18 mL, 0.72 mmol) followed by [Rh(COD)Cl]₂ (7.1 mg, 0.01 mmol) were added to (4-(oxetan-3-yl)phenyl)boronic acid (103 mg, 0.58 mmol) and the reaction mixture was stirred at 50° C. under nitrogen atmosphere for 2 h. EtOAc and water were added. The

Intermediate 73

(2R)-2-((4-Chloro-6-(2-(3-fluorophenyl)propyl)-1,3,5-triazin-2-yl)amino)-4-methylpentan-1-ol

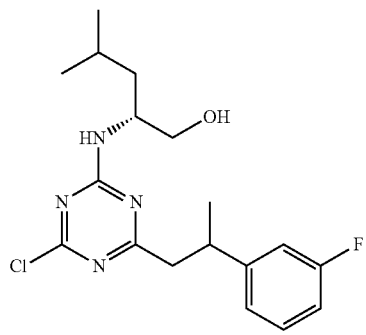 [SMILES: CC(C)C[C@H](CO)Nc1nc(Cl)nc(CC(C)c2cccc(F)c2)n1]

A solution of (R,E)-2-((4-chloro-6-(prop-1-en-1-yl)-1,3,5-triazin-2-yl)amino)-4-methylpentan-1-ol Intermediate 3 (78 mg, 0.29 mmol) in 1,4-dioxane (1.5 mL), a solution of 4 M KOH (aq, 0.18 mL, 0.72 mmol) followed by [Rh(COD)Cl]$_2$ (7.1 mg, 0.01 mmol) were added to (3-fluorophenyl)boronic acid (81 mg, 0.58 mmol). The reaction mixture was stirred at 50° C. under nitrogen atmosphere for 2 h and then EtOAc and water were added. The aqueous phase was acidified and the phases were separated. The organic extract was dried over MgSO$_4$ and filtered through a short pad of silica. The eluate was evaporated to give the crude title compound (assumed quantitative yield); MS (ESI) m/z [M+H]$^+$ 367.3.

Intermediate 74

N-(4-(1-(4-Chloro-6-(((R)-1-hydroxy-4-methylpentan-2-yl)amino)-1,3,5-triazin-2-yl)propan-2-yl)phenyl)acetamide

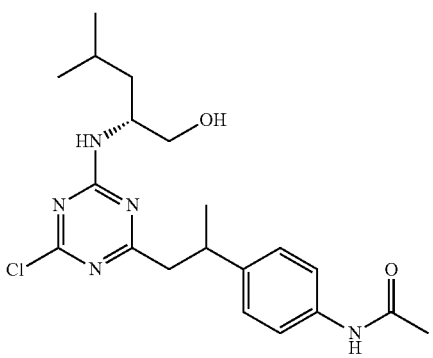 [SMILES: CC(=O)Nc1ccc(C(C)Cc2nc(Cl)nc(N[C@@H](CO)CC(C)C)n2)cc1]

A solution of (R,E)-2-((4-chloro-6-(prop-1-en-1-yl)-1,3,5-triazin-2-yl)amino)-4-methylpentan-1-ol Intermediate 3 (81 mg, 0.30 mmol) in 1,4-dioxane (1.5 mL), a solution of 4 M KOH (aq, 0.15 mL, 0.60 mmol) followed by [Rh(COD)Cl]$_2$ (7.4 mg, 0.02 mmol) were added to N-(4-(4,4,5,5-tetramethyl-1,3,2-dioxaborolan-2-yl)phenyl)acetamide (118 mg, 0.45 mmol). The reaction mixture was stirred at 50° C. under nitrogen atmosphere for 2 h and then DCM and water were added. The aqueous phase was acidified and the phases were separated. The aqueous phase was extracted with EtOAc and the combined organic extract was filtered through a short pad of silica. The eluate was evaporated to give the crude title compound (assumed quantitative yield); MS (ESI) m/z [M+H]$^+$ 406.4.

Intermediate 75

(2R)-2-((4-(2-(1H-Indol-5-yl)propyl)-6-chloro-1,3,5-triazin-2-yl)amino)-4-methylpentan-1-ol

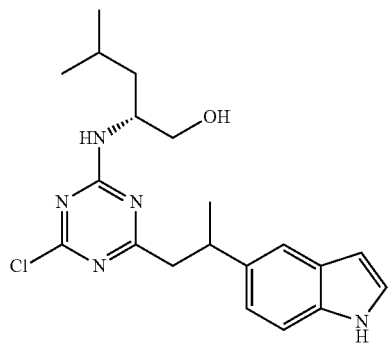 [SMILES: CC(C)C[C@H](CO)Nc1nc(Cl)nc(CC(C)c2ccc3[nH]ccc3c2)n1]

A solution of (R,E)-2-((4-chloro-6-(prop-1-en-1-yl)-1,3,5-triazin-2-yl)amino)-4-methylpentan-1-ol Intermediate 3 (81 mg, 0.30 mmol) in 1,4-dioxane (1.5 mL), a solution of 4 M KOH (aq, 0.15 mL, 0.60 mmol) followed by [Rh(COD)Cl]$_2$ (7.4 mg, 0.02 mmol) were added to (1H-indol-5-yl)boronic acid (95 mg, 0.59 mmol). The reaction mixture was stirred at 50° C. under nitrogen atmosphere for 2 h and then DCM and water were added. The aqueous phase was acidified and the phases were separated. The aqueous phase was extracted with EtOAc and the combined organic extract was filtered through a short pad of silica. The eluate was evaporated to give the crude title compound (assumed quantitative yield); MS (ESI) m/z [M+H]$^+$ 388.3.

Intermediate 76

(2R)-2-((4-(2-(Benzo[d]oxazol-6-yl)propyl)-6-chloro-1,3,5-triazin-2-yl)amino)-4-methylpentan-1-ol

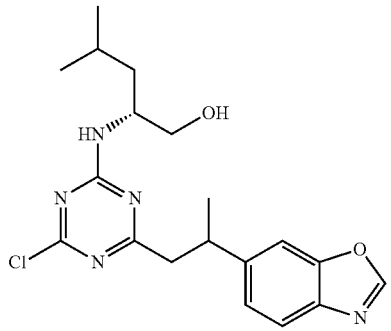 [SMILES: CC(C)C[C@H](CO)Nc1nc(Cl)nc(CC(C)c2ccc3ncoc3c2)n1]

A solution of (R,E)-2-((4-chloro-6-(prop-1-en-1-yl)-1,3,5-triazin-2-yl)amino)-4-methylpentan-1-ol Intermediate 3 (81 mg, 0.30 mmol) in 1,4-dioxane (1.5 mL), a solution of 4 M KOH (aq, 0.15 mL, 0.60 mmol) followed by [Rh(COD)Cl]$_2$ (7.4 mg, 0.02 mmol) were added to 6-(4,4,5,5-tetramethyl-1,3,2-dioxaborolan-2-yl)benzo[d]oxazole (102 mg, 0.42 mmol). The reaction mixture was stirred at 50° C. under nitrogen atmosphere for 2 h and then DCM and water were added. The aqueous phase was acidified and the phases were separated. The aqueous phase was extracted with EtOAc and the combined organic extract was filtered through a short pad of silica. The eluate was evaporated to give the crude title compound (assumed quantitative yield); MS (ESI) m/z [M+H]$^+$ 390.3.

Intermediate 77

(2R)-2-((4-(2-(Benzo[d]oxazol-5-yl)propyl)-6-chloro-1,3,5-triazin-2-yl)amino)-4-methylpentan-1-ol

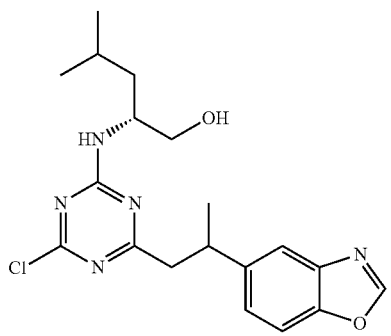 [SMILES: CC(C)C[C@H](CO)Nc1nc(Cl)nc(CC(C)c2ccc3ocnc3c2)n1]

A solution of (R,E)-2-((4-chloro-6-(prop-1-en-1-yl)-1,3,5-triazin-2-yl)amino)-4-methylpentan-1-ol Intermediate 3 (81 mg, 0.30 mmol) in 1,4-dioxane (1.5 mL), a solution of 4 M KOH (aq, 0.15 mL, 0.60 mmol) followed by [Rh(COD)Cl]$_2$ (7.4 mg, 0.02 mmol) were added to 5-(4,4,5,5-tetramethyl-1,3,2-dioxaborolan-2-yl)benzo[d]oxazole (99 mg, 0.40 mmol). The reaction mixture was stirred at 50° C. under nitrogen atmosphere for 2 h and then DCM and water were added. The aqueous phase was acidified and the phases were separated. The aqueous phase was extracted with EtOAc and the combined organic extract was filtered through a short pad of silica. The eluate was evaporated to give the crude title compound (assumed quantitative yield); MS (ESI) m/z [M+H]$^+$ 390.3.

Intermediate 78

((4-(1-(4-Chloro-6-(((R)-1-hydroxy-4-methylpentan-2-yl)amino)-1,3,5-triazin-2-yl)propan-2-yl)phenyl)imino)dimethyl-$\lambda^6$-sulfanone

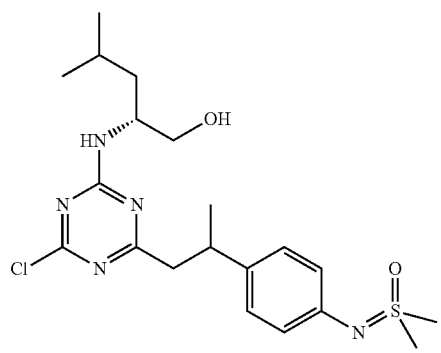 [SMILES: CC(C)C[C@H](CO)Nc1nc(Cl)nc(CC(C)c2ccc(N=S(C)(C)=O)cc2)n1]

A solution of (R,E)-2-((4-chloro-6-(prop-1-en-1-yl)-1,3,5-triazin-2-yl)amino)-4-methylpentan-1-ol Intermediate 3 (81 mg, 0.30 mmol) in 1,4-dioxane (1.5 mL), a solution of 4 M KOH (aq, 0.15 mL, 0.60 mmol) followed by [Rh(COD)Cl]$_2$ (7.4 mg, 0.02 mmol) were added to dimethyl((4-(4,4,5,5-tetramethyl-1,3,2-dioxaborolan-2-yl)phenyl)imino)-$\lambda^6$-sulfanone (96 mg, 0.33 mmol). The reaction mixture was stirred at 50° C. under nitrogen atmosphere for 2 h and then DCM and water were added. The aqueous phase was acidified and the phases were separated. The aqueous phase was extracted with EtOAc and the combined organic extract was filtered through a short pad of silica. The eluate was evaporated to give the crude title compound (assumed quantitative yield); MS (ESI) m/z [M+H]$^+$ 440.4.

Intermediate 79

(2R)-2-((4-(2-(4-(1H-1,2,3-Triazol-1-yl)phenyl)propyl)-6-chloro-1,3,5-triazin-2-yl)amino)-4-methylpentan-1-ol

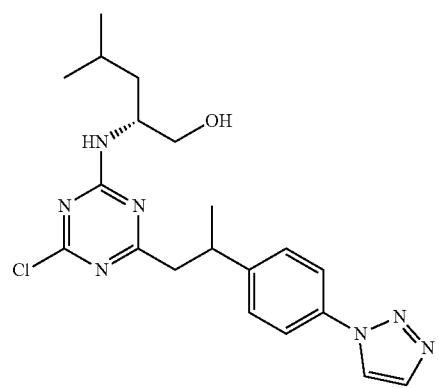 [SMILES: CC(C)C[C@H](CO)Nc1nc(Cl)nc(CC(C)c2ccc(-n3ccnn3)cc2)n1]

A solution of (R,E)-2-((4-chloro-6-(prop-1-en-1-yl)-1,3,5-triazin-2-yl)amino)-4-methylpentan-1-ol Intermediate 3 (81 mg, 0.30 mmol) in 1,4-dioxane (1.5 mL), a solution of 4 M KOH (aq, 0.15 mL, 0.60 mmol) followed by [Rh(COD)Cl]$_2$ (7.4 mg, 0.02 mmol) were added to 1-(4-(4,4,5,5-tetramethyl-1,3,2-dioxaborolan-2-yl)phenyl)-1H-1,2,3-triazole (96 mg, 0.35 mmol). The reaction mixture was stirred at 50° C. under nitrogen atmosphere for 2 h and then DCM and water were added. The aqueous phase was acidified and the phases were separated. The aqueous phase was extracted with EtOAc and the combined organic extract was filtered through a short pad of silica. The eluate was evaporated to give the crude title compound (assumed quantitative yield); MS (ESI) m/z [M+H]$^+$ 416.4.

Intermediate 80

(2R)-2-((4-Chloro-6-(2-(3-chloro-4-fluorophenyl)propyl)-1,3,5-triazin-2-yl)amino)-4-methylpentan-1-ol

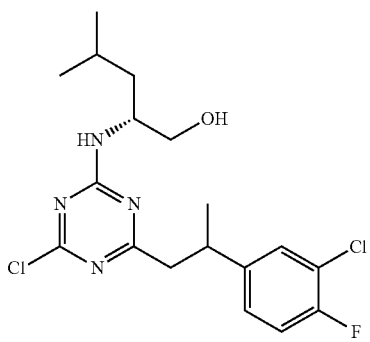 [SMILES: CC(C)C[C@H](CO)Nc1nc(Cl)nc(CC(C)c2ccc(F)c(Cl)c2)n1]

1,4-Dioxane (0.65 mL) and water (72 μL) was added to (R,E)-2-((4-chloro-6-(prop-1-en-1-yl)-1,3,5-triazin-2-yl)amino)-4-methylpentan-1-ol Intermediate 3 (39 mg, 0.14 mmol), (3-chloro-4-fluorophenyl)boronic acid (50.2 mg, 0.29 mmol), [Rh(COD)Cl]$_2$ (3.6 mg, 7.2 μmol) and KOH (16.2 mg, 0.29 mmol) and the reaction mixture was stirred at 50° C. for 3.5 h and then at 60° C. overnight. EtOAc and water were added and the two phases were separated. The organic extract was evaporated and the residue was purified by preparative HPLC, PrepMethod A, (gradient: 40-85%) to yield the title compound (30 mg, 51%); MS (ESI) m/z [M+H]$^+$ 401.3.

Intermediate 81

N-(4-(2-(3-Chloro-4-fluorophenyl)propyl)-6-(((R)-1-hydroxy-4-methylpentan-2-yl)amino)-1,3,5-triazin-2-yl)methanesulfonamide

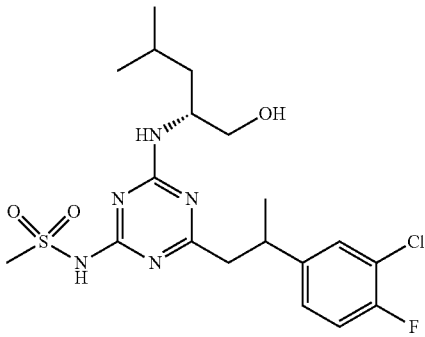 [SMILES: CC(C)C[C@H](CO)Nc1nc(CC(C)c2ccc(F)c(Cl)c2)nc(NS(C)(=O)=O)n1]

THF (0.25 mL) was added to Pd$_2$dba$_3$ (2.7 mg, 2.9 μmol) and X-Phos (5.5 mg, 0.01 mmol) under nitrogen atmosphere. The mixture was stirred for 10 min and then a mixture of (2R)-2-((4-chloro-6-(2-(3-chloro-4-fluorophenyl)propyl)-1,3,5-triazin-2-yl)amino)-4-methylpentan-1-ol Intermediate 80 (29 mg, 0.07 mmol) in THF (0.5 mL), methanesulfonamide (15.5 mg, 0.16 mmol) and K$_2$CO$_3$ (20.47 mg, 0.15 mmol) were added. The reaction mixture was stirred under nitrogen atmosphere at 70° C. overnight. EtOAc and dilute HCl were added and the two phases were separated. The organic phase was washed with brine. The combined aqueous phase was extracted with EtOAc. The combined organic extract was dried over MgSO$_4$, filtered and evaporated. The residue was purified by preparative HPLC, PrepMethod A, (gradient: 30-80%) to yield the title compound (23.8 mg, 72%) as a colourless solid; MS (ESI) m/z [M+H]$^+$ 478.3.

Intermediate 82

2-Ethoxy-4-(prop-1-en-2-yl)pyridine

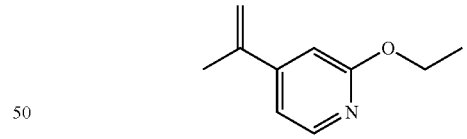

A solution of 4-bromo-2-ethoxypyridine (860 mg, 4.26 mmol) in THF (7.47 mL), followed by Pd(dppf)Cl$_2$·DCM (62 mg, 0.09 mmol) and 4,4,5,5-tetramethyl-2-(prop-1-en-2-yl)-1,3,2-dioxaborolane (1.04 mL, 5.53 mmol) were added to a solution of Cs$_2$CO$_3$ (4.16 g, 12.77 mmol) in water (2.13 mL) and the reaction mixture was degassed and stirred at 80° C. for 20 h under nitrogen atmosphere. Et$_2$O and water were added and the two phases were separated. The organic phase was washed with CsOH (aq) and water and evaporated. The residue was purified by straight phase flash chromatography on silica (gradient: 5-80% Et$_2$O in pentane) to yield the title compound (647 mg, 93%) as a colourless oil; $^1$H NMR (400 MHz, CDCl$_3$) 1.40 (3H, t), 2.09-2.12 (3H, m), 4.36 (2H, q), 5.19-5.23 (1H, m), 5.51-5.54 (1H, m), 6.74 (1H, d), 6.94 (1H, dd), 8.08 (1H, dd).

Intermediate 83

4-(1-(4-Chloro-6-(((R)-1-hydroxy-4-methylpentan-2-yl)amino)-1,3,5-triazin-2-yl)propan-2-yl)benzonitrile

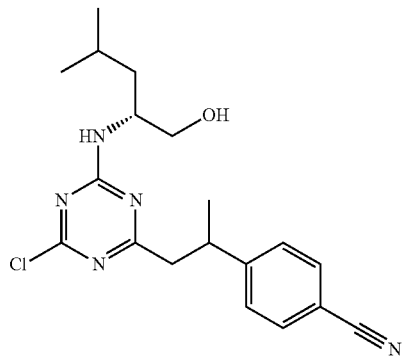 [SMILES: CC(C)C[C@H](CO)Nc1nc(Cl)nc(CC(C)c2ccc(C#N)cc2)n1]

(4-Cyanophenyl)boronic acid (90 mg, 0.61 mmol) and a solution of 4 M KOH (aq, 0.15 mL, 0.61 mmol) were added to (R,E)-2-((4-chloro-6-(prop-1-en-1-yl)-1,3,5-triazin-2-yl)amino)-4-methylpentan-1-ol Intermediate 3 (83 mg, 0.31 mmol) in 1,4-dioxane (1.38 mL). The mixture was degassed and then [Rh(COD)Cl]$_2$ (7.56 mg, 0.02 mmol) was added. The reaction mixture was stirred at 55° C. for 2.5 h under nitrogen atmosphere. EtOAc and dilute acid were added and the two phases were separated. The organic extract was washed with brine and evaporated. The residue was purified by preparative HPLC, PrepMethod A, (gradient: 40-85%) to yield the title compound (89 mg, 78%); MS (ESI) m/z [M+H]$^+$ 374.3.

Intermediate 84

(2R)-2-((4-Chloro-6-(2-(4-(methoxymethyl)phenyl)propyl)-1,3,5-triazin-2-yl)amino)-4-methylpentan-1-ol

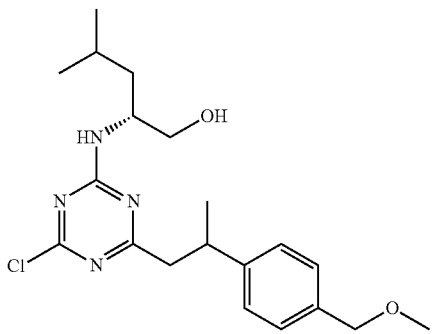 [SMILES: COCc1ccc(C(C)Cc2nc(Cl)nc(N[C@@H](CO)CC(C)C)n2)cc1]

A solution of (R,E)-2-((4-chloro-6-(prop-1-en-1-yl)-1,3,5-triazin-2-yl)amino)-4-methylpentan-1-ol Intermediate 3 (78 mg, 0.29 mmol) in 1,4-dioxane (1.5 mL), a solution of 4 M KOH (aq, 0.18 mL, 0.72 mmol) followed by [Rh(COD)Cl]$_2$ (7.1 mg, 0.01 mmol) were added to (4-(methoxymethyl)phenyl) boronic acid (96 mg, 0.58 mmol). The reaction mixture was stirred at 50° C. under nitrogen atmosphere for 2 h and then EtOAc and water were added. The aqueous phase was acidified and the phases were separated. The organic extract was dried over MgSO$_4$ and filtered through a short pad of silica. The eluate was evaporated to give the crude title compound (assumed quantitative yield); MS (ESI) m/z [M+H]$^+$ 393.4.

Intermediate 85

(2R)-2-((4-Chloro-6-(2-(3,4-dimethylphenyl)propyl)-1,3,5-triazin-2-yl)amino)-4-methylpentan-1-ol

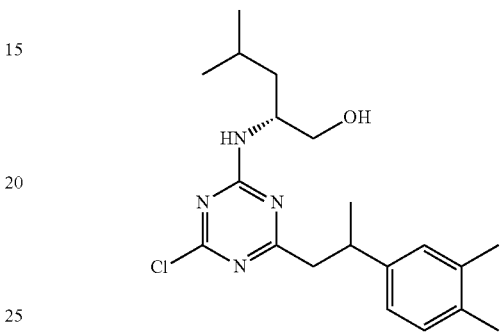

A solution of (R,E)-2-((4-chloro-6-(prop-1-en-1-yl)-1,3,5-triazin-2-yl)amino)-4-methylpentan-1-ol Intermediate 3 (78 mg, 0.29 mmol) in 1,4-dioxane (1.5 mL), a solution of 4 M KOH (aq, 0.18 mL, 0.72 mmol) followed by [Rh(COD)Cl]$_2$ (7.1 mg, 0.01 mmol) were added to (3,4-dimethylphenyl)boronic acid (87 mg, 0.58 mmol). The reaction mixture was stirred at 50° C. under nitrogen atmosphere for 2 h and then EtOAc and water were added. The aqueous phase was acidified and the phases were separated. The organic extract was dried over MgSO$_4$ and filtered through a short pad of silica. The eluate was evaporated to give the crude title compound (assumed quantitative yield); MS (ESI) m/z [M+H]$^+$ 377.4.

Intermediate 86

(2R)-2-((4-Chloro-6-(2-(4-(1,1-difluoroethyl)phenyl)propyl)-1,3,5-triazin-2-yl)amino)-4-methylpentan-1-ol

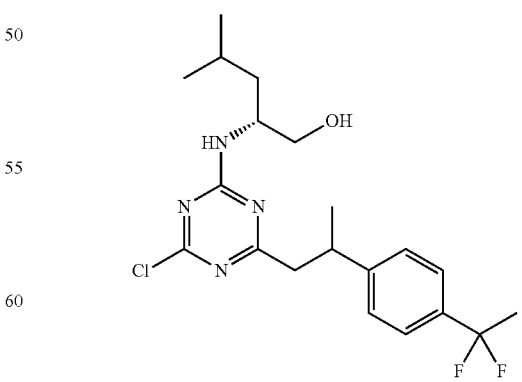

A solution of (R,E)-2-((4-chloro-6-(prop-1-en-1-yl)-1,3,5-triazin-2-yl)amino)-4-methylpentan-1-ol Intermediate 3 (78 mg, 0.29 mmol) in 1,4-dioxane (1.5 mL), a solution of 4 M KOH (aq, 0.18 mL, 0.72 mmol) followed by [Rh(COD)Cl]$_2$ (7.1 mg, 0.01 mmol) were added to (4-(1,1-difluoroethyl)phenyl)boronic acid (108 mg, 0.58 mmol). The reaction mixture was stirred at 50° C. under nitrogen atmosphere for 2 h and then EtOAc and water were added. The aqueous phase was acidified and the phases were separated. The organic extract was dried over MgSO$_4$ and filtered through a short pad of silica. The eluate was evaporated to give the crude title compound (assumed quantitative yield); MS (ESI) m/z [M+H]$^+$ 413.4.

Intermediate 87

(2R)-2-((4-Chloro-6-(2-(3-chlorophenyl)propyl)-1,3,5-triazin-2-yl)amino)-4-methylpentan-1-ol

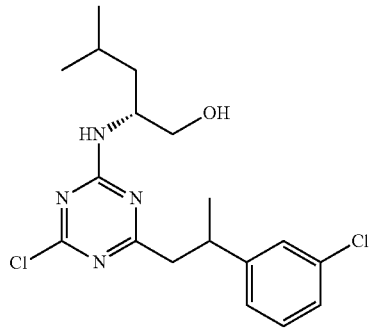 [SMILES: CC(C)C[C@H](CO)Nc1nc(Cl)nc(CC(C)c2cccc(Cl)c2)n1]

A solution of (R,E)-2-((4-chloro-6-(prop-1-en-1-yl)-1,3,5-triazin-2-yl)amino)-4-methylpentan-1-ol Intermediate 3 (78 mg, 0.29 mmol) in 1,4-dioxane (1.5 mL), a solution of 4 M KOH (aq, 0.18 mL, 0.72 mmol) followed by [Rh(COD)Cl]$_2$ (7.1 mg, 0.01 mmol) were added to (3-chlorophenyl)boronic acid (91 mg, 0.58 mmol). The reaction mixture was stirred at 50° C. under nitrogen atmosphere for 2 h and then EtOAc and water were added. The aqueous phase was acidified and the phases were separated. The organic extract was dried over MgSO$_4$ and filtered through a short pad of silica. The eluate was evaporated to give the crude title compound (assumed quantitative yield); MS (ESI) m/z [M+H]$^+$ 383.3.

Intermediate 88

N-(4-(1-(4-Chloro-6-(((R)-1-hydroxy-4-methylpentan-2-yl)amino)-1,3,5-triazin-2-yl)propan-2-yl)phenyl)-N-methylacetamide

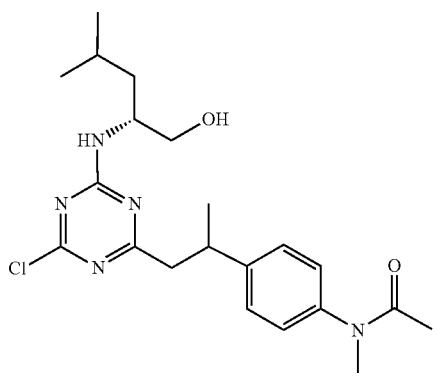 [SMILES: CC(=O)N(C)c1ccc(C(C)Cc2nc(Cl)nc(N[C@@H](CO)CC(C)C)n2)cc1]

A solution of (R,E)-2-((4-chloro-6-(prop-1-en-1-yl)-1,3,5-triazin-2-yl)amino)-4-methylpentan-1-ol Intermediate 3 (81 mg, 0.30 mmol) in 1,4-dioxane (1.5 mL) and a 4 M solution of KOH (aq, 0.15 mL, 0.60 mmol) were added to N-methyl-N-(4-(4,4,5,5-tetramethyl-1,3,2-dioxaborolan-2-yl)phenyl)acetamide (116 mg, 0.42 mmol) followed by the addition of [Rh(COD)Cl]$_2$ (7.4 mg, 0.02 mmol). The reaction mixture was stirred at 50° C. under nitrogen atmosphere for 2 h and then DCM and water were added. The aqueous phase was acidified and the phases were separated. The aqueous phase was extracted with EtOAc and the combined organic extract was filtered through a short pad of silica. The eluate was evaporated and the residue with the crude title compound was used in next step without further purification. Yield assumed quantitative; MS (ESI) m/z [M+H]$^+$ 420.4.

Intermediate 89

(2R)-2-((4-Chloro-6-(2-(4-(trifluoromethyl)phenyl)propyl)-1,3,5-triazin-2-yl)amino)-4-methylpentan-1-ol

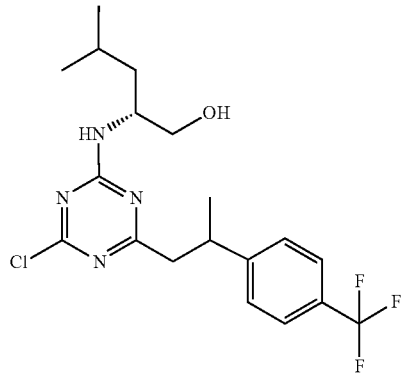 [SMILES: CC(C)C[C@H](CO)Nc1nc(Cl)nc(CC(C)c2ccc(C(F)(F)F)cc2)n1]

A solution of (R,E)-2-((4-chloro-6-(prop-1-en-1-yl)-1,3,5-triazin-2-yl)amino)-4-methylpentan-1-ol Intermediate 3 (81 mg, 0.30 mmol) in 1,4-dioxane (1.5 mL), a solution of 4 M KOH (aq, 0.15 mL, 0.60 mmol) followed by [Rh(COD)Cl]$_2$ (7.4 mg, 0.01 mmol) were added to (4-(trifluoromethyl)phenyl)boronic acid (57 mg, 0.30 mmol) The reaction mixture was stirred at 50° C. under nitrogen atmosphere for 1.5 h and then EtOAc and water were added. The aqueous phase was acidified and the phases were separated. The organic phase was extracted with EtOAc and the combined organic extract was dried over MgSO$_4$, filtered and evaporated. The residue with was purified by straight phase flash chromatography on silica (gradient: 15-75% EtOAc in heptane) to yield the title compound (80 mg, 64%); MS (ESI) m/z [M+H]$^+$ 417.3.

Intermediate 90

2-Methoxy-5-(prop-1-en-2-yl)pyridine

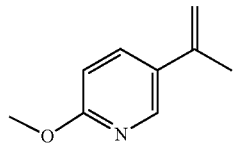

Methyltriphenylphosphonium bromide (23.6 g, 66.2 mmol) was added to a suspension of KOtBu (7.42 g, 66.2 mmol) in THF (50 mL) at −20° C. under nitrogen atmosphere. The reaction mixture was stirred at −20° C. for 1 h. 1-(6-Methoxypyridin-3-yl)ethan-1-one (5.0 g, 33 mmol) was added at −20° C. and stirring was continued at rt for 14 h. The mixture was concentrated, diluted with EtOAc (200 mL) and washed sequentially with sat NH$_4$Cl (2×200 mL), brine (2×200 mL), and water (3×200 mL). The organic layer was dried over Na$_2$SO$_4$, filtered and evaporated. The residue was purified by straight phase flash chromatography on silica (gradient: 10-20% EtOAc in PE) to afford the title compound (3.4 g, 69%) as a dark oil; $^1$H NMR (300 MHz, DMSO-d6) 2.10 (3H, dd), 3.86 (3H, s), 5.00-5.10 (1H, m), 5.30-5.40 (1H, m), 6.80 (1H, dd), 7.87 (1H, dd), 8.29 (1H, dd).

Intermediate 91

N-(4-(((R)-1-Hydroxy-4-methylpentan-2-yl)amino)-6-(2-(6-methoxypyridin-3-yl)propyl)-1,3,5-triazin-2-yl)methanesulfonamide

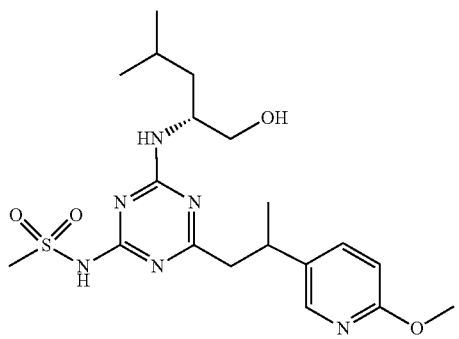

9-BBN (0.5 M, 72.9 mL, 36.5 mmol) in THF (40 mL) was added to 2-methoxy-5-(prop-1-en-2-yl)pyridine Intermediate 90 (3.20 g, 21.4 mmol), and the reaction mixture was stirred at 70° C. for 1 h. Degassed (R)—N-(4-chloro-6-((1-hydroxy-4-methylpentan-2-yl)amino)-1,3,5-triazin-2-yl)methanesulfonamide Intermediate 1 (3.47 g, 10.7 mmol), Pd(dppf)Cl$_2$-DCM (1.31 g, 1.61 mmol) and 3 M K$_3$PO$_4$ (aq, 21.4 mL, 64.4 mmol) were added to the solution. The resulting mixture was purged and stirred at 40° C. for 20 h. The reaction mixture was poured into sat brine (250 mL), acidified with 0.3 M HCl (to pH 1) and extracted with EtOAc (2×200 mL). The pH of the aqueous phase was adjusted to ~7 by the addition of sat NaHCO$_3$ (50 mL) and then extracted with EtOAc (3×200 mL). The combined organic layers were dried over MgSO$_4$, filtered and concentrated (40° C.). The residue was purified by reversed phase flash chromatography on C18-column (gradient: 10-80% water in CH$_3$CN) to afford the title compound (2.80 g, 60%) as a colourless solid; MS (ESI) m/z [M+H]$^+$ 439.20

Intermediate 92

1,3-Difluoro-2-(prop-1-en-2-yl)benzene

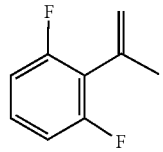

KOtBu (1.72 g, 15.4 mmol) was added to a stirred suspension of methyltriphenylphosphonium bromide (5.49 g, 15.4 mmol) in Et$_2$O (8.6 mL) at rt and the resulting mixture was stirred at rt for 30 min. 1-(2,6-Difluorophenyl)ethanone (1.0 mL, 7.7 mmol) was added and stirring was continued at rt for 30 min. The reaction mixture was filtered and evaporated. The crude product was purified by flash chromatography on silica (20 g) eluting with Et$_2$O to give the title compound (1.3 g, 110%) as an oil; $^1$H NMR (400 MHz, CDCl$_3$) 2.07-2.11 (3H, s), 5.08-5.13 (1H, m), 5.39-5.43 (1H, m), 5.15-5.20 (1H, m), 5.39-5.43 (1H, m), 6.83-6.91 (2H, m), 7.13-7.22 (1H, m).

Intermediate 93

N-(4-(2-(2,6-Difluorophenyl)propyl)-6-(((R)-1-hydroxy-4-methylpentan-2-yl)amino)-1,3,5-triazin-2-yl)methanesulfonamide 9-BBN (0.5 M in THF, 1.69 mL, 0.840 mmol) was added to 1,3-difluoro-2-(prop-1-en-2-yl)benzene Intermediate 92 (65 mg, 0.42 mmol) and the mixture was stirred at 60° C. for 2 h under nitrogen atmosphere. degassed (R)—N-(4-chloro-6-((1-hydroxy-4-methylpentan-2-yl)amino)-1,3,5-triazin-2-yl)methanesulfonamide Intermediate 1 (137 mg, 0.420 mmol), 3 M K$_3$PO$_4$ (aq, 422 μL, 1.26 mmol) and PdCl$_2$(dppf)·DCM (15 mg, 0.02 mmol) were added to the solution. The resulting mixture was stirred at rt for 2 days under nitrogen atmosphere. Water and DCM were added, the water layer was acidified with 1 M KHSO$_4$ and extracted with DCM. The organic portions were concentrated and filtered through SiliaMetS Thiol applied on top of a silica plug eluted with a mixture of DCM and a small amount of MeOH. The organic layer was concentrated and the residue was purified by preparative HPLC, PrepMethod F (gradient: 5-95%) to yield the title compound (15 mg, 8%); MS (ESI) m/z [M+H]$^+$ 444.19

Intermediate 94

N-(4-(2-(4-Fluorophenyl)propyl)-6-(((R)-1-hydroxy-4-methylpentan-2-yl)amino)-1,3,5-triazin-2-yl)methanesulfonamide

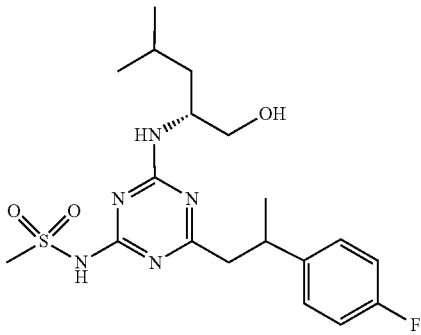 [SMILES: CC(C)C[C@H](CO)Nc1nc(CC(C)c2ccc(F)cc2)nc(NS(C)(=O)=O)n1]

9-BBN (0.5 M in THF, 1.24 mL, 0.620 mmol) was added to an ice-cold solution of 1-fluoro-4-(prop-1-en-2-yl)benzene (42 mg, 0.31 mmol) in THF (0.5 ml) under nitrogen atmosphere. The mixture was stirred at rt for 1.5 h. A degassed mixture of (R)—N-(4-chloro-6-((1-hydroxy-4-methylpentan-2-yl)amino)-1,3,5-triazin-2-yl)methanesulfonamide Intermediate 1 (100 mg, 0.310 mmol), 3 M $K_3PO_4$ (aq, 309 µL, 0.930 mmol) and DMF (250 µl) followed by degassed $PdCl_2$(dppf)DCM (11 mg, 0.02 mmol) were added. The resulting mixture was stirred at rt for 2 days under nitrogen atmosphere. Water and DCM were added, the water layer was acidified with 1 M $KHSO_4$ and extracted with DCM. The organic portions were concentrated and filtered through SiliaMetS Thiol applied on top of a silica plug eluted with a mixture of DCM and a small amount of MeOH. The organic layer was concentrated and the residue was purified by preparative HPLC, PrepMethod F (gradient: 5-95%) to yield the title compound (29 mg, 22%); MS (ESI) m/z $[M+H]^+$ 426.2

Intermediate 95

2-Fluoro-4-methoxy-1-(prop-1-en-2-yl)benzene

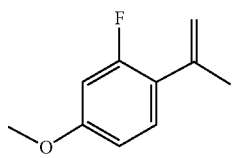

KOtBu (1.34 g, 11.9 mmol) was added to a stirred suspension of methyltriphenylphosphonium bromide (4.25 g, 11.9 mmol) in $Et_2O$ (15 ml) at rt and the resulting mixture was stirred at rt for 30 min. 1-(2-fluoro-4-methoxyphenyl)ethanone (1.0 g, 5.95 mmol) was added dropwise and stirring was continued at rt overnight. The reaction mixture was diluted with $Et_2O$, filtered and evaporated. The residue was purified by straight phase flash chromatography on silica (gradient: 5-30% EtOAc in heptane) to afford the title compound (0.78 g, 79%) as an oil; $^1$H NMR (500 MHz, $CDCl_3$) 2.12 (3H, s), 3.80 (3H, s), 5.14-5.18 (1H, m), 5.18-5.21 (1H, m), 6.57-6.68 (2H, m), 7.22 (1H, t).

Intermediate 96

N-(4-(2-(2-Fluoro-4-methoxyphenyl)propyl)-6-(((R)-1-hydroxy-4-methylpentan-2-yl)amino)-1,3,5-triazin-2-yl)methanesulfonamide

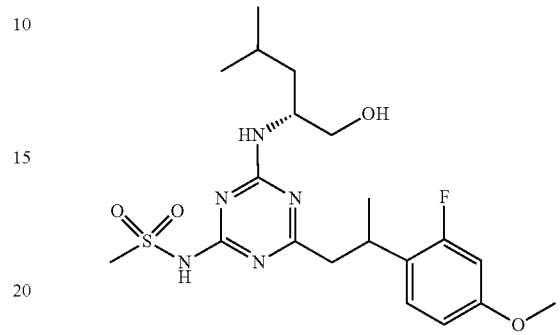

9-BBN Dimer (139 mg, 0.570 mmol) was added to a solution of 2-fluoro-4-methoxy-1-(prop-1-en-2-yl)benzene Intermediate 95 (92 mg, 0.56 mmol) in THF (1.5 mL) under nitrogen atmosphere. The mixture was stirred at rt for 1 h. Degassed $K_3PO_4$ (371 µL, 1.11 mmol), (R)—N-(4-chloro-6-((1-hydroxy-4-methylpentan-2-yl)amino)-1,3,5-triazin-2-yl)methanesulfonamide Intermediate 1 (120 mg, 0.370 mmol) and Pd(dppf)$Cl_2$·DCM (14 mg, 0.02 mmol) were added to the solution. The reaction mixture was degassed and stirred under nitrogen atmosphere at 35° C. for 3 days. The mixture was filtered and concentrated, and the residue was purified by preparative HPLC, PrepMethod F (gradient: 5-95%) to yield the title compound (23 mg, 14%); MS (ESI) m/z $[M+H]^+$ 456.21

Intermediate 97

4-Chloro-2-fluoro-1-(prop-1-en-2-yl)benzene

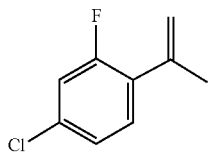

KOtBu (1.33 g, 11.8 mmol) was added to a suspension of methyltriphenylphosphonium bromide (4.14 g, 11.6 mmol) in $Et_2O$ (10 mL) at −10° C. A solution of 1-(4-chloro-2-fluorophenyl)ethanone (1.01 g, 5.83 mmol) in $Et_2O$ (3 mL) was added dropwise, the mixture was allowed to reach rt and stirring was continued overnight. The reaction mixture was diluted with $Et_2O$, filtered and washed sequentially with water, $KHSO_4$ (aq), water, and brine. The organic layer was dried over $MgSO_4$, filtered and evaporated (24° C.). The residue was purified by straight phase flash chromatography on silica (gradient: 0-5% $Et_2O$ in pentane) to give the title compound (0.89 g, 89%); $^1$H NMR (400 MHz, THF-d8) 2.07-2.14 (3H, m), 5.21-5.27 (2H, m), 7.11-7.23 (2H, m), 7.28-7.38 (1H, m).

Intermediate 98

N-(4-(2-(4-Chloro-2-fluorophenyl)propyl)-6-(((R)-1-hydroxy-4-methylpentan-2-yl)amino)-1,3,5-triazin-2-yl)methanesulfonamide

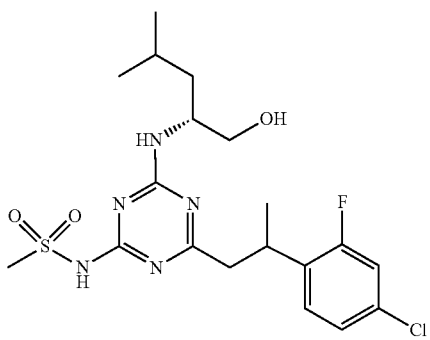 [SMILES: CC(C)C[C@H](CO)Nc1nc(CC(C)c2ccc(Cl)cc2F)nc(NS(C)(=O)=O)n1]

9-BBN (0.5 M in THF, 2.78 mL, 1.39 mmol) was added to 4-chloro-2-fluoro-1-(prop-1-en-2-yl)benzene Intermediate 97 (190 mg, 0.930 mmol) under nitrogen atmosphere. The reaction mixture was stirred at rt for 2.5 h and at 40° C. for 1 h. Degassed $K_3PO_4$ (0.926 mL, 2.78 mmol), (R)—N-(4-chloro-6-((1-hydroxy-4-methylpentan-2-yl)amino)-1,3,5-triazin-2-yl)methanesulfonamide Intermediate 1 (150 mg, 0.460 mmol) and Pd(dppf)Cl$_2$-DCM (57 mg, 0.07 mmol) were added to the solution. The reaction mixture was stirred at 40° C. for 16 h under nitrogen atmosphere. EtOAc and 0.3 M HCl were added. The aqueous phase was acidified with 4 M HCl (to pH 4) and extracted once with EtOAc. The organic phases were combined and treated with SiliaMetS Thiol, filtered and evaporated (40° C.). The residue was purified by preparative HPLC, PrepMethod A (gradient: 30-70%) to give the title compound (128 mg, 60%); MS (ESI) m/z [M+H]$^+$ 460.3

Intermediate 99

2-Fluoro-6-methoxy-3-(prop-1-en-2-yl)pyridine

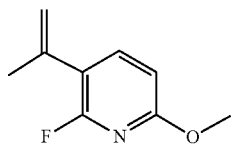

n-BuLi (1.6 M in hexane, 44.3 mL, 70.9 mmol) was added to methyltriphenylphosphonium bromide (25.3 g, 70.9 mmol) in THF (150 mL). The reaction mixture was stirred at rt for 10 min and then a solution of 1-(2-fluoro-6-methoxypyridin-3-yl)ethan-1-one (10.0 g, 59.1 mmol) in THF (50 mL) was added and the reaction mixture was stirred at 40° C. for 1 h. Water and Et$_2$O were added and the two phases were separated. The organic extract was washed with water, dried over MgSO$_4$, filtered and evaporated. The residue was dissolved in boiling heptane. The heptane solution was allowed to reach rt and then filtered. The filtrate was evaporated and the residue was purified by straight phase flash chromatography on silica (heptane/EtOAc, 15/1) to yield the title compound as a colourless oil (8.5 g, 86%);

$^1$H NMR (500 MHz, CDCl$_3$) 2.10-2.13 (3H, m), 3.92 (3H, s), 5.19-5.21 (1H, m), 5.23-5.26 (1H, m), 6.59 (1H, dd), 7.63 (1H, dd).

Intermediate 100

N-(4-(2-(2-Fluoro-6-methoxypyridin-3-yl)propyl)-6-(((R)-1-hydroxy-4-methylpentan-2-yl)amino)-1,3,5-triazin-2-yl)methanesulfonamide

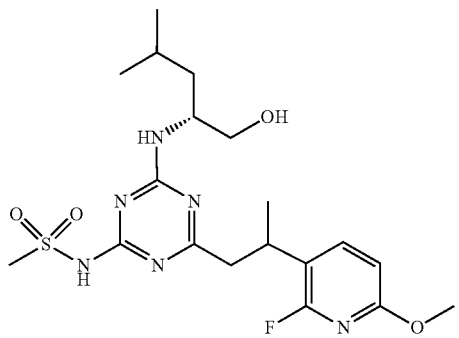

9-BBN (0.5 M in THF, 56.5 ml, 28.3 mmol) in THF (30 mL) was added to 2-fluoro-6-methoxy-3-(prop-1-en-2-yl)pyridine Intermediate 99 (2.70 g, 16.2 mmol) and the mixture was stirred at rt overnight. Degassed 3 M K$_3$PO$_4$ (aq, 16.2 mL, 48.4 mmol), (R)—N-(4-chloro-6-((1-hydroxy-4-methylpentan-2-yl)amino)-1,3,5-triazin-2-yl)methanesulfonamide Intermediate 1 (2.61 g, 8.07 mmol) and Pd(dppf)Cl$_2$·DCM (0.989 g, 1.21 mmol) were added to the solution. The reaction mixture was purged and stirred at 38° C. for 20 h. The reaction mixture was poured into sat brine (100 mL), acidified with 0.3 M HCl (to pH 1) and extracted with EtOAc (3×150 mL). The pH of the aqueous phase was adjusted to ~7 by the addition of sat NaHCO$_3$ and then extracted with EtOAc (2×50 mL). The combined organic layers were treated with SiliaMetS Thiol, dried over MgSO$_4$, filtered and concentrated. The residue was purified by reversed phase flash chromatography on C18-column [gradient: 0-50% MeCN in water (0.2% FA)] to afford the title compound (1.70 g, 46%) as a colourless solid; MS (ESI) m/z [M+H]$^+$ 457.15

Intermediate 101

1,2,3-Trifluoro-4-(prop-1-en-2-yl)benzene

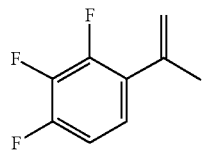

K$_3$PO$_4$ (1.93 g, 17.2 mmol) was added to a suspension of methyltriphenylphosphonium bromide (6.15 g, 17.2 mmol) in Et$_2$O (8 mL) at −10° C. (ice-water bath). A solution of 1-(2,3,4-trifluorophenyl)ethanone (1.50 g, 8.61 mmol) in Et$_2$O (8 mL) was added dropwise, the mixture was allowed to reach rt and stirred overnight. The reaction mixture was diluted with Et$_2$O, filtered and washed sequentially with water, 0.4 M HCl, water and brine. The organic layer was dried over MgSO$_4$, filtered and carefully concentrated (24° C.). Pentane was added and the precipitate was filtered off. The filtrate was evaporated and the residue was purified by straight phase flash chromatography on silica (10% EtOAc in pentane) to yield the title compound (1.16 g, 78%); $^1$H NMR (400 MHz, CDCl$_3$) 2.09-2.15 (3H, m), 5.20-5.30 (2H, m), 6.85-7.05 (2H, m).

Intermediate 102

N-(4-(((R)-1-Hydroxy-4-methylpentan-2-yl)amino)-6-(2-(2,3,4-trifluorophenyl)propyl)-1,3,5-triazin-2-yl)methanesulfonamide

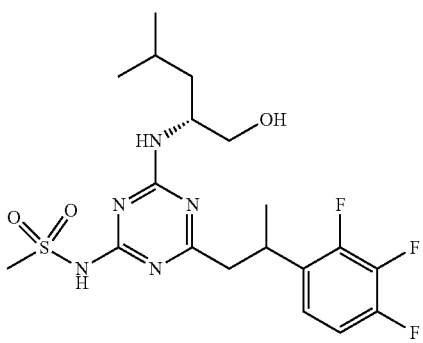 [SMILES: CC(C)C[C@H](CO)Nc1nc(CC(C)c2ccc(F)c(F)c2F)nc(NS(C)(=O)=O)n1]

9-BBN (0.5 M in THF, 5.31 mL, 2.66 mmol) was added to 1,2,3-trifluoro-4-(prop-1-en-2-yl)benzene Intermediate 101 (229 mg, 1.33 mmol) under nitrogen atmosphere. The reaction mixture was stirred at rt for 1 h and then added to a mixture of (R)—N-(4-chloro-6-((1-hydroxy-4-methylpentan-2-yl)amino)-1,3,5-triazin-2-yl)methanesulfonamide Intermediate 1 (430 mg, 1.33 mmol), Pd(dppf)Cl$_2$·DCM (108 mg, 0.130 mmol) and K$_3$PO$_4$ (1.13 g, 5.31 mmol) under nitrogen atmosphere. The reaction mixture was heated at 50° C. for 2.5 h. Water and EtOAc were added and the two phases were separated. The organic layer was extracted with water and brine. The combined aqueous layers were acidified with 1 M HCl (to pH 5) and extracted with EtOAc (×3). The organic extracts were dried over MgSO$_4$, filtered and evaporated. The residue was purified by straight phase flash chromatography on silica using EtOAc as eluent to yield the title compound (75 mg, 12%); MS (ESI) m/z [M+H]$^+$ 462.33

Intermediate 103

1-(But-1-en-2-yl)-2-fluorobenzene

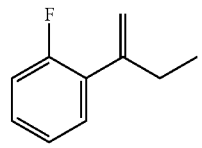

KOtBu (0.796 g, 7.10 mmol) was added to a stirred suspension of methyltriphenylphosphonium bromide (2.54 g, 7.10 mmol) in Et$_2$O (15 ml) and the mixture was stirred at rt for 30 min. 1-(2-Fluorophenyl)propan-1-one (0.503 mL, 3.55 mmol) was added dropwise and stirring was continued at rt overnight. The reaction mixture was filtered and evaporated. The residue was purified by straight phase flash chromatography on silica (gradient: 5-20% EtOAc in heptane) to yield the title compound (0.387 g, 73%); $^1$H NMR (400 MHz, CDCl$_3$) 1.05 (3H, td), 2.44-2.53 (2H, m), 5.12-5.15 (1H, m), 5.19-5.24 (1H, m), 6.98-7.13 (2H, m), 7.19-7.28 (m, partial overlap with CDCl$_3$).

Intermediate 104

2-Fluoro-4-(prop-1-en-2-yl)pyridine

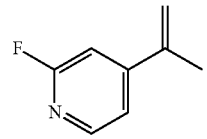

4-Bromo-2-fluoropyridine (5.00 g, 28.4 mmol) was added to 4,4,5,5-tetramethyl-2-(prop-1-en-2-yl)-1,3,2-dioxaborolane (5.25 g, 31.2 mmol), Cs$_2$CO$_3$ (18.5 g, 56.8 mmol) and Pd(dppf)Cl$_2$·DCM (2.32 g, 2.84 mmol) in 1,4-dioxane (50 mL) at 10° C. over a period of 1 min under nitrogen atmosphere. The resulting solution was stirred at 100° C. for 14 h. The reaction mixture was extracted with EtOAc (3×150 mL), the organic layer was dried over Na$_2$SO$_4$, filtered and evaporated. The residue was purified by preparative TLC (PE/EtOAc, 5/1) to afford the title compound (3.70 g, 95%) as an oil which solidified on standing; $^1$H NMR (400 MHz, CDCl$_3$) 1.95-2.12 (m, 3H), 5.17 (d, 1H), 5.46 (d, 1H), 6.75-6.85 (m, 1H), 7.05-7.20 (m, 1H), 8.00 (d, 1H).

Intermediate 105

N-(4-(2-(2-Fluoropyridin-4-yl)propyl)-6-(((R)-1-hydroxy-4-methylpentan-2-yl)amino)-1,3,5-triazin-2-yl)methanesulfonamide

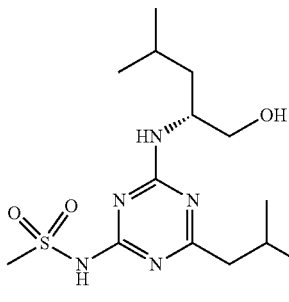

9-BBN (0.5 M in THF, 77.0 mL, 38.3 mmol) in THF (30 mL) was added to 2-fluoro-4-(prop-1-en-2-yl)pyridine Intermediate 104 (3.0 g, 21.9 mmol) and the mixture was stirred at 70° C. overnight. Degassed K$_3$PO$_4$ (21.9 mL, 65.6 mmol), (R)—N-(4-chloro-6-((1-hydroxy-4-methylpentan-2-yl)amino)-1,3,5-triazin-2-yl)methanesulfonamide Intermediate 1 (3.54 g, 10.9 mmol) and Pd(dppf)Cl$_2$-DCM (1.34 g, 1.64 mmol) were added to the solution. The reaction mixture was purged and stirred at 38° C. for 20 h. The reaction mixture was poured into sat brine (250 mL) and extracted with EtOAc (3×150 mL). The aqueous phase was acidified (to pH 5) with 0.3 M HCl and extracted with EtOAc (150 mL). The combined organic layers were treated with SiliaMetS Thiol, dried over MgSO$_4$, filtered and concentrated (40° C.). The residue was purified by reversed phase flash chromatography on C18-column (gradient: 10-70% MeCN in water) to afford the title compound (2.19 g, 47%) as a colourless solid; MS (ESI) m/z [M+H]$^+$ 427.15

Intermediate 106

2-(3-Bromobenzyl)isoxazolidin-3-one

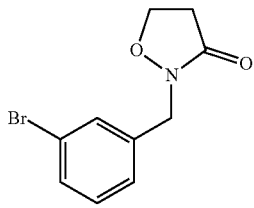 [SMILES: O=C1CCON1Cc1cccc(Br)c1]

K$_2$CO$_3$ (105 g, 0.812 mol) followed by 3-bromobenzyl bromide (105 g, 0.377 mol) were added to a solution of isoxazolidin-3-one (35 g, 0.40 mol) in MeCN (750 mL). The mixture was stirred at rt for 16 h and then filtered and concentrated. The residue was purified by flash chromatography on silica (PE:EtOAc, 1:1) to afford the title compound (74 g, 70%) as a pale yellow solid; MS (ESI) m/z [M+H]$^+$ 255.8.

Intermediate 107

2-(3-(4,4,5,5-Tetramethyl-1,3,2-dioxaborolan-2-yl)benzyl)isoxazolidin-3-one

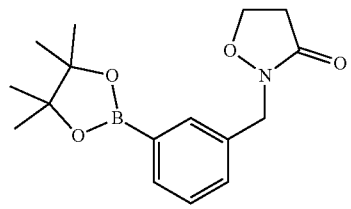 [SMILES: CC1(C)OB(c2cccc(CN3OCCC3=O)c2)OC1(C)C]

Pd(dppf)Cl$_2$ (10 g, 0.013 mol) was added to a solution of 2-(3-bromobenzyl)isoxazolidin-3-one Intermediate 106 (74 g, 0.29 mol), B$_2$pin$_2$ (92.5 g, 0.36 mol) and KOAc (113 g, 1.15 mol) in 1,4-dioxane (750 mL) under an atmosphere of nitrogen and the reaction mixture was stirred at 60° C. for 16 h. The reaction mixture was filtered and concentrated in vacuo. The residue was purified by flash chromatography on silica (PE:EtOAc, 4:1) to afford the title compound (30 g, 34%) as a colourless solid; MS (ESI) m/z [M+H]$^+$ 304.1

Intermediate 108

2-((5,6,7,8-Tetrahydronaphthalen-1-yl)oxy)tetrahydro-2H-pyran

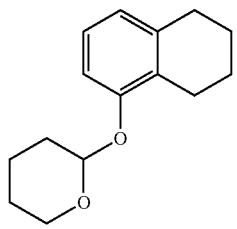 [SMILES: c1cc2c(c(OC3CCCCO3)c1)CCCC2]

Pyridinium pTsOH (0.397 g, 1.58 mmol) was added to a solution of 3,4-dihydro-2H-pyran (2.8 mL, 30.7 mmol) and 5,6,7,8-tetrahydronaphthalen-1-ol (2.3 g, 15.5 mmol) in DCM (60 mL). The resulting mixture was stirred at rt for 6 h and then sat NaHCO$_3$(aq, 50 mL) was added. The layers were separated, and the organic portion was washed with sat NaHCO$_3$(aq, 50 mL) and brine, dried over MgSO$_4$, filtered and evaporated. The residue was purified by flash chromatography on silica (0-20% EtOAc in heptane) to give the title compound (3.40 g, 94%) as a colourless oil; $^1$H NMR (400 MHz, CDCl$_3$) δ 1.56-1.84 (7H, m), 1.84-1.91 (2H, m), 1.97-2.11 (1H, m), 2.64-2.83 (4H, m), 3.60 (1H, dtd), 3.91 (1H, ddd), 5.42 (1H, t), 6.73 (1H, d), 6.89 (1H, d), 7.03 (1H, t).

Intermediate 109

4,4,5,5-Tetramethyl-2-(4-((tetrahydro-2H-pyran-2-yl)oxy)-5,6,7,8-tetrahydronaphthalen-2-yl)-1,3,2-dioxaborolane

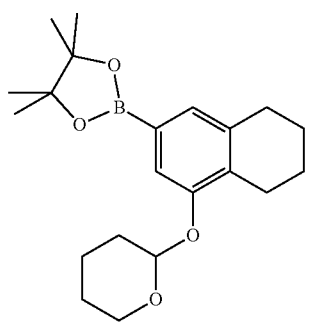 [SMILES: CC1(C)OB(c2cc3c(c(OC4CCCCO4)c2)CCCC3)OC1(C)C]

MTBE (20 mL) was added to a purged mixture of 4-tert-butyl-2-(4-tert-butyl-2-pyridyl)pyridine (0.017 g, 0.06 mmol) and di-mu-methoxobis(1,5-cyclooctadiene)diiridium(I) (0.021 g, 0.03 mmol). B$_2$pin$_2$ (1.72 g, 6.77 mmol) followed by a solution of 2-((5,6,7,8-tetrahydronaphthalen-1-yl)oxy)tetrahydro-2H-pyran Intermediate 108 (1.5 g, 6.46 mmol) in MTBE (5 mL) were added under nitrogen atmosphere. The reaction mixture was heated in a microwave reactor at 80° C. for 4 h. After cooling and standing overnight the reaction mixture was concentrated, and the residue was purified twice by flash chromatography on silica (0-25% EtOAc in heptane) to afford the title compound (1.1 g, 45%) as a colourless crystalline solid; $^1$H NMR (400 MHz, CDCl$_3$) δ 1.32 (12H, s), 1.59-1.83 (7H, m), 1.86 (2H, dt), 1.95-2.1 (1H, m), 2.74 (4H, dt), 3.62 (1H, dtd), 3.89 (1H, ddd), 5.57 (1H, t), 7.20 (1H, s), 7.26 (1H, s).

Intermediate 110

3-(4,4,5,5-Tetramethyl-1,3,2-dioxaborolan-2-yl)-5,6,7,8-tetrahydronaphthalen-1-ol

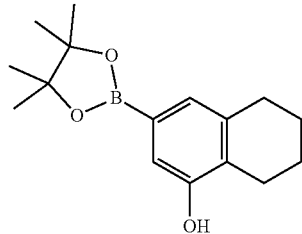 [SMILES: CC1(C)OB(c2cc(O)c3c(c2)CCCC3)OC1(C)C]

A solution of CuBr$_2$ (4.30 g, 19.3 mmol) in water (40 mL) was added to a suspension of 4,4,5,5-tetramethyl-2-(4-((tetrahydro-2H-pyran-2-yl)oxy)-5,6,7,8-tetrahydronaphthalen-2-yl)-1,3,2-dioxaborolane Intermediate 109 (2.3 g, 6.42 mmol) in MeOH (40 mL). The mixture was heated at 80° C. for 4 h and then stirred at rt for 16 h. The reaction mixture was treated with Et$_2$O (75 mL) and water (20 mL). The layers were separated and the aqueous phase was extracted with Et$_2$O (2×75 mL). The combined organic phase was washed with brine, dried over MgSO$_4$, filtered and evaporated. The residue was purified by flash chromatography on silica (0-50% EtOAc in heptane) to give the title compound (0.539 g, 30.6%) as a colourless solid; MS (ESI) m/z [M–H]$^-$ 273.

Intermediate 111

(6-(2-Hydroxyethyl)pyridin-3-yl)boronic acid

A suspension of 2-(5-bromopyridin-2-yl)ethan-1-ol (50 g, 0.25 mol), Pd(dppf)Cl$_2$ (18.1 g, 25 mmol), KOAc (48.6 g, 0.49 mol) and B$_2$pin$_2$ (81.7 g, 0.32 mol) in 1,4-dioxane (1000 mL) was stirred at 80° C. for 16 h. The mixture was filtered and concentrated. 2 M HCl (300 mL) was added and the solution was washed with EtOAc (3×150 mL). The aqueous layer was concentrated to afford the HCl salt of the title compound (25 g, 50%) as a pale yellow solid; MS (ESI) m/z [M+H]$^+$ 168.1.

Intermediate 112

Diphenyl iminodicarbonate

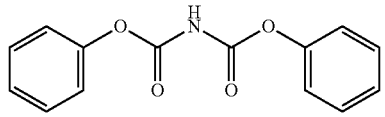 [SMILES: O=C(NC(=O)Oc1ccccc1)Oc1ccccc1]

Step a) Phenyl carbonisocyanatidate

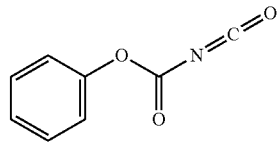 [SMILES: O=C=NC(=O)Oc1ccccc1]

Oxalyl dichloride (20.8 mL, 246 mmol) was added under nitrogen atmosphere to a stirred suspension of phenyl carbamate (30.7 g, 224 mmol) in DCM (165 mL). The mixture was heated under nitrogen atmosphere to gentle reflux for 18 h to obtain a solution. After evaporation, the residue was treated with toluene (150 mL). The slurry was stirred for 20 min, and the insoluble material was removed by filtration. The toluene-filtrate containing the subtitle compound (224 mmol) was used immediately.

Step b) Diphenyl iminodicarbonate

Phenol (23.2 g, 246 mmol) was added in portions within 10 min to the ice cold toluene-filtrate Intermediate 112 step a) (224 mmol). The mixture was stirred with the cooling bath for 30 min and thereafter at rt for 20 h. The mixture was concentrated, the residue was dissolved in DCM and concentrated, after repeated once more the residue solidified. Toluene (200 mL) was added to the solid and the mixture was stirred at rt for 20 min. Heptane (50 mL) was added to the mixture and stirring was continued overnight in order to get a slurry. The crude product was filtered off and the solid was washed with heptane until the filtrate became clear. The mother liquor and washings were combined and concentrated. Toluene (50 mL) and heptane (20 mL) were added to the residue. The mixture was stirred overnight in order to get a slurry. The residue was filtered off and the solid was washed with heptane until the filtrate became clear. Both crops were combined to yield the title compound (38.8 g, 93%). MS (ESI) m/z [M+H]$^+$ 257.9.

Intermediate 113

(E)-3-(2,3-Difluorophenyl)but-2-enenitrile

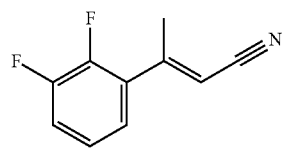

Diethyl cyanomethylphosphonate (4.45 mL, 27.5 mmol) was added at 0° C. to a solution of NaOtBu (2.64 g, 27.5 mmol) in abs EtOH (33 mL). After stirring for 15 min, 1-(2,3-difluorophenyl)ethanone (3.90 g, 25.0 mmol) was added and the mixture was stirred at rt for 2 h. 10% Citric acid (33 mL) was added and the mixture was extracted with PE×3 (bp. 40-60) (×3, 100, 50 and 50 mL). The combined colourless extracts were washed with brine, dried over Na$_2$SO$_4$ and concentrated to give the title compound (3.94 g, 88%). According to $^1$H NMR a mixture of E- and Z-isomer (~4:1) was obtained; $^1$H NMR (400 MHz, CDCl$_3$) 2.28-2.48 (3H, m), 5.54-5.66 (1H, m), 7.03-7.25 (3H, m).

Intermediate 114

3-(2,3-Difluorophenyl)butanenitril

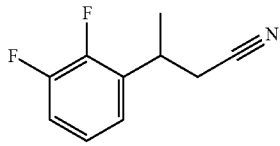

Pd/C 10% (1.20 g, 1.13 mmol) was added under argon atmosphere to a stirred solution of crude (E)-3-(2,3-difluorophenyl)but-2-enenitrile Intermediate 113 (9.92 g, 55.4 mmol) (E/Z-mixture) in EtOAc (240 mL). The mixture was hydrogenated (atmospheric pressure) at rt for 14 h. The catalyst was removed by filtration through silica and celite. The filtrate was concentrated to give the title compound (9.62, 96%) as a colourless oil which was used without further purification; $^1$H NMR (400 MHz, CDCl$_3$) 1.48 (3H, dd), 2.58-2.75 (2H, m), 3.45-3.57 (1H, m), 6.94-7.15 (3H, m).

Intermediate 115

3-(2,3-Difluorophenyl)butanimidamide

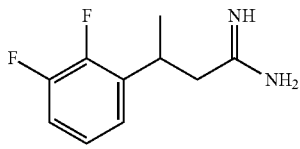

AlMe$_3$ (2 M in toluene, 4.8 mL, 9.6 mmol) was added dropwise under argon atmosphere to an ice cold suspension of NH$_4$Cl (0.551 g, 10.3 mmol) in toluene (6 mL). The resulting mixture was warmed to rt and stirred for 1 h. 3-(2,3-Difluorophenyl)butanenitrile Intermediate 114 (1.09 g, 6.01 mmol) was added and the mixture was stirred at 80° C. overnight. After cooling to rt the mixture was slowly poured into an ice cold slurry of silica (4 g) in CHCl$_3$ (15 mL) and stirred for 15 min. The slurry was filtered and the residue was washed with MeOH (2×40 mL). The combined filtrates were concentrated. The residue was stirred for 5 min with HCl (1.25 M in MeOH, 4 mL) and then concentrated. The colourless residue was stirred with IPA/acetone (4/1, 16 mL) for 45 min, the insolubles were removed by filtration and the filtrate was concentrated. The crude product was dissolved in IPA (5 mL), HCl (1.25 M in MeOH, 0.5 mL) was added under stirring followed by dropwise addition (~10 min) of Et$_2$O (~20 mL). The mixture was stirred at rt for 30 min and then cooled to 5° C. for 1 h. The colourless precipitate was collected by filtration, washed with Et$_2$O and dried in vacuo to yield the HCl salt of the title compound (0.79 g, 56%); $^1$H NMR (400 MHz, D$_2$O) 1.41 (3H, d), 2.68-2.9 (2H, m), 3.53-3.66 (1H, m), 7.12-7.26 (3H, m).

Intermediate 116

6-(2-(2,3-Difluorophenyl)propyl)-1,3,5-triazine-2,4(1H,3H)-dione

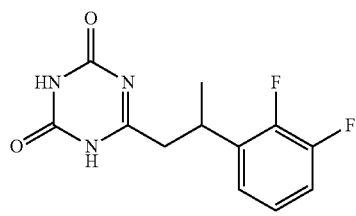 [SMILES: CC(Cc1nc(=O)[nH]c(=O)[nH]1)c1cccc(F)c1F]

A suspension of K$_2$CO$_3$ (462 mg, 3.35 mmol) and 3-(2,3-difluorophenyl)butanimidamide Intermediate 115 (785 mg, 3.35 mmol) in MeCN (15 mL) was stirred under argon atmosphere for 5 min. Diphenyl iminodicarbonate Intermediate 112 (862 mg, 3.35 mmol) was added and stirring was continued at rt for 1 h. Another equivalent of K$_2$CO$_3$ (462 mg, 3.35 mmol) was added and stirring was continued at rt for 1 h and at 60° C. for 2 h. After cooling to rt the resulting thick suspension was dissolved in 1 M HCl (15 mL) and EtOAc (50 mL). The layers were separated, the aqueous phase was extracted with EtOAc (2×25 mL) and the combined organic layers were washed with brine and dried over Na$_2$SO$_4$. The solvent was evaporated and the remaining solid was dried in vacuo. The material, containing phenol (~20 mol %) as impurity, was stirred for 10 min with PE/Et$_2$O (2/1, 30 mL), filtered and dried in vacuo to yield the title compound (791 mg, 88%); MS (ESI) m/z [M+H]$^+$ 268.4.

Intermediate 117

(2R)-2-((4-Chloro-6-(2-(2,3-difluorophenyl)propyl)-1,3,5-triazin-2-yl)amino)-4-methylpentan-1-ol

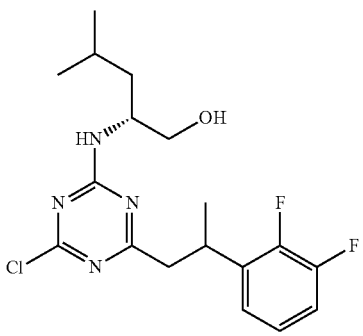 [SMILES: CC(C)C[C@H](CO)Nc1nc(Cl)nc(CC(C)c2cccc(F)c2F)n1]

Step a) 2,4-Dichloro-6-(2-(2,3-difluorophenyl)propyl)-1,3,5-triazine

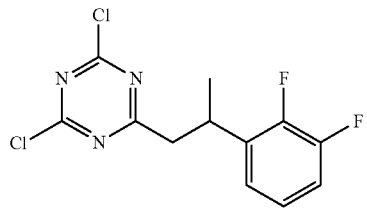 [SMILES: CC(Cc1nc(Cl)nc(Cl)n1)c1cccc(F)c1F]

A mixture of 6-(2-(2,3-difluorophenyl)propyl)-1,3,5-triazine-2,4(1H,3H)-dione Intermediate 116 (0.27 g, 1.0 mmol), POCl₃ (0.28 ml, 3.0 mmol) and N,N-diethylaniline (0.16 ml, 1.0 mmol) was heated at 70° C. for 1.5 h. After cooling to rt the mixture was diluted with CHC13 (10 mL) and toluene (10 mL). The mixture was concentrated to give the subtitle compound as an oil used in step b) (yield assumed quantitative).

Step b) (2R)-2-((4-Chloro-6-(2-(2,3-difluorophenyl)propyl)-1,3,5-triazin-2-yl)amino)-4-methylpentan-1-ol K$_2$CO$_3$ (270 mg, 1.95 mmol) was added in 3 portions over 2 h to a stirred solution of 2,4-dichloro-6-(2-(2,3-difluorophenyl)propyl)-1,3,5-triazine Intermediate 117 step a) and (R)-2-amino-4-methylpentan-1-ol (150 μl, 1.17 mmol) in dry THF (6 mL). Stirring was continued for another 1 h, additional (R)-2-amino-4-methylpentan-1-ol (100 μl, 0.780 mmol) was added and the mixture was stirred overnight. The mixture was diluted with Et$_2$O (40 mL) and the insolubles were removed by filtration. The filtrate was concentrated and the residue was purified by preparative HPLC, PrepMethod A, (gradient: 40-80%) to yield the title compound (80 mg, 21%); MS (ESI) m/z [M+H]$^+$ 385.5

Intermediate 118

N-(4-(2-(2,3-Difluorophenyl)propyl)-6-(((R)-1-hydroxy-4-methylpentan-2-yl)amino)-1,3,5-triazin-2-yl)methanesulfonamide

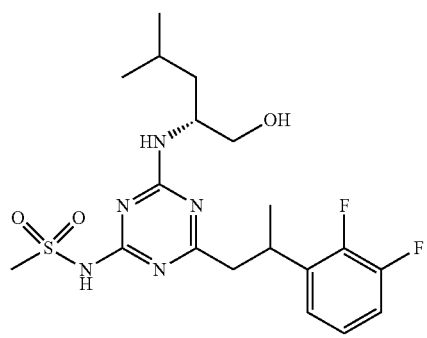 [SMILES: CC(C)C[C@H](CO)Nc1nc(CC(C)c2cccc(F)c2F)nc(NS(C)(=O)=O)n1]

Cs$_2$CO$_3$ (132 mg, 0.410 mmol) was added under argon atmosphere to a suspension of methanesulfonamide (39 mg, 0.41 mmol), Pd$_2$(dba)$_3$ (21 mg, 0.020 mmol), X-Phos (21 mg, 0.040 mmol) and (2R)-2-((4-chloro-6-(2-(2,3-difluorophenyl)propyl)-1,3,5-triazin-2-yl)amino)-4-methylpentan-1-ol Intermediate 117 (80 mg, 0.21 mmol) in THF (3.1 mL) and the reaction mixture was stirred at 64° C. for 6.5 h. After cooling to rt the mixture was diluted with THF (7 mL) and filtered through celite. The filtrate was acidified with HOAc (50 μL) and concentrated.

The remaining oil was purified by preparative HPLC, PrepMethod F, (gradient: 5-95%), to give the title compound (37 mg, 40%); MS (ESI) m/z [M+H]$^+$ 444.19.

Intermediate 119

(E)-3-(2-Fluorophenyl)but-2-enenitrile

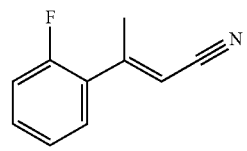

The title compound was prepared from 1-(2-fluorophenyl)ethanone (18.2 mL, 150 mmol), as described for Intermediate 125, to give the title compound (24.0 g, 99%). According to $^1$H NMR a mixture of E- and Z-isomer (~4:1) was obtained; $^1$H NMR (400 MHz, CDCl$_3$) 2.27-2.50 (3H, m), 5.49-5.65 (1H, m), 7.07-7.24 (2H, m), 7.28-7.43 (2H, m).

Intermediate 120

3-(2-Fluorophenyl)butanenitrile

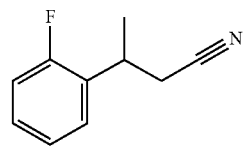

Pd/C 10% (1.50 g, 1.41 mmol) was added under argon to a solution of crude (E)-3-(2-fluorophenyl)but-2-enenitrile Intermediate 119 (24.0 g, 149 mmol) (E/Z-mixture) in EtOAc (300 mL). The mixture was hydrogenated at rt and at 1.3 bar for 17 h and then at 1.6 bar for 5 h. The catalyst was removed by filtration through celite, and the solvent was evaporated (30° C.) to give the title compound (24.0 g, 89%) as a colourless oil; $^1$H NMR (400 MHz, CDCl$_3$) 1.47 (3H, d), 2.54-2.75 (2H, m), 3.40-3.56 (1H, m), 6.7-7.41 (4H, m, overlap with CDCl$_3$).

Intermediate 121

3-(2-Fluorophenyl)butanimidamide

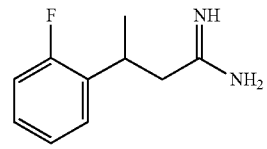

Step a) Ethyl 3-(2-fluorophenyl)butanimidate

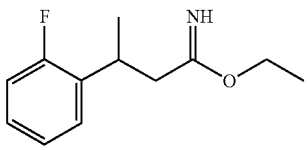

Acetyl chloride (82.3 mL, 1160 mmol) was added dropwise to an ice cooled solution of crude 3-(2-fluorophenyl)butanenitrile Intermediate 120 (23.9 g, 146 mmol) in abs EtOH (106 mL). The solution was kept at ~4° C. for 1 h and thereafter allowed to reach rt and left standing at rt for 22 h. The clear solution was concentrated leaving the HCl salt of the subtitle compound as a colourless solid (34.6 g). The crude compound was stored in the freezer.

Step b) 3-(2-Fluorophenyl)butanimidamide

Cold $NH_3$ (7 M in MeOH, 170 ml, 1190 mmol) was added to ethyl 3-(2-fluorophenyl)butanimidate Intermediate 121 Step a) (34.6 g, 140.8 mmol). After stirring for 15 min a clear solution was formed. After standing at rt for 22 h the solvent was evaporated and the residue was dried in vacuo to yield the HCl salt of the title compound (30.2 g, 99%) as a colourless solid; $^1$H NMR (400 MHz, DMSO-$d_6$) 1.24 (3H, d), 2.65-2.83 (2H, m), 3.51-3.64 (1H, m), 7.12-7.44 (4H, m), 8.73 (2H, br s), 9.11 (2H, br s).

Intermediate 122

6-(2-(2-Fluorophenyl)propyl)-1,3,5-triazine-2,4(1H,3H)-dione

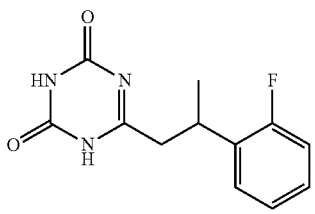 [SMILES: CC(Cc1nc(=O)[nH]c(=O)[nH]1)c1ccccc1F]

A suspension of $K_2CO_3$ (6.05 g, 43.8 mmol) and 3-(2-fluorophenyl)butanimidamide Intermediate 121 (8.67 g, 40.0 mmol) in MeCN (200 ml) was stirred under argon atmosphere for 5 min. Diphenyl iminodicarbonate Intermediate 112 (12.4 g, 45.0 mmol) was added and stirring was continued at rt for 1 h. $K_2CO_3$ (6.05 g, 43.8 mmol) was added and stirring was continued at rt for 1 h and then at 60° C. for 2 h. The mixture was cooled to rt and then concentrated. 2 M HCl (70 mL) and heptane (70 mL) were added, and the resulting mixture was stirred for 1 h. The resulting solid was collected by filtration, washed twice with heptane, dried in vacuo, washed twice with water and dried again to obtain a colourless solid (6.27 g). The filtrates were combined and the top layer was discarded. Both lower layers were concentrated at 60° C. to ~70 mL volume. DIPE (50 mL) was added and immediate precipitation occurred. After stirring at rt for 1 h the precipitate was collected by filtration, washed with heptane and water, dried in vacuo and recrystallised from IPA (35 mL). Another pure material (1.99 g) was obtained and both crops were combined to yield the title compound (8.26 g, 83%); MS (ESI) m/z [M+H]$^+$ 250.1

Intermediate 123

(2R)-2-((4-Chloro-6-(2-(2-fluorophenyl)propyl)-1,3,5-triazin-2-yl)amino)-4-methylpentan-1-ol

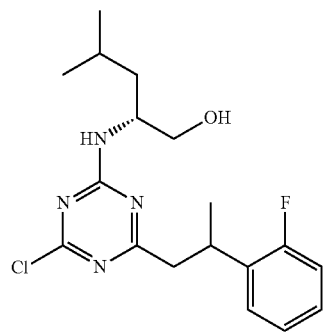 [SMILES: CC(C)C[C@H](CO)Nc1nc(Cl)nc(CC(C)c2ccccc2F)n1]

Step a) 2,4-Dichloro-6-(2-(2-fluorophenyl)propyl)-1,3,5-triazine

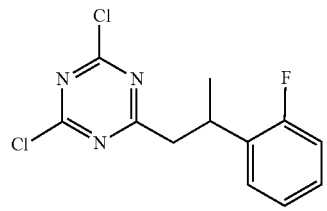 [SMILES: CC(Cc1nc(Cl)nc(Cl)n1)c1ccccc1F]

A mixture of 6-(2-(2-fluorophenyl)propyl)-1,3,5-triazine-2,4(1H,3H)-dione Intermediate 122 (6.23 g, 25.0 mmol) and $POCl_3$ (80.0 mL, 861 mmol) was heated to gentle reflux for 15 h. After cooling to rt the $POCl_3$ was evaporated. The residue was twice taken up in toluene (20 mL) and evaporated to give a brown liquid. The resulting liquid was diluted under argon atmosphere with dry DCM (130 mL). The mixture was cooled to 0° C. and a solution of DIPEA (18 mL) in DCM (10 mL) was added dropwise. After complete addition (~15 min) the still cold solution was shaken with ice/brine, 1/1 (100 mL). The layers were separated, the aqueous phase was extracted with DCM (30 mL) and the combined organic layers were washed twice with a mixture of water/sat $NaHCO_3$/brine (5/2/2, 90 mL), dried over $Na_2SO_4$, filtered and concentrated. The residual oil was taken up in toluene (50 mL) and decanted. The clear toluene solution was concentrated to give the subtitle compound (6.42 g, 22.4 mmol) as a dark orange solid.

Step b) (2R)-2-((4-Chloro-6-(2-(2-fluorophenyl)propyl)-1,3,5-triazin-2-yl)amino)-4-methylpentan-1-ol (R)-2-Amino-4-methylpentan-1-ol (3.16 mL, 24.7 mmol) was added at 5° C. to a stirred suspension of $K_2CO_3$ (3.48 g, 25.2 mmol) and 2,4-dichloro-6-(2-(2-fluorophenyl)propyl)-1,3,5-triazine Intermediate 123 step a) (6.42 g, 22.4 mmol) in MeCN (70 mL). A precipitation occurred and the cooling bath was removed. After stirring for 90 min the reaction mixture was concentrated. The residue was stirred with toluene (60 mL) for 5 min. The insolubles were removed by filtration and the filtrate was washed twice with 10% citric acid and brine, dried over $Na_2SO_4$, filtered and concentrated. The remaining oil was dissolved in EtOAc (25 mL) and filtered through silica. The filtrate was concentrated to give the title compound (6.74 g, 82%) as an orange oil; MS (ESI) m/z [M+H]$^+$ 367.3

Intermediate 124

N-(4-(2-(2-Fluorophenyl)propyl)-6-(((R)-1-hydroxy-4-methylpentan-2-yl)amino)-1,3,5-triazin-2-yl)methanesulfonamide

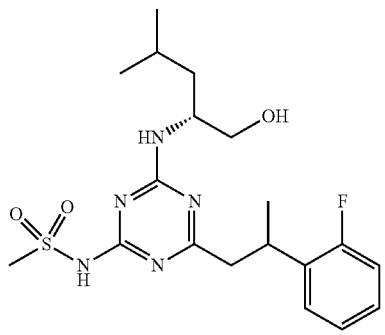 [SMILES: CC(C)C[C@H](CO)Nc1nc(CC(C)c2ccccc2F)nc(NS(C)(=O)=O)n1]

A mixture of methanesulfonamide (3.11 g, 32.7 mmol), (2R)-2-((4-chloro-6-(2-(2-fluorophenyl)propyl)-1,3,5-triazin-2-yl)amino)-4-methylpentan-1-ol Intermediate 123 (6.73 g, 18.3 mmol), X-phos (1.41 g, 2.96 mmol), $Pd_2(dba)_3$ (1.25 g, 1.37 mmol) and THF (80 mL) was stirred under argon atmosphere at rt for 10 min. $K_2CO_3$ (4.52 g, 32.7 mmol) was added and the mixture was heated at 65° C. for 21 h. After cooling to rt, the mixture was partitioned between water (180 mL) and MTBE (50 mL). The dark upper layer was extracted with a mixture of 2 M $K_2CO_3$ (20 mL) and THF (10 mL). The combined aqueous layers were washed with MTBE (2×30 mL). The aqueous layer was concentrated to remove THF, the remaining mixture was cooled 8° C. and neutralised by dropwise addition of conc HCl. MTBE (80 mL) was added and the two layers were separated. The aqueous layer was extracted with MTBE (60 mL). The combined extracts were washed with brine (50 mL), dried over $Na_2SO_4$ and concentrated. The residue was purified by preparative HPLC, PrepMethod B (gradient: 20-65%) to give the title compound (3.83 g, 49%); MS (ESI) m/z [M+H]$^+$ 426.3

Intermediate 125

(E)-3-Phenylbut-2-enenitrile

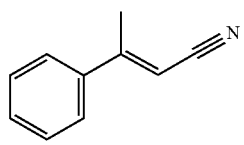

Diethyl cyanomethylphosphonate (26.7 mL, 165 mmol) was added at 0° C. to a solution of NaOtBu (15.8 g, 165 mmol) in abs EtOH (230 mL). After stirring for 15 min, still while cooling in an ice-bath, acetophenone (17.6 mL, 150 mmol) was added in two equal portions within 10 min. The mixture was stirred at 0° C. for additional 30 min and thereafter allowed to reach rt and stirred overnight. The mixture was concentrated and the residue precipitated on cooling. EtOH (30 mL), 10% citric acid (100 mL) and heptane (120 mL) were added and the mixture was thoroughly shaken until all solid had dissolved. On standing three liquid layers were separated, the two lower were combined and extracted with heptane (100, 80 and 50 mL). The combined colourless extracts were washed with brine, dried over $Na_2SO_4$ and concentrated to yield the title compound (20.7 g, 96%). According to $^1$H NMR a mixture of E- and Z-isomer (~9:1) was obtained; $^1$H NMR (400 MHz, $CDCl_3$) 2.26-2.51 (3H, m), 5.38-6.66 (1H, m), 7.37-7.56 (5H, m).

Intermediate 126

3-Phenylbutanenitrile

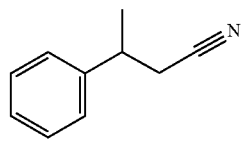

Pd/C 10% (2.0 g, 1.88 mmol) was added under argon atmosphere to a well stirred solution of crude (E)-3-phenylbut-2-enenitrile Intermediate 125 (20.7 g, 144 mmol) (E/Z-mixture) in EtOAc (300 mL). The mixture was hydrogenated (1.3 bar) at rt for 5 h. The catalyst was removed by filtration through celite, and the solvent was evaporated (30° C.) to give the title compound (20.8 g, 99%) as a colourless oil; $^1$H NMR (400 MHz, $CDCl_3$) 1.46 (3H, d), 2.5-2.67 (2H, m), 3.10-3.23 (1H, m), 7.2-7.41 (5H, m, overlap with $CDCl_3$).

Intermediate 127

3-Phenylbutanimidamide

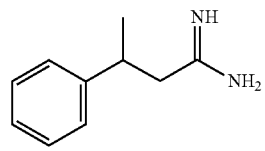

Step a) Ethyl 3-phenylbutanimidate

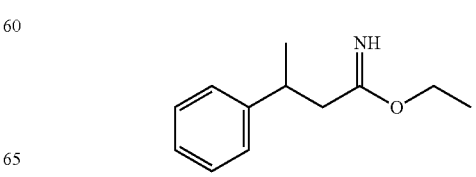

Acetyl chloride (38.7 mL, 544 mmol) was added dropwise to an ice cooled solution of 3-phenylbutanenitrile Intermediate 126 (10.0 g, 68.9 mmol) in abs EtOH (50 mL). The solution was standing at rt for 18 h. The clear solution was concentrated leaving the HCl salt of the subtitle compound as a colourless solid (15.2 g); $^1$H NMR (400 MHz, CD$_3$CN) 1.27 (3H, t), 1.32 (3H, d), 2.91-3.05 (2H, m), 3.27-3.41 (1H, m), 4.29-4.43 (2H, m), 7.2-7.38 (5H, m).

Step b) 3-Phenylbutanimidamide

Cold NH$_3$ (7 M in MeOH, 86.0 mL, 600 mmol) was added to ethyl 3-phenylbutanimidate Intermediate 127 Step a) (15.2 g, 66.8 mmol). After stirring for 15 min a clear solution was formed. After standing for 22 h at rt the solvent was evaporated to leave a colourless solid which was stirred with DIPE (100 mL) for 1 h. The solid was collected by filtration and dried in vacuo to yield the HCl salt of the title compound (12.7 g, 96%); $^1$H NMR (400 MHz, DMSO-d$_6$) 1.22 (3H, d), 2.62-2.7 (2H, m), 3.21-3.36 (1H, m, partial overlap with water in DMSO-d$_6$), 7.19-7.37 (5H, m), 8.66 (2H, br s), 9.03 (2H, br s).

Intermediate 128

6-(2-Phenylpropyl)-1,3,5-triazine-2,4(1H,3H)-dione

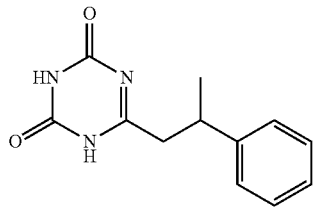 [SMILES: CC(Cc1nc(=O)[nH]c(=O)[nH]1)c1ccccc1]

A suspension of K$_2$CO$_3$ (6.05 g, 43.8 mmol) and 3-phenylbutanimidamide Intermediate 127 (7.55 g, 38.0 mmol) in MeCN (190 mL) was stirred under argon atmosphere for 5 min. Diphenyl iminodicarbonate Intermediate 112 (12.1 g, 43.7 mmol) was added and stirring was continued at rt for 1 h. K$_2$CO$_3$ (6.05 g, 43.8 mmol) was added and stirring was continued at rt for 1 h and at 60° C. for 2 h. The reaction mixture was cooled to rt and concentrated. 2 M HCl (68 mL) followed by heptane/Et$_2$O (2/1, 90 mL) was added to the resulting suspension, and it was stirred for 1 h. The resulting solid was collected by filtration, washed with heptane, dried in vacuo, washed with water and dried again to yield the title compound (5.62 g, 64%); $^1$H NMR (400 MHz, DMSO-d$_6$) 1.23 (3H, d), 2.59-2.73 (2H, m), 3.22-3.34 (m, partial overlap with water in DMSO-d$_6$), 7.15-7.35 (5H, m), 11.19 (1H, s), 12.08 (1H, s).

Intermediate 129

(2R)-2-((4-Chloro-6-(2-phenylpropyl)-1,3,5-triazin-2-yl)amino)-4-methylpentan-1-ol

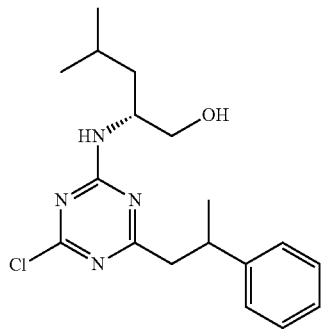 [SMILES: CC(C)C[C@H](CO)Nc1nc(Cl)nc(CC(C)c2ccccc2)n1]

Step a)
2,4-Dichloro-6-(2-phenylpropyl)-1,3,5-triazine

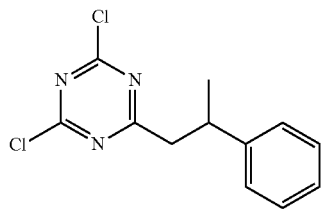 [SMILES: CC(Cc1nc(Cl)nc(Cl)n1)c1ccccc1]

A mixture of 6-(2-phenylpropyl)-1,3,5-triazine-2,4(1H,3H)-dione Intermediate 128 (5.62 g, 24.3 mmol) in distilled POCl$_3$ (80.0 mL, 861 mmol) was heated to gentle reflux for 15 h. After cooling to rt during, the POCl$_3$ was evaporated. The residue was twice taken up in toluene (30 mL) and evaporated to give of an orange liquid. The resulting liquid was diluted under argon atmosphere with dry DCM (130 mL). The mixture was cooled to 0° C. and a solution of DIPEA (17 mL) in DCM (15 mL) was added dropwise. After complete addition the still cold solution was shaken with ice/brine (1/1, 100 mL). The layers were separated, the aqueous phase was extracted with DCM (30 mL). The combined organic layers were washed with a solution of sat NaHCO$_3$/brine (⅓, ×2), dried over Na$_2$SO$_4$, filtered and concentrated. The residual oil was taken up in toluene/EtOAc (1/1, 120 mL) and washed with water and NaHCO$_3$ (aq). The organic layer was dried over Na$_2$SO$_4$, filtered and concentrated to give the subtitle compound (yield assumed quantitative); $^1$H NMR (500 MHz, CDCl$_3$) 1.31-1.35 (3H, m), 3.11-3.24 (2H, m), 3.46-3.57 (1H, m), 7.17-7.32 (m, partial overlap with CDCl$_3$).

Step b) (2R)-2-((4-Chloro-6-(2-phenylpropyl)-1,3,5-triazin-2-yl)amino)-4-methylpentan-1-ol (R)-2-amino-4-methylpentan-1-ol (3.44 mL, 26.9 mmol) was added over 2 min at rt to a stirred suspension of K$_2$CO$_3$ (3.77 g, 27.3 mmol) and 2,4-dichloro-6-(2-phenylpropyl)-1,3,5-triazine Intermediate 129 step a) in MeCN (70 mL). The mixture was heated to ~30° C. After 21 h the mixture was concentrated and the residue was partitioned between toluene (100 mL) and water (100 mL). HCl (12 M, ~25 mL) was added to accelerate the layer separation. The aqueous phase was extracted with toluene (50 mL). The combined organic layers were washed twice with water and brine, dried over $Na_2SO_4$, filtered and concentrated. The remaining oil was dissolved in EtOAc (25 mL) and filtered through silica and the filtrate was concentrated to give the title compound (6.12 g, 72%) as an orange oil; MS (ESI) m/z [M+H]$^+$ 349.2

Intermediate 130

N-(4-(((R)-1-Hydroxy-4-methylpentan-2-yl)amino)-6-(2-phenylpropyl)-1,3,5-triazin-2-yl)methanesulfonamide

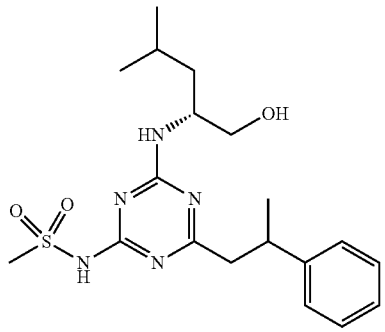 [SMILES: CC(C)C[C@H](CO)Nc1nc(CC(C)c2ccccc2)nc(NS(C)(=O)=O)n1]

A solution of (2R)-2-((4-chloro-6-(2-phenylpropyl)-1,3,5-triazin-2-yl)amino)-4-methylpentan-1-ol Intermediate 129 (5.95 g, 17.1 mmol) in THF (6 mL) (degassed with argon) was added under nitrogen atmosphere to a mixture of $Pd_2(dba)_3$ (0.607 g, 0.670 mmol), X-Phos (1.25 g, 2.62 mmol) and $K_2CO_3$ (3.54 g, 25.6 mmol), stirring at rt for –10 min. Then a degassed solution of methanesulfonamide (1.95 g, 20.5 mmol) in THF (20 mL) was added and the reaction mixture was heated at 60° C. overnight, under nitrogen atmosphere. After cooling to rt the mixture was partitioned between water (180 mL) and MTBE (50 mL). The organic layer was extracted with a mixture of 2 M $K_2CO_3$ (aq, 20 mL) and THF (10 mL. Additional water (20 mL), MTBE (30 mL) and brine (10 mL) were added. The aqueous phase was washed with MTBE (30 mL) and concentrated. The water phase was acidified with 4 M HCl (to pH 4.7) and the precipitated compound was extracted into EtOAc (×2, 130 and 60 mL). The organic layer was dried over $Na_2SO_4$, filtered and evaporated to give the title compound (4.51 g, 65%) as a solid; MS (ESI) m/z [M+H]$^+$ 408.4

Intermediate 131

(E)-3-(5-Chloropyridin-2-yl)but-2-enenitrile

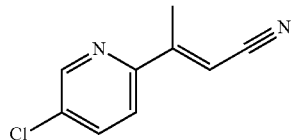

Diethyl cyanomethylphosphonate (4.45 mL, 27.5 mmol) was added at 0° C. to a solution of NaOtBu (2.64 g, 27.5 mmol) in abs EtOH (33 mL). After stirring for 15 min, 1-(5-chloropyridin-2-yl)ethanone (3.89 g, 25.0 mmol) was added and the mixture was stirred at rt for 14 h. 10% Citric acid (33 mL) was added, the mixture was cooled to 5° C. for 1 h, and the precipitate was collected by filtration, washed with EtOH (aq, 50%) and dried in vacuo to yield the title compound (4.02 g, 90%). According to $^1$H NMR, only one (E/Z)-configuration was observed, likely the E-isomer; $^1$H NMR (400 MHz, CDCl$_3$) 2.48 (3H, d), 6.45 (1H, q), 7.46 (1H, dd), 7.73 (1H, dd), 8.57 (1H, dd).

Intermediate 132

3-(5-Chloropyridin-2-yl)butanenitrile

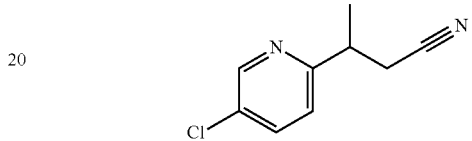

Diphenylsilane (7.98 mL, 43.0 mmol) was added to a stirred mixture of Cu(OAc)$_2$ (118 mg, 0.650 mmol) and DPEphos (0.35 g, 0.65 mmol) in toluene (22 mL) at rt under argon atmosphere and the reaction mixture was stirred for 30 min at rt. Solid (E)-3-(5-chloropyridin-2-yl)but-2-enenitrile Intermediate 131 (3.84 g, 21.5 mmol) and t-BuOH (8 mL) were added and the reaction mixture was stirred at rt for 3 h. The reaction was quenched under vigorous stirring and gas development with water (20 mL), followed by sat NaHCO$_3$. EtOAc (30 mL) was added and the layers were separated, the organic portion was extracted with 1 M HCl (5×50 mL). The combined acidic extracts were washed with pentane (20 mL), and neutralised with conc NH$_3$. The milky mixture was extracted with Et$_2$O (2×50 mL). The combined extracts were dried over Na$_2$SO$_4$, filtered and concentrated (24° C.). The remaining black oil was dissolved in DCM (15 mL) and filtered through silica (5 g) eluted with DCM (45 mL), and the combined filtrates were concentrated to give the title compound (2.96 g, 76%); MS (ESI) m/z [M+H]$^+$ 181.2

Intermediate 133

3-(5-Chloropyridin-2-yl)butanimidamide

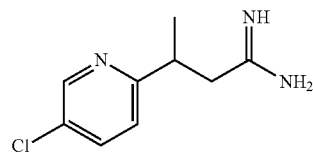

AlMe$_3$ (2 M in toluene, 13.1 mL, 26.2 mmol) was added dropwise under argon atmosphere to an ice cold suspension of NH$_4$Cl (1.51 g, 28.2 mmol) in toluene (16 mL) (gas formation). The resulting mixture was warmed to rt and stirred for 1 h. 3-(5-Chloropyridin-2-yl)butanenitrile Intermediate 132 (2.96 g, 16.4 mmol) was added and the mixture was stirred at 80° C. overnight. After cooling to rt the mixture was slowly poured into an ice cold slurry of silica (15 g) in CHCl$_3$ (40 mL), stirring was continued at rt for 15 min. The mixture was filtered and the residue was washed with MeOH (2×60 mL). The combined filtrates were concentrated and the residue was stirred for 10 min in 1.25 M HCl in MeOH (13.1 mL) and then concentrated. The residue was stirred with IPA/acetone (4/1, 45 mL) for 10 min, the colourless insolubles were removed by filtration and the filtrate was concentrated to ~20 mL of volume. Et$_2$O (20 mL) was added dropwise (~15 min) under vigorous stirring. The stirring was continued at rt for 30 min and the mixture was left standing at 5° C. for 1 h. The precipitate was collected by filtration, washed with IPA/Et$_2$O (1/1), Et$_2$O and dried in vacuo to yield the HCl salt of the title compound (2.17 g, 57%); $^1$H NMR (400 MHz, D$_2$O) 1.49 (3H, d), 2.86-2.95 (2H, m), 3.54-3.68 (1H, m), 7.82 (1H, d), 8.36 (1H, dd), 8.74 (1H, d).

Intermediate 134

6-(2-(5-Chloropyridin-2-yl)propyl)-1,3,5-triazine-2,4 (1H,3H)-dione

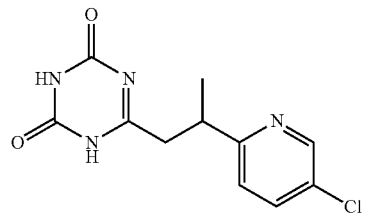 [SMILES: CC(Cc1nc(=O)[nH]c(=O)[nH]1)c1ccc(Cl)cn1]

A suspension of K$_2$CO$_3$ (1.17 g, 8.50 mmol) and 3-(5-chloropyridin-2-yl)butanimidamide Intermediate 133 (1.98 g, 8.44 mmol) in MeCN (35 mL) was stirred under argon atmosphere for 1 h. Diphenyl iminodicarbonate Intermediate 112 (2.17 g, 8.44 mmol) was added and stirring was continued at rt for 1 h. K$_2$CO$_3$ (1.17 g, 8.50 mmol) was added and stirring was continued at rt for 1 and then at 60° C. for 2 h. After cooling to rt the resulting thick suspension was dissolved in 0.4 M citric acid (aq, 50 mL) and concentrated to ~60 mL volume. The remaining solution was extracted with EtOAc (3×50 mL). The combined extracts were washed with brine and dried over Na$_2$SO$_4$, filtered and the solvent was evaporated. The remaining solid was dried in vacuo for 3 h. The semi-solid residue was stirred for 20 min with PE/Et$_2$O (2/1, 60 mL), filtered, washed with DIPE and dried in vacuo to give the title compound (1.59 g, 71%); MS (ESI) m/z [M+H]$^+$ 267.4

Intermediate 135

(2R)-2-((4-Chloro-6-(2-(5-chloropyridin-2-yl)propyl)-1,3,5-triazin-2-yl)amino)-4-methylpentan-1-ol

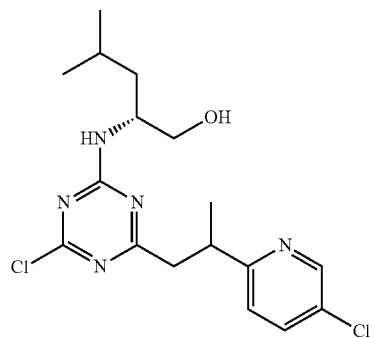 [SMILES: CC(C)C[C@H](CO)Nc1nc(Cl)nc(CC(C)c2ccc(Cl)cn2)n1]

Step a) 2,4-Dichloro-6-(2-(5-chloropyridin-2-yl) propyl)-1,3,5-triazine

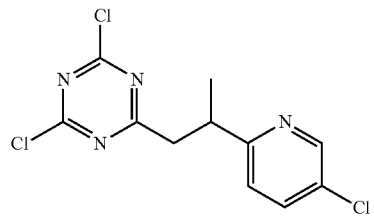 [SMILES: CC(Cc1nc(Cl)nc(Cl)n1)c1ccc(Cl)cn1]

A mixture of 6-(2-(5-chloropyridin-2-yl)propyl)-1,3,5-triazine-2,4(1H,3H)-dione Intermediate 134 (267 mg, 1.00 mmol), POCl$_3$ (280 µL, 3.00 mmol) and N,N-diethylaniline (159 µL, 1.00 mmol) was heated at 70° C. for 1.5 h. After cooling to rt the mixture was diluted with CHCl$_3$ (10 mL) and toluene (10 mL). The mixture was concentrated to give the subtitle compound (assumed quantitative yield) as an oil used in step b).

Step b) (2R)-2-((4-Chloro-6-(2-(5-chloropyridin-2-yl)propyl)-1,3,5-triazin-2-yl)amino)-4-methylpentan-1-ol K$_2$CO$_3$ (270 mg, 1.95 mmol) was added in 3 portions over 2 h to a stirred solution of 2,4-dichloro-6-(2-(5-chloropyridin-2-yl)propyl)-1,3,5-triazine Intermediate 135 step a) and (R)-2-amino-4-methylpentan-1-ol (150 µl, 1.17 mmol) in dry THF (6 mL). Stirring was continued for another 1 h, additional (R)-2-amino-4-methylpentan-1-ol (100 µl, 0.780 mmol) was added and the mixture was stirred overnight. 3 more portions of (R)-2-amino-4-methylpentan-1-ol (100 µL each) were added during 8 h, and stirring was continued overnight. The mixture was diluted with Et$_2$O (40 mL) and the insoluble gum was removed by decantation and filtration through celite. The filtrate was concentrated and the residue was purified by preparative HPLC, PrepMethod B, (gradient: 35-75%) to give the title compound (58 mg, 15%); MS (ESI) m/z [M+H]$^+$ 384.5/386.5

Intermediate 136

N-(4-(2-(5-Chloropyridin-2-yl)propyl)-6-(((R)-1-hydroxy-4-methylpentan-2-yl)amino)-1,3,5-triazin-2-yl)methanesulfonamide

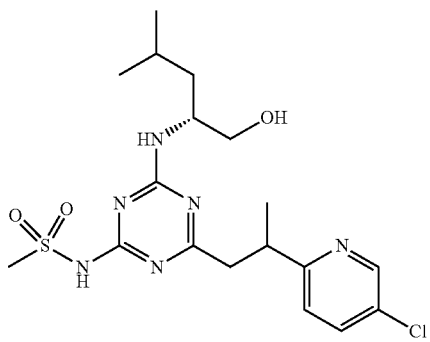 [SMILES: CC(C)C[C@H](CO)Nc1nc(CC(C)c2ccc(Cl)cn2)nc(NS(C)(=O)=O)n1]

The title compound was prepared from (2R)-2-((4-chloro-6-(2-(5-chloropyridin-2-yl)propyl)-1,3,5-triazin-2-yl)amino)-4-methylpentan-1-ol Intermediate 135 (58 mg, 0.15 mmol) as described for Example 118; to give the title compound (33 mg, 49%); MS (ESI) m/z [M+H]+ 443.17

Intermediate 137

(Z)-4,4,4-Trifluoro-3-phenylbut-2-enenitrile

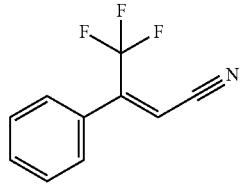 [SMILES: N#C/C=C(/c1ccccc1)C(F)(F)F]

A solution of diethyl cyanomethylphosphonate (4.52 g, 25.5 mmol) in THF (5 mL) was added to a slurry of NaH (1.02 g, 25.5 mmol) in THF (10 mL) at rt during 15 min under nitrogen atmosphere and the resulting yellow solution was stirred for 1 h. 2,2,2-trifluoro-1-phenylethan-1-one (2.96 g, 17 mmol) was added and the reaction mixture was stirred at rt for 3 h. THF (10 mL) was added to the thick reaction mixture and it was stirred at rt overnight. Water (50 mL) was added and the mixture was extracted with EtOAc (×2, 150 and 50 mL). The combined organic layers were dried over Na$_2$SO$_4$, filtered and concentrated. The residue was purified by straight phase flash chromatography on silica (gradient: 5-40% EtOAc in heptane) to give the title compound as two separated E- and Z-isomers (in total 1.80 g, 54%). First eluted isomer (1.07 g): $^1$H NMR (400 MHz, CDCl$_3$) 6.15-6.19 (1H, m), 7.46-7.59 (5H, m); Second eluted isomer (0.728 g): $^1$H NMR (400 MHz, CDCl$_3$) 5.92-5.96 (1H, m), 7.41-7.56 (5H, m).

Intermediate 138

4,4,4-Trifluoro-3-phenylbutanenitrile

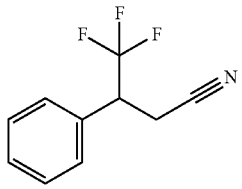 [SMILES: N#CCC(c1ccccc1)C(F)(F)F]

NaBH$_4$ (0.616 g, 16.3 mmol) was added to a mixture of (Z)-4,4,4-trifluoro-3-phenylbut-2-enenitrile Intermediate 137 first eluted isomer (1.07 g, 5.43 mmol) (E or Z-isomer) in MeOH (20 mL) at 0° C. After 5 min the mixture was allowed to reach rt and stirred for 2 h. The reaction mixture was quenched with 2 M HCl (10 mL), stirred for 45 min and thereafter concentrated. Brine (10 mL) was added and the aqueous phase was extracted with DCM (50 mL). The organic phase was dried by passing through a phase separator and concentrated to give the title compound (1.0 g, 92%) as a colourless oil; $^1$H NMR (400 MHz, CDCl$_3$) 2.88-3.11 (2H, m), 3.63-3.78 (1H, m), 7.31-7.49 (5H, m).

Intermediate 139

4,4,4-Trifluoro-3-phenylbutanimidamide

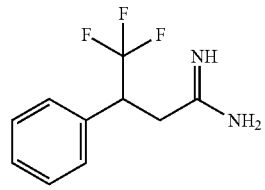 [SMILES: N=C(N)CC(c1ccccc1)C(F)(F)F]

AlMe$_3$ (2 M in toluene, 12.5 mL, 25.0 mmol) was added dropwise (~10 min) under nitrogen atmosphere to an ice cold suspension of NH$_4$Cl (1.62 g, 30.2 mmol) in toluene (10 mL). The resulting mixture was warmed to rt and stirred for 1 h. A solution of 4,4,4-trifluoro-3-phenylbutanenitrile Intermediate 138 (1.66 g, 8.33 mmol) in toluene (5 mL) was added, and the clear solution was heated at 70° C. overnight. The mixture was allowed to reach rt and then cooled on an ice-water bath. MeOH (24 mL) was added slowly and the resulting mixture was stirred for 15 min and then allowed to reach rt. Silica (2 g) was added as filtering agent and insolubles were removed by filtration. The insolubles were washed with MeOH (44 mL) and the combined filtrates were concentrated to give a solid. MeOH (25 mL) followed by HCl (4 M in dioxane, 4 mL) were added to the solid, and the suspension was concentrated. The residue was stirred for ~45 min with a mixture of IPA/acetone (4/1, 50 mL). The insoluble precipitate was removed by filtration and the filtrate was concentrated. The oily residue was dried in vacuo overnight to give a syrup like foam. Et$_2$O (10 mL) was added to the residue and the mixture was concentrated. MTBE was added to the residue and the mixture was concentrated to give a gum-like solid that was dried in vacuo over weekend to give the HCl salt of the title compound (1.96 g, 93%); $^1$H NMR (400 MHz, DMSO-$d_6$) 3.1-3.29 (2H, m), 4.38-4.53 (1H, m), 7.39-7.46 (5H, m). According to $^1$H NMR the product contains some TBME.

Intermediate 140

2,4-Dichloro-6-(3,3,3-trifluoro-2-phenylpropyl)-1,3,5-triazine

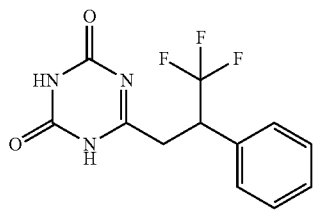 [SMILES: O=c1nc(CC(c2ccccc2)C(F)(F)F)[nH]c(=O)[nH]1]

A suspension of $K_2CO_3$ (1.26 g, 9.13 mmol) and 4,4,4-trifluoro-3-phenylbutanimidamide Intermediate 139 (1.96 g, 7.76 mmol) in MeCN (40 mL) was stirred under nitrogen atmosphere for 5 min. Diphenyl iminodicarbonate Intermediate 112 (2.36 g, 9.19 mmol) was added and stirring was continued at rt for 1.5 h. $K_2CO_3$ (1.26 g, 9.13 mmol) was added and stirring was continued at rt for 20 min and then at 60° C. overnight. The mixture was stirred with MTBE (35 mL) for 1 h. The solid was filtered, washed with MTBE (10 mL) and dried in vacuo. 2 M HCl (24 mL) was added to the solid and the mixture was stirred for 45 min. The precipitate was collected by filtration, washed with 0.2 M HCl (15 mL) and water (10 mL) and then dried in vacuo at 50° C. overnight to give the title compound (1.98 g, 89%) as a colourless solid; MS (ESI) m/z [M+H]$^+$ 286.2

Intermediate 141

(2R)-2-((4-Chloro-6-(3,3,3-trifluoro-2-phenylpropyl)-1,3,5-triazin-2-yl)amino)-4-methylpentan-1-ol

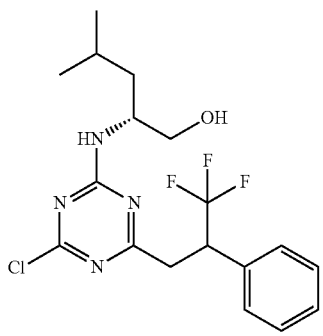 [SMILES: CC(C)C[C@H](CO)Nc1nc(Cl)nc(CC(c2ccccc2)C(F)(F)F)n1]

Step a) 2,4-Dichloro-6-(3,3,3-trifluoro-2-phenylpropyl)-1,3,5-triazine

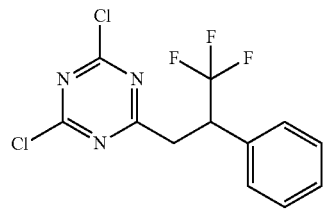 [SMILES: FC(F)(F)C(Cc1nc(Cl)nc(Cl)n1)c1ccccc1]

A mixture of 6-(3,3,3-trifluoro-2-phenylpropyl)-1,3,5-triazine-2,4(1H,3H)-dione Intermediate 140 (1.97 g, 6.91 mmol) and POCl$_3$ (31.5 mL, 338 mmol) was heated to a gentle reflux for 48 h. After cooling to rt the mixture was concentrated and coevaporated twice from toluene. The residue was dissolved in DCM (85 mL) and the solution was cooled to 0° C. on an ice bath. DIPEA (4.83 mL, 27.6 mmol) was added carefully during 15 min followed by the slow addition of water (1 mL). The orange solution was diluted with DCM (25 mL) and water (12 mL). The organic layer was washed with water (18 mL) followed by sat NaHCO$_3$ (12 mL) and water (18 mL), dried by passing through a phase separator and concentrated to give the subtitle compound (assumed quantitative yield) as a dark oil.

Step b) (2R)-2-((4-Chloro-6-(3,3,3-trifluoro-2-phenylpropyl)-1,3,5-triazin-2-yl)amino)-4-methylpentan-1-ol $K_2CO_3$ (1.05 g, 7.60 mmol) was added to an ice cold solution of 2,4-dichloro-6-(3,3,3-trifluoro-2-phenylpropyl)-1,3,5-triazine Intermediate 141 step a) in MeCN (25 mL). (R)-2-amino-4-methylpentan-1-ol (0.927 mL, 7.26 mmol) was added dropwise during ~1 min at 0° C., and the reaction mixture was stirred at 0° C. for 20 min. The mixture was allowed to reach rt and stirred for 1.5 h and then DCM (150 mL) and water (20 mL) were added. The organic layer was washed with water/brine (2/1, 30 mL), dried over MgSO$_4$, filtered and concentrated. The residue was purified by straight phase flash chromatography on silica (gradient: 12-100% EtOAc in heptane) to give the title compound (0.526 g, 19%) as a thick yellow oil; MS (ESI) m/z [M+H]$^+$ 403.4.

Intermediate 142

(3-(1-Hydroxycyclopropyl)phenyl)boronic acid

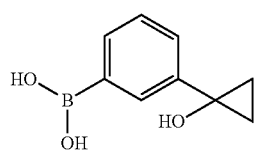 [SMILES: OB(O)c1cccc(C2(O)CC2)c1]

n-BuLi (291 mL, 0.73 mol) was added dropwise to a solution of 1-(3-bromophenyl)cyclopropan-1-ol (70 g, 0.33 mol) in THF (1.5 L) at −65° C. and under an atmosphere of N$_2$(g). The reaction mixture was stirred at −65° C. for 30 min. A solution of triisopropyl borate (75.2 g, 0.40 mol) in THF (200 mL) was added dropwise at −65° C. The reaction mixture was slowly warmed to −30° C. for 2 h. The reaction was quenched with NH$_4$Cl (aq). The organic layer was separated, dried over anhydrous Na$_2$SO$_4$, filtered and evaporated to give the crude solid product, which was washed with 2-methoxy-2-methylpropane to give the title compound (27 g, 46%); MS (ESI) m/z [M−18+H]$^+$161.1; $^1$H NMR (400 MHz, DMSO-d$_6$) δ 1.05 (m, 2H), 1.32 (m, 2H), 2.38 (brs, 1H), 7.18 (m, 2H), 7.34 (m, 1H), 7.46 (m, 1H).

Intermediate 143

6-(2-Methyl-2-phenylpropyl)-1,3,5-triazine-2,4(1H,3H)-dione

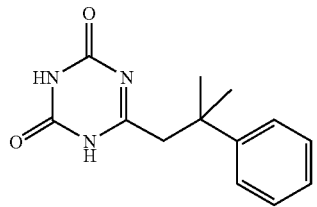 [SMILES: CC(C)(Cc1nc(=O)[nH]c(=O)[nH]1)c1ccccc1]

A suspension of K$_2$CO$_3$ (374 mg, 2.71 mmol) and 3-methyl-3-phenylbutanimidamide, HCl US20140194431 (0.490 g, 2.30 mmol) in dry MeCN (13 mL) was stirred at rt under an atmosphere of N$_2$(g) for 5 min. Diphenyl iminodicarbonate (0.702 g, 2.73 mmol) was added and the reaction mixture was stirred at rt for 1 h. K$_2$CO$_3$ (374 mg, 2.71 mmol) was added, and the reaction mixture was stirred for 20 min at rt and then at 60° C. for 2 h 20 min. The reaction mixture was cooled to rt and concentrated in vacuo. MTBE (10 mL) was added to the residue and the mixture was stirred for 30 min. The insoluble material was isolated by filtration, washed with MTBE (2-3 mL), and dried in vacuo. The solid was stirred with 2 N HCl (8 mL) for 45 min. The precipitate was collected by filtration, washed with 0.2 N HCl (5 mL) and dried in vacuo to give the title compound (0.302 g, 54%) as an off white solid; MS (ESI) m/z [M+H]$^+$ 246.3.

Intermediate 144

2,4-Dichloro-6-(2-methyl-2-phenylpropyl)-1,3,5-triazine

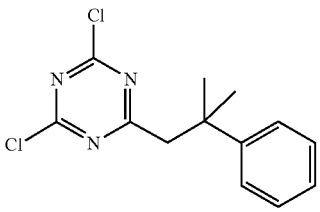 [SMILES: CC(C)(Cc1nc(Cl)nc(Cl)n1)c1ccccc1]

POCl$_3$ (5.38 mL, 57.73 mmol) was added to 6-(2-methyl-2-phenylpropyl)-1,3,5-triazine-2,4(1H,3H)-dione Intermediate 143 (0.289 g, 1.18 mmol) and the reaction mixture was heated to gentle reflux for 18 h and then cooled to rt. The reaction mixture was concentrated in vacuo to dryness, co-evaporated twice from toluene, and dried under an atmosphere of N2(g) overnight upon which it solidified. The crude product was dissolved in DCM (15 mL) and the solution was cooled to 0° C. on an ice bath. DIPEA (0.823 mL, 4.71 mmol) was added very carefully over 15 min, followed by slow addition of water (1 mL) over 10 min. The mixture was partitioned between DCM (4 mL) and water (2 mL). The organic phase was washed with water (3 mL), aq NaHCO$_3$(sat, 2 mL), and water (3 mL). The organic layer was dried over MgSO$_4$, filtered and concentrated to give the crude title compound (386 mg) as a brown oil which solidified upon standing at rt; $^1$H NMR (400 MHz, CD$_3$CN) δ1.45 (6H, s), 3.15 (2H, s), 7.16-7.21 (1H, m), 7.26-7.32 (2H, m), 7.35-7.4 (2H, m). The crude product was used without further purification in the next step.

Intermediate 145

(R)-2-((4-Chloro-6-(2-methyl-2-phenylpropyl)-1,3,5-triazin-2-yl)amino)-4-methylpentan-1-ol

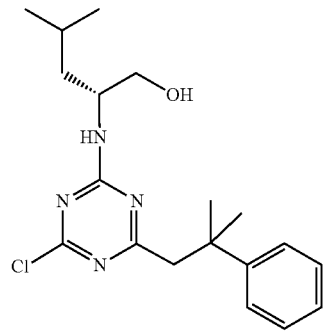 [SMILES: CC(C)C[C@H](CO)Nc1nc(Cl)nc(CC(C)(C)c2ccccc2)n1]

K$_2$CO$_3$ (0.179 g, 1.30 mmol) was added to a cooled solution of 2,4-dichloro-6-(2-methyl-2-phenylpropyl)-1,3,5-triazine Intermediate 144 (0.333 g, 1.18 mmol) in MeCN (4 mL). (R)-2-Amino-4-methylpentan-1-ol (0.158 mL, 1.24 mmol) was added dropwise at 0° C. and the reaction mixture was stirred at 0° C. for 15 min. The reaction mixture was allowed to attain rt and DCM (60 mL) and water (10 mL) were added. The organic layer was washed with water (10 mL), dried over MgSO$_4$, filtered, and concentrated. The crude product was purified by straight phase flash chromatography on silica (heptane:EtOAc, 1:1) to give the title compound (211 mg, 49%) as a yellow oil; MS (ESI) m/z [M+H]$^+$ 363.4.

Intermediate 146

1-(1,1-Difluoroallyl)-4-fluorobenzene

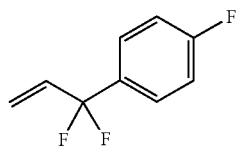

3-Bromo-3,3-difluoroprop-1-ene (235 mg, 1.50 mmol) was added to a mixture of (4-fluorophenyl)boronic acid (140 mg, 1 mmol), Pd$_2$dba$_3$ (5 mg, 5.46 µmol) and K$_2$CO$_3$ (415 mg, 3.00 mmol) in dioxane (5 mL) and water (8.65 µl) in a microwave vial. The vessel was sealed and heated at 80° C. overnight and then stirred at rt for 20 h. The reaction mixture was diluted with Et$_2$O and filtered through a pad of MgSO$_4$. The filtrate was washed several times with water and then concentrated. The crude product was dissolved in pentane, washed with water, and concentrated. The crude product was purified by straight phase flash chromatography on silica (0-5% Et$_2$O in pentane) to give the title compound (60 mg, 35%); $^1$H NMR (400 MHz, CDCl$_3$) δ 5.46-5.61 (2H, m), 6.06-6.22 (1H, m), 7.11 (2H, t), 7.49 (2H, dd).

Intermediate 147

3-Fluoro-6-methyl-2-(prop-1-en-2-yl)pyridine

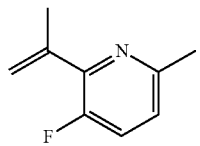

Et$_2$O (7 mL) and PdCl$_2$(dppf) (0.046 g, 0.06 mmol) were added to a degassed solution of K$_2$CO$_3$ (2.182 g, 15.79 mmol) in water (2 mL) and the reaction mixture was degassed. 2-Bromo-3-fluoro-6-methylpyridine (1 g, 5.26 mmol) and 4,4,5,5-tetramethyl-2-(prop-1-en-2-yl)-1,3,2-dioxaborolane (1.088 mL, 5.79 mmol) were added in one portion, followed by THF (1.5 mL), and the reaction mixture was refluxed under an atmosphere of N2(g) for 72 h. The reaction mixture was diluted with Et$_2$O and washed with water and brine. The organic layer was carefully concentrated, and the residue was purified by straight phase flash chromatography on silica (2-5% Et$_2$O in pentane). The first compound containing fraction was collected and heated with K$_2$CO$_3$ (aq) in a microwave reactor at 100° C. for 15 min and then partitioned between Et$_2$O and water. The organic layer was treated with CsOH monohydrate (0.23 g, 1.37 mmol) in water (0.5 mL) at rt. The aqueous layer was extracted with Et$_2$O and the combined organic layer was carefully concentrated. The second compound containing fraction was collected and treated with CsOH monohydrate (0.23 g, 1.37 mmol) at rt and then extracted with Et$_2$O. The organic layer was carefully concentrated, and the residues were combined to give the title compound (0.505 g, 64%) as a colourless liquid; $^1$H NMR (500 MHz, CDCl$_3$) δ 2.20 (3H, td), 2.51 (3H, d), 5.45 (1H, h), 5.66 (1H, tq), 6.99 (1H, dd), 7.24 (1H, dd).

Example 1

N-(4-((S*)-2-(3,4-Dichlorophenyl)propyl)-6-(((R)-1-hydroxy-4-methylpentan-2-yl)amino)-1,3,5-triazin-2-yl)methanesulfonamide (Isomer 1)

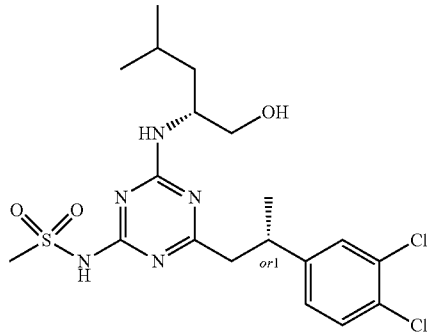

Isomer 1

Example 2

N-(4-((R*)-2-(3,4-Dichlorophenyl)propyl)-6-(((R)-1-hydroxy-4-methylpentan-2-yl)amino)-1,3,5-triazin-2-yl)methanesulfonamide (Isomer 2)

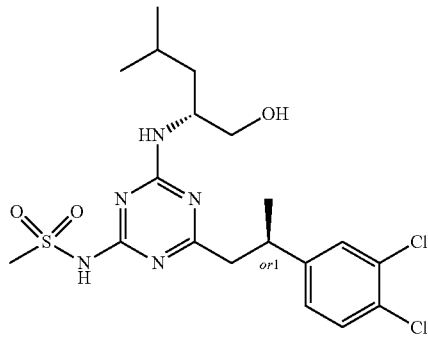

Isomer 2

The diastereomers of N-(4-(2-(3,4-dichlorophenyl)propy-6-(((R)-1-hydroxy-4-methylpentan-2-yl)amino)-1,3,5-triazin-2-yl)methanesulfonamide Intermediate 6 (70 mg, 0.15 mmol) were separated by preparative chiral HPLC on a Chiralpak IA column (250×30 mm, 5 µm), eluted with 15% MeOH/DEA (100/0.5) in CO$_2$, 120 bar at a flow rate of 150 mL/min and detected at 220 nm, to give the first eluting compound N-(4-((S*)-2-(3,4-dichlorophenyl)propyl)-6-(((R)-1-hydroxy-4-methylpentan-2-yl)amino)-1,3,5-triazin-2-yl)methanesulfonamide (Isomer 1) Example 1 (28 mg, 40%); IRMS (ESI) m/z [M+H]$^+$ calcd for C19H$_{28}$Cl$_2$N$_5$O$_3$S: 476.1284, found: 476.1292; $^1$H NMR (500 MHz, CDCl$_3$) 0.91 (6H, dd), 1.25 (m, partial overlap with DEA residues), 1.31-1.47 (2H, m), 1.57-1.75 (1H, m), 2.64-2.82 (2H, m), 3.13 (3H, s), 3.33 (1H, sext), 3.55 (1H, dd), 3.69 (1H, dd), 4.07 (1H, br s), 6.10 (2H, br s), 7.05 (1H, dd), 7.28-7.33 (2H, m), and the second eluting compound N-(4-((R*)-2-(3,4-dichlorophenyl)propyl)-6-(((R)-1-hydroxy-4-methylpentan-2-yl)amino)-1,3,5-triazin-2-yl)methanesulfonamide (Isomer 2) Example 2 (27 mg, 39%); IRMS (ESI) m/z [M+H]+ calcd for C19H28Cl2N5O3S: 476.1284, found: 476.1280; $^1$H NMR (500 MHz, CDCl$_3$) 0.85-0.98 (6H, m), 1.21-1.49 (m, partial overlap with DEA residues), 1.54-1.75 (1H, m), 2.69-2.91 (2H, m), 2.97-3.10 (2H, m), 3.16 (3H, s), 3.26-3.40 (1H, m), 3.51-3.63 (1H, m), 3.64-3.77 (1H, m), 4.14 (1H, br s), 6.80 (1H, br s), 7.07 (1H, d), 7.28-7.34 (2H, m).

Example 3

N-(4-((S*)-2-(3-Chloro-2-fluorophenyl)propyl)-6-(((R)-1-hydroxy-4-methylpentan-2-yl)amino)-1,3,5-triazin-2-yl)methanesulfonamide (Isomer 1)

Isomer 1

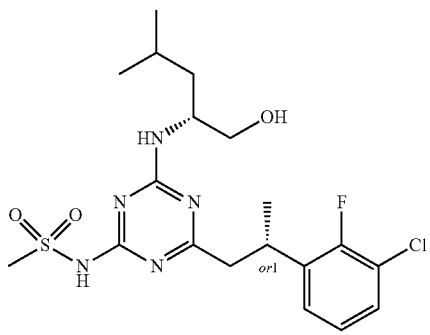

Example 4

N-(4-((R*)-2-(3-Chloro-2-fluorophenyl)propyl)-6-(((R)-1-hydroxy-4-methylpentan-2-yl)amino)-1,3,5-triazin-2-yl)methanesulfonamide (Isomer 2)

Isomer 2

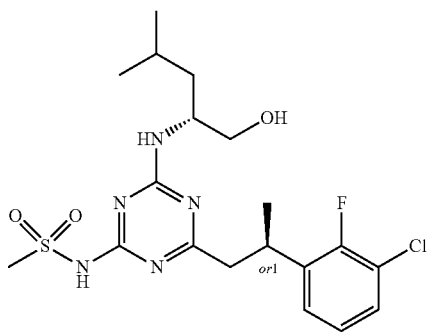

The diastereomers of N-(4-(2-(3-chloro-2-fluorophenyl)propyl)-6-(((R)-1-hydroxy-4-methylpentan-2-yl)amino)-1,3,5-triazin-2-yl)methanesulfonamide Intermediate 8 (150 mg, 0.33 mmol) were separated by preparative chiral HPLC on a Chiralcel OJ column (250×30 mm, 5 µm), eluted with 15% EtOH/DEA (100/0.5) in CO$_2$, 120 bar at a flow rate of 80 mL/min and detected at 220 nm, to give the first eluting compound N-(4-((S*)-2-(3-chloro-2-fluorophenyl)propyl)-6-(((R)-1-hydroxy-4-methylpentan-2-yl)amino)-1,3,5-triazin-2-yl)methanesulfonamide (Isomer 1) Example 3 that was dissolved in EtOAc and washed with acidic water (pH 4) and brine. The organic extract was evaporated to yield (36 mg, 24%); HRMS (ESI) m/z [M+H]+ calcd for C19H28ClFN5O3S: 460.1580, found: 460.1580; $^1$H NMR (500 MHz, MeOD) 0.83-0.97 (6H, m), 1.31-1.53 (5H, m), 1.56-1.69 (1H, m), 2.84 (1H, d), 2.88-2.98 (1H, m), 3.16 (3H, d), 3.45-3.59 (2H, m), 3.67-3.82 (1H, m), 4.13-4.27 (1H, m), 7.07-7.13 (1H, m), 7.23-7.28 (1H, m), 7.28-7.34 (1H, m). The second eluting compound from the chiral separation, N-(4-((R*)-2-(3-chloro-2-fluorophenyl)propyl)-6-(((R)-1-hydroxy-4-methylpentan-2-yl)amino)-1,3,5-triazin-2-yl)methanesulfonamide (Isomer 2) Example 4 was dissolved in EtOAc and washed with acidic water (pH 4) and brine. The organic extract was evaporated to yield (38 mg, 26%); HRMS (ESI) m/z [M+H]+ calcd for C19H28ClFN5O3S: 460.1580, found: 460.1580; $^1$H NMR (500 MHz, MeOD) 0.89-0.96 (6H, m), 1.31-1.53 (5H, m), 1.57-1.71 (1H, m), 2.84 (1H, d), 2.87-2.98 (1H, dd), 3.16 (3H, d), 3.41-3.61 (2H, m), 3.70-3.81 (1H, m), 4.17-4.27 (1H, m), 7.07-7.13 (1H, m), 7.23-7.28 (1H, m), 7.28-7.34 (1H, m).

Example 5

N-(4-((S*)-2-(2,4-Difluorophenyl)propyl)-6-(((R)-1-hydroxy-4-methylpentan-2-yl)amino)-1,3,5-triazin-2-yl)methanesulfonamide (Isomer 1)

Isomer 1

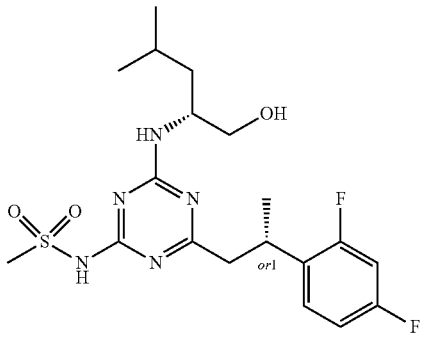

Example 6

N-(4-((R*)-2-(2,4-Difluorophenyl)propyl)-6-(((R)-1-hydroxy-4-methylpentan-2-yl)amino)-1,3,5-triazin-2-yl)methanesulfonamide (Isomer 2)

Isomer 2

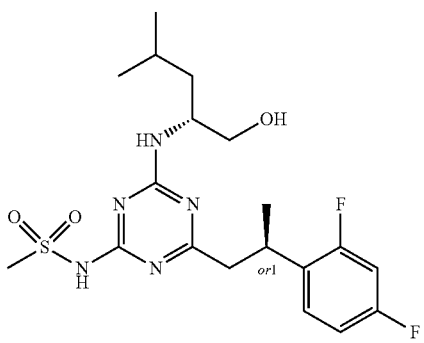

The diastereomers of N-(4-(2-(2,4-difluorophenyl)propyl)-6-(((R)-1-hydroxy-4-methylpentan-2-yl)amino)-1,3,5-triazin-2-yl)methanesulfonamide Intermediate 10 (90 mg, 0.20 mmol) were separated by preparative chiral HPLC on a Chiralcel OJ column (250×30 mm, 5 μm), eluted with 15% EtOH/DEA (100/0.5) in $CO_2$, 120 bar at a flow rate of 80 mL/min and detected at 220 nm, to give the first eluting compound N-(4-((S*)-2-(2,4-difluorophenyl)propyl)-6-(((R)-1-hydroxy-4-methylpentan-2-yl)amino)-1,3,5-triazin-2-yl)methanesulfonamide (Isomer 1) Example 5 that was dissolved in EtOAc and washed with dilute HCl. The organic extract was dried over $MgSO_4$, filtered and evaporated to yield (22 mg, 24%); HRMS (ESI) m/z [M+H]$^+$ calcd for $C_{19}H_{28}F_2N_5O_3S$: 444.1876, found: 444.1894; $^1$H NMR (500 MHz, MeOD) 0.86-0.97 (6H, m), 1.34 (3H, d), 1.36-1.51 (2H, m), 1.57-1.68 (1H, m), 2.77-2.85 (1H, m), 2.85-2.93 (1H, m), 3.15 (3H, d), 3.45-3.59 (2H, m), 3.60-3.75 (1H, m), 4.15-4.27 (1H, m), 6.82-6.93 (2H, m), 7.28-7.36 (1H, m). The second eluting compound from the chiral separation, N-(4-((R*)-2-(2,4-difluorophenyl)propyl)-6-(((R)-1-hydroxy-4-methylpentan-2-yl)amino)-1,3,5-triazin-2-yl)methanesulfonamide (Isomer 2) Example 6 was dissolved in EtOAc and washed with dilute HCl. The organic extract was dried over $MgSO_4$, filtered and evaporated to yield (14 mg, 16%); HRMS (ESI) m/z [M+H]$^+$ calcd for $C_{19}H_{28}F2N5O3S$: 444.1876, found: 444.1856; $^1$H NMR (500 MHz, MeOD) 0.87-0.97 (6H, m), 1.30-1.35 (3H, m), 1.36-1.55 (2H, m), 1.50-1.69 (1H, m), 2.82 (1H, d), 2.89 (1H, d), 3.16 (3H, d), 3.48 (1H, d), 3.50-3.60 (1H, m), 3.64-3.74 (1H, m), 4.23 (1H, hept), 6.83-6.93 (2H, m), 7.29-7.37 (1H, m).

Example 7

N-(4-((R*)-2-(5-Fluoro-6-methoxypyridin-3-yl)propyl)-6-(((R)-1-hydroxy-4-methylpentan-2-yl)amino)-1,3,5-triazin-2-yl)methanesulfonamide (Isomer 1)

Isomer 1

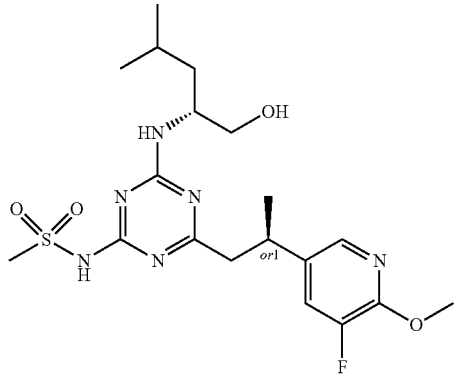

Example 8

N-(4-((S*)-2-(5-Fluoro-6-methoxypyridin-3-yl)propyl)-6-(((R)-1-hydroxy-4-methylpentan-2-yl)amino)-1,3,5-triazin-2-yl)methanesulfonamide (Isomer 2)

Isomer 2

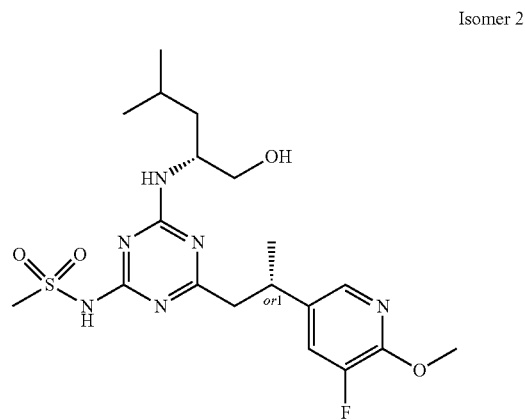

The diastereomers of N-(4-(2-(5-fluoro-6-methoxypyridin-3-yl)propyl)-6-(((R)-1-hydroxy-4-methylpentan-2-yl)amino)-1,3,5-triazin-2-yl)methanesulfonamide Intermediate 12 (33 mg, 0.07 mmol) were separated by preparative chiral HPLC on a Chiralpak IC column (250×20 mm, 5 μm), eluted with 20% EtOH/DEA (100/0.5) in $CO_2$, 120 bar at a flow rate of 70 mL/min and detected at 230 nm, to give the first eluting compound N-(4-((R*)-2-(5-fluoro-6-methoxypyridin-3-yl)propyl)-6-(((R)-1-hydroxy-4-methylpentan-2-yl)amino)-1,3,5-triazin-2-yl)methanesulfonamide (Isomer 1) Example 7 that was dissolved in EtOAc and washed with aqueous citric acid and brine. The organic extract was dried over $Na_2SO_4$, filtered and evaporated to yield (15 mg, 45%); HRMS (ESI) m/z [M+H]$^+$ calcd for $C_{19}H_{30}FN_6O_4S$: 457.2028, found: 457.2020; $^1$H NMR (400 MHz, MeOD) 0.84-0.99 (6H, m), 1.31-1.54 (5H, m), 1.54-1.71 (1H, m), 2.67-2.98 (m, partial overlap with citric acid residues), 3.16 (3H, d), 3.37-3.63 (3H, m), 3.95 (3H, d), 4.18-4.28 (1H, m), 7.44 (1H, ddd), 7.77 (1H, dd). The second eluting compound from the chiral separation, N-(4-((S*)-2-(5-fluoro-6-methoxypyridin-3-yl)propyl)-6-(((R)-1-hydroxy-4-methylpentan-2-yl)amino)-1,3,5-triazin-2-yl)methanesulfonamide (Isomer 2) Example 8 was dissolved in EtOAc and washed with aqueous citric acid and brine. The organic extract was dried over $Na_2SO_4$, filtered and evaporated to yield (13 mg, 39%); HRMS (ESI) m/z [M+H]$^+$ calcd for $C_{19}H_{30}FN_6O_4S$: 457.2028, found: 457.2010; $^1$H NMR (400 MHz, MeOD) 0.87-0.99 (6H, m), 1.31-1.53 (5H, m), 1.55-1.71 (1H, m), 2.68-2.97 (m, partial overlap with citric acid residues), 3.16 (3H, d), 3.34-3.61 (3H, m), 3.95 (3H, d), 4.15-4.27 (1H, m), 7.44 (1H, dt), 7.74-7.79 (1H, m).

Example 9

N-(4-((R*)-2-(5-Chloro-6-methoxypyridin-3-yl)propyl)-6-(((R)-1-hydroxy-4-methylpentan-2-yl)amino)-1,3,5-triazin-2-yl)methanesulfonamide (Isomer 1)

Isomer 1

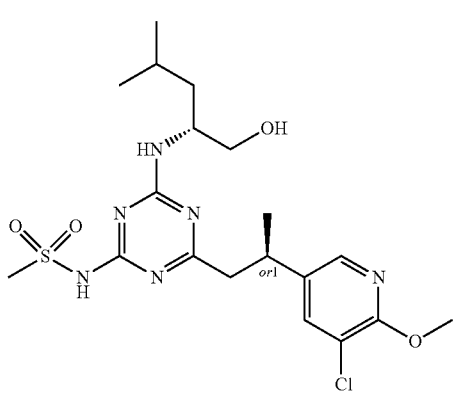

Example 10

N-(4-((S*)-2-(5-Chloro-6-methoxypyridin-3-yl)propyl)-6-(((R)-1-hydroxy-4-methylpentan-2-yl)amino)-1,3,5-triazin-2-yl)methanesulfonamide (Isomer 2)

Isomer 2

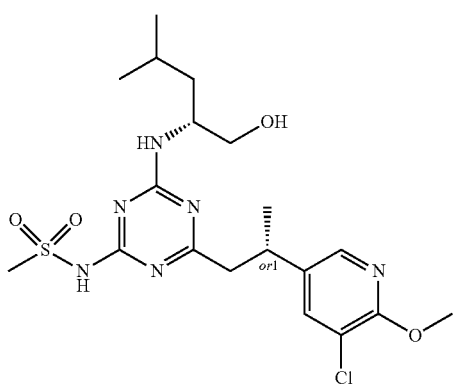

The diastereomers of N-(4-(2-(5-chloro-6-methoxypyridin-3-yl)propyl)-6-(((R)-1-hydroxy-4-methylpentan-2-yl)amino)-1,3,5-triazin-2-yl)methanesulfonamide Intermediate 14 (23 mg, 0.05 mmol) were separated by preparative chiral HPLC on a Chiralpak IC column (250×20 mm, 5 μm), eluted with 20% EtOH/DEA (100/0.5) in $CO_2$, 120 bar at a flow rate of 70 mL/min and detected at 230 nm, to give the first eluting compound N-(4-((R*)-2-(5-chloro-6-methoxypyridin-3-yl)propyl)-6-(((R)-1-hydroxy-4-methylpentan-2-yl)amino)-1,3,5-triazin-2-yl)methanesulfonamide (Isomer 1) Example 9 that was dissolved in EtOAc and washed with aqueous citric acid and brine. The organic extract was dried over $Na_2SO_4$, filtered and evaporated to yield (7.9 mg, 34%); IRMS (ESI) m/z [M+H]$^+$ calcd for $C_{19}H_{30}ClN_6O_4S$: 473.1732, found: 473.1724; $^1$H NMR (500 MHz, MeOD) 0.83-0.99 (6H, m), 1.32-1.54 (5H, m), 1.55-1.73 (1H, m), 2.68-2.94 (m, partial overlap with citric acid residues), 3.16 (3H, d), 3.35-3.43 (1H, m), 3.47-3.60 (2H, m), 3.94 (3H, d), 4.17-4.28 (1H, m), 7.70 (1H, dd), 7.91 (1H, dd). The second eluting compound from the chiral separation, N-(4-((S*)-2-(5-chloro-6-methoxypyridin-3-yl)propyl)-6-(((R)-1-hydroxy-4-methylpentan-2-yl)amino)-1,3,5-triazin-2-yl)methanesulfonamide (Isomer 2) Example 10 was dissolved in EtOAc and washed with aqueous citric acid and brine. The organic extract was dried over $Na_2SO_4$, filtered and evaporated to yield (8.2 mg, 36%); IRMS (ESI) m/z [M+H]$^+$ calcd for $C_{19}H_{30}ClN_6O_4S$: 473.1732, found: 473.1734; $^1$H NMR (500 MHz, MeOD) 0.87-0.98 (6H, m), 1.32-1.52 (5H, m), 1.58-1.69 (1H, m), 2.69-2.93 (m, partial overlap with citric acid residues), 3.16 (3H, d), 3.35-3.43 (1H, m), 3.46-3.60 (2H, m), 3.95 (3H, d), 4.15-4.26 (1H, m), 7.68-7.71 (1H, m), 7.88-7.92 (1H, m).

Example 11

N-(4-((S*)-2-(2-Cyclopropylpyrimidin-5-yl)propyl)-6-(((R)-1-hydroxy-4-methylpentan-2-yl)amino)-1,3,5-triazin-2-yl)methanesulfonamide (Isomer 1)

Isomer 1

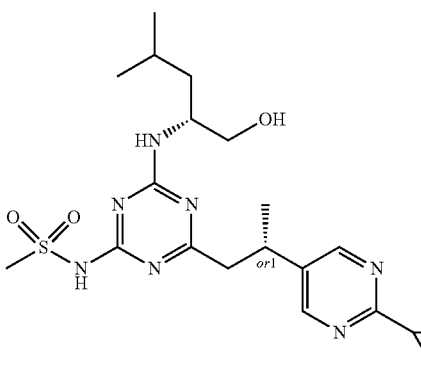

Example 12

N-(4-((R*)-2-(2-Cyclopropylpyrimidin-5-yl)propyl)-6-(((R)-1-hydroxy-4-methylpentan-2-yl)amino)-1,3,5-triazin-2-yl)methanesulfonamide (Isomer 2)

Isomer 2

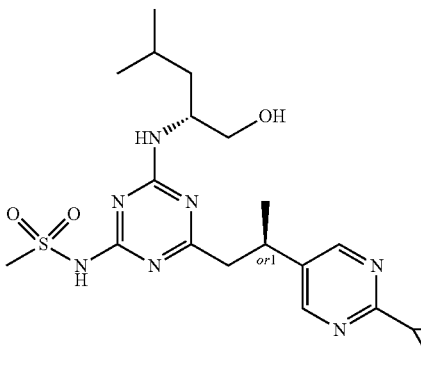

The diastereomers of N-(4-(2-(2-cyclopropylpyrimidin-5-yl)propyl)-6-(((R)-1-hydroxy-4-methylpentan-2-yl)amino)-1,3,5-triazin-2-yl)methanesulfonamide Intermediate 16 (49 mg, 0.11 mmol) were separated by preparative chiral HPLC on a Chiralpak AD column (250×20 mm, 5 μm), eluted with 20% EtOH/DEA (100/0.5) in $CO_2$, 120 bar at a flow rate of 70 mL/min and detected at 230 nm, to give the first eluting compound N-(4-((S*)-2-(2-cyclopropylpyrimidin-5-yl)propyl)-6-(((R)-1-hydroxy-4-methylpentan-2-yl)amino)-1,3,5-triazin-2-yl)methanesulfonamide (Isomer 1) Example 11 that was dissolved in EtOAc and washed with aqueous citric acid and brine. The organic extract was dried over $Na_2SO_4$, filtered and evaporated to yield (28 mg, 57%); HRMS (ESI) m/z $[M+H]^+$ calcd for $C_{20}H_{32}N_7O_3S$: 450.2282, found: 450.2276; $^1H$ NMR (500 MHz, MeOD) 0.84-0.97 (6H, m), 1.04-1.09 (4H, m), 1.33-1.53 (5H, m), 1.57-1.68 (1H, m), 2.14-2.22 (1H, m), 2.76-2.96 (m, partial overlap with citric acid residues), 3.16-3.19 (3H, m), 3.37-3.60 (3H, m), 4.09-4.26 (1H, m), 8.50-8.53 (2H, m). The second eluting compound from the chiral separation, N-(4-((R*)-2-(2-cyclopropylpyrimidin-5-yl)propyl)-6-(((R)-1-hydroxy-4-methylpentan-2-yl)amino)-1,3,5-triazin-2-yl)methanesulfonamide (Isomer 2) Example 12 was dissolved in EtOAc and washed with aqueous citric acid and brine. The organic extract was dried over $Na_2SO_4$, filtered and evaporated to yield (28 mg, 57%); HRMS (ESI) m/z $[M+H]^+$ calcd for $C_{20}H_{32}N_7O_3S$: 450.2282, found: 450.2292; $^1H$ NMR (500 MHz, MeOD) 0.85-0.98 (6H, m), 1.03-1.10 (4H, m), 1.33-1.53 (5H, m), 1.55-1.70 (1H, m), 2.13-2.22 (1H, m), 2.76-2.98 (m, partial overlap with citric acid residues), 3.16-3.19 (3H, m), 3.39-3.63 (3H, m), 4.15-4.26 (1H, m), 8.50-8.53 (2H, m).

Example 13

N-(4-(((R)-1-Hydroxy-4-methylpentan-2-yl)amino)-6-((R*)-2-(6-methoxy-4-methylpyridin-3-yl)propyl)-1,3,5-triazin-2-yl)methanesulfonamide (Isomer 1)

Isomer 1

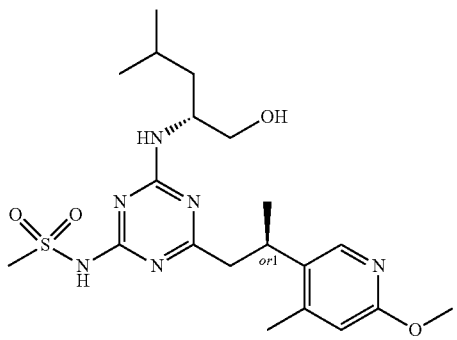

Example 14

N-(4-(((R)-1-Hydroxy-4-methylpentan-2-yl)amino)-6-((S*)-2-(6-methoxy-4-methylpyridin-3-yl)propyl)-1,3,5-triazin-2-yl)methanesulfonamide (Isomer 2)

Isomer 2

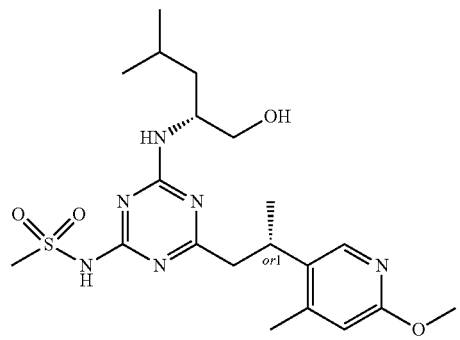

The diastereomers of N-(4-(((R)-1-hydroxy-4-methylpentan-2-yl)amino)-6-(2-(6-methoxy-4-methylpyridin-3-yl)propyl)-1,3,5-triazin-2-yl)methanesulfonamide Intermediate 19 (52 mg, 0.11 mmol) were separated by preparative chiral HPLC on a Chiralpak IB column (250×30 mm, 5 μm), eluted with 15% EtOH/DEA (100/0.5) in $CO_2$, 120 bar at a flow rate of 150 mL/min and detected at 230 nm, to give the first eluting compound N-(4-(((R)-1-hydroxy-4-methylpentan-2-yl)amino)-6-((R*)-2-(6-methoxy-4-methylpyridin-3-yl)propyl)-1,3,5-triazin-2-yl)methanesulfonamide (Isomer 1) Example 13 that was dissolved in EtOAc and washed with dilute acetic acid (0.5%) and brine. The organic extract was dried over $Na_2SO_4$, filtered and evaporated to yield (25 mg, 48%); HRMS (ESI) m/z $[M+H]^+$ calcd for $C_{20}H_{33}N_6O_4S$: 453.2278, found: 453.2254; $^1H$ NMR (500 MHz, $CDCl_3$) 0.85-0.98 (6H, m), 1.24-1.51 (5H, m), 1.56-1.73 (1H, m), 2.30 (3H, s), 2.78-3.04 (2H, m), 3.27 (3H, d), 3.46-3.61 (2H, m), 3.63-3.81 (1H, m), 3.87 (3H, d), 4.15-4.26 (1H, d), 6.51 (1H, s), 8.00 (1H, d). The second eluting compound from the chiral separation, N-(4-(((R)-1-hydroxy-4-methylpentan-2-yl)amino)-6-((S*)-2-(6-methoxy-4-methylpyridin-3-yl)propyl)-1,3,5-triazin-2-yl)methanesulfonamide (Isomer 2) Example 14 was dissolved in EtOAc and washed with dilute acetic acid (0.5%) and brine. The organic extract was dried over $Na_2SO_4$, filtered and evaporated to yield (17 mg, 33%); HRMS (ESI) m/z $[M+H]^+$ calcd for $C_{20}H_{33}N_6O_4S$: 453.2278, found: 453.2274; $^1H$ NMR (500 MHz, $CDCl_3$) 0.86-0.97 (6H, m), 1.24-1.51 (5H, m), 1.56-1.72 (1H, m), 2.26-2.32 (3H, m), 2.80-3.04 (2H, m), 3.28 (3H, d), 3.47-3.61 (2H, m), 3.63-3.81 (1H, m), 3.87 (3H, d), 4.16-4.26 (1H, m), 6.51 (1H, d), 8.02 (1H, d).

Example 15

N-(4-(((R)-1-Hydroxy-4-methylpentan-2-yl)amino)-6-((R*)-2-(6-methoxy-5-methylpyridin-3-yl)propyl)-1,3,5-triazin-2-yl)methanesulfonamide (Isomer 1)

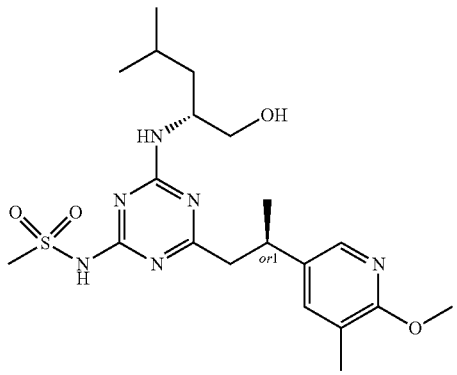

Example 16

N-(4-(((R)-1-Hydroxy-4-methylpentan-2-yl)amino)-6-((S*)-2-(6-methoxy-5-methylpyridin-3-yl)propyl)-1,3,5-triazin-2-yl)methanesulfonamide (Isomer 2)

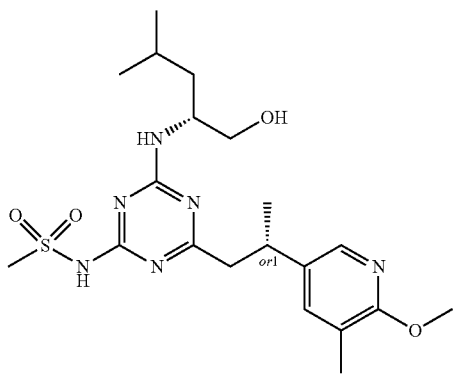

The diastereomers of N-(4-(((R)-1-hydroxy-4-methylpentan-2-yl)amino)-6-(2-(6-methoxy-5-methylpyridin-3-yl)propyl)-1,3,5-triazin-2-yl)methanesulfonamide Intermediate 21 (52 mg, 0.11 mmol) were separated by preparative chiral HPLC on a Chiralpak IC column (250×20 mm, 5 μm), eluted with 35% EtOH/DEA (100/0.5) in $CO_2$, 120 bar at a flow rate of 60 mL/min and detected at 230 nm, to give the first eluting compound N-(4-(((R)-1-hydroxy-4-methylpentan-2-yl)amino)-6-((R*)-2-(6-methoxy-5-methylpyridin-3-yl)propyl)-1,3,5-triazin-2-yl)methanesulfonamide (Isomer 1) Example 15 that was dissolved in EtOAc and washed with dilute acetic acid (0.5%) and brine. The organic extract was dried over $Na_2SO_4$, filtered and evaporated to yield (23 mg, 44%); HRMS (ESI) m/z [M+H]$^+$ calcd for $C_{20}H_{33}N_6O_4S$: 453.2278, found: 453.2272; $^1$H NMR (500 MHz, CDCl$_3$) 0.86-0.97 (6H, m), 1.24-1.32 (3H, m), 1.33-1.49 (2H, m), 1.56-1.72 (1H, m), 2.13-2.17 (3H, m), 2.89 (2H, dd), 3.20-3.40 (4H, m), 3.45-3.80 (2H, m), 3.88-3.93 (3H, m), 4.16-4.27 (1H, m), 7.28-7.33 (1H, m), 7.81 (1H, dd). The second eluting compound from the chiral separation, N-(4-(((R)-1-hydroxy-4-methylpentan-2-yl)amino)-6-((S*)-2-(6-methoxy-5-methylpyridin-3-yl)propyl)-1,3,5-triazin-2-yl)methanesulfonamide (Isomer 2) Example 16 was dissolved in EtOAc and washed with dilute acetic acid (0.5%) and brine. The organic extract was dried over $Na_2SO_4$, filtered and evaporated to yield (24 mg, 46%); HRMS (ESI) m/z [M+H]$^+$ calcd for $C_{20}H_{33}N_6O_4S$: 453.2278, found: 453.2270; 0.85-0.97 (6H, m), 1.24-1.50 (5H, m), 1.55-1.72 (1H, m), 2.15 (3H, s), 2.80-2.95 (2H, m), 3.21-3.32 (4H, m), 3.51-3.80 (2H, m), 3.91 (3H, s), 4.09-4.25 (1H, m), 7.30 (1H, ddd), 7.80 (1H, dd).

Example 17

N-(4-(((R)-1-Hydroxy-4-methylpentan-2-yl)amino)-6-((R*)-2-(2-methoxypyridin-3-yl)propyl)-1,3,5-triazin-2-yl)methanesulfonamide (Isomer 1)

Isomer 1

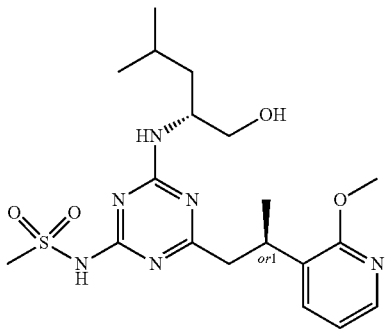

Example 18

N-(4-(((R)-1-Hydroxy-4-methylpentan-2-yl)amino)-6-((S*)-2-(2-methoxypyridin-3-yl)propyl)-1,3,5-triazin-2-yl)methanesulfonamide (Isomer 2)

Isomer 2

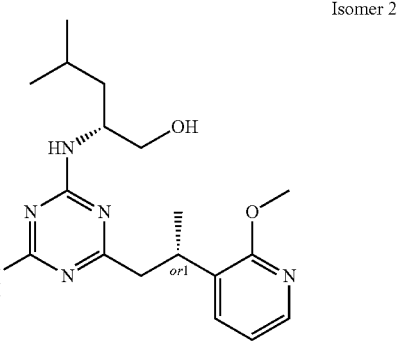

The diastereomers of N-(4-(((R)-1-hydroxy-4-methylpentan-2-yl)amino)-6-(2-(2-methoxypyridin-3-yl)propyl)-1,3,5-triazin-2-yl)methanesulfonamide Intermediate 23 (166 mg, 0.38 mmol) were separated by preparative chiral HPLC on a Chiralcel OJ column (250×30 mm, 5 μm), eluted with 15% EtOH/TEA (100/0.5) in $CO_2$, 120 bar at a flow rate of 130 mL/min and detected at 230 nm, to give the first eluting compound N-(4-(((R)-1-hydroxy-4-methylpentan-2-yl)amino)-6-((R*)-2-(2-methoxypyridin-3-yl)propyl)-1,3,5-triazin-2-yl)methanesulfonamide (Isomer 1) Example 17 that was dissolved in EtOAc and washed with dilute HCl (aq) and brine. The organic extract was dried over $MgSO_4$, filtered and evaporated to yield (50 mg, 30%); HRMS (ESI) m/z $[M+H]^+$ calcd for $C_{19}H_{31}N_6O_4S$: 439.2122, found: 439.2126; $^1$H NMR (500 MHz, MeOD) 0.86-0.97 (6H, m), 1.29-1.52 (5H, m), 1.57-1.72 (1H, m), 2.73-2.91 (2H, m), 3.08-3.18 (m, partial overlap with TEA residues), 3.44-3.70 (3H, m), 3.89 (3H, d), 4.10-4.28 (1H, m), 6.90 (1H, dd), 7.58 (1H, d), 7.96 (1H, d). The second eluting compound from the chiral separation, N-(4-(((R)-1-hydroxy-4-methylpentan-2-yl)amino)-6-((S*)-2-(2-methoxypyridin-3-yl)propyl)-1,3,5-triazin-2-yl)methanesulfonamide (Isomer 2) Example 18 was dissolved in EtOAc and washed with dilute HCl (aq) and brine. The organic extract was dried over $MgSO_4$, filtered and evaporated to yield (42 mg, 25%); HRMS (ESI) m/z $[M+H]^+$ calcd for $C_{19}H_{31}N_6O_4S$: 439.2122, found: 439.2124; $^1$H NMR (500 MHz, MeOD) 0.87-0.97 (6H, m), 1.31-1.52 (m, partial overlap with TEA residues), 1.55-1.72 (1H, m), 2.72-2.91 (2H, m), 3.15 (3H, d), 3.44-3.72 (3H, m), 3.89 (3H, d), 4.12-4.27 (1H, m), 6.91 (1H, dd), 7.58 (1H, dt), 7.97 (1H, dt).

Example 19

N-(4-((R*)-2-(3-Fluoro-4-methoxyphenyl)propyl)-6-(((R)-1-hydroxy-4-methylpentan-2-yl)amino)-1,3,5-triazin-2-yl)methanesulfonamide (Isomer 1)

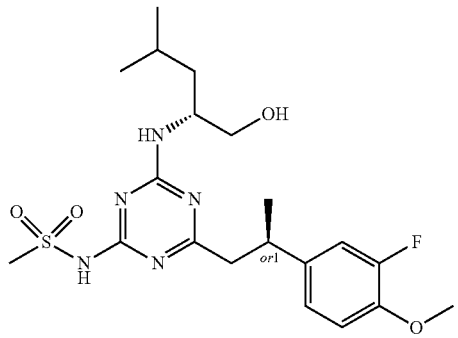

Isomer 1

Example 20

N-(4-((S*)-2-(3-Fluoro-4-methoxyphenyl)propyl)-6-(((R)-1-hydroxy-4-methylpentan-2-yl)amino)-1,3,5-triazin-2-yl)methanesulfonamide (Isomer 2)

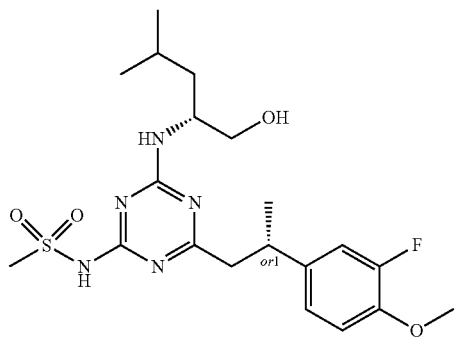

Isomer 2

The diastereomers of N-(4-(2-(3-fluoro-4-methoxyphenyl)propyl)-6-(((R)-1-hydroxy-4-methylpentan-2-yl)amino)-1,3,5-triazin-2-yl)methanesulfonamide Intermediate 25 (64 mg, 0.14 mmol) were separated by preparative chiral HPLC on a Chiralpak IC column (250×20 mm, 5 μm), eluted with 30% EtOH/DEA (100/0.5) in $CO_2$, 120 bar at a flow rate of 80 mL/min and detected at 254 nm, to give the first eluting compound N-(4-((R*)-2-(3-fluoro-4-methoxyphenyl)propyl)-6-(((R)-1-hydroxy-4-methylpentan-2-yl)amino)-1,3,5-triazin-2-yl)methanesulfonamide (Isomer 1) Example 19 that was dissolved in EtOAc and washed with dilute HCl and brine. The organic extract was dried over $MgSO_4$, filtered and evaporated to yield (30 mg, 47%); HRMS (ESI) m/z $[M+H]^+$ calcd for $C_{20}H_{31}FN_5O_4S$: 456.2076, found: 456.2088; $^1$H NMR (400 MHz, $CDCl_3$) 0.87-0.98 (6H, m), 1.22-1.54 (m, partial overlap with solvent residues), 1.55-1.73 (1H, m), 2.86-2.98 (2H, m), 3.19-3.40 (4H, m), 3.52-3.89 (5H, m), 4.16-4.31 (1H, m), 6.80-7.01 (3H, m). The second eluting compound from the chiral separation, N-(4-((S*)-2-(3-fluoro-4-methoxyphenyl)propyl)-6-(((R)-1-hydroxy-4-methylpentan-2-yl)amino)-1,3,5-triazin-2-yl)methanesulfonamide (Isomer 2) Example 20 was dissolved in EtOAc and washed with dilute HCl and brine. The organic extract was dried over $MgSO_4$, filtered and evaporated to yield (28 mg, 44%); HRMS (ESI) m/z $[M+H]^+$ calcd for $C_{20}H_{31}FN_5O_4S$: 456.2076, found: 456.2092; $^1$H NMR (400 MHz, $CDCl_3$) 0.88-0.98 (6H, m), 1.22-1.54 (m, partial overlap with solvent residues), 1.55-1.73 (1H, m), 2.81-2.95 (2H, m), 3.18-3.36 (4H, m), 3.53-3.87 (5H, m), 4.17-4.29 (1H, d), 6.80-7.02 (3H, m).

Example 21

N-(4-(((R)-1-Hydroxy-4-methylpentan-2-yl)amino)-6-((S*)-2-(3,4,5-trifluorophenyl)propyl)-1,3,5-triazin-2-yl)methanesulfonamide (Isomer 1)

Isomer 1

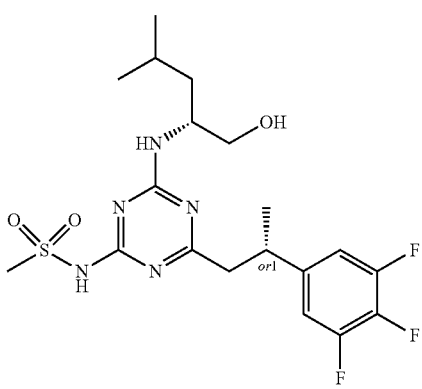

Example 22

N-(4-(((R)-1-Hydroxy-4-methylpentan-2-yl)amino)-6-((R*)-2-(3,4,5-trifluorophenyl)propyl)-1,3,5-triazin-2-yl)methanesulfonamide (Isomer 2)

Isomer 2

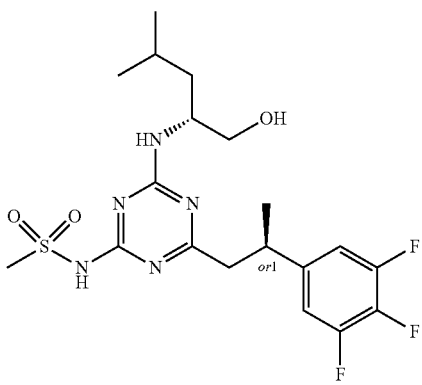

The diastereomers of N-(4-(((R)-1-hydroxy-4-methylpentan-2-yl)amino)-6-(2-(3,4,5-trifluorophenyl)propyl)-1,3,5-triazin-2-yl)methanesulfonamide Intermediate 27 (98 mg, 0.21 mmol) were separated by preparative chiral HPLC on a Chiralpak IA column (250×20 mm, 5 μm), eluted with 15% EtOH/DEA (100/0.5) in $CO_2$, 120 bar at a flow rate of 70 mL/min and detected at 254 nm, to give the first eluting compound N-(4-(((R)-1-hydroxy-4-methylpentan-2-yl)amino)-6-((S*)-2-(3,4,5-trifluorophenyl)propyl)-1,3,5-triazin-2-yl)methanesulfonamide (Isomer 1) Example 21 that was dissolved in EtOAc and washed with dilute HCl and brine. The organic extract was dried over $MgSO_4$, filtered and evaporated to yield (22 mg, 22%); HRMS (ESI) m/z $[M+H]^+$ calcd for $C_{19}H_{27}F_3N_5O_3S$: 462.1780, found: 462.1792; $^1$H NMR (400 MHz, $CDCl_3$) 0.85-1.01 (6H, m), 1.22-1.54 (m, partial overlap with solvent residues), 1.55-1.74 (1H, m), 2.84-2.99 (2H, m), 3.22-3.41 (4H, m), 3.53-3.65 (1H, m), 3.66-3.83 (1H, m), 4.16-4.30 (1H, m), 6.82-6.94 (2H, m). The second eluting compound from the chiral separation, N-(4-(((R)-1-hydroxy-4-methylpentan-2-yl)amino)-6-((R*)-2-(3,4,5-trifluorophenyl)propyl)-1,3,5-triazin-2-yl)methanesulfonamide (Isomer 2) Example 22 was dissolved in EtOAc and washed with dilute HCl and brine. The organic extract was dried over $MgSO_4$, filtered and evaporated to yield (27 mg, 28%); HRMS (ESI) m/z $[M+H]^+$ calcd for $C_{19}H_{27}F_3N_5O_3S$: 462.1780, found: 462.1792; 0.85-1.01 (6H, m), 1.22-1.54 (m, partial overlap with solvent residues), 1.55-1.74 (1H, m), 2.81-3.00 (2H, m), 3.23-3.43 (4H, m), 3.54-3.65 (1H, m), 3.66-3.84 (1H, m), 4.18-4.32 (1H, m), 6.83-6.95 (2H, m).

Example 23

N-(4-((S*)-2-(2,5-Difluorophenyl)propyl)-6-(((R)-1-hydroxy-4-methylpentan-2-yl)amino)-1,3,5-triazin-2-yl)methanesulfonamide (Isomer 1)

Isomer 1

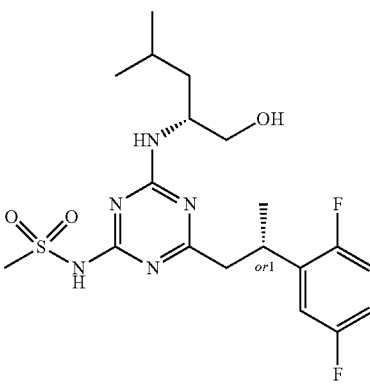

Example 24

N-(4-((R*)-2-(2,5-Difluorophenyl)propyl)-6-(((R)-1-hydroxy-4-methylpentan-2-yl)amino)-1,3,5-triazin-2-yl)methanesulfonamide (Isomer 2)

Isomer 2

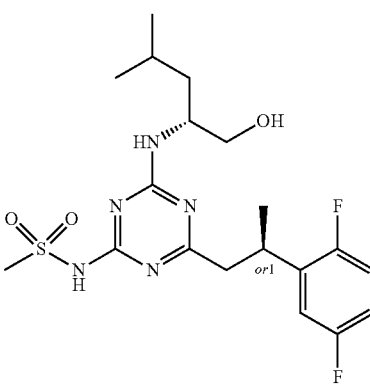

The diastereomers of N-(4-(2-(2,5-difluorophenyl)propyl)-6-(((R)-1-hydroxy-4-methylpentan-2-yl)amino)-1,3,5-triazin-2-yl)methanesulfonamide Intermediate 29 (28 mg, 0.06 mmol) were separated by preparative chiral HPLC on a Chiralcel OJ column (250×30 mm, 5 µm), eluted with 15% EtOH/DEA (100/0.5) in $CO_2$, 120 bar at a flow rate of 70 mL/min and detected at 260 nm, to give the first eluting compound N-(4-((S*)-2-(2,5-difluorophenyl)propyl)-6-(((R)-1-hydroxy-4-methylpentan-2-yl)amino)-1,3,5-triazin-2-yl)methanesulfonamide (Isomer 1) Example 23 that was dissolved in EtOAc and washed with dilute HCl and brine. The organic extract was dried over $MgSO_4$, filtered and evaporated to yield (10 mg, 36%); IRMS (ESI) m/z [M+H]$^+$ calcd for $C_{19}H_{28}F_2N_5O_3S$: 444.1876, found: 444.1900; $^1$H NMR (400 MHz, $CDCl_3$) 0.84-1.00 (6H, m), 1.28-1.53 (5H, m), 1.55-1.73 (1H, m), 2.87-3.03 (2H, m), 3.23-3.34 (3H, m), 3.52-3.81 (3H, m), 4.15-4.26 (1H, m), 6.77-6.86 (1H, m), 6.89-7.01 (2H, m). The second eluting compound from the chiral separation, N-(4-((R*)-2-(2,5-difluorophenyl)propyl)-6-(((R)-1-hydroxy-4-methylpentan-2-yl)amino)-1,3,5-triazin-2-yl)methanesulfonamide (Isomer 2) Example 24 was dissolved in EtOAc and washed with dilute HCl and brine. The organic extract was dried over $MgSO_4$, filtered and evaporated to yield (11 mg, 39%); IRMS (ESI) m/z [M+H]$^+$ calcd for $C_{19}H_{28}F_2N_5O_3S$: 444.1876, found: 444.1888; $^1$H NMR (400 MHz, $CDCl_3$) 0.85-0.98 (6H, m), 1.25-1.53 (m, partial overlap with solvent residues), 1.54-1.70 (1H, m), 2.83-3.04 (2H, m), 3.22-3.31 (3H, m), 3.52-3.80 (3H, m), 4.16-4.28 (1H, m), 6.77-6.86 (1H, m), 6.88-7.01 (2H, m).

Example 25

N-(4-((S*)-2-(2-Chloropyridin-4-yl)propyl)-6-(((R)-1-hydroxy-4-methylpentan-2-yl)amino)-1,3,5-triazin-2-yl)methanesulfonamide (Isomer 1)

Isomer 1

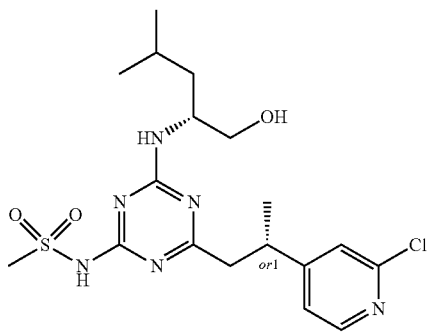

Example 26

N-(4-((R*)-2-(2-Chloropyridin-4-yl)propyl)-6-(((R)-1-hydroxy-4-methylpentan-2-yl)amino)-1,3,5-triazin-2-yl)methanesulfonamide (Isomer 2)

Isomer 2

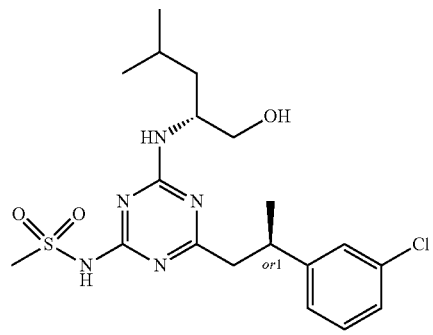

The diastereomers of N-(4-(2-(2-chloropyridin-4-yl)propyl)-6-(((R)-1-hydroxy-4-methylpentan-2-yl)amino)-1,3,5-triazin-2-yl)methanesulfonamide Intermediate 31 (23 mg, 0.05 mmol) were separated by preparative chiral HPLC on a Chiralcel OJ column (250×30 mm, 5 µm), eluted with 20% EtOH/TEA (100/0.5) in $CO_2$, 120 bar at a flow rate of 87.5 mL/min and detected at 230 nm, to give the first eluting compound N-(4-((S*)-2-(2-chloropyridin-4-yl)propyl)-6-(((R)-1-hydroxy-4-methylpentan-2-yl)amino)-1,3,5-triazin-2-yl)methanesulfonamide (Isomer 1) Example 25 that was dissolved in EtOAc and washed with dilute HCl and brine. The organic extract was dried over $MgSO_4$, filtered and evaporated. The residue was purified by preparative HPLC, PrepMethod C, (gradient: 20-60%) to yield (4.6 mg, 20%); IRMS (ESI) m/z [M+H]$^+$ calcd for $C_{18}H_{28}C_1N_6O_3S$: 443.1626, found: 443.1626; $^1$H NMR (400 MHz, $CDCl_3$) 0.87-0.99 (6H, m), 1.30-1.54 (5H, m), 1.55-1.71 (1H, m), 2.82-3.02 (2H, m), 3.29-3.45 (m, partial overlap with byproduct), 3.56-3.64 (1H, m), 3.66-3.83 (1H, m), 4.13-4.28 (1H, m), 7.12 (1H, dd), 7.20-7.24 (1H, m), 8.24-8.32 (1H, m). The second eluting compound from the chiral separation, N-(4-((R*)-2-(2-chloropyridin-4-yl)propyl)-6-(((R)-1-hydroxy-4-methylpentan-2-yl)amino)-1,3,5-triazin-2-yl)methanesulfonamide (Isomer 2) Example 26 was dissolved in EtOAc and washed with dilute HCl and brine. The organic extract was dried over $MgSO_4$, filtered and evaporated to yield (5.6 mg, 24%); IRMS (ESI) m/z [M+H]$^+$ calcd for $C_{18}H_{28}C_1N_6O_3S$: 443.1626, found: 443.1618; $^1$H NMR (500 MHz, $CDCl_3$) 0.87-0.98 (6H, m), 1.28-1.52 (5H, m), 1.55-1.71 (1H, m), 2.82-3.02 (2H, m), 3.25-3.45 (4H, m), 3.53-3.61 (1H, m), 3.63-3.81 (1H, m), 4.16-4.26 (1H, m), 7.09-7.14 (1H, m), 7.22 (1H, d), 8.26 (1H, d).

Example 27

N-(4-((R*)-2-(6-Ethoxypyridin-3-yl)propyl)-6-(((R)-1-hydroxy-4-methylpentan-2-yl)amino)-1,3,5-triazin-2-yl)methanesulfonamide (Isomer 1)

Isomer 1

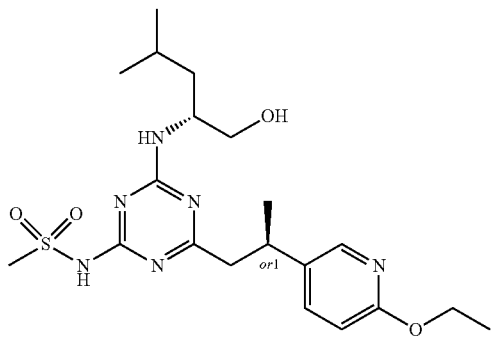

Example 28

N-(4-((S*)-2-(6-Ethoxypyridin-3-yl)propyl)-6-(((R)-1-hydroxy-4-methylpentan-2-yl)amino)-1,3,5-triazin-2-yl)methanesulfonamide (Isomer 2)

Isomer 2

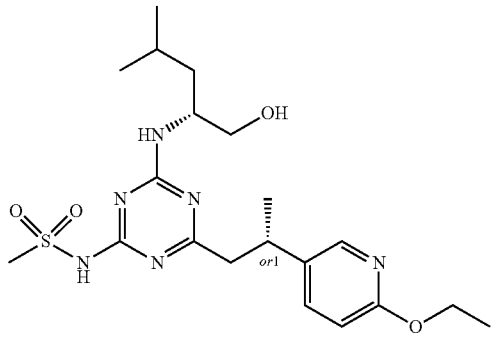

The diastereomers of N-(4-(2-(6-ethoxypyridin-3-yl)propyl)-6-(((R)-1-hydroxy-4-methylpentan-2-yl)amino)-1,3,5-triazin-2-yl)methanesulfonamide Intermediate 33 (23.5 mg, 0.05 mmol) were separated by preparative chiral HPLC on a Chiralpak IC column (250×30 mm, 5 μm), eluted with 27% EtOH/DEA (100/0.5) in $CO_2$, 100 bar at a flow rate of 160 mL/min and detected at 230 nm, to give the first eluting compound N-(4-((R*)-2-(6-ethoxypyridin-3-yl)propyl)-6-(((R)-1-hydroxy-4-methylpentan-2-yl)amino)-1,3,5-triazin-2-yl)methanesulfonamide (Isomer 1) Example 27 that was dissolved in EtOAc and washed with dilute HCl and brine. The organic extract was dried over $MgSO_4$, filtered and evaporated to yield (10.6 mg, 45%); HRMS (ESI) m/z [M+H]$^+$ calcd for $C_{20}H_{33}N_6O_4S$: 453.2278, found: 453.2306; $^1$H NMR (400 MHz, CDCl$_3$) 0.86-0.97 (6H, m), 1.22-1.50 (8H, m), 1.54-1.70 (1H, m), 2.86-3.00 (2H, m), 3.21-3.40 (4H, m), 3.46-3.82 (2H, m), 4.16-4.33 (3H, m), 6.65 (1H, d), 7.46-7.52 (1H, m), 7.95-8.00 (1H, m). The second eluting compound from the chiral separation, N-(4-((S*)-2-(6-ethoxypyridin-3-yl)propyl)-6-(((R)-1-hydroxy-4-methylpentan-2-yl)amino)-1,3,5-triazin-2-yl)methanesulfonamide (Isomer 2) Example 28 was dissolved in EtOAc and washed with dilute HCl and brine. The organic extract was dried over $MgSO_4$, filtered and evaporated to yield (10.6 mg, 45%); HRMS (ESI) m/z [M+H]$^+$ calcd for $C_{20}H_{33}N_6O_4S$: 453.2278, found: 453.2302; $^1$H NMR (400 MHz, CDCl$_3$) 0.84-0.98 (6H, m), 1.22-1.51 (8H, m), 1.54-1.72 (1H, m), 2.81-2.98 (2H, m), 3.21-3.38 (4H, m), 3.50-3.60 (1H, m), 3.61-3.82 (1H, m), 4.09-4.23 (1H, m), 4.28 (2H, q), 6.65 (1H, d), 7.44-7.53 (1H, m), 7.92-7.99 (1H, m).

Example 29

N-(4-((S*)-2-(5-Chloro-2-fluorophenyl)propyl)-6-(((R)-1-hydroxy-4-methylpentan-2-yl)amino)-1,3,5-triazin-2-yl)methanesulfonamide (Isomer 1)

Isomer 1

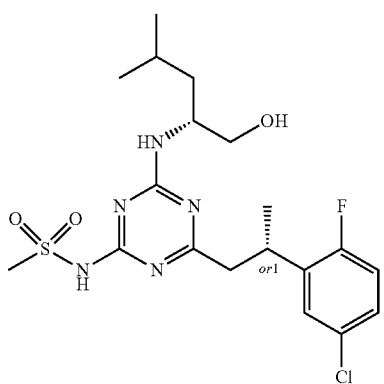

Example 30

N-(4-((R*)-2-(5-Chloro-2-fluorophenyl)propyl)-6-(((R)-1-hydroxy-4-methylpentan-2-yl)amino)-1,3,5-triazin-2-yl)methanesulfonamide (Isomer 2)

Isomer 2

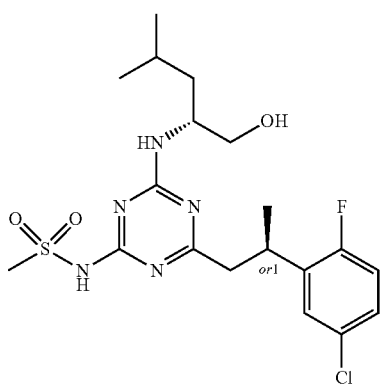

The diastereomers of N-(4-(2-(5-chloro-2-fluorophenyl)propyl)-6-(((R)-1-hydroxy-4-methylpentan-2-yl)amino)-1,3,5-triazin-2-yl)methanesulfonamide Intermediate 35 (12.8 mg, 0.03 mmol) were separated by preparative chiral HPLC on a Chiralcel OJ column (250×30 mm, 5 μm), eluted with 15% EtOH/DEA (100/0.5) in $CO_2$, 100 bar at a flow rate of 70 mL/min and detected at 260 nm, to give the first eluting compound N-(4-((S*)-2-(5-chloro-2-fluorophenyl)propyl)-6-(((R)-1-hydroxy-4-methylpentan-2-yl)amino)-1,3,5-triazin-2-yl)methanesulfonamide (Isomer 1) Example 29 that was dissolved in EtOAc and washed with dilute HCl and brine. The organic extract was dried over $MgSO_4$, filtered and evaporated to yield (4.2 mg, 33%); HRMS (ESI) m/z [M+H]$^+$ calcd for $C_{19}H_{28}ClFN_5O_3S$: 460.1580, found: 460.1610; $^1$H NMR (400 MHz, CDCl$_3$) 0.85-0.99 (6H, m), 1.29-1.53 (5H, m), 1.55-1.73 (1H, m), 2.85-3.03 (2H, m), 3.26-3.35 (3H, m), 3.54-3.79 (3H, m), 4.15-4.26 (1H, m), 6.88-6.96 (1H, m), 7.08-7.15 (1H, m), 7.24 (1H, dd). The second eluting compound from the chiral separation, N-(4-((R*)-2-(5-chloro-2-fluorophenyl)propyl)-6-(((R)-1-hydroxy-4-methylpentan-2-yl)amino)-1,3,5-triazin-2-yl)methanesulfonamide (Isomer 2) Example 30 was dissolved in EtOAc and washed with dilute HCl and brine. The organic extract was dried over $MgSO_4$, filtered and evaporated to yield (4.5 mg, 35%); HRMS (ESI) m/z [M+H]$^+$ calcd for $C_{19}H_{28}ClFN_5O_3S$: 460.1580, found: 460.1608; $^1$H NMR (400 MHz, CDCl$_3$) 0.86-0.98 (6H, m), 1.28-1.53 (5H, m), 1.55-1.73 (1H, m), 2.85-3.01 (2H, m), 3.26-3.35 (3H, m), 3.52-3.81 (3H, m), 4.16-4.30 (1H, m), 6.92 (1H, dd), 7.08-7.15 (1H, m), 7.23 (1H, dd).

Example 31

N-(4-((R*)-2-(4-Chloro-3,5-difluorophenyl)propyl)-6-(((R)-1-hydroxy-4-methylpentan-2-yl)amino)-1,3,5-triazin-2-yl)methanesulfonamide (Isomer 1)

Isomer 1

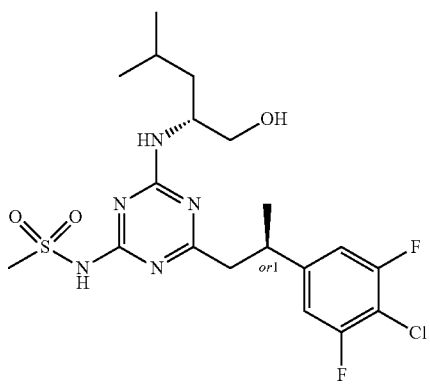

Example 32

N-(4-((S*)-2-(4-Chloro-3,5-difluorophenyl)propyl)-6-(((R)-1-hydroxy-4-methylpentan-2-yl)amino)-1,3,5-triazin-2-yl)methanesulfonamide (Isomer 2)

Isomer 2

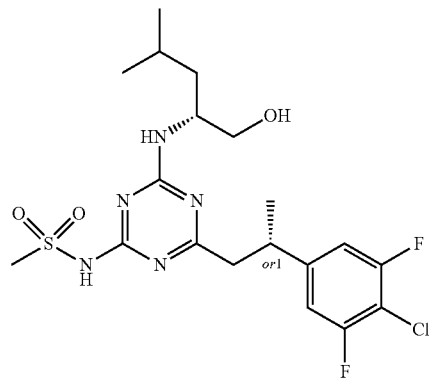

The diastereomers of N-(4-(2-(4-chloro-3,5-difluorophenyl)propyl)-6-(((R)-1-hydroxy-4-methylpentan-2-yl)amino)-1,3,5-triazin-2-yl)methanesulfonamide Intermediate 37 (25 mg, 0.05 mmol) were separated by preparative chiral HPLC on a Chiralcel IA column (250×30 mm, 5 μm), eluted with 10% EtOH/DEA (100/0.5) in $CO_2$, 120 bar at a flow rate of 100 mL/min and detected at 230 nm, to give the first eluting compound N-(4-((R*)-2-(4-chloro-3,5-difluorophenyl)propyl)-6-(((R)-1-hydroxy-4-methylpentan-2-yl)amino)-1,3,5-triazin-2-yl)methanesulfonamide (Isomer 1) Example 31 that was dissolved in EtOAc and washed with dilute HCl and brine. The organic extract was dried over $MgSO_4$, filtered and evaporated to yield (10.3 mg, 41%); HRMS (ESI) m/z [M+H]$^+$ calcd for $C_{19}H_{27}ClF_2N_5O_3S$: 478.1486, found: 478.1516; $^1$H NMR (400 MHz, CDCl$_3$) 0.85-0.98 (6H, m), 1.27-1.53 (5H, m), 1.54-1.74 (1H, m), 2.83-3.00 (2H, m), 3.22-3.46 (4H, m), 3.53-3.64 (1H, m), 3.65-3.83 (1H, m), 4.16-4.30 (1H, m), 6.84-6.95 (2H, m). The second eluting compound from the chiral separation, N-(4-((S*)-2-(4-chloro-3,5-difluorophenyl)propyl)-6-(((R)-1-hydroxy-4-methylpentan-2-yl)amino)-1,3,5-triazin-2-yl)methanesulfonamide (Isomer 2) Example 32 was dissolved in EtOAc and washed with dilute HCl and brine. The organic extract was dried over $MgSO_4$, filtered and evaporated to yield (8.2 mg, 33%); HRMS (ESI) m/z [M+H]$^+$ calcd for $C_{19}H_{27}ClF_2N_5O_3S$: 478.1486, found: 478.1466; $^1$H NMR (400 MHz, CDCl$_3$) 0.85-0.98 (6H, m), 1.27-1.54 (5H, m), 1.55-1.72 (1H, m), 2.83-2.96 (2H, m), 3.25-3.42 (4H, m), 3.54-3.64 (1H, m), 3.66-3.82 (1H, m), 4.15-4.26 (1H, m), 6.83-6.92 (2H, m).

Example 33

N-(4-((S*)-2-(4-Chloro-2,3-difluorophenyl)propyl)-6-(((R)-1-hydroxy-4-methylpentan-2-yl)amino)-1,3,5-triazin-2-yl)methanesulfonamide (Isomer 1)

Isomer 1

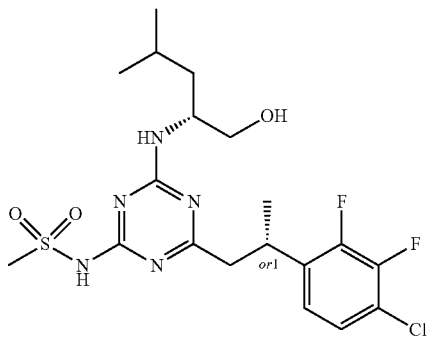

Example 34

N-(4-((R*)-2-(4-Chloro-2,3-difluorophenyl)propyl)-6-(((R)-1-hydroxy-4-methylpentan-2-yl)amino)-1,3,5-triazin-2-yl)methanesulfonamide (Isomer 2)

Isomer 2

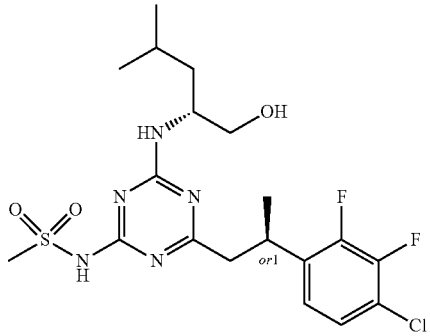

The diastereomers of N-(4-(2-(4-chloro-2,3-difluorophenyl)propyl)-6-(((R)-1-hydroxy-4-methylpentan-2-yl)amino)-1,3,5-triazin-2-yl)methanesulfonamide Intermediate 39 (60 mg, 0.13 mmol) were separated by preparative chiral HPLC on a Chiralcel OJ column (250×30 mm, 5 μm), eluted with 10% IPA/TEA (100/0.5) in $CO_2$, 120 bar at a flow rate of 80 mL/min and detected at 230 nm, to give the first eluting compound N-(4-((S*)-2-(4-chloro-2,3-difluorophenyl)propyl)-6-(((R)-1-hydroxy-4-methylpentan-2-yl)amino)-1,3,5-triazin-2-yl)methanesulfonamide (Isomer 1) Example 33 that was dissolved in EtOAc and washed with dilute HCl and brine. The organic extract was dried over $MgSO_4$, filtered and evaporated to yield (23 mg, 38%); HRMS (ESI) m/z [M+H]$^+$ calcd for $C_{19}H_{27}ClF_2N_5O_3S$: 478.1486, found: 478.1484; $^1$H NMR (400 MHz, $CDCl_3$) 0.82-0.99 (6H, m), 1.28-1.74 (6H, m), 2.89-3.08 (2H, m), 3.23-3.36 (3H, m), 3.52-3.63 (1H, m), 3.64-3.81 (2H, m), 4.08-4.26 (1H, m), 6.92-7.14 (2H, m). The second eluting compound from the chiral separation, N-(4-((R*)-2-(4-chloro-2,3-difluorophenyl)propyl)-6-(((R)-1-hydroxy-4-methylpentan-2-yl)amino)-1,3,5-triazin-2-yl)methanesulfonamide (Isomer 2) Example 34 was dissolved in EtOAc and washed with dilute HCl and brine. The organic extract was dried over $MgSO_4$, filtered and evaporated to yield (20 mg, 33%); HRMS (ESI) m/z [M+H]$^+$ calcd for $C_{19}H_{27}ClF_2N_5O_3S$: 478.1486, found: 478.1488; $^1$H NMR (400 MHz, $CDCl_3$) 0.87-0.99 (6H, m), 1.28-1.72 (6H, m), 2.91-3.07 (2H, m), 3.24-3.38 (3H, m), 3.53-3.83 (3H, m), 4.16-4.30 (1H, m), 6.93-7.14 (2H, m).

Example 35

N-(4-(((R)-1-Hydroxy-4-methylpentan-2-yl)amino)-6-((S*)-2-(2,4,5-trifluorophenyl)propyl)-1,3,5-triazin-2-yl)methanesulfonamide (Isomer 1)

Isomer 1

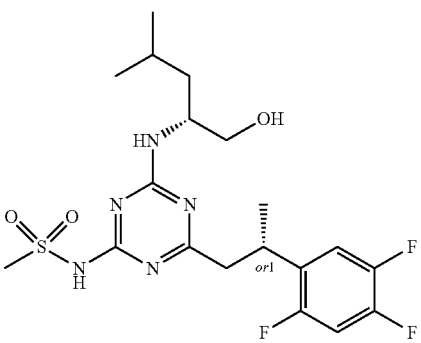

Example 36

N-(4-(((R)-1-Hydroxy-4-methylpentan-2-yl)amino)-6-((R*)-2-(2,4,5-trifluorophenyl)propyl)-1,3,5-triazin-2-yl)methanesulfonamide (Isomer 2)

Isomer 2

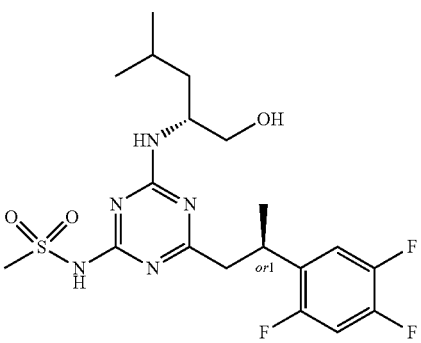

The diastereomers of N-(4-(((R)-1-hydroxy-4-methylpentan-2-yl)amino)-6-(2-(2,4,5-trifluorophenyl)propyl)-1,3,5-triazin-2-yl)methanesulfonamide Intermediate 41 (118 mg, 0.26) were separated by preparative chiral HPLC on a Chiralcel OJ column (250×30 mm, 5 μm), eluted with 13% IPA/TEA (100/0.5) in CO$_2$, 120 bar at a flow rate of 80 mL/min and detected at 230 nm, to give the first eluting compound N-(4-(((R)-1-hydroxy-4-methylpentan-2-yl)amino)-6-((S*)-2-(2,4,5-trifluorophenyl)propyl)-1,3,5-triazin-2-yl)methanesulfonamide (Isomer 1) Example 35 that was dissolved in EtOAc and washed with dilute HCl and brine. The organic extract was dried over MgSO$_4$, filtered and evaporated to yield (39 mg, 33%); HRMS (ESI) m/z [M+H]$^+$ calcd for C$_{19}$H$_{27}$F$_3$N$_5$O$_3$S: 462.1780, found: 462.1790; $^1$H NMR (400 MHz, CDCl$_3$) 0.83-0.98 (6H, m), 1.27-1.73 (6H, m), 2.83-3.01 (2H, m), 3.24-3.31 (3H, m), 3.53-3.81 (3H, m), 4.15-4.27 (1H, m), 6.79-6.89 (1H, m), 7.05-7.17 (1H, m). The second eluting compound from the chiral separation, N-(4-(((R)-1-hydroxy-4-methylpentan-2-yl)amino)-6-((R*)-2-(2,4,5-trifluorophenyl)propyl)-1,3,5-triazin-2-yl)methanesulfonamide (Isomer 2) Example 36 was dissolved in EtOAc and washed with dilute HCl and brine. The organic extract was dried over MgSO$_4$, filtered and evaporated to yield (35 mg, 30%); HRMS (ESI) m/z [M+H]$^+$ calcd for C$_{19}$H$_{27}$F$_3$N$_5$O$_3$S: 462.1780, found: 462.1772; $^1$H NMR (400 MHz, CDCl$_3$) 0.86-0.98 (6H, m), 1.26-1.73 (6H, m), 2.76-3.01 (2H, m), 3.23-3.33 (3H, m), 3.54-3.82 (3H, m), 4.16-4.31 (1H, m), 6.79-6.89 (1H, m), 7.05-7.16 (1H, m).

Example 37

N-(4-((S*)-2-(4-Chloro-2,5-difluorophenyl)propyl)-6-(((R)-1-hydroxy-4-methylpentan-2-yl)amino)-1,3,5-triazin-2-yl)methanesulfonamide (Isomer 1)

Isomer 1

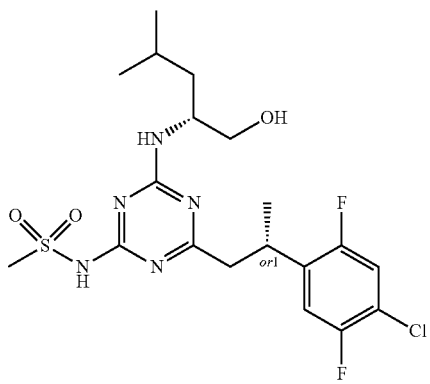

Example 38

N-(4-((R*)-2-(4-Chloro-2,5-difluorophenyl)propyl)-6-(((R)-1-hydroxy-4-methylpentan-2-yl)amino)-1,3,5-triazin-2-yl)methanesulfonamide (Isomer 2)

Isomer 2

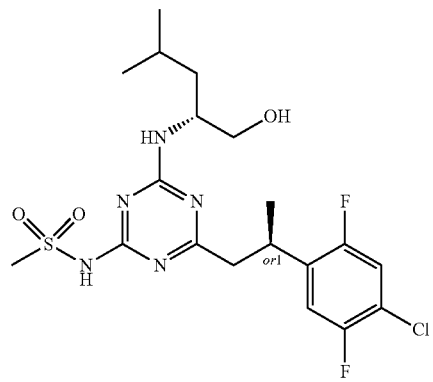

The diastereomers of N-(4-(2-(4-chloro-2,5-difluorophenyl)propyl)-6-(((R)-1-hydroxy-4-methylpentan-2-yl)amino)-1,3,5-triazin-2-yl)methanesulfonamide Intermediate 43 (99 mg, 0.20 mmol) were separated by preparative chiral HPLC on a Chiralcel OJ column (250×30 mm, 5 μm), eluted with 13% EtOH/DEA (100/0.5) in CO$_2$, 120 bar at a flow rate of 80 mL/min and detected at 230 nm, to give the first eluting compound N-(4-((S*)-2-(4-chloro-2,5-difluorophenyl)propyl)-6-(((R)-1-hydroxy-4-methylpentan-2-yl)amino)-1,3,5-triazin-2-yl)methanesulfonamide (Isomer 1) Example 37 (43 mg, 43%); HRMS (ESI) m/z [M+H]$^+$ calcd for C$_{19}$H$_{27}$ClF$_2$N$_5$O$_3$S: 478.1486, found: 478.1472; $^1$H NMR (400 MHz, CDCl$_3$) 0.79-0.98 (6H, m), 1.19-1.49 (m, partial overlap with DEA residues), 1.53-1.76 (1H, m), 2.70-2.96 (2H, m), 3.12-3.26 (3H, m), 3.50-3.78 (3H, m), 4.04-4.19 (1H, m), 6.98-7.13 (2H, m), and the second eluting compound N-(4-((R*)-2-(4-chloro-2,5-difluorophenyl)propyl)-6-(((R)-1-hydroxy-4-methylpentan-2-yl)amino)-1,3,5-triazin-2-yl)methanesulfonamide (Isomer 2) Example 38 (44 mg, 44%); HRMS (ESI) m/z [M+H]$^+$ calcd for C$_{19}$H$_{27}$ClF$_2$N$_5$O$_3$S: 478.1486, found: 478.1478; $^1$H NMR (400 MHz, CDCl$_3$) 0.84-0.98 (6H, m), 1.22-1.49 (m, partial overlap with DEA residues), 1.53-1.75 (1H, m), 2.70-2.96 (2H, m), 3.14-3.24 (3H, m), 3.50-3.77 (3H, m), 4.08-4.22 (1H, m), 7.00-7.13 (2H, m).

Example 39

N-(4-(((R)-1-Hydroxy-4-methylpentan-2-yl)amino)-6-((S*)-2-(2,4,6-trifluorophenyl)propyl)-1,3,5-triazin-2-yl)methanesulfonamide (Isomer 1)

Isomer 1

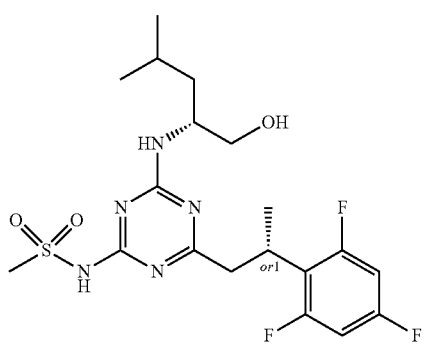

Example 40

N-(4-(((R)-1-Hydroxy-4-methylpentan-2-yl)amino)-6-((R*)-2-(2,4,6-trifluorophenyl)propyl)-1,3,5-triazin-2-yl)methanesulfonamide (Isomer 2)

Isomer 2

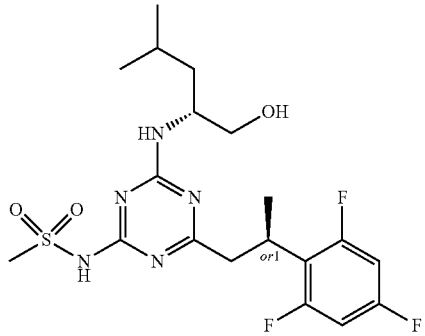

The diastereomers of N-(4-(((R)-1-hydroxy-4-methylpentan-2-yl)amino)-6-(2-(2,4,6-trifluorophenyl)propyl)-1,3,5-triazin-2-yl)methanesulfonamide Intermediate 47 (140 mg, 0.30 mmol) were separated by preparative chiral HPLC on a Chiralcel OJ column (250×30 mm, 5 μm), eluted with 13% EtOH/DEA (100/0.5) in $CO_2$, 120 bar at a flow rate of 80 mL/min and detected at 230 nm, to give the first eluting compound N-(4-(((R)-1-hydroxy-4-methylpentan-2-yl)amino)-6-((S*)-2-(2,4,6-trifluorophenyl)propyl)-1,3,5-triazin-2-yl)methanesulfonamide (Isomer 1) Example 39 that was dissolved in EtOAc and washed with water and brine. The organic extract was dried over $MgSO_4$, filtered and evaporated to yield (57 mg, 41%); HRMS (ESI) m/z [M+H]$^+$ calcd for $C_{19}H_{27}F_3N_5O_3S$: 462.1780, found: 462.1778; $^1$H NMR (400 MHz, CDCl$_3$) 0.84-0.98 (6H, m), 1.29-1.54 (5H, m), 1.55-1.73 (1H, m), 2.92-3.16 (2H, m), 3.25-3.38 (3H, m), 3.51-3.62 (1H, m), 3.65-3.86 (2H, m), 3.73-3.84 (1H, m), 4.09-4.25 (m, partial overlap with solvent residues), 6.53-6.64 (2H, m). The second eluting compound from the chiral separation, N-(4-(((R)-1-hydroxy-4-methylpentan-2-yl)amino)-6-((R*)-2-(2,4,6-trifluorophenyl)propyl)-1,3,5-triazin-2-yl)methanesulfonamide (Isomer 2) Example 40 was dissolved in EtOAc and washed with water and brine. The organic extract was dried over $MgSO_4$, filtered and evaporated to yield (55 mg, 39%); HRMS (ESI) m/z [M+H]$^+$ calcd for $C_{19}H_{27}F_3N_5O_3S$: 462.1780, found: 462.1770; $^1$H NMR (400 MHz, CDCl$_3$) 0.85-0.97 (6H, m), 1.31-1.52 (5H, m), 1.53-1.72 (1H, m), 2.94-3.16 (2H, m), 3.24-3.37 (3H, m), 3.53-3.61 (1H, m), 3.61-3.70 (1H, m), 3.73-3.89 (1H, m), 4.16-4.30 (1H, m), 6.52-6.64 (2H, m).

Example 41

N-(4-(((R)-1-Hydroxy-4-methylpentan-2-yl)amino)-6-((S*)-2-(2,3,6-trifluorophenyl)propyl)-1,3,5-triazin-2-yl)methanesulfonamiede (Isomer 1)

Isomer 1

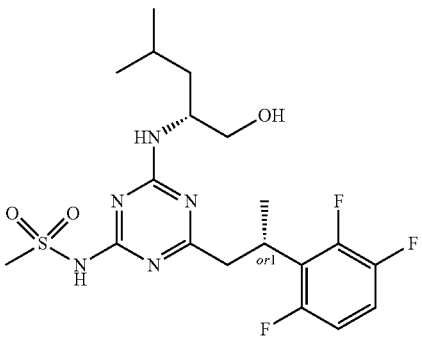

Example 42

N-(4-(((R)-1-Hydroxy-4-methylpentan-2-yl)amino)-6-((R*)-2-(2,3,6-trifluorophenyl)propyl)-1,3,5-triazin-2-yl)methanesulfonamide (Isomer 2)

Isomer 2

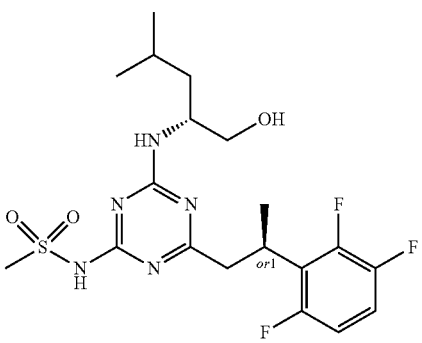

The diastereomers of N-(4-(((R)-1-hydroxy-4-methylpentan-2-yl)amino)-6-(2-(2,3,6-trifluorophenyl)propyl)-1,3,5-triazin-2-yl)methanesulfonamide Intermediate 51 (54 mg, 0.12 mmol) were separated by preparative chiral HPLC on a Chiralcel OJ column (250×30 mm, 5 μm), eluted with 12% EtOH/DEA (100/0.5) in $CO_2$, 120 bar at a flow rate of 80 mL/min and detected at 230 nm, to give the first eluting compound N-(4-(((R)-1-hydroxy-4-methylpentan-2-yl)amino)-6-((S*)-2-(2,3,6-trifluorophenyl)propyl)-1,3,5-triazin-2-yl)methanesulfonamide (Isomer 1) Example 41 that was dissolved in EtOAc and washed with dilute HCl and brine. The organic extract was dried over $Na_2SO_4$, filtered and evaporated to yield (13 mg, 24%); IRMS (ESI) m/z $[M+H]^+$ calcd for $C_{19}H_{27}F_3N_5O_3S$: 462.1780, found: 462.1780; $^1$H NMR (400 MHz, $CDCl_3$) 0.79-0.97 (6H, m), 1.23-1.71 (6H, m), 2.98-3.20 (2H, m), 3.25-3.36 (3H, m), 3.41-3.90 (3H, m), 4.10-4.23 (m, partial overlap with solvent residues), 6.68-6.79 (1H, m), 6.88-7.01 (2H, m). The second eluting compound from the chiral separation, N-(4-(((R)-1-hydroxy-4-methylpentan-2-yl)amino)-6-((R*)-2-(2,3,6-trifluorophenyl)propyl)-1,3,5-triazin-2-yl)methanesulfonamide (Isomer 2) Example 42 was dissolved in EtOAc and washed with dilute HCl and brine. The organic extract was dried over $Na_2SO_4$, filtered and evaporated to yield (14 mg, 26%); IRMS (ESI) m/z $[M+H]^+$ calcd for $C_{19}H_{27}F_3N_5O_3S$: 462.1780, found: 462.1768; $^1$H NMR (400 MHz, $CDCl_3$) 0.86-0.97 (6H, m), 1.30-1.71 (6H, m), 2.99-3.22 (2H, m), 3.25-3.36 (3H, m), 3.51-3.94 (3H, m), 4.16-4.31 (1H, m), 6.69-6.80 (1H, m), 6.89-7.01 (2H, m).

Example 43

N-(4-((S*)-2-(4-Chloro-2,6-difluorophenyl)propyl)-6-(((R)-1-hydroxy-4-methylpentan-2-yl)amino)-1,3,5-triazin-2-yl)methanesulfonamide (Isomer 1)

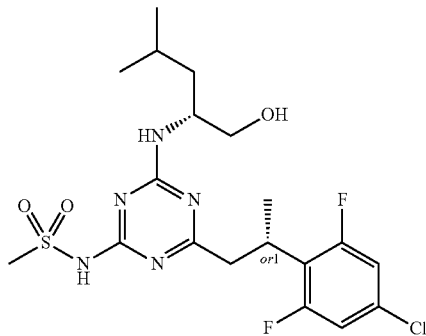

Isomer 1

Example 44

N-(4-((R*)-2-(4-Chloro-2,6-difluorophenyl)propyl)-6-(((R)-1-hydroxy-4-methylpentan-2-yl)amino)-1,3,5-triazin-2-yl)methanesulfonamide (Isomer 2)

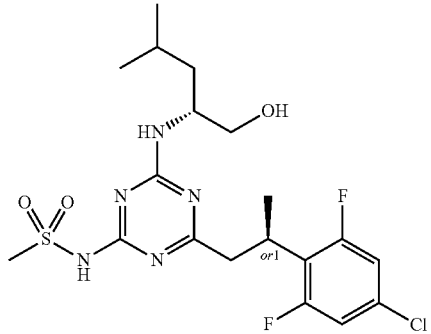

Isomer 2

The diastereomers of N-(4-(2-(4-chloro-2,6-difluorophenyl)propyl)-6-(((R)-1-hydroxy-4-methylpentan-2-yl)amino)-1,3,5-triazin-2-yl)methanesulfonamide Intermediate 55 (59 mg, 0.12 mmol) were separated by preparative chiral HPLC on a Chiralcel OJ column (250×30 mm, 5 μm), eluted with 17% EtOH/DEA (100/0.5) in $CO_2$, 120 bar at a flow rate of 70 mL/min and detected at 230 nm, to give the first eluting compound N-(4-((S*)-2-(4-chloro-2,6-difluorophenyl)propyl)-6-(((R)-1-hydroxy-4-methylpentan-2-yl)amino)-1,3,5-triazin-2-yl)methanesulfonamide (Isomer 1) Example 43 that was dissolved in EtOAc and washed with two portions of dilute HCl. The aqueous phase was extracted with EtOAc and the combined organic extract was dried over $MgSO_4$, filtered and evaporated to yield (31 mg, 52%); HRMS (ESI) m/z $[M+H]^+$ calcd for $C_{19}H_{27}ClF_2N_5O_3S$: 478.1486, found: 478.1476; $^1$H NMR (400 MHz, $CDCl_3$) 0.82-0.97 (6H, m), 1.29-1.68 (6H, m), 2.97-3.15 (2H, m), 3.27-3.32 (3H, m), 3.52-3.61 (1H, m), 3.64-3.84 (2H, m), 4.10-4.22 (m, partial overlap with solvent residues), 6.80-6.89 (2H, m). The second eluting compound from the chiral separation, N-(4-((R*)-2-(4-chloro-2,6-difluorophenyl)propyl)-6-(((R)-1-hydroxy-4-methylpentan-2-yl)amino)-1,3,5-triazin-2-yl)methanesulfonamide (Isomer 2) Example 44 was dissolved in EtOAc and washed twice with dilute HCl. The aqueous phase was extracted with EtOAc and the combined organic extract was dried over $MgSO_4$, filtered and evaporated to yield (32 mg, 54%); HRMS (ESI) m/z $[M+H]^+$ calcd for $C_{19}H_{27}ClF_2N_5O_3S$: 478.1486, found: 478.1470; $^1$H NMR (400 MHz, $CDCl_3$) 0.84-0.98 (6H, m), 1.32-1.75 (6H, m), 2.92-3.16 (2H, m), 3.24-3.35 (3H, m), 3.52-3.68 (2H, m), 3.71-3.89 (1H, m), 4.16-4.27 (1H, m), 6.80-6.89 (2H, m).

Example 45

N-(4-((S*)-2-(4-Fluoro-6-methoxypyridin-3-yl)propyl)-6-(((R)-1-hydroxy-4-methylpentan-2-yl)amino)-1,3,5-triazin-2-yl)methanesulfonamide (Isomer 1)

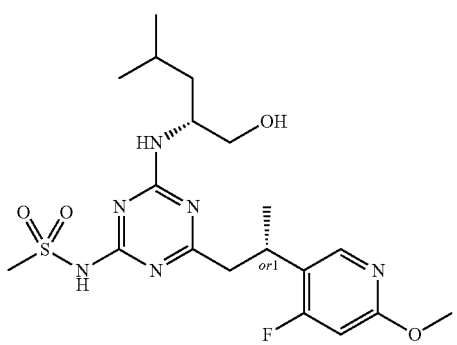

Isomer 1

Example 46

N-(4-((R*)-2-(4-Fluoro-6-methoxypyridin-3-yl)propyl)-6-(((R)-1-hydroxy-4-methylpentan-2-yl)amino)-1,3,5-triazin-2-yl)methanesulfonamide (Isomer 2)

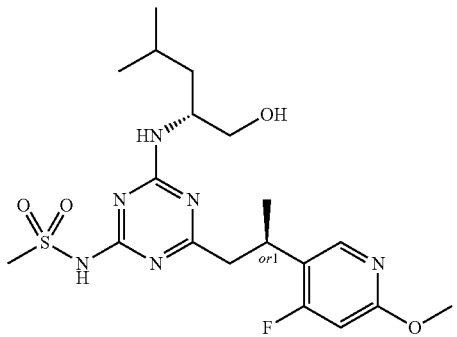

Isomer 2

The diastereomers of N-(4-(2-(4-fluoro-6-methoxypyridin-3-yl)propyl)-6-(((R)-1-hydroxy-4-methylpentan-2-yl)amino)-1,3,5-triazin-2-yl)methanesulfonamide Intermediate 58 (494 mg, 1.08 mmol) were separated by preparative chiral HPLC on a Lux $C_3$ (OJ) column (250×30 mm, 5 μm), eluted with 20% MeCN:MeOH/DEA (85:15/20 mM) in $CO_2$, at 120 bar, and at a flow rate of 140 mL/min and detected at 240 nm, to give the first eluting compound N-(4-((S*)-2-(4-fluoro-6-methoxypyridin-3-yl)propyl)-6-(((R)-1-hydroxy-4-methylpentan-2-yl)amino)-1,3,5-triazin-2-yl)methanesulfonamide (Isomer 1) Example 45 (227 mg, 46%); HRMS (ESI) m/z [M+H]$^+$ calcd for $C_{19}H_{30}FN_6O_4S$: 457.2028, found: 457.2002; $^1$H NMR (500 MHz, DMSO) 0.77-0.89 (6H, m), 1.24-1.46 (5H, m), 1.47-1.60 (1H, m), 2.74-2.88 (2H, m), 3.02-3.16 (3H, m), 3.23-3.54 (m, partial overlap with solvent residues), 3.80-3.86 (3H, m), 3.96-4.06 (1H, m), 4.57-4.78 (1H, m), 6.67 (1H, dd), 8.10 (1H, dd), and the second eluting compound N-(4-((R*)-2-(4-fluoro-6-methoxypyridin-3-yl)propyl)-6-(((R)-1-hydroxy-4-methylpentan-2-yl)amino)-1,3,5-triazin-2-yl)methanesulfonamide (Isomer 2) Example 46 (217 mg, 44%); HRMS (ESI) m/z [M+H]$^+$ calcd for $C_{19}H_{30}FN_6O_4S$: 457.2028, found: 457.2030; $^1$H NMR (500 MHz, DMSO) 0.77-0.90 (6H, m), 1.23-1.46 (5H, m), 1.46-1.60 (1H, m), 2.75-2.87 (2H, m), 3.04-3.17 (3H, m), 3.25-3.41 (m, partial overlap with solvent residues), 3.45-3.54 (1H, m), 3.83 (3H, d), 3.97-4.08 (1H, m), 4.63-4.71 (1H, m), 6.67 (1H, dd), 8.07-8.13 (1H, m).

Example 47

N-(4-((R*)-2-(2,3-Difluorophenyl)butyl)-6-(((R)-1-hydroxy-4-methylpentan-2-yl)amino)-1,3,5-triazin-2-yl)methanesulfonamide (Isomer 1)

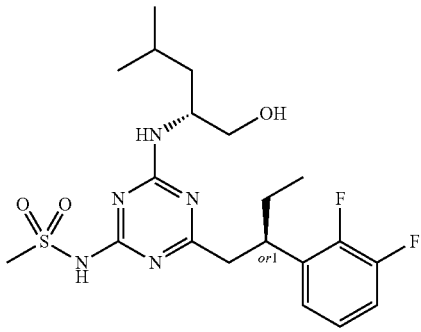

Isomer 1

Example 48

N-(4-((S*)-2-(2,3-Difluorophenyl)butyl)-6-(((R)-1-hydroxy-4-methylpentan-2-yl)amino)-1,3,5-triazin-2-yl)methanesulfonamide (Isomer 2)

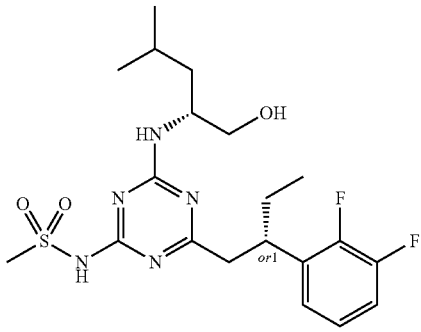

Isomer 2

The diastereomers of N-(4-(2-(2,3-difluorophenyl)butyl)-6-(((R)-1-hydroxy-4-methylpentan-2-yl)amino)-1,3,5-triazin-2-yl)methanesulfonamide Intermediate 60 (70 mg, 0.15 mmol) were separated by preparative chiral HPLC on a Chiralpak IC column (250×30 mm, 5 μm), eluted with 30-35% EtOH/DEA (100/20 mM) in $CO_2$, 120 bar at a flow rate of 100 mL/min and detected at 230 nm, to give the first eluting compound N-(4-((R*)-2-(2,3-difluorophenyl)butyl)-6-(((R)-1-hydroxy-4-methylpentan-2-yl)amino)-1,3,5-triazin-2-yl)methanesulfonamide (Isomer 1) Example 47 (31 mg, 44%); IRMS (ESI) m/z [M+H]$^+$ calcd for $C_{20}H_{30}F_2N_5O_3S$: 458.2032, found: 458.2028; $^1$H NMR (500 MHz, CDCl₃) 0.71-0.81 (3H, m), 0.85-0.95 (6H, m), 1.30-1.46 (2H, m), 1.56-1.79 (3H, m), 2.72-2.94 (2H, m), 3.09-3.18 (3H, m), 3.46-3.59 (2H, m), 3.60-3.73 (1H, m), 4.05-4.16 (1H, m), 6.90-7.00 (3H, m), and the second eluting compound N-(4-((S*)-2-(2,3-difluorophenyl)butyl)-6-(((R)-1-hydroxy-4-methylpentan-2-yl)amino)-1,3,5-triazin-2-yl)methanesulfonamide (Isomer 2) Example 48 (31 mg, 44%); HRMS (ESI) m/z [M+H]⁺ calcd for $C_{20}H_{30}F_2N_5O_3S$: 458.2032, found: 458.2046; ¹H NMR (500 MHz, CDCl₃) 0.71-0.82 (3H, m), 0.83-0.95 (6H, m), 1.31-1.45 (2H, m), 1.55-1.80 (3H, m), 2.70-2.95 (2H, m), 3.07-3.19 (3H, m), 3.44-3.58 (2H, m), 3.63-3.73 (1H, m), 4.03-4.13 (1H, m), 6.90-7.01 (3H, m).

Example 49

N-(4-(2-(4-Fluoro-6-methoxypyridin-3-yl)butyl)-6-(((R)-1-hydroxy-4-methylpentan-2-yl)amino)-1,3,5-triazin-2-yl)methanesulfonamide

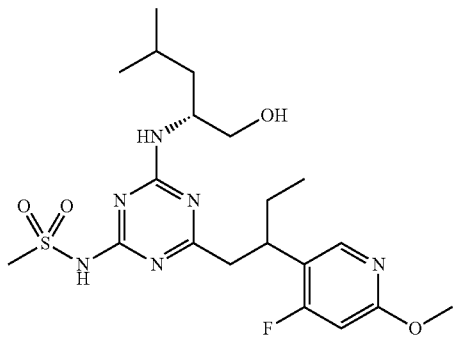

A solution of 0.5 M 9-BBN in THF (3.40 mL, 1.70 mmol) was added to 5-(but-1-en-2-yl)-4-fluoro-2-methoxypyridine Intermediate 62 (162 mg, 0.89 mmol) under nitrogen atmosphere. The reaction mixture was stirred at rt for 45 min and then added to (R)—N-(4-chloro-6-((1-hydroxy-4-methylpentan-2-yl)amino)-1,3,5-triazin-2-yl)methanesulfonamide Intermediate 1 (275 mg, 0.85 mmol), Pd(dppf)Cl₂·DCM (69.4 mg, 0.08 mmol) and K₃PO₄ (721 mg, 3.40 mmol) under nitrogen atmosphere. The reaction mixture was heated at 50° C. for 4 h. Water and EtOAc were added and the two phases were separated. The organic extract was washed with water. The combined aqueous phase was acidified to pH5 by the addition of 1 M HCl. The acidified aqueous phase was extracted with three portions of EtOAc. The organic extract was dried over MgSO₄, filtered and evaporated. The residue was purified by straight phase flash chromatography on silica (gradient: 75-100% EtOAc in heptane). Fractions with product were combined, evaporated and the residue was repurified by straight phase flash chromatography on silica a second time (5% MeOH in DCM as eluent) to yield the title compound (21 mg, 5%) as a colourless solid; HRMS (ESI) m/z [M+H]⁺ calcd for $C_{20}H_{32}FN_6O_4S$: 471.2184, found: 471.2174; ¹H NMR (500 MHz, CDCl₃) 0.77-0.96 (9H, m), 1.3-1.51 (2H, m), 1.52-1.84 (3H, m), 2.92-3.11 (2H, m), 3.21-3.37 (4H, m), 3.49-3.78 (2H, m), 3.85-3.92 (3H, m), 4.08-4.25 (1H, m), 6.36 (1H, dd), 7.96 (1H, dd).

Example 50

N-(4-((S*)-2-(6-Aminopyridin-3-yl)propyl)-6-(((R)-1-hydroxy-4-methylpentan-2-yl)amino)-1,3,5-triazin-2-yl)methanesulfonamide (Isomer 1)

Isomer 1

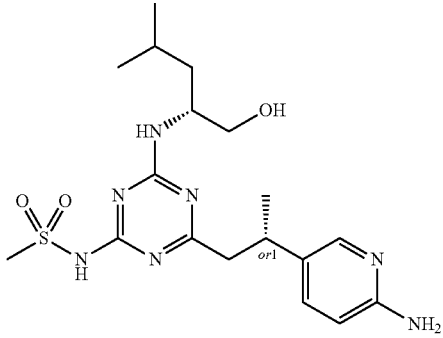

Example 51

N-(4-((R*)-2-(6-Aminopyridin-3-yl)propyl)-6-(((R)-1-hydroxy-4-methylpentan-2-yl)amino)-1,3,5-triazin-2-yl)methanesulfonamide (Isomer 2)

Isomer 2

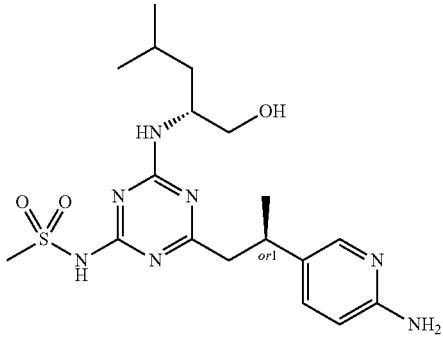

The diastereomers of N-(4-(2-(6-aminopyridin-3-yl)propyl)-6-(((R)-1-hydroxy-4-methylpentan-2-yl)amino)-1,3,5-triazin-2-yl)methanesulfonamide Intermediate 65 (90 mg, 0.17 mmol) were separated by preparative chiral HPLC on a Chiralpak AS column (250×30 mm, 5 µm), eluted with 16% EtOH/DEA (100/20 mM) in CO₂, 120 bar at a flow rate of 120 mL/min and detected at 230 nm, to give the first eluting compound N-(4-((S*)-2-(6-aminopyridin-3-yl)propyl)-6-(((R)-1-hydroxy-4-methylpentan-2-yl)amino)-1,3,5-triazin-2-yl)methanesulfonamide (Isomer 1) Example 50 (19 mg, 26%); IRMS (ESI) m/z [M+H]⁺ calcd for $C_{18}H_{30}N_7O_3S$: 424.2126, found: 424.2138, and the second eluting compound N-(4-((R*)-2-(6-aminopyridin-3-yl)propyl)-6-(((R)-1-hydroxy-4-methylpentan-2-yl)amino)-1,3,5-triazin-2-yl)methanesulfonamide (Isomer 2) Example 51 (18 mg, 25%); IRMS (ESI) m/z [M+H]⁺ calcd for $C_{18}H_{30}N_7O_3S$: 424.2126, found: 424.2106.

Example 52

N-(4-((R*)-2-(2,6-Dimethoxypyridin-3-yl)propyl)-6-(((R)-1-hydroxy-4-methylpentan-2-yl)amino)-1,3,5-triazin-2-yl)methanesulfonamide (Isomer 1)

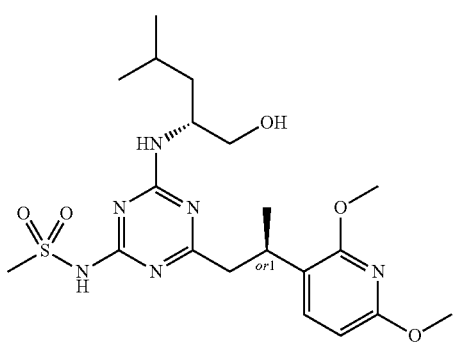

Isomer 1

Example 53

N-(4-((S*)-2-(2,6-Dimethoxypyridin-3-yl)propyl)-6-(((R)-1-hydroxy-4-methylpentan-2-yl)amino)-1,3,5-triazin-2-yl)methanesulfonamide (Isomer 2)

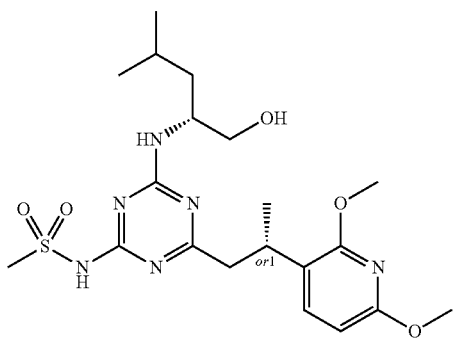

Isomer 2

The diastereomers of N-(4-(2-(2,6-dimethoxypyridin-3-yl)propyl)-6-(((R)-1-hydroxy-4-methylpentan-2-yl)amino)-1,3,5-triazin-2-yl)methanesulfonamide Intermediate 67 (57 mg, 0.12 mmol) were separated by preparative chiral HPLC on a Chiralcel OJ column (250×30 mm, 5 μm), eluted with 25% EtOH/DEA (100/0.5) in $CO_2$, 120 bar at a flow rate of 80 mL/min and detected at 230 nm, to give the first eluting compound N-(4-((R*)-2-(2,6-dimethoxypyridin-3-yl)propyl)-6-(((R)-1-hydroxy-4-methylpentan-2-yl)amino)-1,3,5-triazin-2-yl)methanesulfonamide (Isomer 1) Example 52 that was dissolved in EtOAc and washed with water and brine. The organic extract was dried over $Na_2SO_4$, filtered and evaporated to yield (24 mg, 42%); HRMS (ESI) m/z $[M+H]^+$ calcd for $C_{20}H_{33}N_6O_5S$: 469.2228, found: 469.2222; $^1H$ NMR (500 MHz, $CDCl_3$) 0.86-0.97 (6H, m), 1.23-1.30 (3H, m), 1.33-1.52 (2H, m), 1.57-1.72 (1H, m), 2.80-2.99 (2H, m), 3.21 (3H, d), 3.46-3.60 (2H, m), 3.65-3.81 (1H, m), 3.84-3.92 (6H, m), 4.13-4.29 (1H, m), 6.23 (1H, dd), 7.40 (1H, dd). The second eluting compound from the chiral separation, N-(4-((S*)-2-(2,6-dimethoxypyridin-3-yl)propyl)-6-(((R)-1-hydroxy-4-methylpentan-2-yl)amino)-1,3,5-triazin-2-yl)methanesulfonamide (Isomer 2) Example 53 was dissolved in EtOAc and washed with water and brine. The organic extract was dried over $Na_2SO_4$, filtered and evaporated to yield (24 mg, 42%); IRMS (ESI) m/z $[M+H]^+$ calcd for $C_{20}H_{33}N_6O_5S$: 469.2228, found: 469.2210; $^1H$ NMR (500 MHz, $CDCl_3$) 0.89-0.98 (6H, m), 1.22-1.30 (3H, m), 1.33-1.52 (2H, m), 1.57-1.73 (1H, m), 2.82-3.02 (2H, m), 3.23 (3H, d), 3.46-3.63 (2H, m), 3.65-3.81 (1H, m), 3.85-3.94 (6H, m), 4.18-4.28 (1H, m), 6.20-6.27 (1H, m), 7.36-7.43 (1H, m).

Example 54

N-(4-(((R)-1-Hydroxy-4-methylpentan-2-yl)amino)-6-(2-(4-(piperazin-1-yl)phenyl)propyl)-1,3,5-triazin-2-yl)methanesulfonamide

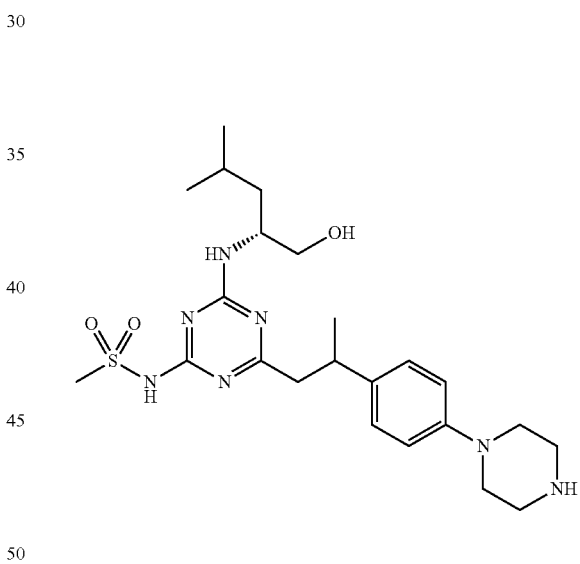

6 M HCl (0.5 mL, 3.0 mmol) was added to a solution of tert-butyl 4-(4-(1-(4-(((R)-1-hydroxy-4-methylpentan-2-yl)amino)-6-(methylsulfonamido)-1,3,5-triazin-2-yl)propan-2-yl)phenyl)piperazine-1-carboxylate Intermediate 69 (172 mg, 0.29 mmol) in 1,4-dioxane (2 mL). The reaction mixture was stirred at rt for 2 h and then concentrated. The residue was purified by preparative HPLC, PrepMethod F, (gradient: 5-95%) to yield the title compound (8.5 mg, 6%); IRMS (ESI) m/z $[M+H]^+$ calcd for $C_{23}H_{38}N_7O_3S$: 492.2752, found: 469.2732; $^1H$ NMR (600 MHz, DMSO) 0.81-0.91 (6H, m), 1.13-1.20 (3H, m), 1.28-1.45 (2H, m), 1.51-1.62 (1H, m), 2.56-2.70 (2H, m), 2.87-2.92 (4H, m), 3.00-3.07 (8H, m), 3.20-3.60 (m, partial overlap with water), 3.97-4.15 (1H, m), 6.80-6.87 (2H, m), 7.05-7.10 (2H, m).

Example 55

N-(4-(2-(4-(Cyanomethyl)phenyl)propyl)-6-(((R)-1-hydroxy-4-methylpentan-2-yl)amino)-1,3,5-triazin-2-yl)methanesulfonamide

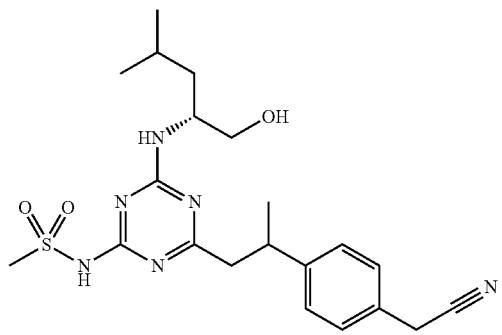 [SMILES: CC(C)C[C@H](CO)Nc1nc(CC(C)c2ccc(CC#N)cc2)nc(NS(C)(=O)=O)n1]

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then 2-(4-(1-(4-chloro-6-(((R)-1-hydroxy-4-methylpentan-2-yl)amino)-1,3,5-triazin-2-yl)propan-2-yl)phenyl)acetonitrile Intermediate 70 (112 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was made acidic by the addition of 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod G, to yield the title compound (66 mg, 50%); IRMS (ESI) m/z [M+H]$^+$ calcd for C$_{21}$H$_{31}$N$_6$O$_3$S: 447.2172, found: 447.2168; $^1$H NMR (600 MHz, DMSO) 0.81-0.90 (6H, m), 1.20-1.25 (3H, m), 1.29-1.45 (2H, m), 1.50-1.60 (1H, m), 2.64-2.82 (2H, m), 3.27-3.40 (m, partial overlap with water), 3.93-4.15 (3H, m), 4.63-4.78 (1H, m), 7.23-7.30 (4H, m).

Example 56

N-(4-(2-(3-Fluoro-4-methylphenyl)propyl)-6-(((R)-1-hydroxy-4-methylpentan-2-yl)amino)-1,3,5-triazin-2-yl)methanesulfonamide

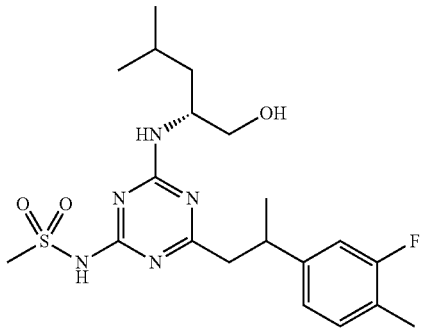

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then (2R)-2-((4-chloro-6-(2-(3-fluoro-4-methylphenyl)propyl)-1,3,5-triazin-2-yl)amino)-4-methylpentan-1-ol Intermediate 71 (110 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was made acidic by the addition of 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod E, (gradient: 5-95%) to yield the title compound (78 mg, 61%); HRMS (ESI) m/z [M+H]$^+$ calcd for C$_{20}$H$_{31}$FN$_5$O$_3$S: 440.2126, found: 440.2136; $^1$H NMR (600 MHz, DMSO) 0.81-0.89 (6H, m), 1.17-1.25 (3H, m), 1.28-1.45 (2H, m), 1.48-1.60 (1H, m), 2.17 (3H, d), 2.63-2.79 (2H, m), 3.25-3.40 (m, partial overlap with water), 3.97-4.13 (1H, m), 4.64-4.76 (1H, m), 6.93-7.04 (2H, m), 7.13-7.21 (1H, m).

Example 57

N-(4-(((R)-1-Hydroxy-4-methylpentan-2-yl)amino)-6-(2-(4-(oxetan-3-yl)phenyl)propyl)-1,3,5-triazin-2-yl)methanesulfonamide

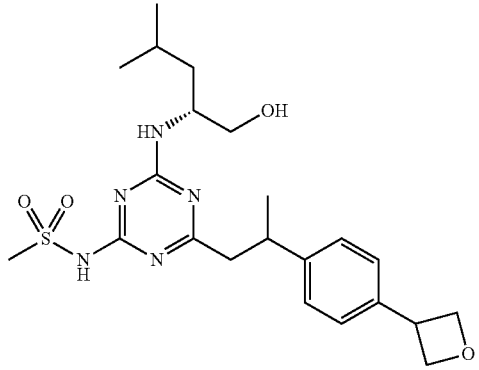 [SMILES: CC(C)C[C@H](CO)Nc1nc(CC(C)c2ccc(C3COC3)cc2)nc(NS(C)(=O)=O)n1]

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then (2R)-2-((4-chloro-6-(2-(4-(oxetan-3-yl)phenyl)propyl)-1,3,5-triazin-2-yl)amino)-4-methylpentan-1-ol Intermediate 72 (117 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was made acidic by the addition of 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod H, to yield the title compound (66 mg, 49%); HRMS (ESI) m/z [M+H]$^+$ calcd for C$_{22}$H$_{34}$N$_5$O$_4$S: 464.2326, found: 464.2336; $^1$H NMR (600 MHz, DMSO) 0.81-0.90 (6H, m), 1.19-1.25 (3H, m), 1.28-1.45 (2H, m), 1.50-1.60 (1H, m), 2.63-2.82 (2H, m), 3.26-3.42 (m, partial overlap with water), 3.97-4.14 (1H, m), 4.19

(1H, sext), 4.56-4.61 (2H, m), 4.64-4.76 (1H, m), 4.88-4.93 (2H, m), 7.21-7.26 (2H, m), 7.29-7.35 (2H, m).

Example 58

N-(4-(2-(3-Fluorophenyl)propyl)-6-(((R)-1-hydroxy-4-methylpentan-2-yl)amino)-1,3,5-triazin-2-yl)methanesulfonamide

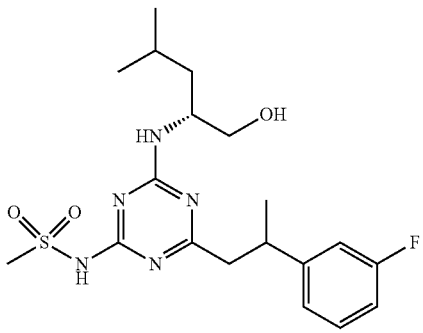 [SMILES: CC(C)C[C@H](CO)Nc1nc(CC(C)c2cccc(F)c2)nc(NS(C)(=O)=O)n1]

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then (2R)-2-((4-chloro-6-(2-(3-fluorophenyl)propyl)-1,3,5-triazin-2-yl)amino)-4-methylpentan-1-ol Intermediate 73 (106 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was acidified with 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod G, to yield the title compound (69 mg, 56%); HRMS (ESI) m/z [M+H]$^+$ calcd for C$_{19}$H$_{29}$FN$_5$O$_3$S: 426.1970, found: 426.1962; $^1$H NMR (600 MHz, DMSO) 0.81-0.89 (6H, m), 1.21-1.27 (3H, m), 1.28-1.45 (2H, m), 1.49-1.60 (1H, m), 2.65-2.84 (2H, m), 3.25-3.42 (m, partial overlap with water), 3.97-4.14 (1H, m), 4.64-4.76 (1H, m), 6.97-7.05 (1H, m), 7.05-7.12 (2H, m), 7.28-7.36 (1H, m).

Example 59

N-(4-(1-(4-(((R)-1-Hydroxy-4-methylpentan-2-yl)amino)-6-(methylsulfonamido)-1,3,5-triazin-2-yl)propan-2-yl)phenyl)acetamide

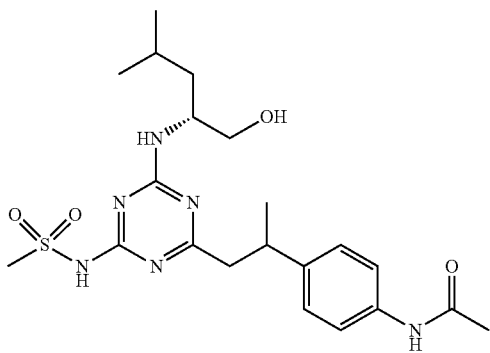 [SMILES: CC(=O)Nc1ccc(C(C)Cc2nc(N[C@@H](CO)CC(C)C)nc(NS(C)(=O)=O)n2)cc1]

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then N-(4-(1-(4-chloro-6-(((R)-1-hydroxy-4-methylpentan-2-yl)amino)-1,3,5-triazin-2-yl)propan-2-yl)phenyl)acetamide Intermediate 74 (106 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was acidified with of 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod H, to yield the title compound (45 mg, 33%); HRMS (ESI) m/z [M+H]$^+$ calcd for C$_{21}$H$_{33}$N$_6$O$_4$S: 465.2278, found: 465.2282; $^1$H NMR (600 MHz, DMSO) 0.81-0.90 (6H, m), 1.17-1.23 (3H, m), 1.28-1.46 (2H, m), 1.50-1.60 (1H, m), 2.01 (3H, d), 2.59-2.78 (2H, m), 3.98-4.16 (1H, m), 4.63-4.79 (1H, m), 7.11-7.17 (2H, m), 7.44-7.50 (2H, m), 9.86 (1H, d).

Example 60

N-(4-(2-(1H-Indol-5-yl)propyl)-6-(((R)-1-hydroxy-4-methylpentan-2-yl)amino)-1,3,5-triazin-2-yl)methanesulfonamide

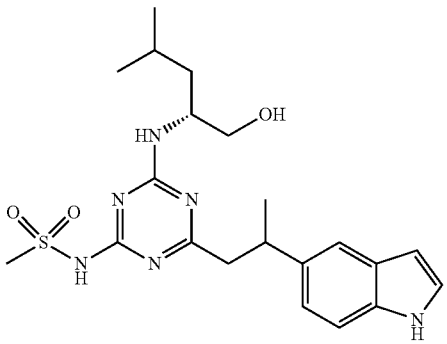 [SMILES: CC(C)C[C@H](CO)Nc1nc(CC(C)c2ccc3[nH]ccc3c2)nc(NS(C)(=O)=O)n1]

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then (2R)-2-((4-(2-(1H-indol-5-yl)propyl)-6-chloro-1,3,5-triazin-2-yl)amino)-4-methylpentan-1-ol Intermediate 75 (112 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight.

EtOAc and water were added. The mixture was acidified with 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod H, to yield the title compound (45 mg, 35%); HRMS (ESI) m/z [M+H]$^+$ calcd for C$_{21}$H$_{31}$N$_6$O$_3$S: 447.2172, found: 447.2166; $^1$H NMR (600 MHz, DMSO) 0.80-0.93 (6H, m), 1.23-1.47 (5H, m), 1.49-1.62 (1H, m), 2.64-2.86 (2H, m), 3.27-3.45 (m, partial overlap with water), 3.98-4.20 (1H, m), 4.63-4.79 (1H, m), 6.31-6.37 (1H, m), 6.94-6.99 (1H, m), 7.26-7.32 (2H, m), 7.36-7.40 (1H, m), 10.93-11.00 (1H, m).

Example 61

N-(4-(2-(Benzo[d]oxazol-6-yl)propyl)-6-(((R)-1-hydroxy-4-methylpentan-2-yl)amino)-1,3,5-triazin-2-yl)methanesulfonamide

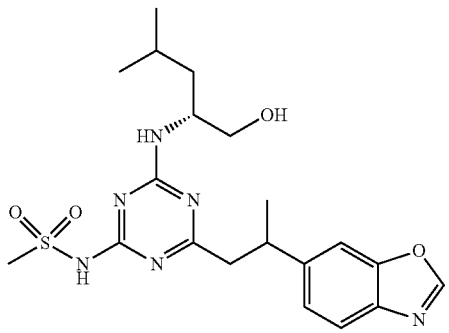 [SMILES: CC(C)C[C@H](CO)Nc1nc(CC(C)c2ccc3ncoc3c2)nc(NS(C)(=O)=O)n1]

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then (2R)-2-((4-(2-(benzo[d]oxazol-6-yl)propyl)-6-chloro-1,3,5-triazin-2-yl)amino)-4-methylpentan-1-ol Intermediate 76 (113 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was acidified with 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod G, to yield the title compound (3.2 mg, 2.5%); HRMS (ESI) m/z [M+H]$^+$ calcd for C$_{20}$H$_{29}$N$_6$O$_4$S: 449.1966, found: 449.1970.

Example 62

N-(4-(2-(Benzo[d]oxazol-5-yl)propyl)-6-(((R)-1-hydroxy-4-methylpentan-2-yl)amino)-1,3,5-triazin-2-yl)methanesulfonamide

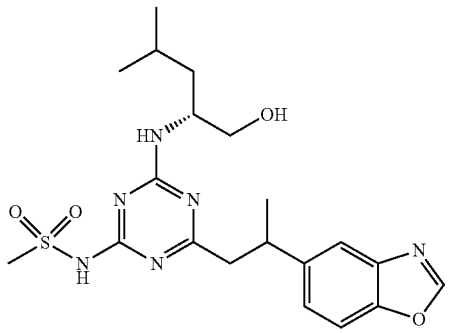 [SMILES: CC(C)C[C@H](CO)Nc1nc(CC(C)c2ccc3ocnc3c2)nc(NS(C)(=O)=O)n1]

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then (2R)-2-((4-(2-(benzo[d]oxazol-5-yl)propyl)-6-chloro-1,3,5-triazin-2-yl)amino)-4-methylpentan-1-ol Intermediate 77 (113 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was acidified with 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod F, (gradient: 5-95%) to yield the title compound (22 mg, 17%); HRMS (ESI) m/z [M+H]$^+$ calcd for C$_{20}$H$_{29}$N$_6$O$_4$S: 449.1966, found: 449.1960; $^1$H NMR (600 MHz, DMSO) 0.74-0.89 (6H, m), 1.26-1.60 (6H, m), 2.71-2.90 (2H, m), 2.95-3.13 (3H, m), 3.25-3.53 (m, partial overlap with water), 3.96-4.13 (1H, m), 4.61-4.77 (1H, m), 7.28-7.35 (1H, m), 7.62-7.70 (2H, m), 8.67-8.71 (1H, m).

Example 63

N-(4-(2-(4-((Dimethyl(oxo)-λ$^6$-sulfaneylidene)amino)phenyl)propyl)-6-(((R)-1-hydroxy-4-methylpentan-2-yl)amino)-1,3,5-triazin-2-yl)methanesulfonamide

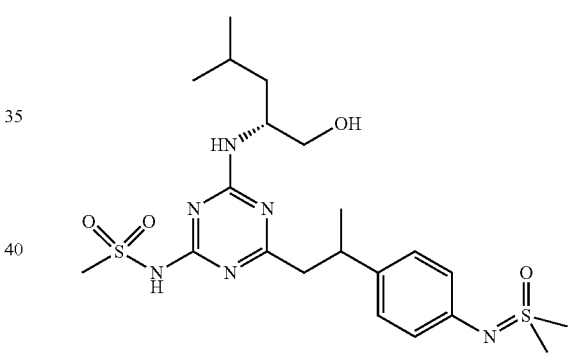

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then ((4-(1-(4-chloro-6-(((R)-1-hydroxy-4-methylpentan-2-yl)amino)-1,3,5-triazin-2-yl)propan-2-yl)phenyl)imino)dimethyl-λ$^6$-sulfanone Intermediate 78 (128 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was acidified with 3.8 M HCl and the two phases were separated. The aqueous phase was extracted with EtOAc and the aqueous phase was evaporated and treated with DMSO. The DMSO slurry was filtered and the filtrate was combined with the organic extract, dried over MgSO$_4$ and treated with SiliaMetS Thiol for 30 min, filtered and evaporated. The residue was purified by preparative HPLC, PrepMethod G, to yield the title compound (26 mg, 17%); HRMS (ESI) m/z [M+H]+ calcd for $C_{21}H_{35}N_6O_4S_2$: 499.2156, found: 499.2150; $^1$H NMR (600 MHz, DMSO) 0.82-0.92 (6H, m), 1.15-1.23 (3H, m), 1.30-1.47 (2H, m), 1.52-1.62 (1H, m), 2.57-2.76 (2H, m), 2.95-3.12 (2H, m), 3.13-3.18 (6H, m), 3.19-3.29 (1H, m), 3.35-3.42 (m, partial overlap with water), 3.99-4.19 (1H, m), 4.64-4.77 (1H, m), 6.81-6.88 (2H, m), 7.02-7.07 (2H, m).

Example 64

N-(4-(2-(4-(1H-1,2,3-Triazol-1-yl)phenyl)propyl)-6-(((R)-1-hydroxy-4-methylpentan-2-yl)amino)-1,3,5-triazin-2-yl)methanesulfonamide

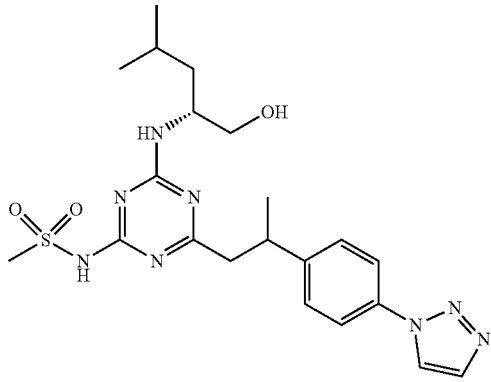 [SMILES: CC(C)C[C@H](CO)Nc1nc(CC(C)c2ccc(-n3ccnn3)cc2)nc(NS(C)(=O)=O)n1]

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then (2R)-2-((4-(2-(4-(1H-1,2,3-triazol-1-yl)phenyl)propyl)-6-chloro-1,3,5-triazin-2-yl)amino)-4-methylpentan-1-ol Intermediate 79 (121 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was acidified with 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod F, (gradient: 5-95%) to yield the title compound (47 mg, 34%); HRMS (ESI) m/z [M+H]+ calcd for $C_{21}H_{31}N_8O_3S$: 475.2234, found: 475.2236; $^1$H NMR (600 MHz, DMSO) 0.76-0.89 (6H, m), 1.25-1.45 (5H, m), 1.46-1.60 (1H, m), 2.69-2.90 (2H, m), 2.98-3.16 (3H, m), 3.40-3.48 (m, partial overlap with water), 3.97-4.15 (1H, m), 4.62-4.79 (1H, m), 7.43-7.50 (2H, m), 7.79-7.85 (2H, m), 7.93-7.97 (1H, m), 8.75-8.79 (1H, m).

Example 65

N-(4-((S*)-2-(3-Chloro-4-fluorophenyl)propyl)-6-(((R)-1-hydroxy-4-methylpentan-2-yl)amino)-1,3,5-triazin-2-yl)methanesulfonamide (Isomer 1)

Isomer 1

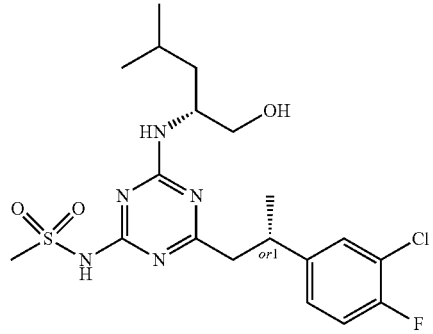

Example 66

N-(4-((R*)-2-(3-Chloro-4-fluorophenyl)propyl)-6-(((R)-1-hydroxy-4-methylpentan-2-yl)amino)-1,3,5-triazin-2-yl)methanesulfonamide (Isomer 2)

Isomer 2

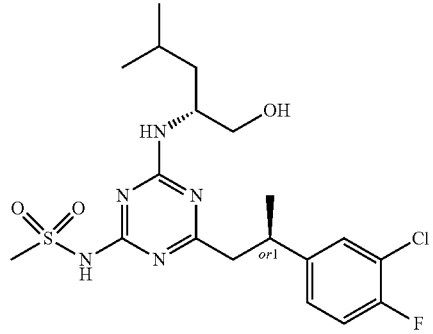

The diastereomers of N-(4-(2-(3-chloro-4-fluorophenyl)propyl)-6-(((R)-1-hydroxy-4-methylpentan-2-yl)amino)-1,3,5-triazin-2-yl)methanesulfonamide Intermediate 81 (24 mg, 0.05 mmol) were separated by preparative chiral HPLC on a Chiralpak IA column (250×20 mm, 5 µm), eluted with 10% EtOH/DEA (100/0.5) in CO$_2$, 120 bar at a flow rate of 70 mL/min and detected at 260 nm, to give the first eluting compound N-(4-((S*)-2-(3-chloro-4-fluorophenyl)propyl)-6-(((R)-1-hydroxy-4-methylpentan-2-yl)amino)-1,3,5-triazin-2-yl)methanesulfonamide (Isomer 1) Example 65 that was dissolved in EtOAc and washed with dilute HCl and brine. The organic extract was dried over MgSO$_4$, filtered and evaporated to yield (9 mg, 38%); HRMS (ESI) m/z [M+H]+ calcd for $C_{19}H_{28}ClFN_5O_3S$: 460.1580, found: 469.1566; $^1$H NMR (400 MHz, CDCl$_3$) 0.87-0.98 (6H, m), 1.26-1.54 (5H, m), 1.56-1.71 (1H, m), 2.84-2.95 (2H, m), 3.24-3.41 (4H, m), 3.54-3.62 (1H, m), 3.66-3.80 (1H, m), 4.16-4.27 (1H, m), 6.98-7.13 (2H, m), 7.24-7.29 (m, partial overlap with NMR solvent). The second eluting compound from the chiral separation, N-(4-((R*)-2-(3-chloro-4-fluorophenyl)propyl)-6-(((R)-1-hydroxy-4-methylpentan-2-yl)amino)-1,3,5-triazin-2-yl)methanesulfonamide (Isomer 2) Example 66 was dissolved in EtOAc and washed with dilute HCl and brine. The organic extract was dried over MgSO$_4$, filtered and evaporated to yield (9 mg, 38%); HRMS (ESI) m/z [M+H]$^+$ calcd for C$_{19}$H$_{28}$ClFN$_5$O$_3$S: 460.1580, found: 469.1584; $^1$H NMR (400 MHz, CDCl$_3$) 0.87-0.98 (6H, m), 1.25-1.53 (m, partial overlap with solvent residues), 1.55-1.72 (1H, m), 2.84-2.95 (2H, m), 3.23-3.41 (4H, m), 3.54-3.63 (1H, m), 3.65-3.81 (1H, m), 4.17-4.29 (1H, m), 6.98-7.05 (1H, m), 7.05-7.13 (1H, m), 7.24-7.29 (m, partial overlap with NMR solvent).

Example 67

N-(4-(2-(2-Ethoxypyridin-4-yl)propyl)-6-(((R)-1-hydroxy-4-methylpentan-2-yl)amino)-1,3,5-triazin-2-yl)methanesulfonamide

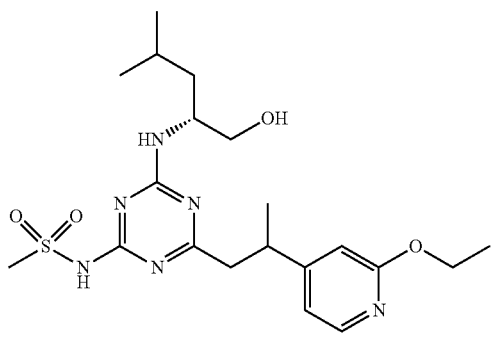 [SMILES: CCOc1cc(C(C)Cc2nc(N[C@@H](CO)CC(C)C)nc(NS(C)(=O)=O)n2)ccn1]

9-BBN Dimer (88 mg, 0.37 mmol) was added to a solution of 2-ethoxy-4-(prop-1-en-2-yl)pyridine Intermediate 82 (119 mg, 0.73 mmol) in THF (2.52 mL) under nitrogen atmosphere. The mixture was stirred at 35° C. for 1 h and then a degassed solution of 3 M K$_3$PO$_4$ (aq, 0.73 mL, 2.19 mmol) was added followed by the addition of (R)—N-(4-((1-(((tert-butyldimethylsilyl)oxy)-4-methylpentan-2-yl)amino)-6-chloro-1,3,5-triazin-2-yl)methanesulfonamide Intermediate 2 (160 mg, 0.37 mmol) and Pd(dppf)Cl$_2$·DCM (44.3 mg, 0.05 mmol). The reaction mixture was stirred at 35° C. under nitrogen atmosphere for 68 h. EtOAc and water were added and the two phases were separated. The organic extract was evaporated and redissolved in a small amount heptane/EtOAc (3/1) and filtered through a short column of silica, eluted with a gradient of EtOAc in heptane. The solvent was evaporated and the residue was dissolved in EtOH (2 mL) and HCl (0.4 mL), and the solution was stirred at rt for 30 min. The solvent was evaporated and the residue was dissolved in DMSO and SiliaMetS Thiol was added, stirred for a minute, filtered and purified by preparative HPLC, PrepMethod F, (gradient: 5-95%) to yield the title compound (15 mg, 9%); IRMS (ESI) m/z [M+H]$^+$ calcd for C$_{20}$H$_{33}$N$_6$O$_4$S: 453.2278, found: 453.2270; $^1$H NMR (600 MHz, DMSO) 0.77-0.90 (6H, m), 1.17-1.25 (3H, m), 1.25-1.44 (5H, m), 1.47-1.61 (1H, m), 2.63-2.83 (2H, m), 2.97-3.16 (3H, m), 3.24-3.42 (m, partial overlap with water), 3.95-4.10 (1H, m), 4.21-4.29 (2H, m), 4.62-4.74 (1H, m), 6.61-6.66 (1H, m), 6.81-6.87 (1H, m), 7.99-8.06 (1H, m).

Example 68

N-(4-(2-(4-Cyanophenyl)propyl)-6-(((R)-1-hydroxy-4-methylpentan-2-yl)amino)-1,3,5-triazin-2-yl)methanesulfonamide

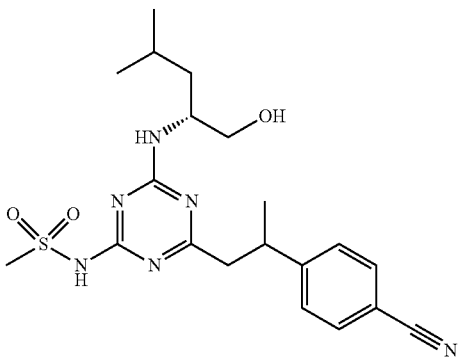 [SMILES: CC(C)C[C@H](CO)Nc1nc(CC(C)c2ccc(C#N)cc2)nc(NS(C)(=O)=O)n1]

THF (0.25 mL) was added to Pd$_2$dba$_3$ (8.7 mg, 0.01 mmol) and X-Phos (18.2 mg, 0.04 mmol) and the mixture was stirred under nitrogen atmosphere at rt for 10 min and then 4-(1-(4-chloro-6-(((R)-1-hydroxy-4-methylpentan-2-yl)amino)-1,3,5-triazin-2-yl)propan-2-yl)benzonitrile Intermediate 83 (89 mg, 0.24 mmol) in THF (0.75 mL), methanesulfonamide (52 mg, 0.55 mmol) and K$_2$CO$_3$ (67 mg, 0.49 mmol) were added. The reaction mixture was stirred at 70° C. overnight. EtOAc and dilute HCl were added. The two phases were separated and the organic extract was washed with brine. The combined aqueous phase was extracted with EtOAc. The combined organic extract was dried over MgSO$_4$, filtered and evaporated. The residue was purified by preparative HPLC, PrepMethod A, (gradient: 20-70%) to yield the title compound (66 mg, 64%); HRMS (ESI) m/z [M+H]$^+$ calcd for C$_{20}$H$_{29}$N$_6$O$_3$S: 433.2016, found: 433.2042; $^1$H NMR (400 MHz, CDCl$_3$) 0.87-0.98 (6H, m), 1.28-1.71 (m, partial overlap with water), 2.83-2.97 (2H, m), 3.29-3.35 (3H, m), 3.41-3.51 (1H, m), 3.53-3.62 (1H, m), 3.64-3.80 (1H, m), 4.13-4.24 (1H, m), 7.31-7.38 (2H, m), 7.54-7.60 (2H, m).

Example 69

N-(4-(((R)-1-Hydroxy-4-methylpentan-2-yl)amino)-6-(2-(4-(methoxymethyl)phenyl)propyl)-1,3,5-triazin-2-yl)methanesulfonamide

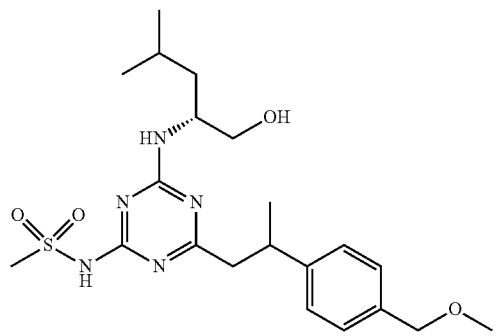

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then (2R)-2-((4-chloro-6-(2-(4-(methoxymethyl)phenyl)propyl)-1,3,5-triazin-2-yl)amino)-4-methylpentan-1-ol Intermediate 84 (114 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was acidified with 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod H, to yield the title compound (69 mg, 52%); HRMS (ESI) m/z [M+H]$^+$ calcd for C$_{21}$H$_{34}$N$_5$O$_4$S: 452.2326, found: 452.2338; $^1$H NMR (600 MHz, DMSO) 0.81-0.90 (6H, m), 1.19-1.45 (5H, m), 1.50-1.60 (1H, m), 2.63-2.79 (2H, m), 2.93-3.09 (2H, s), 3.20-3.45 (m, partial overlap with water), 3.97-4.15 (1H, m), 4.33-4.37 (2H, m), 4.64-4.76 (1H, m), 7.20-7.33 (m, partial overlap with impurity).

Example 70

N-(4-(2-(3,4-Dimethylphenyl)propyl)-6-(((R)-1-hydroxy-4-methylpentan-2-yl)amino)-1,3,5-triazin-2-yl)methanesulfonamide

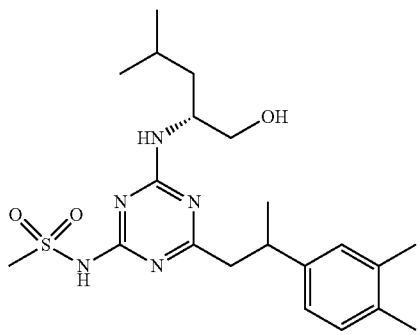

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then (2R)-2-((4-chloro-6-(2-(3,4-dimethylphenyl)propyl)-1,3,5-triazin-2-yl)amino)-4-methylpentan-1-ol Intermediate 85 (109 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was acidified with 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod G, to yield the title compound (62 mg, 49%); HRMS (ESI) m/z [M+H]$^+$ calcd for C$_{21}$H$_{34}$N$_5$O$_3$S: 436.2376, found: 436.2368; $^1$H NMR (600 MHz, DMSO) 0.81-0.91 (6H, m), 1.17-1.22 (3H, m), 1.28-1.47 (2H, m), 1.50-1.60 (1H, m), 2.13-2.20 (6H, m), 2.60-2.78 (2H, m), 2.95-3.12 (2H, m), 3.21-3.41 (m, partial overlap with water), 3.98-4.16 (1H, m), 4.64-4.76 (1H, m), 6.90-7.06 (3H, m).

Example 71

N-(4-(2-(4-(1,1-Difluoroethyl)phenyl)propyl)-6-(((R)-1-hydroxy-4-methylpentan-2-yl)amino)-1,3,5-triazin-2-yl)methanesulfonamide

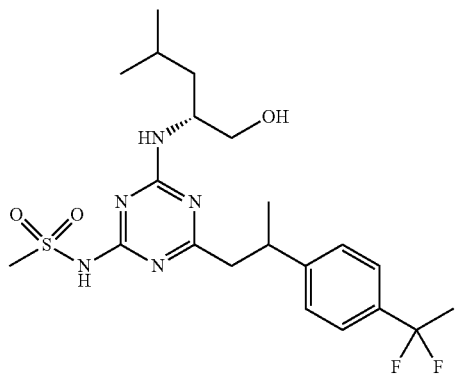 [SMILES: CC(C)C[C@H](CO)Nc1nc(CC(C)c2ccc(C(C)(F)F)cc2)nc(NS(C)(=O)=O)n1]

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then (2R)-2-((4-chloro-6-(2-(4-(1,1-difluoroethyl)phenyl)propyl)-1,3,5-triazin-2-yl)amino)-4-methylpentan-1-ol Intermediate 86 (120 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was acidified with 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod H, to yield the title compound (67 mg, 47%); HRMS (ESI) m/z [M+H]$^+$ calcd for C$_{21}$H$_{32}$F$_2$N$_5$O$_3$S: 472.2188, found: 472.2192; $^1$H NMR (600 MHz, DMSO) 0.80-0.91 (6H, m), 1.21-1.46 (5H, m), 1.49-1.60 (1H, m), 1.89-2.00 (3H, m), 2.64-2.86 (2H, m), 2.95-3.17 (2H, m), 3.25-3.45 (m, partial overlap with water), 3.98-4.14 (1H, m), 4.63-4.77 (1H, m), 7.32-7.39 (2H, m), 7.44-7.51 (2H, m).

Example 72

N-(4-(2-(3-Chlorophenyl)propyl)-6-(((R)-1-hydroxy-4-methylpentan-2-yl)amino)-1,3,5-triazin-2-yl)methanesulfonamide

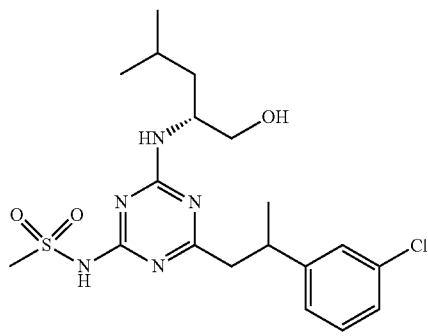

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then (2R)-2-((4-chloro-6-(2-(3-chlorophenyl)propyl)-1,3,5-triazin-2-yl)amino)-4-methylpentan-1-ol Intermediate 87 (111 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was acidified with 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod G, to yield the title compound (67 mg, 51%); HRMS (ESI) m/z [M+H]$^+$ calcd for C$_{19}$H$_{29}$ClN$_5$O$_3$S: 442.1674, found: 442.1682; $^1$H NMR (600 MHz, DMSO) 0.80-0.90 (6H, m), 1.21-1.46 (5H, m), 1.49-1.62 (1H, m), 2.64-2.83 (2H, m), 2.90-3.15 (2H, m), 3.26-3.45 (m, partial overlap with water), 3.95-4.14 (1H, m), 4.63-4.76 (1H, m), 7.18-7.36 (4H, m).

Example 73

N-(4-(1-(4-(((R)-1-Hydroxy-4-methylpentan-2-yl)amino)-6-(methylsulfonamido)-1,3,5-triazin-2-yl)propan-2-yl)phenyl)-N-methylacetamide

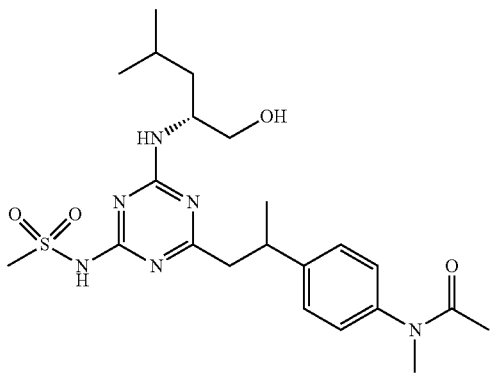 [SMILES: CC(=O)N(C)c1ccc(C(C)Cc2nc(N[C@@H](CO)CC(C)C)nc(NS(C)(=O)=O)n2)cc1]

THF (0.3 mL) was added to Pd$_2$dba$_3$ (10.6 mg, 0.01 mmol) and X-Phos (22 mg, 0.05 mmol) and the mixture was stirred under nitrogen atmosphere at rt for 10 min and then N-(4-(1-(4-chloro-6-(((R)-1-hydroxy-4-methylpentan-2-yl)amino)-1,3,5-triazin-2-yl)propan-2-yl)phenyl)-N-methylacetamide Intermediate 88 (122 mg, 0.29 mmol) in THF (1 mL), methanesulfonamide (55 mg, 0.58 mmol) in THF (0.5 mL) and K$_2$CO$_3$ (82 mg, 0.59 mmol) were added. The reaction mixture was stirred at 70° C. overnight. EtOAc and water were added. The mixture was acidified with 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod H, to yield the title compound (51 mg, 36%); HRMS (ESI) m/z [M+H]$^+$ calcd for C$_{22}$H$_{35}$N$_6$O$_4$S: 479.2434, found: 479.2434; $^1$H NMR (600 MHz, DMSO) 0.81-0.91 (6H, m), 1.22-1.27 (3H, m), 1.28-1.45 (2H, m), 1.51-1.60 (1H, m), 1.72 (3H, s), 2.63-2.82 (2H, m), 2.96-3.19 (5H, m), 3.25-3.45 (m, partial overlap with water), 3.98-4.17 (1H, m), 4.62-4.77 (1H, m), 7.17-7.35 (4H, m).

Example 74

N-(4-(((R)-1-Hydroxy-4-methylpentan-2-yl)amino)-6-(2-(4-(trifluoromethyl)phenyl)propyl)-1,3,5-triazin-2-yl)methanesulfonamide

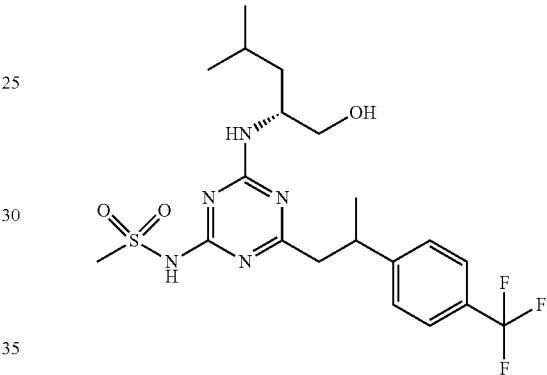

THF (0.3 mL) was added to Pd$_2$dba$_3$ (7.0 mg, 7.7 μmol) and X-Phos (14.6 mg, 0.03 mmol) and the mixture was stirred under nitrogen atmosphere at rt for a few min and then (2R)-2-((4-chloro-6-(2-(4-(trifluoromethyl)phenyl)propyl)-1,3,5-triazin-2-yl)amino)-4-methylpentan-1-ol Intermediate 89 (80 mg, 0.19 mmol) in THF (0.5 mL), methanesulfonamide (36.5 mg, 0.38 mmol) in THF (0.5 mL) and K$_2$CO$_3$ (53.0 mg, 0.38 mmol) were added. The reaction mixture was stirred at 70° C. overnight. EtOAc and water were added. The mixture was acidified with 3.8 M HCl and the two phases were separated. The aqueous phase was extracted with EtOAc and the combined organic extract was dried over MgSO$_4$, treated with SiliaMetS Thiol for 30 min, filtered and evaporated. The residue was purified by preparative HPLC, PrepMethod H, to yield the title compound (8 mg, 9%); HRMS (ESI) m/z [M+H]$^+$ calcd for C$_{20}$H$_{29}$F$_3$NSO$_3$S: 476.1938, found: 476.1894; $^1$H NMR (600 MHz, DMSO) 0.77-0.89 (6H, m), 1.23-1.45 (5H, m), 1.47-1.58 (1H, m), 2.68-2.87 (2H, m), 2.98-3.16 (2H, m), 3.25-3.47 (m, partial overlap with water), 3.97-4.10 (1H, m), 4.64-4.76 (1H, m), 7.45-7.51 (2H, m), 7.61-7.68 (2H, m).

Example 75

N-(4-(((R)-1-Hydroxy-4-methylpentan-2-yl)amino)-6-((S*)-2-(6-methoxypyridin-3-yl)propyl)-1,3,5-triazin-2-yl)methanesulfonamide (Isomer 1)

Isomer 1

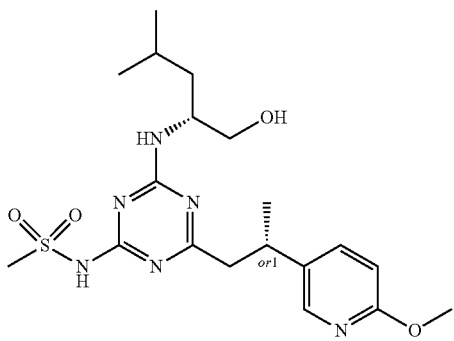

Example 76

N-(4-(((R)-1-Hydroxy-4-methylpentan-2-yl)amino)-6-((R*)-2-(6-methoxypyridin-3-yl)propyl)-1,3,5-triazin-2-yl)methanesulfonamide (Isomer 2)

Isomer 2

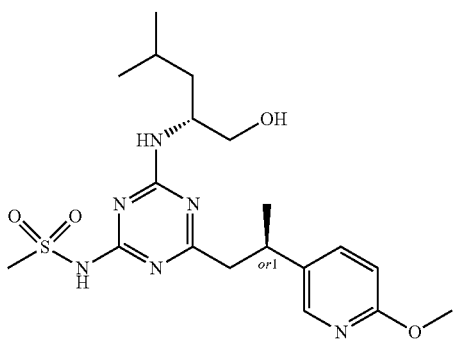

The diastereomers of N-(4-(((R)-1-hydroxy-4-methylpentan-2-yl)amino)-6-(2-(6-methoxypyridin-3-yl)propyl)-1,3,5-triazin-2-yl)methanesulfonamide Intermediate 91 (2.8 g, 6.38 mmol) were separated by preparative chiral HPLC on a Lux 5 µm Cellulose-4 column (5 µm, 250×30) using 35% MeOH (0.1% 2 M NH$_3$-MeOH) in CO$_2$, 100 bar, at a flow rate of 70 mL/min and detected at 220 nm, to yield the first eluted compound N-(4-(((R)-1-hydroxy-4-methylpentan-2-yl)amino)-6-((S*)-2-(6-methoxypyridin-3-yl)propyl)-1,3,5-triazin-2-yl)methanesulfonamide (Isomer 1) Example 75 (1.04 g, 37%) as a white solid; HRMS (ESI) m/z [M+H]$^+$ calcd for C$_{19}$H$_{31}$N$_6$O$_4$S: 439.2122, found: 439.2116; $^1$H NMR (400 MHz, CDCl$_3$) 0.83-1.0 (6H, m), 1.2-1.55 (5H, m), 1.55-1.78 (1H, m), 2.82-3.02 (2H, m), 3.2-3.4 (4H, m), 3.52-3.82 (2H, m), 3.89 (3H, s), 4.12-4.35 (1H, m), 6.69 (1H, d), 6.98 (1H, br s), 7.47-7.58 (1H, m), 7.95-8.03 (1H, m), and the second eluted compound N-(4-(((R)-1-hydroxy-4-methylpentan-2-yl)amino)-6-((R*)-2-(6-methoxypyridin-3-yl)propyl)-1,3,5-triazin-2-yl)methanesulfonamide (Isomer 2) Example 76 (0.856 g, 31%) as a white solid; HRMS (ESI) m/z [M+H]$^+$ calcd for C$_{19}$H$_{31}$N$_6$O$_4$S: 439.2122, found: 439.2122; $^1$H NMR (300 MHz, CDCl$_3$) 0.85-1.02 (6H, m), 1.25-1.55 (5H, m), 1.55-1.78 (1H, m), 2.83-3.0 (2H, m), 3.25-3.48 (4H, m), 3.48-3.81 (2H, m), 3.93 (3H, d), 4.15-4.33 (1H, m), 6.74 (1H, d), 6.80-6.89 (1H, m), 7.48-7.65 (1H, m), 8.01-8.13 (1H, m).

Example 77

N-(4-((S*)-2-(2,6-Difluorophenyl)propyl)-6-(((R)-1-hydroxy-4-methylpentan-2-yl)amino)-1,3,5-triazin-2-yl)methanesulfonamide (Isomer 1)

Isomer 1

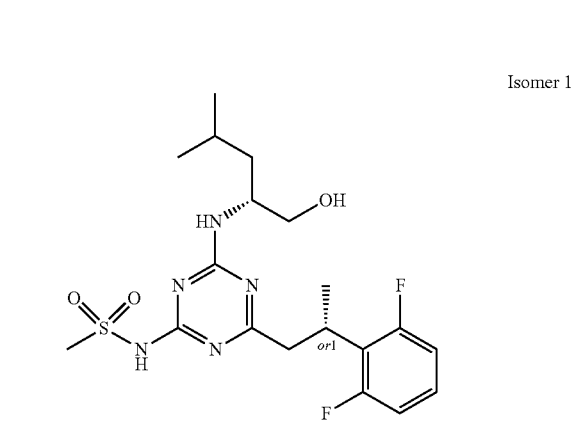 [SMILES: CC(C)C[C@H](CO)Nc1nc(C[C@H](C)c2c(F)cccc2F)nc(NS(C)(=O)=O)n1]

Example 78

N-(4-((R*)-2-(2,6-Difluorophenyl)propyl)-6-(((R)-1-hydroxy-4-methylpentan-2-yl)amino)-1,3,5-triazin-2-yl)methanesulfonamide (Isomer 2)

Isomer 2

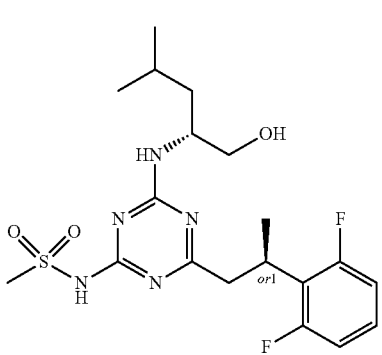

The diastereomers of N-(4-(2-(2,6-difluorophenyl)propyl)-6-(((R)-1-hydroxy-4-methylpentan-2-yl)amino)-1,3,5-triazin-2-yl)methanesulfonamide Intermediate 93 (15 mg, 0.03 mmol) were separated by preparative chiral HPLC on a Chiralcel OJ column (5 µm, 250×30 mm ID) eluted with 20% EtOH/DEA (100/0.5) in CO$_2$, 120 bar at a flow rate of 80 mL/min and detected at 230 nm, to give the first eluted compound N-(4-((S*)-2-(2,6-difluorophenyl)propyl)-6-(((R)-1-hydroxy-4-methylpentan-2-yl)amino)-1,3,5-triazin-2-yl)methanesulfonamide (Isomer 1) Example 77 that was dissolved in DCM/0.25 M KHSO$_4$ and extracted with DCM (×3), dried through a phase separator and evaporated to yield (8 mg, 53%); HRMS (ESI) m/z [M+H]+ calcd for $C_{19}H_{28}F_2N_5O_3S$: 444.1876, found: 444.1870; $^1H$ NMR (500 MHz, CDCl$_3$) 0.85-0.97 (6H, m), 1.30-1.50 (5H, m), 1.55-1.71 (1H, m), 2.95-3.18 (2H, m), 3.25-3.34 (3H, m), 3.52-3.60 (1H, m), 3.68 (0.7H, dd), 3.75 (0.3H, dd), 3.78-3.9 (1H, m), 4.12-4.22 (1H, m), 6.76-6.85 (2H, m), 7.04-7.16 (1H, m). The second eluted compound from the chiral separation, N-(4-((R*)-2-(2,6-difluorophenyl)propyl)-6-(((R)-1-hydroxy-4-methylpentan-2-yl)amino)-1,3,5-triazin-2-yl)methanesulfonamide (Isomer 2) Example 78 was dissolved in DCM/0.25 M KHSO$_4$ and extracted with DCM (×3), dried through a phase separator and evaporated to yield (6 mg, 40%); IRMS (ESI) m/z [M+H]+ calcd for $C_{19}H_{28}F_2N_5O_3S$: 444.1876, found: 444.1880; $^1H$ NMR (500 MHz, CDCl$_3$) 0.88-0.96 (6H, m), 1.31-1.50 (5H, m), 1.55-1.71 (1H, m), 2.95-3.19 (2H, m), 3.25-3.35 (3H, m), 3.51-3.60 (1H, m), 3.64 (0.7H, dd), 3.76 (0.3H, dd), 3.79-3.93 (1H, m), 4.15-4.28 (1H, m), 6.76-6.84 (2H, m), 7.04-7.16 (1H, m).

Example 79

N-(4-((R*)-2-(4-Fluorophenyl)propyl)-6-(((R)-1-hydroxy-4-methylpentan-2-yl)amino)-1,3,5-triazin-2-yl)methanesulfonamide (Isomer 1)

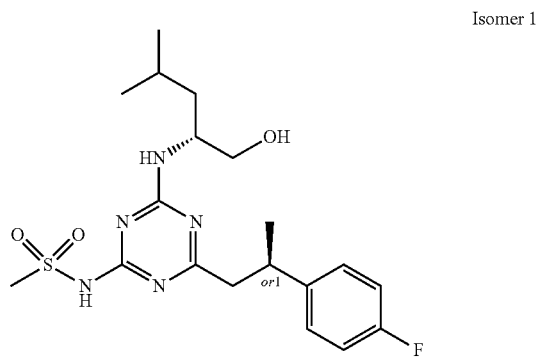 [SMILES: CC(C)C[C@H](CO)Nc1nc(C[C@@H](C)c2ccc(F)cc2)nc(NS(C)(=O)=O)n1]

Example 80

N-(4-((S*)-2-(4-Fluorophenyl)propyl)-6-(((R)-1-hydroxy-4-methylpentan-2-yl)amino)-1,3,5-triazin-2-yl)methanesulfonamide (Isomer 2)

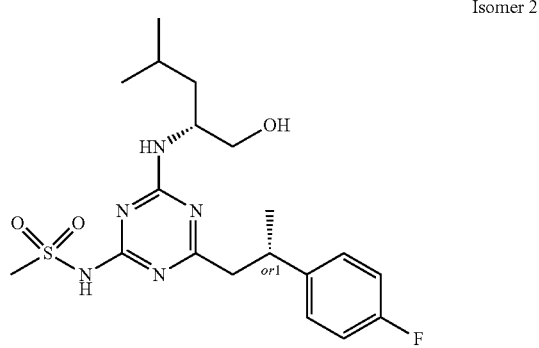 [SMILES: CC(C)C[C@H](CO)Nc1nc(C[C@H](C)c2ccc(F)cc2)nc(NS(C)(=O)=O)n1]

The diastereomers of N-(4-(2-(4-fluorophenyl)propyl)-6-(((R)-1-hydroxy-4-methylpentan-2-yl)amino)-1,3,5-triazin-2-yl)methanesulfonamide Intermediate 94 (60 mg, 0.14 mmol) were separated by preparative chiral HPLC on a Chiralpak IC column (5 μm, 250×20 mm ID) using heptane/(DCM/MeOH, 9/1)/TEA (60/40/0.1) as mobile phase, at a flow rate of 25 mL/min and detected at 270 nm, to yield the first eluted compound N-(4-((R*)-2-(4-fluorophenyl)propyl)-6-(((R)-1-hydroxy-4-methylpentan-2-yl)amino)-1,3,5-triazin-2-yl)methanesulfonamide (Isomer 1) Example 79, that was dissolved in DCM/0.25 M KHSO$_4$ and extracted with DCM (×3), dried through a phase separator and evaporated to yield (22 mg, 35%); HRMS (ESI) m/z [M+H]+ calcd for $C_{19}H_{29}FN_5O_3S$: 426.1970, found: 426.1984; $^1H$ NMR (500 MHz, CDCl$_3$) 0.90-0.97 (6H, m), 1.25-1.53 (5H, m), 1.57-1.72 (1H, m), 2.85-2.95 (2H, m), 3.20-3.25 (3H, m), 3.27-3.39 (1H, m), 3.54-3.62 (1H, m), 3.69 (0.6H, dd). 3.79 (0.4H, dd), 4.17-4.27 (1H, m), 6.90-6.99 (3H, m), 7.14-7.21 (2H, m). The second eluted compound from the chiral separation, N-(4-((S*)-2-(4-fluorophenyl)propyl)-6-(((R)-1-hydroxy-4-methylpentan-2-yl)amino)-1,3,5-triazin-2-yl)methanesulfonamide (Isomer 2) Example 80 was dissolved in DCM/0.25 M KHSO$_4$ and extracted with DCM (×3), dried through a phase separator and evaporated to yield (21 mg, 33%); IRMS (ESI) m/z [M+H]+ calcd for $C_{19}H_{29}FN_5O_3S$: 426.1970, found: 426.1972; $^1H$ NMR (500 MHz, CDCl$_3$) 0.89-0.97 (6H, m), 1.24-1.38 (4H, m), 1.39-1.51 (1H, m), 1.54-1.74 (1H, m), 2.83-2.94 (2H, m), 3.22-3.28 (3H, m), 3.29-3.42 (1H, m), 3.55-3.62 (1H, m), 3.70 (0.7H, dd), 3.77 (0.3H, dd), 4.16-4.23 (1H, m), 6.89-6.99 (2H, m), 7.14-7.22 (2H, m).

Example 81

N-(4-((R*)-2-(2-Fluoro-4-methoxyphenyl)propyl)-6-(((R)-1-hydroxy-4-methylpentan-2-yl)amino)-1,3,5-triazin-2-yl)methanesulfonamide (Isomer 1)

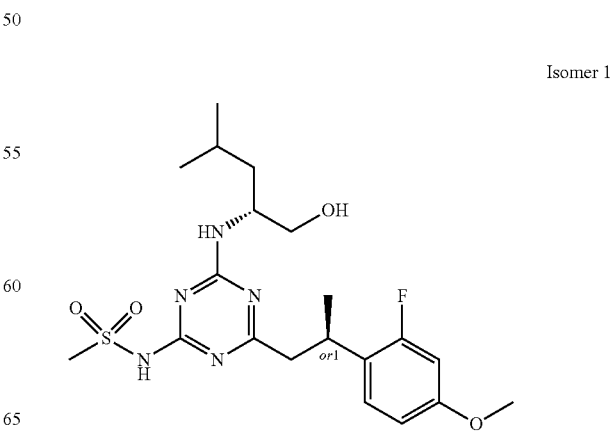

Example 82

N-(4-((S*)-2-(2-Fluoro-4-methoxyphenyl)propyl)-6-(((R)-1-hydroxy-4-methylpentan-2-yl)amino)-1,3,5-triazin-2-yl)methanesulfonamide (Isomer 2)

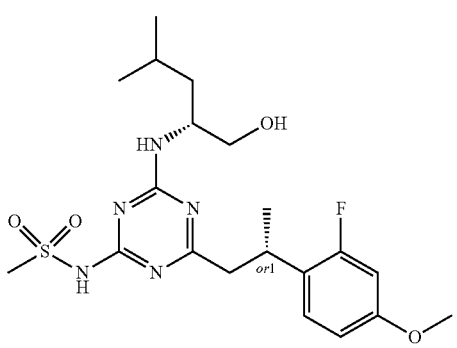

Isomer 2

The diastereomers of N-(4-(2-(2-fluoro-4-methoxyphenyl)propyl)-6-(((R)-1-hydroxy-4-methylpentan-2-yl)amino)-1,3,5-triazin-2-yl)methanesulfonamide Intermediate 96 (23 mg, 0.05 mmol) were separated by preparative chiral HPLC on a Chiralpak IC (5 μm, 250×20 mm) using 30% EtOH/DEA (100/0.5) in $CO_2$, 120 bar as mobile phase, at a flow rate of 70 mL/min and detected at 230 nm, to give the first eluted compound N-(4-((R*)-2-(2-fluoro-4-methoxyphenyl)propyl)-6-(((R)-1-hydroxy-4-methylpentan-2-yl)amino)-1,3,5-triazin-2-yl)methanesulfonamide (Isomer 1) Example 81 that was dissolved in DCM/0.25 M $KHSO_4$. The organic phase was dried through a phase separator and evaporated to yield (7 mg, 30%); HRMS (ESI) m/z $[M+H]^+$ calcd for $C_{20}H_{31}FN_5O_4S$: 456.2076, found: 456.2080; $^1H$ NMR (500 MHz, $CDCl_3$) 0.88-0.97 (6H, m), 1.26-1.51 (5H, m), 1.55-1.73 (1H, m), 2.84-3.03 (2H, m), 3.22-3.29 (3H, m), 3.53-3.80 (6H, m), 4.16-4.29 (1H, m), 6.50-6.58 (1H, m), 6.58-6.66 (1H, m), 7.10-7.17 (1H, m). The second eluted compound from the chiral separation, N-(4-((S*)-2-(2-fluoro-4-methoxyphenyl)propyl)-6-(((R)-1-hydroxy-4-methylpentan-2-yl)amino)-1,3,5-triazin-2-yl)methanesulfonamide (Isomer 2) Example 82 was dissolved in DCM/0.25 M $KHSO_4$. The organic phase was evaporated to yield (6 mg, 26%); HRMS (ESI) m/z $[M+H]^+$ calcd for $C_{20}H_{31}FN_5O_4S$: 456.2076, found: 456.2080; $^1H$ NMR (500 MHz, $CDCl_3$) 0.86-0.97 (6H, m), 1.25-1.52 (5H, m), 1.57-1.72 (1H, m), 2.86-3.01 (2H, m), 3.22-3.28 (3H, m), 3.52-3.80 (6H, m), 4.16-4.26 (1H, m), 6.50-6.57 (1H, m), 6.59-6.64 (1H, m), 7.10-7.18 (1H, m).

Example 83

N-(4-((S*)-2-(4-Chloro-2-fluorophenyl)propyl)-6-(((R)-1-hydroxy-4-methylpentan-2-yl)amino)-1,3,5-triazin-2-yl)methanesulfonamide (Isomer 1)

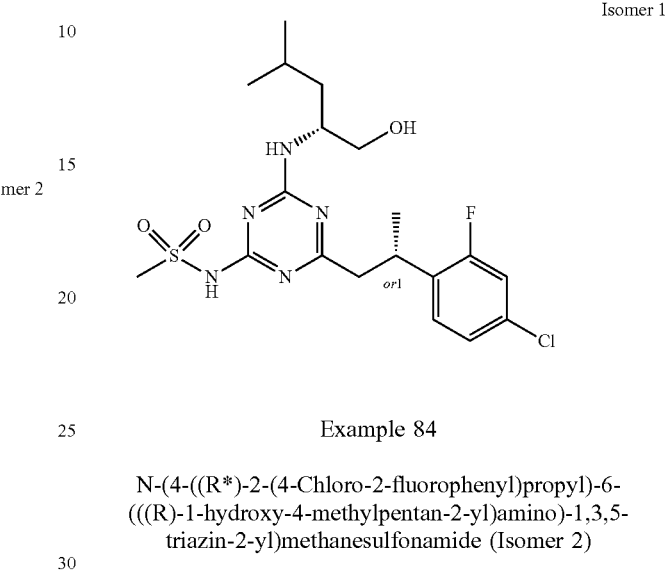

Isomer 1

Example 84

N-(4-((R*)-2-(4-Chloro-2-fluorophenyl)propyl)-6-(((R)-1-hydroxy-4-methylpentan-2-yl)amino)-1,3,5-triazin-2-yl)methanesulfonamide (Isomer 2)

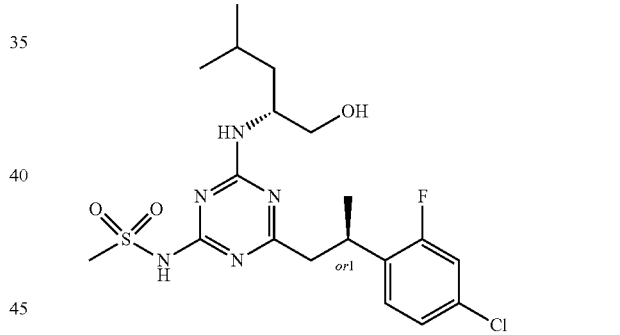

Isomer 2

The diastereomers of N-(4-(2-(4-chloro-2-fluorophenyl)propyl)-6-(((R)-1-hydroxy-4-methylpentan-2-yl)amino)-1,3,5-triazin-2-yl)methanesulfonamide Intermediate 98 (128 mg, 0.278 mmol) were separated by preparative chiral HPLC on a Chiralcel OJ (5 μm, 250×30 mm) using 25% EtOH/$NH_3$ in $CO_2$, 120 bar as mobile phase, at a flow rate of 80 mL/min and detected at 230 nm, to give the first eluted compound N-(4-((S*)-2-(4-chloro-2-fluorophenyl)propyl)-6-(((R)-1-hydroxy-4-methylpentan-2-yl)amino)-1,3,5-triazin-2-yl)methanesulfonamide (Isomer 1) Example 83 that was dissolved in EtOAc (35 mL). The organic layer was washed with water (2×5 mL) and brine, dried over $MgSO_4$, filtered and concentrated to yield (29 mg, 23%); HRMS (ESI) m/z $[M+H]^+$ calcd for $C_{19}H_{28}ClFN_5O_3S$: 460.1580, found: 460.1590; $^1H$ NMR (400 MHz, $CDCl_3$) 0.84-0.98 (6H, m), 1.28-1.52 (5H, m, partial overlap with EtOAc), 1.53-1.72 (1H, m), 2.86-3.05 (2H, m), 3.21-3.29 (3H, m), 3.52-3.81 (3H, m), 4.11-4.26 (m, partial overlap with EtOAc), 6.95-7.09 (3H, m), 7.16-7.25 (1H, m). The second eluted compound from the chiral separation, N-(4-((R*)-2-

(4-chloro-2-fluorophenyl)propyl)-6-(((R)-1-hydroxy-4-methylpentan-2-yl)amino)-1,3,5-triazin-2-yl)methanesulfonamide (Isomer 2) Example 84 was dissolved in EtOAc (35 mL) and washed with water (2×5 mL). The combined aqueous layers were extracted with EtOAc. The combined organic phases were washed with brine, dried over MgSO$_4$, filtered and concentrated to yield to yield (37 mg, 29%); HRMS (ESI) m/z [M+H]$^+$ calcd for $C_{19}H_{28}ClFN_5O_3S$: 460.1580, found: 460.1556; $^1$H NMR (400 MHz, CDCl$_3$) 0.86-0.96 (6H, m), 1.27-1.51 (5H, m, partial overlap with EtOAc), 1.52-1.73 (1H, m), 2.91-3.05 (2H, m), 3.20-3.28 (3H, m), 3.52-3.79 (3H, m), 4.16-4.28 (1H, m), 6.95-7.12 (3H, m), 7.16-7.24 (1H, m).

Example 85

N-(4-((R*)-2-(2-Fluoro-6-methoxypyridin-3-yl)propyl)-6-(((R)-1-hydroxy-4-methylpentan-2-yl)amino)-1,3,5-triazin-2-yl)methanesulfonamide (Isomer 1)

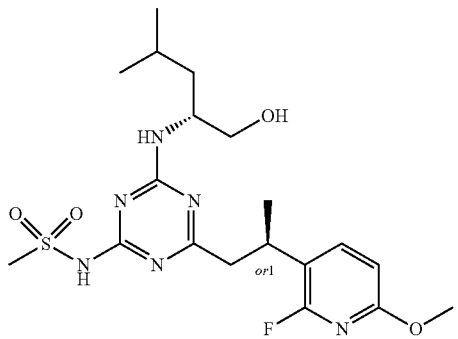

Isomer 1

Example 86

N-(4-((S*)-2-(2-Fluoro-6-methoxypyridin-3-yl)propyl)-6-(((R)-1-hydroxy-4-methylpentan-2-yl)amino)-1,3,5-triazin-2-yl)methanesulfonamide (Isomer 2)

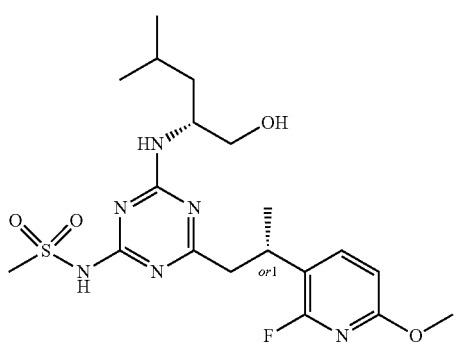

Isomer 2

The diastereomers of N-(4-(2-(2-fluoro-6-methoxypyridin-3-yl)propyl)-6-(((R)-1-hydroxy-4-methylpentan-2-yl)amino)-1,3,5-triazin-2-yl)methanesulfonamide Intermediate 100 (1.70 g, 3.72 mmol) were separated by preparative chiral HPLC on a CHIRAL ART Cellulose-SC (5 μm, 250×20 mm) column using 40% EtOH in hexane (0.1% FA), at a flow rate of 20 mL/min and detected at 220/254 nm, to yield the first eluted compound N-(4-((R*)-2-(2-fluoro-6-methoxypyridin-3-yl)propyl)-6-(((R)-1-hydroxy-4-methylpentan-2-yl)amino)-1,3,5-triazin-2-yl)methanesulfonamide (Isomer 1) Example 85 (0.64 g, 38%) as a white solid; HRMS (ESI) m/z [M+H]$^+$ calcd for $C_{19}H_{30}FN_6O_4S$: 457.2028, found: 457.2012; $^1$H NMR (400 MHz, CDCl$_3$) 0.89-0.99 (6H, m), 1.25-1.54 (5H, m), 1.54-1.73 (1H, m), 2.95-3.06 (2H, m), 3.26-3.33 (3H, m), 3.52-3.81 (3H, m), 3.83-3.92 (3H, m), 4.16-4.33 (1H, m), 6.53-6.62 (1H, m), 7.56-7.68 (1H, m), and the second eluted compound N-(4-((S*)-2-(2-fluoro-6-methoxypyridin-3-yl)propyl)-6-(((R)-1-hydroxy-4-methylpentan-2-yl)amino)-1,3,5-triazin-2-yl)methanesulfonamide (Isomer 2) Example 86 (0.67 g, 39%) as a white solid; HRMS (ESI) m/z [M+H]$^+$ calcd for $C_{19}H_{30}FN_6O_4S$: 457.2028, found: 457.2016; $^1$H NMR (300 MHz, CDCl$_3$) 0.82-1.0 (6H, m), 1.22-1.75 (6H, m), 2.88-3.05 (2H, m), 3.22-3.35 (3H, m), 3.50-3.84 (3H, m), 3.88 (3H, s), 4.12-4.3 (1H, m), 6.57 (1H, d), 7.54-7.72 (1H, m).

Example 87

N-(4-(((R)-1-Hydroxy-4-methylpentan-2-yl)amino)-6-((S*)-2-(2,3,4-trifluorophenyl)propyl)-1,3,5-triazin-2-yl)methanesulfonamide (Isomer 1)

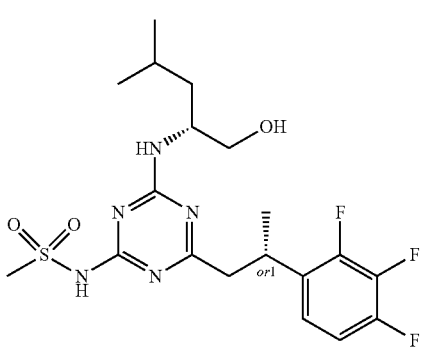

Isomer 1

Example 88

N-(4-(((R)-1-Hydroxy-4-methylpentan-2-yl)amino)-6-((R*)-2-(2,3,4-trifluorophenyl)propyl)-1,3,5-triazin-2-yl)methanesulfonamide (Isomer 2)

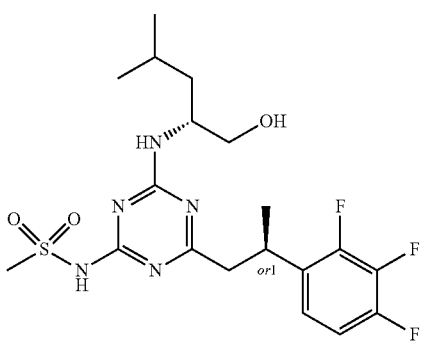

Isomer 2

The diastereomers of N-(4-(((R)-1-hydroxy-4-methylpentan-2-yl)amino)-6-(2-(2,3,4-trifluorophenyl)propyl)-1,3,5-triazin-2-yl)methanesulfonamide Intermediate 102 (68 mg, 0.15 mmol) were separated by preparative chiral HPLC on a Lux C₃ (OJ) column (5 µm, 250×20 mm ID) using 8% MeOH/DEA (100/20 mM) in CO₂, 130 bar as mobile phase, at a flow rate of 70 mL/min and detected at 230 nm, to yield the first eluted compound N-(4-(((R)-1-hydroxy-4-methylpentan-2-yl)amino)-6-((S*)-2-(2,3,4-trifluorophenyl)propyl)-1,3,5-triazin-2-yl)methanesulfonamide (Isomer 1) Example 87 (26 mg, 38%); HRMS (ESI) m/z [M+H]⁺ calcd for $C_{19}H_{27}F_3N_5O_3S$: 462.1780, found: 462.1780; ¹H NMR (400 MHz, CDCl₃) 0.84-0.98 (6H, m), 1.28-1.52 (5H, m), 1.53-1.73 (1H, m), 2.86-3.07 (2H, m), 3.22-3.32 (3H, m), 3.52-3.81 (3H, m), 4.14-4.27 (1H, m), 6.83-7.05 (3H, m), and the second eluted compound N-(4-(((R)-1-hydroxy-4-methylpentan-2-yl)amino)-6-((R*)-2-(2,3,4-trifluorophenyl)propyl)-1,3,5-triazin-2-yl)methanesulfonamide (Isomer 2) Example 88 (28 mg, 41%); HRMS (ESI) m/z [M+H]⁺ calcd for $C_{19}H_{27}F_3N_5O_3S$: 462.1780, found: 462.1786; ¹H NMR (400 MHz, CDCl₃) 0.86-0.97 (6H, m), 1.28-1.52 (5H, m), 1.52-1.72 (1H, m), 2.92-3.08 (2H, m), 3.21-3.33 (3H, m), 3.53-3.81 (3H, m), 4.15-4.31 (1H, m), 6.83-6.93 (1H, m), 6.93-7.03 (1H, m), 7.06-7.12 (1H, m).

Example 89

N-(4-(2-(2-Fluorophenyl)butyl)-6-(((R)-1-hydroxy-4-methylpentan-2-yl)amino)-1,3,5-triazin-2-yl)methanesulfonamide

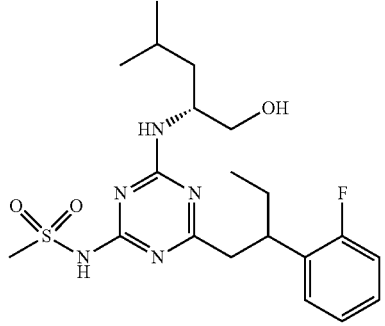 [SMILES: CCC(Cc1nc(N[C@@H](CO)CC(C)C)nc(NS(C)(=O)=O)n1)c1ccccc1F]

9-BBN Dimer (174 mg, 0.720 mmol) was added to 1-(but-1-en-2-yl)-2-fluorobenzene Intermediate 103 (104 mg, 0.690 mmol) in THF (1.85 mL), and the reaction mixture was stirred at rt for 35 min and then 3 M K₃PO₄ (aq, 463 µL, 1.39 mmol), (R)—N-(4-chloro-6-((1-hydroxy-4-methylpentan-2-yl)amino)-1,3,5-triazin-2-yl)methanesulfonamide Intermediate 1 (150 mg, 0.460 mmol) and PdCl₂(dppf).DCM (17 mg, 0.02 mmol) were added. The resulting mixture was degassed and stirred at 35° C. overnight. DCM and 1 M KHSO₄ were added. The organic layer was concentrated and the residue was purified by preparative HPLC, PrepMethod F (gradient: 5-95%) to give the title compound (19 mg, 9%); HRMS (ESI) m/z [M+H]⁺ calcd for $C_{20}H_{31}FN_5O_3S$: 440.2126, found: 440.2104; ¹H NMR (600 MHz, DMSO-d₆) 0.69-0.76 (3H, m), 0.80-0.89 (6H, m), 1.27-1.72 (5H, m), 2.68-2.93 (2H, m), 2.96-2.16 (3H, m), 3.38-3.52 (m, partial overlap with water), 3.92-4.13 (1H, m), 4.59-4.75 (1H, m), 7.05-7.35 (4H, m).

Example 90

N-(4-((S*)-2-(2-Fluoropyridin-4-yl)propyl)-6-(((R)-1-hydroxy-4-methylpentan-2-yl)amino)-1,3,5-triazin-2-yl)methanesulfonamide (Isomer 1)

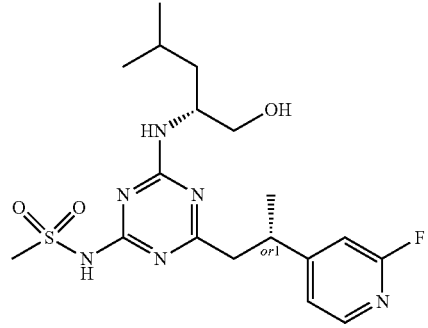

Isomer 1

Example 91

N-(4-((R*)-2-(2-Fluoropyridin-4-yl)propyl)-6-(((R)-1-hydroxy-4-methylpentan-2-yl)amino)-1,3,5-triazin-2-yl)methanesulfonamide (Isomer 2)

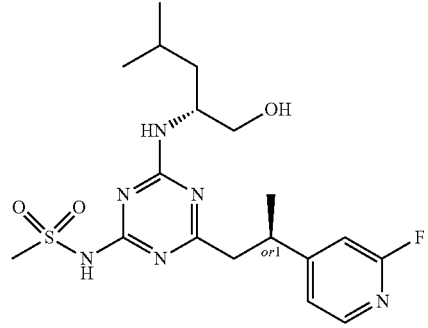

Isomer 2

The diastereomers of N-(4-(2-(2-fluoropyridin-4-yl)propyl)-6-(((R)-1-hydroxy-4-methylpentan-2-yl)amino)-1,3,5-triazin-2-yl)methanesulfonamide Intermediate 105 (2.19 g, 4.92 mmol) were separated by preparative chiral HPLC on a CHIRAL ART Cellulose-SB (5 µm, 250×30 mm) column using 25% IPA (0.5% 2 M NH₃ in MeOH) in CO₂, 100 bar as eluent at a flow rate of 60 mL/min and detected at 220 nm, to yield the first eluted compound N-(4-((S*)-2-(2-fluoropyridin-4-yl)propyl)-6-(((R)-1-hydroxy-4-methylpentan-2-yl)amino)-1,3,5-triazin-2-yl)methanesulfonamide (Isomer 1) Example 90 (0.92 g, 44%) as a white solid; HRMS (ESI) m/z [M+H]⁺ calcd for $C_{18}H_{28}FN_6O_3S$: 427.1922, found: 427.1956; NMR (400 MHz, CDCl₃) 0.83-1.01 (6H, m), 1.29-1.54 (5H, m), 1.54-1.75 (1H, m), 2.90-3.08 (2H, m), 3.22-3.35 (3H, m), 3.38-3.51 (1H, m), 3.53-3.62 (1H, m) 3.65-3.85 (1H, m), 4.15-4.3 (1H, m), 6.83 (1H, d), 7.03-7.12 (1H, m), 8.05-8.15 (1H, m), and the second eluted compound N-(4-((R*)-2-(2-fluoropyridin-4-yl)propyl)-6-(((R)-1-hydroxy-4-methylpentan-2-yl)amino)-1,3,5-triazin-2-yl)methanesulfonamide (Isomer 2) Example 91 (0.81 g, 39%)

as a white solid; HRMS (ESI) m/z [M+H]+ calcd for $C_{18}H_{28}FN_6O_3S$: 427.1922, found: 427.1928; $^1$H NMR (400 MHz, CDCl$_3$) 0.83-1.01 (6H, m), 1.28-1.54 (5H, m), 1.54-1.75 (1H, m), 2.90-3.10 (2H, m), 3.22-3.35 (3H, m), 3.38-3.51 (1H, m), 3.52-3.62 (1H, m) 3.62-3.85 (1H, m), 4.15-4.3 (1H, m), 6.83 (1H, s), 7.0-7.13 (1H, m), 8.05-8.15 (1H, m).

Examples 92-142

The following Examples 92 to 142 were prepared as described in General Synthesis Scheme 1 and General Preparation Method A from Intermediate 4 and appropriate boronic acid or boronic ester Intermediate B as described below. Intermediates B are commercially available if not otherwise stated.

General Synthesis Scheme 1

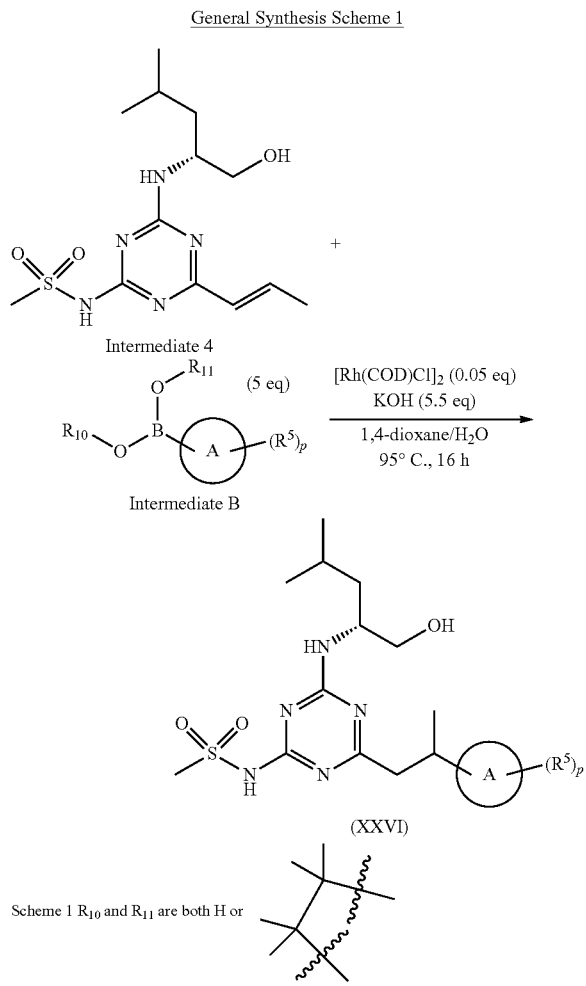

General Preparation Method A

A vial (2 mL) with (R,E)-N-(4-(((1-hydroxy-4-methylpentan-2-yl)amino)-6-(prop-1-en-1-yl)-1,3,5-triazin-2-yl)methanesulfonamide Intermediate 4 (16.5 mg, 50 µmol) and appropriate boronic acid/ester Intermediate B (5 eq) was placed in a glovebox with nitrogen atmosphere. A solution of [Rh(COD)Cl]$_2$ (1.2 mg, 2.5 µmol) in 1,4-dioxane (240 µL) was prepared in the glovebox and added to the reaction vial, which was capped and taken out from the glovebox. A solution of KOH (15.4 mg, 275 µmol) in degassed water (24 µL) was added via syringe, and the resulting reaction mixture was heated at 95° C. for 16 h. After cooling, the mixture was concentrated and DMSO (0.8 mL) was added to the residue. The solution was treated with SiliaMetS Thiol (5 mg) during stirring at rt for 16 h, then filtered and purified by preparative HPLC to give the title compound as a mixture of diastereoisomers.

Example 92

N-(4-(((R)-1-Hydroxy-4-methylpentan-2-yl)amino)-6-(2-(3-methoxyphenyl)propyl)-1,3,5-triazin-2-yl)methanesulfonamide

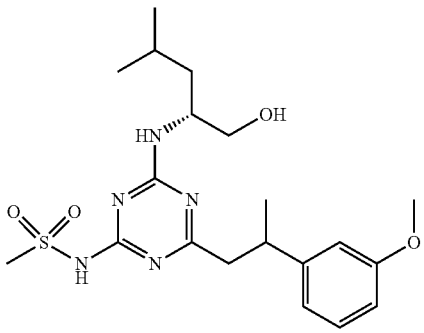

Prepared according to General Preparation Method A using 2-(3-methoxyphenyl)-4,4,5,5-tetramethyl-1,3,2-dioxaborolane as Intermediate B (59 mg, 250 µmol) and purified by preparative HPLC, PrepMethod I, (gradient 5-95%) to give the title compound (3.0 mg, 14%). HRMS (ESI) m/z [M+H]+ calcd for $C_{20}H_{32}N_5O_4S$: 438.2170, found: 438.2172; $^1$H NMR (600 MHz, DMSO-d$_6$) δ 7.74-8.16 (m, 1H), 7.16-7.25 (m, 1H), 6.73-6.85 (m, 3H), 4.52-4.82 (m, 1H), 3.99-4.17 (m, 1H), 3.72-3.75 (m, 3H), 3.34-3.41 (m, partially overlapping with the solvent), 3.04 (m, partially overlapping with the solvent), 2.62-2.77 (m, partially overlapping with the solvent), 1.52-1.61 (m, 1H), 1.29-1.46 (m, 2H), 1.19-1.26 (m, 3H), 0.82-0.92 (m, 6H).

Example 93

N-(4-(2-(1H-Pyrrolo[2,3-b]pyridin-3-yl)propyl)-6-(((R)-1-hydroxy-4-methylpentan-2-yl)amino)-1,3,5-triazin-2-yl)methanesulfonamide

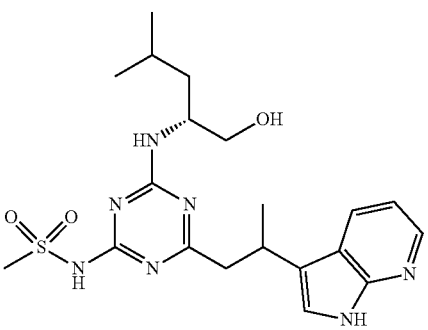 [SMILES: CC(C)C[C@H](CO)Nc1nc(CC(C)c2c[nH]c3ncccc23)nc(NS(C)(=O)=O)n1]

Prepared according to General Preparation Method A using 3-(4,4,5,5-tetramethyl-1,3,2-dioxaborolan-2-yl)-1H- pyrrolo[2,3-b]pyridine as Intermediate B (61 mg, 250 µmol) and purified by preparative HPLC, PrepMethod J (gradient: 15-20%), to give the title compound (2.6 mg, 11%). HRMS (ESI) m/z [M+H]⁺ calcd for $C_{20}H_3N_7O_3S$: 448.2126, found: 448.2110; ¹H NMR (600 MHz, DMSO-$d_6$) δ 8.17-8.23 (m, 1H), 7.9-7.96 (m, 1H), 7.81 (s, 1H), 7.61-7.67 (m, 1H), 7.03-7.1 (m, 1H), 6.43-6.49 (m, 1H), 5.45-5.53 (m, 1H), 4.65 (s, 1H), 3.96-4.18 (m, 2H), 3.36-3.41 (m, partially overlapping with the solvent), 3.00-3.12 (m, partially overlapping with the solvent), 2.56-2.59 (m, partially overlapping with the solvent), 1.47-1.6 (m, 4H), 1.23-1.44 (m, 2H), 0.76-0.9 (m, 6H).

Example 94

N-(4-(((R)-1-Hydroxy-4-methylpentan-2-yl)amino)-6-(2-(2-methylpyridin-4-yl)propyl)-1,3,5-triazin-2-yl)methanesulfonamide

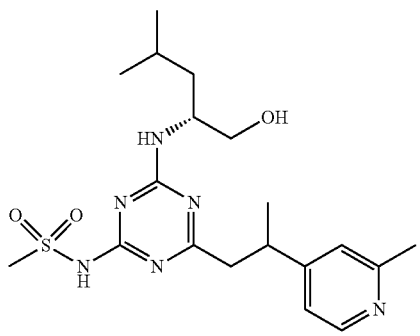

Prepared according to General Preparation Method A using (2-methylpyridin-4-yl)boronic acid as Intermediate B (34 mg, 250 µmol) and purified by preparative HPLC, PrepMethod K (gradient: 15-20%), to give the title compound (10 mg, 46%). HRMS (ESI) m/z [M+H]⁺ calcd for $C_{19}H_{31}N_6O_3S$: 423.2172, found: 423.2150; ¹H NMR (600 MHz, DMSO-$d_6$) δ 8.27-8.35 (m, 1H), 7.32-7.61 (m, 1H), 7.1-7.15 (m, 1H), 7.03-7.08 (m, 1H), 4.39-4.85 (m, 1H), 3.97-4.1 (m, 1H), 3.36-3.39 (m, partially overlapping with the solvent), 2.99-3.04 (m, partially overlapping with the solvent), 2.6-2.78 (m, partially overlapping with the solvent), 2.41-2.43 (m, partially overlapping with the solvent), 1.53-1.63 (m, 1H), 1.3-1.44 (m, 2H), 1.19-1.24 (m, 3H), 0.82-0.9 (m, 6H).

Example 95

N-(4-(((R)-1-Hydroxy-4-methylpentan-2-yl)amino)-6-(2-(4-(morpholinomethyl)phenyl)propyl)-1,3,5-triazin-2-yl)methanesulfonamide

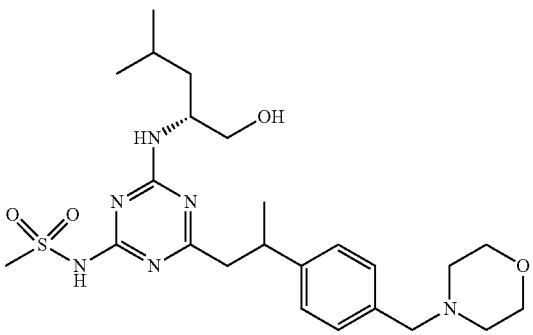 [SMILES: CC(C)C[C@H](CO)Nc1nc(CC(C)c2ccc(CN3CCOCC3)cc2)nc(NS(C)(=O)=O)n1]

Prepared according to General Preparation Method A using 4-(4-(4,4,5,5-tetramethyl-1,3,2-dioxaborolan-2-yl)benzyl)morpholine as Intermediate B (76 mg, 250 µmol) and purified by preparative HPLC, PrepMethod I, (gradient 5-95%) to give the title compound (0.7 mg, 3%). HRMS (ESI) m/z [M+H]⁺ calcd for $C_{24}H_{39}N_6O_4S$: 507.2748, found: 507.2758; ¹H NMR (600 MHz, DMSO-$d_6$) δ 7.14-7.25 (m, 4H), 6.57 (s, 1H), 3.96-4.16 (m, 1H), 3.33-3.59 (m, partially overlapping with the solvent), 2.97-3.05 (m, partially overlapping with the solvent), 2.56-2.63 (m, partially overlapping with the solvent), 2.49-2.52 (m, partially overlapping with the solvent), 2.3-2.34 (m, partially overlapping with the solvent), 1.54-1.62 (m, 1H), 1.29-1.43 (m, 2H), 1.19-1.24 (m, 3H), 0.82-0.9 (m, 6H).

Example 96

N-(4-(2-(3,4-Dimethoxyphenyl)propyl)-6-(((R)-1-hydroxy-4-methylpentan-2-yl)amino)-1,3,5-triazin-2-yl)methanesulfonamide

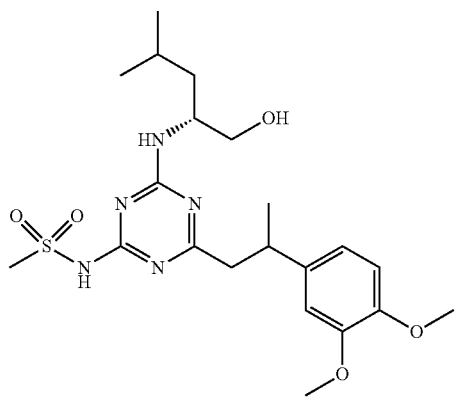

Prepared according to General Preparation Method A using (3,4-dimethoxyphenyl)boronic acid as Intermediate B (45 mg, 250 µmol) and purified by preparative HPLC, PrepMethod L, (gradient 15-20%) to give the title compound (12 mg, 49%). HRMS (ESI) m/z [M+H]⁺ calcd for $C_{21}H_{34}N_5O_5S$: 468.2276, found: 468.2272; ¹H NMR (600

MHz, DMSO-$d_6$) δ 7.97-8.19 (m, 1H), 6.71-6.89 (m, 3H), 4.01-4.16 (m, 2H), 3.7-3.75 (m, partially overlapping with the solvent), 3.26-3.48 (m, partially overlapping with the solvent), 3.05-3.09 (m, partially overlapping with the solvent), 2.66-2.78 (m, 2H), 1.51-1.61 (m, 1H), 1.3-1.46 (m, 2H), 1.2-1.27 (m, 3H), 0.82-0.91 (m, 6H).

Example 97

N-(4-(((R)-1-Hydroxy-4-methylpentan-2-yl)amino)-6-(2-(8-methoxyquinolin-5-yl)propyl)-1,3,5-triazin-2-yl)methanesulfonamide

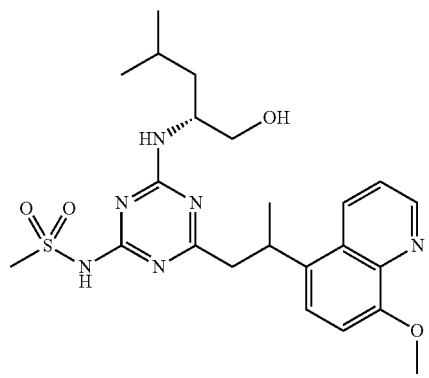

Prepared according to General Preparation Method A using (8-methoxyquinolin-5-yl)boronic acid as Intermediate B (51 mg, 250 μmol) and purified by preparative HPLC, PrepMethod K, (gradient: 15-20%) to give the title compound (4.8 mg, 20%). HRMS (ESI) m/z [M+H]⁺ calcd for $C_{23}H_{33}N_6O_4S$: 489.2278, found: 489.2276; ¹H NMR (600 MHz, DMSO-$d_6$) δ 8.79-8.88 (m, 1H), 8.54-8.64 (m, 1H), 7.81-8.14 (m, 1H), 7.54-7.61 (m, 1H), 7.41-7.5 (m, 1H), 7.11-7.21 (m, 1H), 4.61-4.78 (m, 1H), 3.98-4.16 (m, 2H), 3.92-3.97 (m, 3H), 3.35-3.38 (m, partially overlapping with the solvent), 3.05-3.2 (m, partially overlapping with the solvent), 2.71-3 (m, partially overlapping with the solvent), 1.49-1.58 (m, 1H), 1.21-1.46 (m, 6H), 0.59-0.9 (m, 6H).

Example 98

N-(4-(2-(3-Chloro-4-ethoxyphenyl)propyl)-6-(((R)-1-hydroxy-4-methylpentan-2-yl)amino)-1,3,5-triazin-2-yl)methanesulfonamide

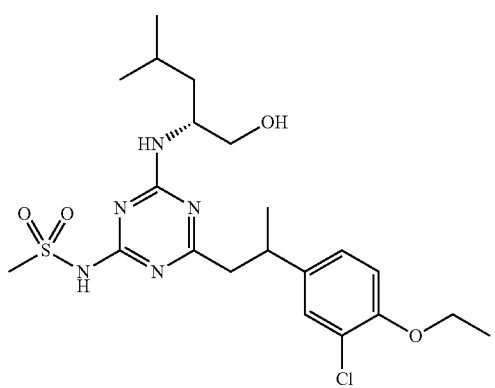 [SMILES: CCOc1ccc(C(C)Cc2nc(N[C@@H](CO)CC(C)C)nc(NS(C)(=O)=O)n2)cc1Cl]

Prepared according to General Preparation Method A using (3-chloro-4-ethoxyphenyl)boronic acid as Intermediate B (50 mg, 250 μmol) and purified by preparative HPLC, PrepMethod L, (gradient: 12-17%) to give the title compound (10.1 mg, 39%). HRMS (ESI) m/z [M+H]⁺ calcd for $C_{21}H_{33}ClNSO_4S$: 486.1936, found: 486.1940; ¹H NMR (600 MHz, DMSO-$d_6$) δ 8.06 (s, 1H), 7.25-7.32 (m, 1H), 7.14 (ddd, 1H), 7.03 (dd, 1H), 3.99-4.14 (m, 3H), 3.24-3.44 (m, partially overlapping with the solvent), 3.08 (m, partially overlapping with the solvent), 2.64-2.77 (m, partially overlapping with the solvent), 1.5-1.62 (m, 1H), 1.28-1.46 (m, 5H), 1.22 (dd, 3H), 0.78-0.93 (m, 6H).

Example 99

N-(4-(2-(2-Fluoro-3-methoxyphenyl)propyl)-6-(((R)-1-hydroxy-4-methylpentan-2-yl)amino)-1,3,5-triazin-2-yl)methanesulfonamide

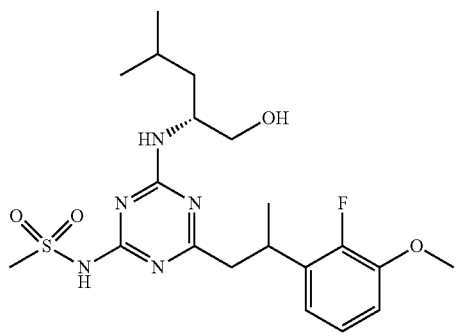

Prepared according to General Preparation Method A using (2-fluoro-3-methoxyphenyl)boronic acid as Intermediate B (42 mg, 250 μmol) and purified by preparative HPLC, PrepMethod E, (gradient 5-95%) to give the title compound (1.7 mg, 7%). HRMS (ESI) m/z [M+H]⁺ calcd for $C_{20}H_{31}FN_5O_4S$: 456.2076, found: 456.2080; ¹H NMR (600 MHz, DMSO-$d_6$) δ 8.19 (s, 1H), 6.96-7.11 (m, 2H), 6.85-6.89 (m, 1H), 4.67 (s, 1H), 3.99-4.13 (m, 1H), 3.79-3.82 (m, 3H), 3.59-3.69 (m, 1H), 3.33-3.38 (m, partially overlapping with the solvent), 3.03-3.21 (m, partially overlapping with the solvent), 2.61-2.85 (m, partially overlapping with the solvent), 1.49-1.61 (m, 1H), 1.28-1.46 (m, 2H), 1.18-1.26 (m, 3H), 0.77-0.91 (m, 6H).

Example 100

N-(4-(((R)-1-Hydroxy-4-methylpentan-2-yl)amino)-6-(2-(3-methyl-2-oxo-2,3-dihydrobenzo[d]oxazol-6-yl)propyl)-1,3,5-triazin-2-yl)methanesulfonamide

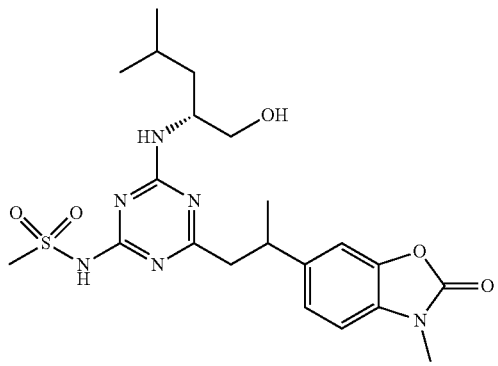 [SMILES: CC(C)C[C@H](CO)Nc1nc(CC(C)c2ccc3c(c2)oc(=O)n3C)nc(NS(C)(=O)=O)n1]

Prepared according to General Preparation Method A using 3-methyl-6-(4,4,5,5-tetramethyl-1,3,2-dioxaborolan-2-yl)benzo[d]oxazol-2(3H)-one as Intermediate B (69 mg, 250 μmol) and purified by preparative HPLC, PrepMethod I, (gradient 2-94%) to give the title compound (3.4 mg, 14%). HRMS (ESI) m/z [M+H]$^+$ calcd for $C_{21}H_{31}N_6O_5S$: 479.2070, found: 479.2074; $^1$H NMR (600 MHz, DMSO-d$_6$) 7.97-8.19 (m, 1H), 7.22-7.28 (m, 1H), 7.05-7.17 (m, 2H), 3.97-4.1 (m, partially overlapping with the solvent), 3.8-3.38 (m, partially overlapping with the solvent), 3.36-3.4 (m, partially overlapping with the solvent), 3.3-3.32 (m, partially overlapping with the solvent), 3.06-3.1 (m, partially overlapping with the solvent), 2.71-2.81 (m, 2H), 1.47-1.62 (m, 1H), 1.3-1.46 (m, 2H), 1.23-1.28 (m, 2H), 0.77-0.9 (m, 6H).

Example 101

N-(4-(((R)-1-Hydroxy-4-methylpentan-2-yl)amino)-6-(2-(3-((3-oxoisoxazolidin-2-yl)methyl)phenyl)propyl)-1,3,5-triazin-2-yl)methanesulfonamide

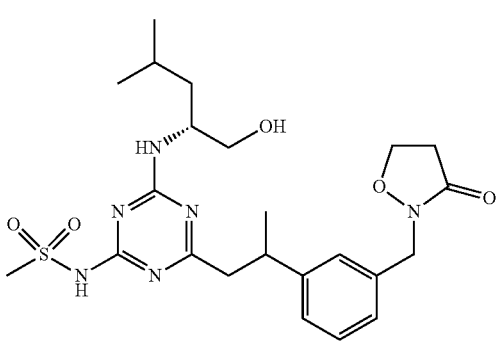 [SMILES: CC(C)C[C@H](CO)Nc1nc(CC(C)c2cccc(CN3OCCC3=O)c2)nc(NS(C)(=O)=O)n1]

Prepared according to General Preparation Method A using 2-(3-(4,4,5,5-tetramethyl-1,3,2-dioxaborolan-2-yl)benzyl)isoxazolidin-3-one Intermediate 107 as Intermediate B (76 mg, 250 μmol) and purified by preparative HPLC, PrepMethod H, (gradient: 12-17%) to give the title compound (1.8 mg, 7%). IRMS (ESI) m/z [M+H]$^+$ calcd for $C_{23}H_{35}N_6O_5S$: 507.2384, found: 507.2398; $^1$H NMR (600 MHz, DMSO-d$_6$) δ 7.77-8.18 (m, 1H), 7.23-7.34 (m, 1H), 7.08-7.22 (m, 3H), 4.56-4.79 (m, 3H), 4.21-4.32 (m, 2H), 3.99-4.17 (m, 2H), 3.34-3.38 (m, partially overlapping with the solvent), 3.04-3.11 (m, partially overlapping with the solvent), 2.69-2.8 (m, partially overlapping with the solvent), 1.52-1.62 (m, 1H), 1.3-1.47 (m, 2H), 1.19-1.26 (m, 3H), 0.82-0.91 (m, 6H).

Example 102

N-(4-(((R)-1-Hydroxy-4-methylpentan-2-yl)amino)-6-(2-(4-(tetrahydro-2H-pyran-4-yl)phenyl)propyl)-1,3,5-triazin-2-yl)methanesulfonamide

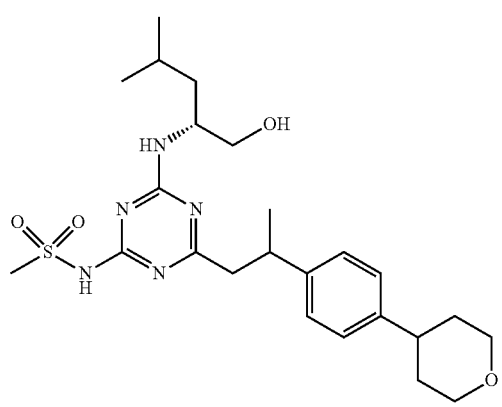 [SMILES: CC(C)C[C@H](CO)Nc1nc(CC(C)c2ccc(C3CCOCC3)cc2)nc(NS(C)(=O)=O)n1]

Prepared according to General Preparation Method A using 4,4,5,5-tetramethyl-2-(4-(tetrahydro-2H-pyran-4-yl)phenyl)-1,3,2-dioxaborolane as Intermediate B (72 mg, 250 μmol) and purified by preparative HPLC, PrepMethod E, (gradient 5-95%) to give the title compound (6.6 mg, 27%). HRMS (ESI) m/z [M+H]$^+$ calcd for $C_{24}H_{38}N_5O_4S$: 492.2638, found: 492.2632; $^1$H NMR (600 MHz, DMSO-d$_6$) δ 7.96-8.34 (m, 1H), 7.15-7.2 (m, 4H), 4.62-4.77 (m, 1H), 3.98-4.16 (m, 1H), 3.91-3.97 (m, 2H), 3.27-3.47 (m, partially overlapping with the solvent), 3.04-3.11 (m, partially overlapping with the solvent), 2.62-2.81 (m, partially overlapping with the solvent), 1.53-1.7 (m, 5H), 1.3-1.47 (m, 2H), 1.19-1.24 (m, 3H), 0.81-0.91 (m, 6H).

Example 103

N-(4-(((R)-1-Hydroxy-4-methylpentan-2-yl)amino)-6-(2-(quinolin-8-yl)propyl)-1,3,5-triazin-2-yl)methanesulfonamide

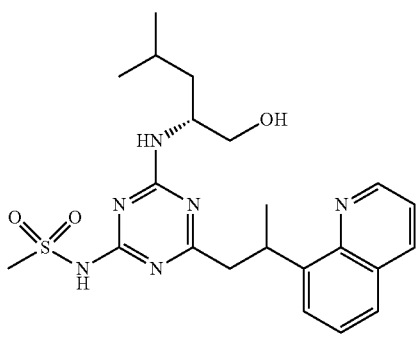 [SMILES: CC(C)C[C@H](CO)Nc1nc(CC(C)c2cccc3cccnc23)nc(NS(C)(=O)=O)n1]

Prepared according to General Preparation Method A using quinolin-8-ylboronic acid as Intermediate B (43 mg, 250 µmol) and purified by preparative HPLC, PrepMethod H, (gradient 12-17%) to give the title compound (0.3 mg, 1%). HRMS (ESI) m/z [M+H]$^+$ calcd for $C_{22}H_{31}N_6O_3S$: 459.2172, found: 459.2154; $^1$H NMR (600 MHz, DMSO-d$_6$) δ 8.85-8.93 (m, 1H), 8.3-8.37 (m, 1H), 7.88-8.18 (m, 1H), 7.79-7.86 (m, 1H), 7.66-7.71 (m, 1H), 7.49-7.61 (m, 2H), 4.63-4.78 (m, 1H), 3.85-4.08 (m, partially overlapping with the solvent), 2.98-3.11 (m, partially overlapping with the solvent), 2.77-2.91 (m, partially overlapping with the solvent), 1.16-1.46 (m, 7H), 0.73-0.89 (m, 6H).

Example 104

N-(4-(((R)-1-Hydroxy-4-methylpentan-2-yl)amino)-6-(2-(4-hydroxy-5,6,7,8-tetrahydronaphthalen-2-yl)propyl)-1,3,5-triazin-2-yl)methanesulfonamide

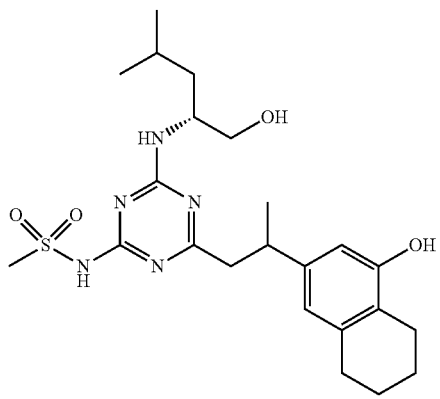 [SMILES: CC(C)C[C@H](CO)Nc1nc(CC(C)c2cc(O)c3c(c2)CCCC3)nc(NS(C)(=O)=O)n1]

Prepared according to General Preparation Method A using 3-(4,4,5,5-tetramethyl-1,3,2-dioxaborolan-2-yl)-5,6,7,8-tetrahydronaphthalen-1-ol Intermediate 110 as Intermediate B (69 mg, 250 µmol) and purified by preparative HPLC, PrepMethod L, (gradient 15-20%) to give the title compound (2.6 mg, 10%). HRMS (ESI) m/z [M+H]$^+$ calcd for $C_{23}H_{36}N_5O_4S$: 478.2482, found: 478.2482; $^1$H NMR (600 MHz, DMSO-d$_6$) δ 8.9-9.18 (m, 1H), 7.86-8.17 (m, 1H), 6.33-6.49 (m, 2H), 4.49-4.94 (m, partially overlapping with the solvent), 3.94-4.18 (m, partially overlapping with the solvent), 3.36-3.4 (m, partially overlapping with the solvent), 3.06-3.17 (m, partially overlapping with the solvent), 2.58-2.7 (m, partially overlapping with the solvent), 2.45-2.5 (m, partially overlapping with the solvent), 1.51-1.76 (m, 5H), 1.29-1.47 (m, 2H), 1.11-1.2 (m, 3H), 0.8-0.92 (m, 6H).

Example 105

N-(4-(((R)-1-Hydroxy-4-methylpentan-2-yl)amino)-6-(2-(3-(oxetan-3-yl)phenyl)propyl)-1,3,5-triazin-2-yl)methanesulfonamide

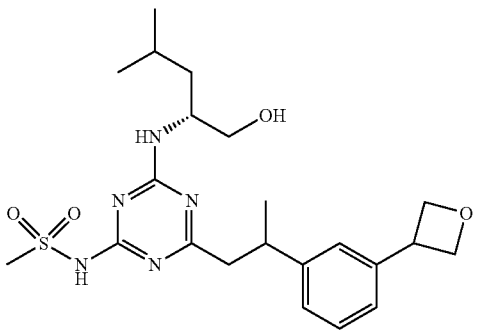 [SMILES: CC(C)C[C@H](CO)Nc1nc(CC(C)c2cccc(C3COC3)c2)nc(NS(C)(=O)=O)n1]

Prepared according to General Preparation Method A using 4,4,5,5-tetramethyl-2-(3-(oxetan-3-yl)phenyl)-1,3,2-dioxaborolane as Intermediate B (65 mg, 250 µmol) and purified by preparative HPLC, PrepMethod I, (gradient 2-94%) to give the title compound (4.3 mg, 19%). HRMS (ESI) m/z [M+H]$^+$ calcd for $C_{22}H_{34}N_5O_4S$: 464.2326, found: 464.2312; $^1$H NMR (600 MHz, DMSO-d$_6$) δ 8-8.4 (m, 1H), 7.2-7.33 (m, 3H), 7.12-7.18 (m, 1H), 4.9-4.95 (m, 2H), 4.64-4.75 (m, 1H), 4.57-4.62 (m, 2H), 4.19-4.25 (m, 1H), 3.98-4.15 (m, 1H), 3.36-3.37 (m, partially overlapping with the solvent), 3.01-3.15 (m, partially overlapping with the solvent), 2.67-2.82 (m, partially overlapping with the solvent), 1.76 (s, 1H), 1.51-1.62 (m, 1H), 1.29-1.47 (m, 2H), 1.22-1.28 (m, 3H), 0.82-0.91 (m, 6H).

Example 106

N-(4-(2-(2,3-Dimethyl-2H-indazol-6-yl)propyl)-6-(((R)-1-hydroxy-4-methylpentan-2-yl)amino)-1,3,5-triazin-2-yl)methanesulfonamide

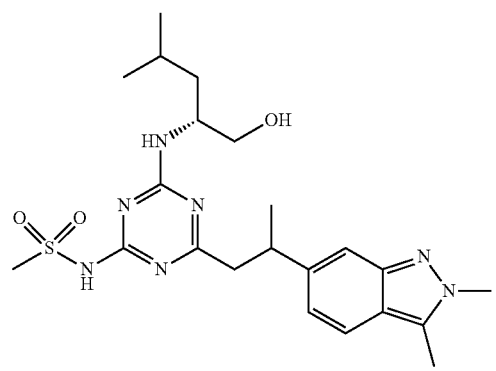

Prepared according to General Preparation Method A using 2,3-dimethyl-6-(4,4,5,5-tetramethyl-1,3,2-dioxaborolan-2-yl)-2H-indazole as Intermediate B (68 mg, 250 µmol) and purified by preparative HPLC, PrepMethod I, (gradient 5-95%) to give the title compound (7.3 mg, 29%). HRMS (ESI) m/z [M+H]$^+$ calcd for $C_{22}H_{34}N_7O_3S$: 476.2438, found: 476.2438; $^1$H NMR (600 MHz, DMSO-d$_6$) δ 7.97-

8.26 (m, 1H), 7.53-7.58 (m, 1H), 7.26-7.31 (m, 1H), 6.85-6.9 (m, 1H), 4.58-4.83 (m, 1H), 3.96-4.17 (m, partially overlapping with the solvent), 3.02-3.1 (m, partially overlapping with the solvent), 2.67-2.88 (m, 2H), 2.5-2.52 (m, partially overlapping with the solvent), 1.49-1.61 (m, 1H), 1.22-1.46 (m, 5H), 0.79-0.92 (m, 6H).

Example 107

N-(4-(2-(5-Chloro-2-hydroxyphenyl)propyl)-6-(((R)-1-hydroxy-4-methylpentan-2-yl)amino)-1,3,5-triazin-2-yl)methanesulfonamide

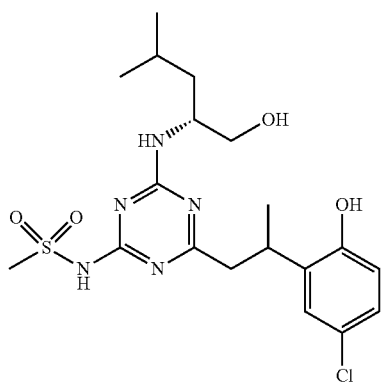 [SMILES: CC(C)C[C@H](CO)Nc1nc(CC(C)c2cc(Cl)ccc2O)nc(NS(C)(=O)=O)n1]

Prepared according to General Preparation Method A using (5-chloro-2-hydroxyphenyl)boronic acid as Intermediate B (43 mg, 250 μmol) and purified by preparative HPLC, PrepMethod I, (gradient 5-95%) to give the title compound (2.5 mg, 10%). HRMS (ESI) m/z [M+H]+ calcd for $C_{19}H_{29}ClN_5O_4S$: 458.1624, found: 458.1628; $^1$H NMR (600 MHz, DMSO-d$_6$) δ 7.77-8.12 (m, 1H), 7.11-7.15 (m, 1H), 7.01-7.07 (m, 1H), 6.76-6.82 (m, 1H), 4.56-4.75 (m, 1H), 3.99-4.14 (m, 1H), 3.58-3.7 (m, 1H), 3.36-3.42 (m, partially overlapping with the solvent), 3.04-3.11 (m, partially overlapping with the solvent), 2.66 (m, partially overlapping with the solvent), 1.5-1.63 (m, 1H), 1.28-1.48 (m, 2H), 1.14-1.22 (m, 3H), 0.81-0.91 (m, 6H).

Example 108

N-(4-(2-(Benzo[d][1,3]dioxol-5-yl)propyl)-6-(((R)-1-hydroxy-4-methylpentan-2-yl)amino)-1,3,5-triazin-2-yl)methanesulfonamide

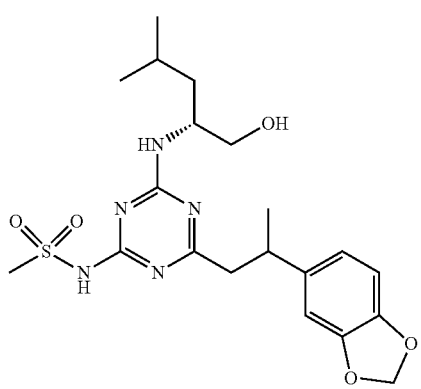 [SMILES: CC(C)C[C@H](CO)Nc1nc(CC(C)c2ccc3c(c2)OCO3)nc(NS(C)(=O)=O)n1]

Prepared according to General Preparation Method A using benzo[d][1,3]dioxol-5-ylboronic acid as Intermediate B (41 mg, 250 μmol) and purified by preparative HPLC, PrepMethod L, (gradient 12-17%) to give the title compound (8.2 mg, 35%). HRMS (ESI) m/z [M+H]+ calcd for $C_{20}H_{30}N_5O_5S$: 452.1962, found: 452.1956; $^1$H NMR (600 MHz, DMSO-d$_6$) δ 7.93-8.36 (m, 1H), 6.75-6.87 (m, 2H), 6.63-6.71 (m, 1H), 5.92-6 (m, 2H), 4.62-4.77 (m, 1H), 3.97-4.17 (m, 1H), 3.22-3.41 (m, partially overlapping with the solvent), 3.03-3.13 (m, partially overlapping with the solvent), 2.63-2.74 (m, partially overlapping with the solvent), 2.5-2.52 (m, partially overlapping with the solvent), 1.51-1.63 (m, 1H), 1.29-1.46 (m, 2H), 1.17-1.24 (m, 3H), 0.81-0.91 (m, 6H).

Example 109

N-(4-(((R)-1-Hydroxy-4-methylpentan-2-yl)amino)-6-(2-(3-methyl-4-oxo-3,4-dihydroquinazolin-8-yl)propyl)-1,3,5-triazin-2-yl)methanesulfonamide

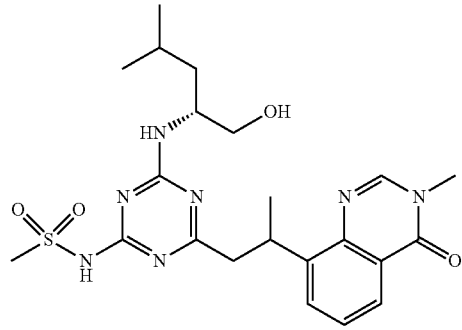 [SMILES: CC(C)C[C@H](CO)Nc1nc(CC(C)c2cccc3c(=O)n(C)cnc23)nc(NS(C)(=O)=O)n1]

Prepared according to General Preparation Method A using (3-methyl-4-oxo-3,4-dihydroquinazolin-8-yl)boronic acid Eur. J. Med. Chem. 2021, 225, 113764 as Intermediate B (46 mg, 250 μmol) and purified by preparative HPLC, PrepMethod L, (gradient 20-25%) to give the title compound (0.5 mg, 2%). HRMS (ESI) m/z [M+H]+ calcd for $C_{22}H_{32}N_7O_4S$: 490.2230, found: 490.2230; $^1$H NMR (600 MHz, DMSO-d$_6$) δ 8.32-8.38 (m, 1H), 8.1-8.2 (m, 1H), 7.99-8.06 (m, 1H), 7.71-7.77 (m, 1H), 7.47-7.55 (m, 1H), 4.59-4.74 (m, 1H), 4.35-4.44 (m, 1H), 3.89-4.05 (m, 1H), 3.47-3.5 (m, partially overlapping with the solvent), 3.05-3.1 (m, partially overlapping with the solvent), 2.87-2.95 (m, 1H), 2.75-2.84 (m, 1H), 1.2-1.6 (m, 6H), 0.75-0.89 (m, 6H).

Example 110

N-(4-(2-(3,5-Difluoro-4-(hydroxymethyl)phenyl)propyl)-6-(((R)-1-hydroxy-4-methylpentan-2-yl)amino)-1,3,5-triazin-2-yl)methanesulfonamide

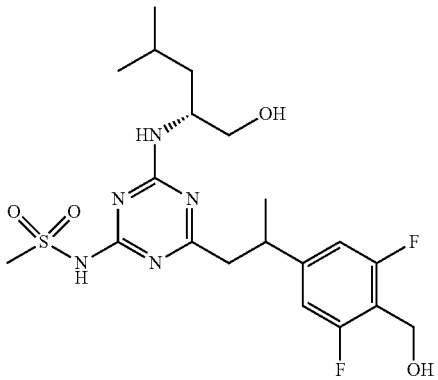 [SMILES: CC(C)C[C@H](CO)Nc1nc(CC(C)c2cc(F)c(CO)c(F)c2)nc(NS(C)(=O)=O)n1]

Prepared according to General Preparation Method A using (3,5-difluoro-4-(hydroxymethyl)phenyl)boronic acid as Intermediate B (47 mg, 250 μmol) and purified by preparative HPLC, PrepMethod L, (gradient 15-20%) to give the title compound (6.8 mg, 27%). HRMS (ESI) m/z [M+H]+ calcd for $C_{20}H_{30}F_2N_5O_4S$: 474.1980, found: 474.1978; $^1$H NMR (600 MHz, DMSO-$d_6$) δ 7.89-8.14 (m, 1H), 6.92-7.02 (m, 2H), 4.99-5.36 (m, partially overlapping with the solvent), 4.42-4.49 (m, partially overlapping with the solvent), 3.96-4.13 (m, partially overlapping with the solvent), 3.29-3.37 (m, partially overlapping with the solvent), 3.07-3.11 (m, partially overlapping with the solvent), 2.69-2.81 (m, 2H), 1.5-1.62 (m, 1H), 1.29-1.47 (m, 2H), 1.24 (dt, 3H), 0.79-0.91 (m, 6H).

Example 111

N-(4-(2-(4-Fluoro-3--methylphenyl)propyl)-6-(((R)-1-hydroxy-4-methylpentan-2-yl)amino)-1,3,5-triazin-2-yl)methanesulfonamide

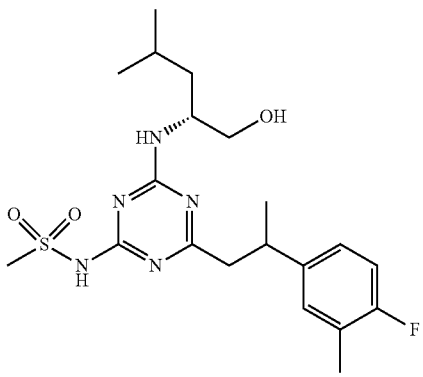 [SMILES: Cc1cc(C(C)Cc2nc(N[C@@H](CO)CC(C)C)nc(NS(C)(=O)=O)n2)ccc1F]

Prepared according to General Preparation Method A using (4-fluoro-3-methylphenyl)boronic acid as Intermediate B (39 mg, 250 μmol) and purified by preparative HPLC, PrepMethod L, (gradient 12-17%) to give the title compound (11.7 mg, 52%). HRMS (ESI) m/z [M+H]+ calcd for $C_{20}H_{31}FN_5O_3S$: 440.2126, found: 440.2114; $^1$H NMR (600 MHz, DMSO-$d_6$) δ 7.95-8.17 (m, 1H), 7.12-7.17 (m, 1H), 6.98-7.1 (m, 2H), 4-4.14 (m, 1H), 3.26-3.4 (m, partially overlapping with the solvent), 3.06-3.1 (m, partially overlapping with the solvent), 2.65-2.76 (m, partially overlapping with the solvent), 2.19-2.22 (m, 3H), 1.49-1.61 (m, 1H), 1.29-1.47 (m, 3H), 1.21 (dd, 3H), 0.81-0.91 (m, 6H).

Example 112

N-(4-(2-(4-Aminophenyl)propyl)-6-(((R)-1-hydroxy-4-methylpentan-2-yl)amino)-1,3,5-triazin-2-yl)methanesulfonamide

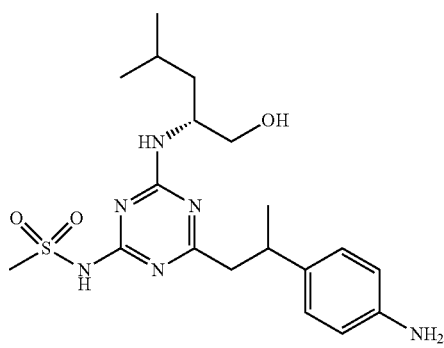 [SMILES: CC(C)C[C@H](CO)Nc1nc(CC(C)c2ccc(N)cc2)nc(NS(C)(=O)=O)n1]

Prepared according to General Preparation Method A using 4-(4,4,5,5-tetramethyl-1,3,2-dioxaborolan-2-yl)aniline as Intermediate B (38 mg, 250 μmol) and purified by preparative HPLC, PrepMethod J, (gradient 15-20%) to give the title compound (11.7 mg, 52%). HRMS (ESI) m/z [M+H]+ calcd for $C_{19}H_{31}N_6O_3S$: 423.2172, found: 423.2184; $^1$H NMR (600 MHz, DMSO-$d_6$) δ 7.93-8.2 (m, 1H), 6.85-6.91 (m, 2H), 6.45-6.52 (m, 2H), 4.48-4.9 (m, partially overlapping with the solvent), 3.96-4.24 (m, partially overlapping with the solvent), 3.32-3.44 (m, partially overlapping with the solvent), 3.04-3.16 (m, partially overlapping with the solvent), 2.56-2.69 (m, partially overlapping with the solvent), 1.53-1.62 (m, 1H), 1.3-1.46 (m, 2H), 1.12-1.18 (m, 3H), 0.82-0.94 (m, 6H).

Example 113

N-(4-(((R)-1-Hydroxy-4-methylpentan-2-yl)amino)-6-(2-(4-methoxyphenyl)propyl)-1,3,5-triazin-2-yl)methanesulfonamide

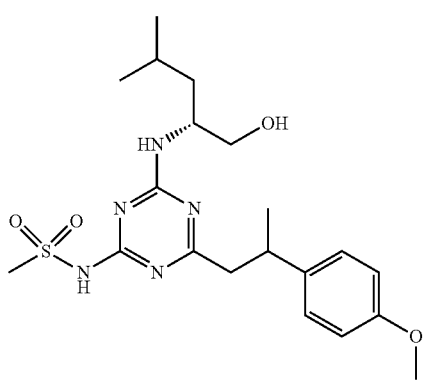

Prepared according to General Preparation Method A using (4-methoxyphenyl)boronic acid as Intermediate B (38 mg, 250 µmol) and purified by preparative HPLC, PrepMethod L, (gradient 12-17%) to give the title compound (8.3 mg, 36%). HRMS (ESI) m/z [M+H]$^+$ calcd for $C_{20}H_{32}N_5O_4S$: 438.2170, found: 438.2162; $^1$H NMR (600 MHz, DMSO-d$_6$) δ 7.92-8.4 (m, 1H), 7.11-7.19 (m, 2H), 6.81-6.89 (m, 2H), 4.64-4.78 (m, 1H), 3.99-4.15 (m, 1H), 3.69-3.73 (m, 3H), 3.24-3.35 (m, partially overlapping with the solvent), 3.02-3.1 (m, partially overlapping with the solvent), 2.63-2.77 (m, partially overlapping with the solvent), 1.5-1.61 (m, 1H), 1.3-1.46 (m, 2H), 1.17-1.24 (m, 3H), 0.81-0.92 (m, 6H).

Example 114

N-(4-(2-(3-Amino-4-methylphenyl)propyl)-6-(((R)-1-hydroxy-4-methylpentan-2-yl)amino)-1,3,5-triazin-2-yl)methanesulfonamide

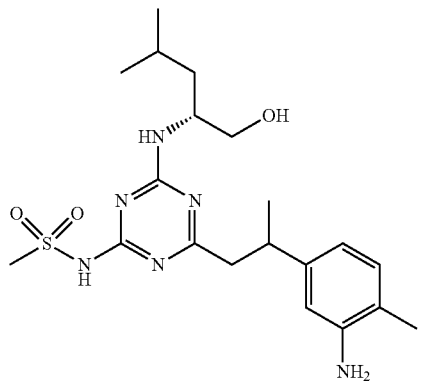

Prepared according to General Preparation Method A using (3-amino-4-methylphenyl)boronic acid as Intermediate B (38 mg, 250 µmol) and purified by preparative HPLC, PrepMethod H, (gradient 15-20%) to give the title compound (2.2 mg, 10%). HRMS (ESI) m/z [M+H]$^+$ calcd for $C_{20}H_{33}N_6O_3S$: 437.2330, found: 437.2340; $^1$H NMR (600 MHz, DMSO-d$_6$) δ 7.95-8.33 (m, 1H), 7.1-7.37 (m, 2H), 6.78-6.86 (m, 1H), 6.50 (d, 1H), 6.36 (dt, 1H), 4.58-5.1 (m, partially overlapping with the solvent), 3.97-4.2 (m, partially overlapping with the solvent), 3.3-3.38 (m, partially overlapping with the solvent), 3.05-3.16 (m, partially overlapping with the solvent), 2.58-2.74 (m, partially overlapping with the solvent), 2.07 (s, 1H), 2.00 (d, 3H), 1.52-1.63 (m, 1H), 1.28-1.47 (m, 2H), 1.15 (dd, 3H), 0.82-0.91 (m, 6H).

Example 115

N-(4-(((R)-1-Hydroxy-4-methylpentan-2-yl)amino)-6-(2-(4-(2-morpholinoethoxy)phenyl)propyl)-1,3,5-triazin-2-yl)methanesulfonamide

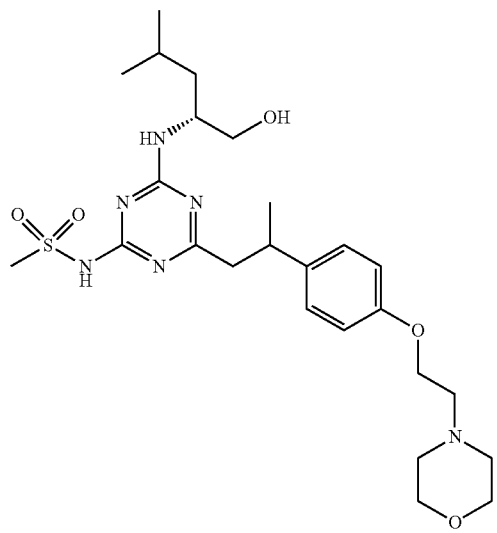 [SMILES: CC(C)C[C@H](CO)Nc1nc(CC(C)c2ccc(OCCN3CCOCC3)cc2)nc(NS(C)(=O)=O)n1]

Prepared according to General Preparation Method A using 4-(2-(4-(4,4,5,5-tetramethyl-1,3,2-dioxaborolan-2-yl)phenoxy)ethyl)morpholine as Intermediate B (83 mg, 250 µmol) and purified by preparative HPLC, PrepMethod H, (gradient 20-25%) to give the title compound (3.5 mg, 13%). HRMS (ESI) m/z [M+H]$^+$ calcd for $C_{25}H_{41}N_6O_5S$: 537.2854, found: 537.2864; $^1$H NMR (600 MHz, DMSO-d$_6$) δ 7.89-8.16 (m, 1H), 7.1-7.18 (m, 2H), 6.81-6.89 (m, 2H), 4.73 (s, 1H), 3.99-4.15 (m, 3H), 3.55-3.59 (m, partially overlapping with the solvent), 3.25-3.34 (m, partially overlapping with the solvent), 3.04-3.08 (m, partially overlapping with the solvent), 2.62-2.74 (m, partially overlapping with the solvent), 2.43-2.48 (m, partially overlapping with the solvent), 1.51-1.62 (m, 1H), 1.29-1.46 (m, 2H), 1.16-1.23 (m, 3H), 0.82-0.91 (m, 6H).

Example 116

2-Fluoro-4-(1-(4-(((R)-1-hydroxy-4-methylpentan-2-yl)amino)-6-(methylsulfonamido)-1,3,5-triazin-2-yl)propan-2-yl)-N,N-dimethylbenzamide

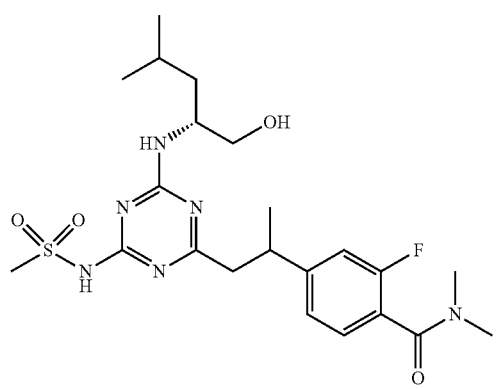

Prepared according to General Preparation Method A using 2-fluoro-N,N-dimethyl-4-(4,4,5,5-tetramethyl-1,3,2-dioxaborolan-2-yl)benzamide as Intermediate B (53 mg, 250 µmol) and purified by preparative HPLC, PrepMethod H, (gradient 15-20%) to give the title compound (1.2 mg, 5%). HRMS (ESI) m/z [M+H]$^+$ calcd for $C_{22}H_{34}FN_6O_4S$: 497.2340, found: 497.2352; $^1$H NMR (600 MHz, DMSO-$d_6$) δ 7.94-8.41 (m, 1H), 7.26-7.33 (m, 1H), 7.11-7.21 (m, 2H), 4.63-4.76 (m, 1H), 3.99-4.15 (m, 1H), 3.28-3.35 (m, partially overlapping with the solvent), 3.01-3.15 (m, partially overlapping with the solvent), 2.97-3.01 (m, 3H), 2.69-2.84 (m, partially overlapping with the solvent), 1.51-1.6 (m, 1H), 1.24-1.47 (m, 5H), 0.8-0.92 (m, 6H).

Example 117

N-(4-(((R)-1-Hydroxy-4-methylpentan-2-yl)amino)-6-(2-(1-methyl-1H-pyrrolo[2,3-b]pyridin-5-yl)propyl)-1,3,5-triazin-2-yl)methanesulfonamide

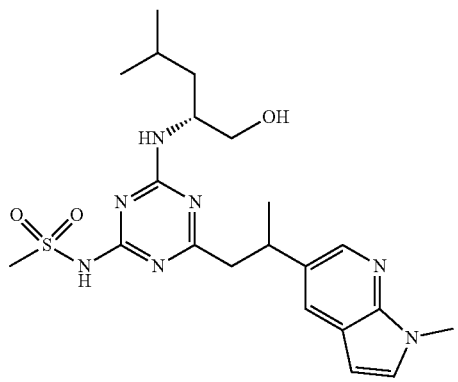

Prepared according to General Preparation Method A using 1-methyl-5-(4,4,5,5-tetramethyl-1,3,2-dioxaborolan-2-yl)-1H-pyrrolo[2,3-b]pyridine as Intermediate B (65 mg, 250 µmol) and purified by preparative HPLC, PrepMethod G, (gradient 20-25%) to give the title compound (2.1 mg, 9%). HRMS (ESI) m/z [M+H]$^+$ calcd for $C_{21}H_{32}N_7O_3S$: 462.2282, found: 462.2284; $^1$H NMR (600 MHz, DMSO-$d_6$) δ 7.89-8.19 (m, 2H), 7.83 (s, 1H), 7.43-7.52 (m, 1H), 6.36-6.43 (m, 1H), 4.58-4.84 (m, 1H), 3.96-4.2 (m, 2H), 3.78 (s, 3H), 3.42-3.5 (m, partially overlapping with the solvent), 3.03-3.09 (m, partially overlapping with the solvent), 2.75-2.88 (m, 2H), 1.46-1.62 (m, 1H), 1.27-1.45 (m, 5H), 0.74-0.9 (m, 6H).

Example 118

N-(4-(((R)-1-Hydroxy-4-methylpentan-2-yl)amino)-6-(2-(4-(3-oxomorpholino)phenyl)propyl)-1,3,5-triazin-2-yl)methanesulfonamide

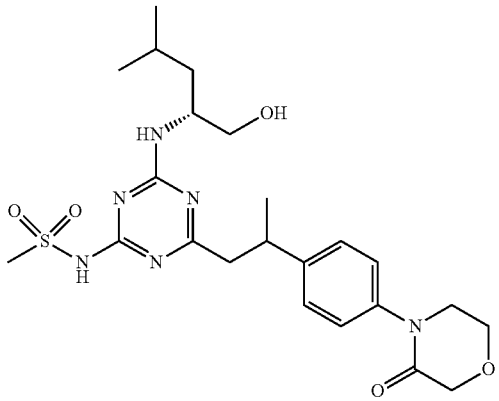 [SMILES: CC(C)C[C@H](CO)Nc1nc(CC(C)c2ccc(N3CCOCC3=O)cc2)nc(NS(C)(=O)=O)n1]

Prepared according to General Preparation Method A using 4-(4-(4,4,5,5-tetramethyl-1,3,2-dioxaborolan-2-yl)phenyl)morpholin-3-one as Intermediate B (76 mg, 250 µmol) and purified by preparative HPLC, PrepMethod G, (gradient 20-25%) to give the title compound (1.5 mg, 6%). HRMS (ESI) m/z [M+H]$^+$ calcd for C23H35N6O5S: 507.2384, found: 507.2386; $^1$H NMR (600 MHz, DMSO-$d_6$) δ 7.86-8.23 (m, 1H), 7.26-7.36 (m, 4H), 4.58-4.83 (m, 1H), 4.17-4.2 (m, 2H), 4.07-4.16 (m, 1H), 4-4.06 (m, 1H), 3.94-3.98 (m, 2H), 3.68-3.74 (m, 2H), 3.04-3.1 (m, partially overlapping with the solvent), 2.71-2.82 (m, partially overlapping with the solvent), 1.53-1.62 (m, 1H), 1.3-1.46 (m, 2H), 1.21-1.27 (m, 3H), 0.81-0.93 (m, 6H).

Example 119

N-(4-(2-(4-Ethoxy-3-fluorophenyl)propyl)-6-(((R)-1-hydroxy-4-methylpentan-2-yl)amino)-1,3,5-triazin-2-yl)methanesulfonamide

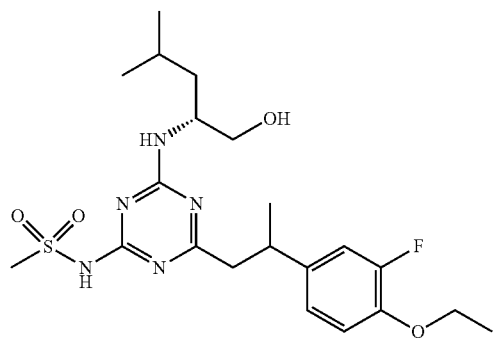 [SMILES: CCOc1ccc(C(C)Cc2nc(N[C@@H](CO)CC(C)C)nc(NS(C)(=O)=O)n2)cc1F]

Prepared according to General Preparation Method A using (4-ethoxy-3-fluorophenyl)boronic acid as Intermediate B (46 mg, 250 µmol) and purified by preparative HPLC, PrepMethod H, (gradient 12-17%) to give the title compound (2.5 mg, 10%). HRMS (ESI) m/z [M+H]$^+$ calcd for $C_{21}H_{33}FN_5O_4S$: 470.2232, found: 470.2228; $^1$H NMR (600

MHz, DMSO-$d_6$) δ 7.93-8.28 (m, 1H), 7-7.13 (m, 2H), 6.93-6.99 (m, 1H), 4.63-4.8 (m, 1H), 3.99-4.18 (m, 4H), 3.24-3.34 (m, partially overlapping with the solvent), 3.03-3.12 (m, partially overlapping with the solvent), 2.61-2.76 (m, partially overlapping with the solvent), 1.49-1.61 (m, 1H), 1.29-1.46 (m, 5H), 1.18-1.25 (m, 3H), 0.8-0.9 (m, 6H).

Example 120

2-Fluoro-4-(1-(4-(((R)-1-hydroxy-4-methylpentan-2-yl)amino)-6-(methylsulfonamido)-1,3,5-triazin-2-yl)propan-2-yl)-N-methylbenzamide

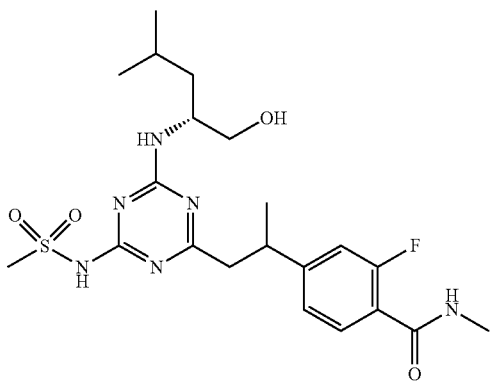

Prepared according to General Preparation Method A using (3-fluoro-4-(methylcarbamoyl)phenyl)boronic acid as Intermediate B (49 mg, 250 μmol) and purified by preparative HPLC, PrepMethod G, (gradient 22-27%) to give the title compound (2.0 mg, 8%). HRMS (ESI) m/z [M+H]$^+$ calcd for $C_{21}H_{32}FN_6O_4S$: 483.2184, found: 483.2200; $^1$H NMR (600 MHz, DMSO-$d_6$) δ 8.1-8.19 (m, 1H), 7.74-8.03 (m, 1H), 7.51-7.58 (m, 1H), 7.11-7.23 (m, 2H), 4.56-4.86 (m, partially overlapping with the solvent), 3.97-4.23 (m, partially overlapping with the solvent), 3.04-3.1 (m, partially overlapping with the solvent), 2.67-2.81 (m, partially overlapping with the solvent), 1.52-1.62 (m, 1H), 1.3-1.45 (m, 2H), 1.21-1.28 (m, 3H), 0.8-0.91 (m, 6H).

Example 121

N-(4-(2-(3-Aminophenyl)propyl)-6-(((R)-1-hydroxy-4-methylpentan-2-yl)amino)-1,3,5-triazin-2-yl)methanesulfonamide

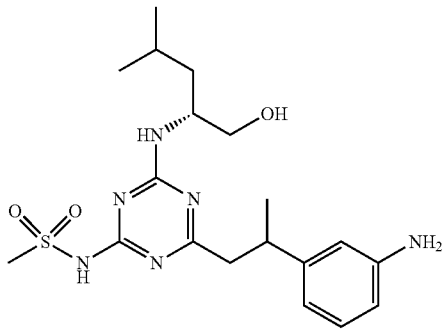 [SMILES: CC(C)C[C@H](CO)Nc1nc(CC(C)c2cccc(N)c2)nc(NS(C)(=O)=O)n1]

Prepared according to General Preparation Method A using 3-(4,4,5,5-tetramethyl-1,3,2-dioxaborolan-2-yl)aniline as Intermediate B (55 mg, 250 μmol) and purified by preparative HPLC, PrepMethod K, (gradient 15-20%) to give the title compound (0.9 mg, 4%). HRMS (ESI) m/z [M+H]$^+$ calcd for $C_{19}H_{31}N_6O_3S$: 423.2172, found: 423.2174; $^1$H NMR (600 MHz, DMSO-$d_6$) δ 7.69-8.06 (m, 1H), 6.9-6.97 (m, 1H), 6.43-6.48 (m, 1H), 6.36-6.42 (m, 2H), 4.58-5.18 (m, 1H), 3.99-4.21 (m, 1H), 3.32-3.4 (m, 3H), 3.02-3.08 (m, partially overlapping with the solvent), 2.68-2.73 (m, partially overlapping with the solvent), 1.54-1.64 (m, 1H), 1.3-1.46 (m, 2H), 1.11-1.19 (m, 3H), 0.81-0.92 (m, 6H).

Example 122

N-(4-(2-(4-Fluoro-3-(hydroxymethyl)phenyl)propyl)-6-(((R)-1-hydroxy-4-methylpentan-2-yl)amino)-1,3,5-triazin-2-yl)methanesulfonamide

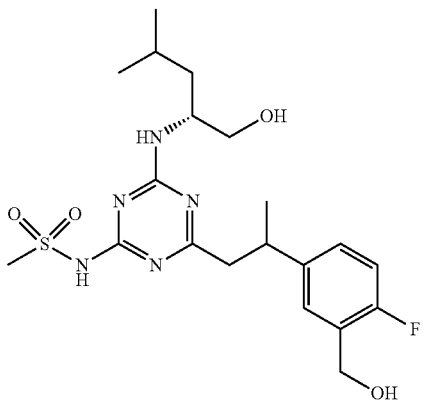 [SMILES: CC(C)C[C@H](CO)Nc1nc(CC(C)c2ccc(F)c(CO)c2)nc(NS(C)(=O)=O)n1]

Prepared according to General Preparation Method A using (4-fluoro-3-(hydroxymethyl)phenyl)boronic acid as Intermediate B (43 mg, 250 μmol) and purified by preparative HPLC, PrepMethod G, (gradient 22-27%) to give the title compound (2.3 mg, 10%). HRMS (ESI) m/z [M+H]$^+$ calcd for $C_{20}H_{31}FN_5O_4S$: 456.2076, found: 456.2090; $^1$H NMR (600 MHz, DMSO-$d_6$) δ 7.78-8.13 (m, 1H), 7.31-7.41 (m, 1H), 7.13-7.21 (m, 1H), 7-7.09 (m, 1H), 5.25 (s, 1H), 4.69 (d, 1H), 4.49-4.57 (m, 2H), 3.98-4.2 (dd, 2H), 3.32-3.42 (m, 2H), 3.04-3.09 (m, partially overlapping with the solvent), 2.68-2.78 (m, partially overlapping with the solvent), 1.53-1.63 (m, 1H), 1.29-1.48 (m, 2H), 1.22 (dd, 3H), 0.8-0.93 (m, 6H).

Example 123

N-(4-(2-(4-Ethoxyphenyl)propyl)-6-(((R)-1-hydroxy-4-methylpentan-2-yl)amino)-1,3,5-triazin-2-yl)methanesulfonamide

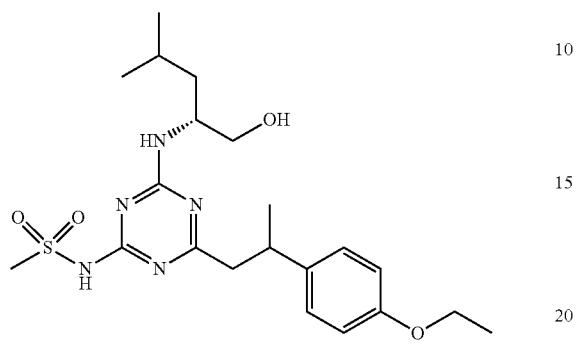

Prepared according to General Preparation Method A using (4-ethoxyphenyl)boronic acid as Intermediate B (42 mg, 250 μmol) and purified by preparative HPLC, PrepMethod H, (gradient 10-15%) to give the title compound (2.6 mg, 11%). HRMS (ESI) m/z [M+H]$^+$ calcd for $C_{21}H_{34}N_5O_4S$: 452.2326, found: 452.2346; $^1$H NMR (600 MHz, DMSO-d$_6$) δ 7.92-8.29 (m, 1H), 7.1-7.17 (m, 2H), 6.79-6.88 (m, 2H), 4.61-4.8 (m, 1H), 4.08-4.16 (m, 1H), 3.94-4.06 (m, 3H), 3.24-3.33 (m, partially overlapping with the solvent), 3.03-3.11 (m, partially overlapping with the solvent), 2.6-2.76 (m, partially overlapping with the solvent), 1.56 (s, 1H), 1.28-1.46 (m, 5H), 1.18-1.23 (m, 3H), 0.82-0.92 (m, 6H).

Example 124

N-(4-(((R)-1-Hydroxy-4-methylpentan-2-yl)amino)-6-(2-(3-methyl-4-oxo-3,4-dihydroquinazolin-6-yl)propyl)-1,3,5-triazin-2-yl methanesulfonamide

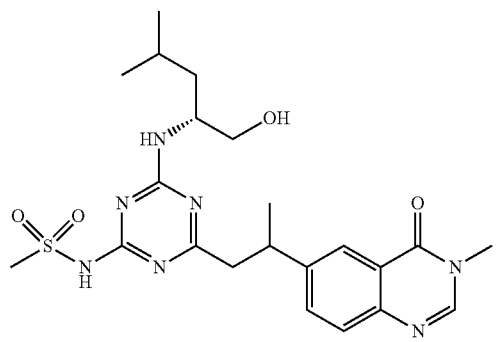

Prepared according to General Preparation Method A using (3-methyl-4-oxo-3,4-dihydroquinazolin-6-yl)boronic acid as Intermediate B (71 mg, 250 μmol) and purified by preparative HPLC, PrepMethod G, (gradient 22-27%) to give the title compound (1.0 mg, 4%). HRMS (ESI) m/z [M+H]$^+$ calcd for $C_{22}H_{32}N_7O_4S$: 490.2230, found: 490.2242; $^1$H NMR (600 MHz, DMSO-d$_6$) δ 8.3-8.36 (m, 1H), 7.97-8.02 (m, 1H), 7.7-7.76 (m, 1H), 7.57-7.64 (m, 1H), 4.54-4.81 (m, 1H), 3.94-4.19 (m, partially overlapping with the solvent), 3.5-3.55 (m, partially overlapping with the solvent), 3.26-3.35 (m, partially overlapping with the solvent), 2.99-3.05 (m, partially overlapping with the solvent), 2.68-2.81 (m, partially overlapping with the solvent), 1.48-1.62 (m, 1H), 1.24-1.43 (m, 5H), 0.76-0.92 (m, 6H).

Example 125

N-(4-(((R)-1-Hydroxy-4-methylpentan-2-yl)amino)-6-(2-(4-methyl-3-oxo-3,4-dihydro-2H-pyrido[3,2-b][1,4]oxazin-7-yl)propyl)-1,3,5-triazin-2-yl)methanesulfonamide

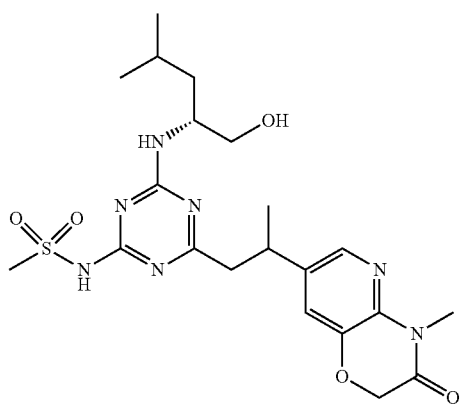

Prepared according to General Preparation Method A using 4-methyl-7-(4,4,5,5-tetramethyl-1,3,2-dioxaborolan-2-yl)-2H-pyrido[3,2-b][1,4]oxazin-3(4H)-one as Intermediate B (73 mg, 250 μmol) and purified by preparative HPLC, PrepMethod H, (gradient 12-17%) to give the title compound (0.6 mg, 2%). IRMS (ESI) m/z [M+H]$^+$ calcd for $C_{21}H_{32}N_7O_5S$: 494.2180, found: 494.2158; $^1$H NMR (600 MHz, DMSO-d$_6$) δ 7.86-7.93 (m, 1H), 7.32-7.36 (m, 1H), 4.63-4.8 (m, 2H), 3.98-4.15 (m, partially overlapping with the solvent), 3.29-3.31 (m, partially overlapping with the solvent), 3.16-3.2 (m, partially overlapping with the solvent), 2.7-2.82 (m, partially overlapping with the solvent), 2.7-2.82 (m, partially overlapping with the solvent), 1.28-1.6 (m, 2H), 1.23-1.27 (m, 3H), 0.8-0.89 (m, 6H).

Example 126

N-(4-(((R)-1-Hydroxy-4-methylpentan-2-yl)amino)-6-(2-(3-methyl-4-oxo-3,4-dihydroquinazolin-7-yl)propyl)-1,3,5-triazin-2-yl)methanesulfonamide

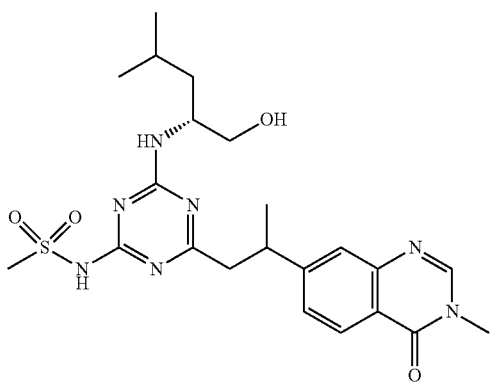

Prepared according to General Preparation Method A using 3-methyl-7-(4,4,5,5-tetramethyl-1,3,2-dioxaborolan-2-yl)quinazolin-4(3H)-one as Intermediate B (72 mg, 250 μmol) and purified by preparative HPLC, PrepMethod G, (gradient 22-27%) to give the title compound (1.4 mg, 6%). HRMS (ESI) m/z [M+H]$^+$ calcd for $C_{22}H_{32}N_7O_4S$: 490.2230, found: 490.2230; $^1$H NMR (600 MHz, DMSO-d$_6$) δ 8.31-8.37 (m, 1H), 8.03-8.1 (m, 1H), 7.56-7.8 (m, 1H), 7.43-7.54 (m, 2H), 4.57-4.82 (m, partially overlapping with the solvent), 3.93-4.24 (m, partially overlapping with the solvent), 3.43-3.55 (m, partially overlapping with the solvent), 2.99-3.05 (m, partially overlapping with the solvent), 2.7-2.83 (m, partially overlapping with the solvent), 1.46-1.61 (m, 1H), 1.26-1.44 (m, 6H), 0.75-0.89 (m, 6H).

Example 127

N-(4-(2-(6-(Difluoromethoxy)pyridin-3-yl)propyl)-6-(((R)-1-hydroxy-4-methylpentan-2-yl)amino)-1,3,5-triazin-2-yl)methanesulfonamide

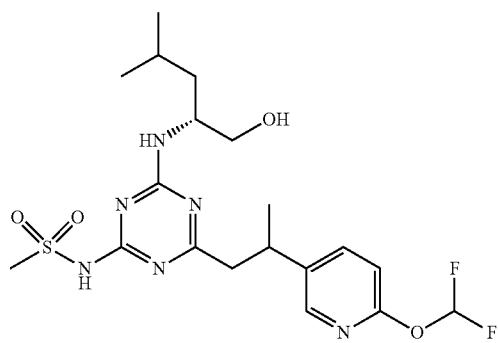 [SMILES: CC(C)C[C@H](CO)Nc1nc(CC(C)c2ccc(OC(F)F)nc2)nc(NS(C)(=O)=O)n1]

Prepared according to General Preparation Method A using 2-(difluoromethoxy)-5-(4,4,5,5-tetramethyl-1,3,2-dioxaborolan-2-yl)pyridine as Intermediate B (67 mg, 250 μmol) and purified by preparative HPLC, PrepMethod H, (gradient: 10-15%) to give the title compound (0.7 mg, 3%). HRMS (ESI) m/z [M+H]$^+$ calcd for $C_{19}H_{29}F_2N_6O_4S$: 475.1934, found: 475.1938; $^1$H NMR (600 MHz, DMSO-d$_6$) δ 8.06-8.17 (m, 1H), 7.81-7.88 (m, 1H), 7.65 (t, 1H), 6.94-7.02 (m, 1H), 6.51-6.82 (m, 1H), 4.52-4.79 (m, partially overlapping with the solvent), 3.92-4.18 (m, partially overlapping with the solvent), 3.26-3.36 (m, partially overlapping with the solvent), 2.88-2.94 (m, partially overlapping with the solvent), 2.73-2.88 (m, partially overlapping with the solvent), 1.52-1.64 (m, 1H), 1.28-1.4 (m, 2H), 1.2-1.26 (m, 3H), 0.79-0.91 (m, 6H).

Example 128

N-(4-(((R)-1-Hydroxy-4-methylpentan-2-yl)amino)-6-(2-(2-methyl-3-oxo-1,2,3,4-tetrahydroisoquinolin-6-yl)propyl)-1,3,5-triazin-2-yl)methanesulfonamide

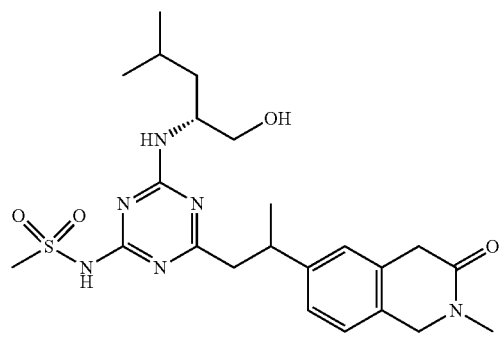

Prepared according to General Preparation Method A using 2-methyl-6-(4,4,5,5-tetramethyl-1,3,2-dioxaborolan-2-yl)-1,4-dihydroisoquinolin-3(2H)-one as Intermediate B (72 mg, 250 μmol) and purified by preparative HPLC, PrepMethod K, (gradient 15-20%) to give the title compound (2.6 mg, 11%). HRMS (ESI) m/z [M+H]$^+$ calcd for $C_{23}H_{35}N_6O_4S$: 491.2434, found: 491.2438; $^1$H NMR (600 MHz, DMSO-d$_6$) δ 7.78-8.11 (m, 1H), 7.14-7.19 (m, 1H), 7.06-7.13 (m, 2H), 4.58-4.87 (m, 1H), 4.41-4.5 (m, 2H), 3.97-4.21 (m, 2H), 3.47-3.5 (m, partially overlapping with the solvent), 3.31-3.37 (m, partially overlapping with the solvent), 3.03-3.09 (m, partially overlapping with the solvent), 2.94-2.97 (m, partially overlapping with the solvent), 2.67-2.78 (m, partially overlapping with the solvent), 1.51-1.61 (m, 1H), 1.29-1.47 (m, 2H), 1.18-1.26 (m, 3H), 0.81-0.92 (m, 6H).

Example 129

N-(4-(((R)-1-Hydroxy-4-methylpentan-2-yl)amino)-6-(2-(4-methyl-3-oxo-3,4-dihydro-2H-benzo[b][1,4]oxazin-7-yl)propyl)-1,3,5-triazin-2-yl)methanesulfonamide

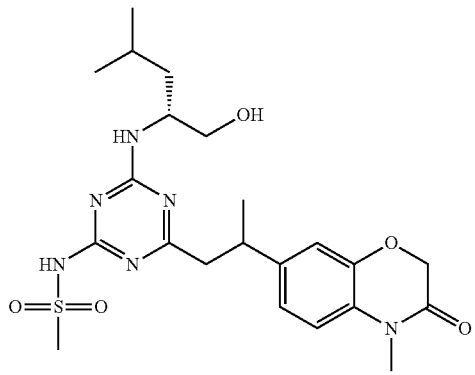 [SMILES: CC(C)C[C@H](CO)Nc1nc(CC(C)c2ccc3c(c2)OCC(=O)N3C)nc(NS(C)(=O)=O)n1]

Prepared according to General Preparation Method A using 4-methyl-7-(4,4,5,5-tetramethyl-1,3,2-dioxaborolan-2-yl)-2H-benzo[b][1,4]oxazin-3(4H)-one as Intermediate B (72 mg, 250 μmol) and purified by preparative HPLC, PrepMethod H, (gradient 12-17%) to give the title compound (2.6 mg, 11%). HRMS (ESI) m/z [M+H]$^+$ calcd for $C_{22}H_{33}N_6O_5S$: 493.2228, found: 493.2216; $^1$H NMR (600 MHz, DMSO-d$_6$) δ 7.91-8.22 (m, 1H), 7.02-7.09 (m, 1H), 6.88-6.96 (m, 2H), 4.65-4.78 (m, 1H), 4.6-4.63 (m, 2H), 3.98-4.22 (m, 2H), 3.28-3.34 (m, partially overlapping with the solvent), 3.23-3.26 (m, partially overlapping with the solvent), 3.04-3.1 (m, partially overlapping with the solvent), 2.67-2.77 (m, partially overlapping with the solvent), 1.5-1.61 (m, 1H), 1.29-1.46 (m, 2H), 1.18-1.25 (m, 3H), 0.81-0.91 (m, 6H).

Example 130

N-(4-(((R)-1-Hydroxy-4-methylpentan-2-yl)amino)-6-(2-(2-methyl-3-oxo-1,2,3,4-tetrahydroisoquinolin-7-yl)propyl)-1,3,5-triazin-2-yl)methanesulfonamide

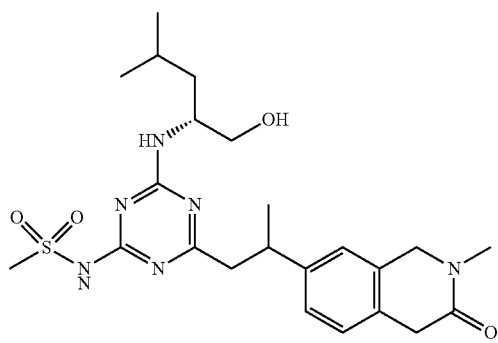

Prepared according to General Preparation Method A using 2-methyl-7-(4,4,5,5-tetramethyl-1,3,2-dioxaborolan-2-yl)-1,4-dihydroisoquinolin-3(2H)-one as Intermediate B (71 mg, 250 μmol) and purified by preparative HPLC, PrepMethod K, (gradient 25-30%) to give the title compound (0.3 mg, 1%). IRMS (ESI) m/z [M+H]$^+$ calcd for $C_{23}H_{35}N_6O_4S$: 491.2434, found: 491.2422; $^1$H NMR (600 MHz, DMSO-d$_6$) δ 7.83-8.17 (m, 1H), 7.07-7.16 (m, 3H), 4.65-4.8 (m, 1H), 4.41-4.5 (m, 2H), 3.97-4.17 (m, 2H), 3.45-3.48 (m, partially overlapping with the solvent), 2.93-2.97 (m, 3H), 3.01-3.09 (m, 3H), 2.68-2.78 (m, partially overlapping with the solvent), 1.49-1.6 (m, 1H), 1.27-1.45 (m, 2H), 1.18-1.25 (m, 3H), 0.8-0.9 (m, 6H).

Example 131

N-(4-(2-(5-Amino-6-methylpyridin-3-yl)propyl)-6-(((R)-1-hydroxy-4-methylpentan-2-yl)amino)-1,3,5-triazin-2-yl)methanesulfonamide

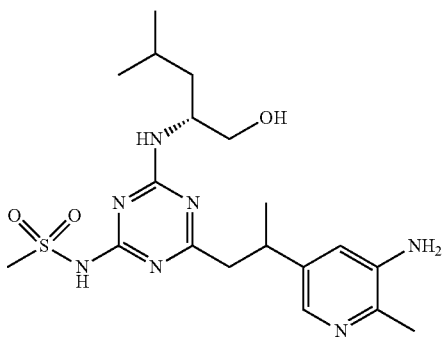

Prepared according to General Preparation Method A using 2-methyl-5-(4,4,5,5-tetramethyl-1,3,2-dioxaborolan-2-yl)pyridin-3-amine as Intermediate B (59 mg, 250 μmol) and purified by preparative HPLC, PrepMethod H, (gradient 22-27%) to give the title compound (1.2 mg, 5%). HRMS (ESI) m/z [M+H]$^+$ calcd for $C_{19}H_{32}N_7O_3S$: 438.2282, found: 438.2272; $^1$H NMR (600 MHz, DMSO-d$_6$) δ 7.93-8.24 (m, 1H), 7.5-7.59 (m, 1H), 6.75-6.86 (m, 1H), 4.89-5.04 (m, 2H), 4.64-4.82 (m, 1H), 3.97-4.17 (m, 3H), 3.16-3.24 (m, partially overlapping with the solvent), 3.05-3.1 (m, 3H), 2.66-2.72 (m, partially overlapping with the solvent), 2.19-2.23 (m, 3H), 1.53-1.63 (m, 1H), 1.3-1.47 (m, 2H), 1.15-1.22 (m, 3H), 0.81-0.91 (m, 6H).

Example 132

N-(4-(((R)-1-Hydroxy-4-methylpentan-2-yl)amino)-6-(2-(6-(2-hydroxyethyl)pyridin-3-yl)propyl)-1,3,5-triazin-2-yl)methanesulfonamide

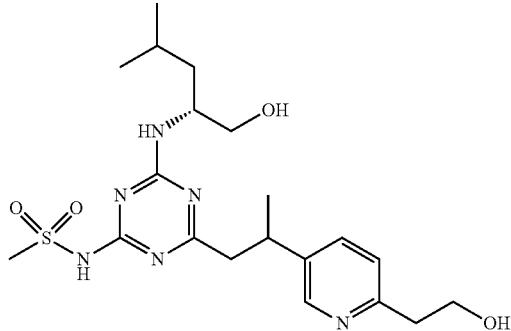 [SMILES: CC(C)C[C@H](CO)Nc1nc(CC(C)c2ccc(CCO)nc2)nc(NS(C)(=O)=O)n1]

Prepared according to General Preparation Method A using (6-(2-hydroxyethyl)pyridin-3-yl)boronic acid Intermediate 111 as Intermediate B (41 mg, 250 μmol) and purified by preparative HPLC, PrepMethod M, (gradient 5-95%) to give the title compound (0.9 mg, 3%). HRMS (ESI) m/z [M+H]$^+$ calcd for $C_{20}H_{33}N_6O_4S$: 453.2278, found: 453.2284; $^1$H NMR (600 MHz, DMSO-$d_6$) δ 8.24-8.4 (m, 1H), 7.68-7.99 (m, 1H), 7.55-7.61 (m, 1H), 7.15-7.24 (m, 1H), 4.48-4.83 (m, partially overlapping with the solvent), 3.98-4.11 (m, partially overlapping with the solvent), 3.69-3.74 (m, partially overlapping with the solvent), 3.31-3.37 (m, partially overlapping with the solvent), 3.02-3.08 (m, partially overlapping with the solvent), 2.67-2.87 (m, partially overlapping with the solvent), 1.29-1.61 (m, 4H), 1.22-1.28 (m, 3H), 0.8-0.91 (m, 6H).

Example 133

N-(4-(2-(3-Fluoro-4-(hydroxymethyl)phenyl)propyl)-6-(((R)-1-hydroxy-4-methylpentan-2-yl)amino)-1,3,5-triazin-2-yl)methanesulfonamide

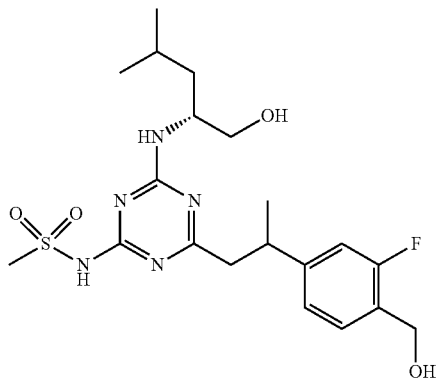 [SMILES: CC(C)C[C@H](CO)Nc1nc(CC(C)c2ccc(CO)c(F)c2)nc(NS(C)(=O)=O)n1]

Prepared according to General Preparation Method A using (2-fluoro-4-(4,4,5,5-tetramethyl-1,3,2-dioxaborolan-2-yl)phenyl)methanol as Intermediate B (63 mg, 250 μmol) and purified by preparative HPLC, PrepMethod H, (gradient 15-20%) to give the title compound (7.1 mg, 30%). HRMS (ESI) m/z [M+H]$^+$ calcd for $C_{20}H_{31}FN_5O_4S$: 456.2076, found: 456.2064; $^1$H NMR (600 MHz, DMSO-$d_6$) δ 7.6-8.04 (m, 1H), 7.29-7.43 (m, 1H), 6.99-7.14 (m, 2H), 5.11-5.24 (m, 1H), 4.59-4.79 (m, 1H), 4.44-4.55 (m, 2H), 3.94-4.25 (m, 2H), 3.01-3.07 (m, 3H), 2.68-2.76 (m, partially overlapping with the solvent), 1.51-1.62 (m, 1H), 1.29-1.45 (m, 2H), 1.16-1.27 (m, 3H), 0.81-0.92 (m, 6H).

Example 134

N-(4-(((R)-1-Hydroxy-4-methylpentan-2-yl)amino)-6-(2-(quinolin-3-yl)propyl)-1,3,5-triazin-2-yl)methanesulfonamide

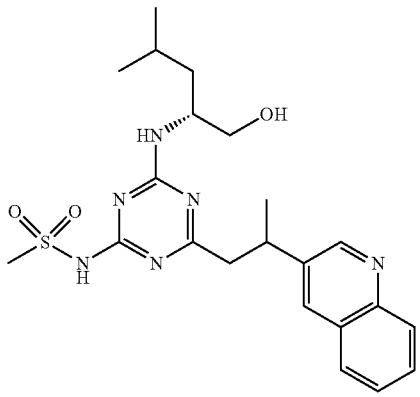 [SMILES: CC(C)C[C@H](CO)Nc1nc(CC(C)c2cnc3ccccc3c2)nc(NS(C)(=O)=O)n1]

Prepared according to General Preparation Method A using quinolin-3-ylboronic acid as Intermediate B (43 mg, 250 μmol) and purified by preparative HPLC, PrepMethod H, (gradient 12-17%) to give the title compound (0.5 mg, 2%). HRMS (ESI) m/z [M+H]$^+$ calcd for $C_{22}H_{31}N_6O_3S$: 459.2172, found: 459.2178; $^1$H NMR (600 MHz, DMSO-$d_6$) δ 8.78-8.87 (m, 1H), 8.16-8.24 (m, 1H), 7.88-8 (m, 2H), 7.66-7.73 (m, 1H), 7.53-7.61 (m, 1H), 6.3-6.79 (m, 1H), 4.49-4.82 (m, 1H), 3.89-4.22 (m, 1H), 3.57-3.66 (m, partially overlapping with the solvent), 3.21-3.36 (m, partially overlapping with the solvent), 2.69-2.79 (m, partially overlapping with the solvent), 1.51-1.66 (m, 1H), 1.25-1.41 (m, 5H), 0.71-0.91 (m, 7H).

Example 135

N-(4-(2-(3-Fluoro-2-hydroxyphenyl)propyl)-6-(((R)-1-hydroxy-4-methylpentan-2-yl)amino)-1,3,5-triazin-2-yl)methanesulfonamide

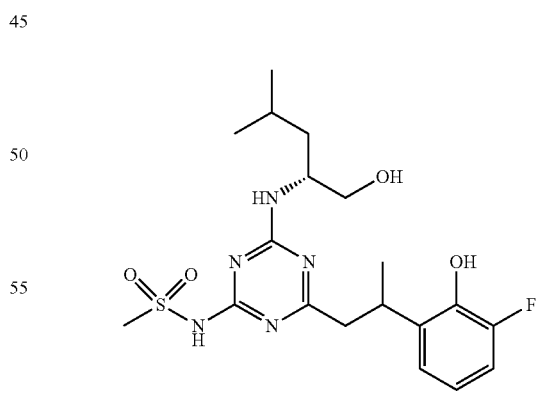

Prepared according to General Preparation Method A using (3-fluoro-2-hydroxyphenyl)boronic acid as Intermediate B (39 mg, 250 μmol) and purified by preparative HPLC, PrepMethod H, (gradient 15-20%) to give the title compound (8.1 mg, 36%). HRMS (ESI) m/z [M+H]$^+$ calcd for $C_{19}H_{29}FN_5O_4S$: 442.1918, found: 442.1924; $^1$H NMR (600 MHz, DMSO-$d_6$) δ 7.67-8.08 (m, 1H), 6.93-7.03 (m, 2H), 6.72-6.82 (m, 1H), 4.47-4.89 (m, 1H), 3.97-4.25 (m, partially overlapping with the solvent), 3.66-3.75 (m, partially overlapping with the solvent), 3.27-3.32 (m, partially overlapping with the solvent), 3.03-3.1 (m, partially overlapping with the solvent), 2.66-2.84 (m, 3H), 1.51-1.61 (m, 1H), 1.29-1.46 (m, 2H), 1.17-1.22 (m, 3H), 0.8-0.9 (m, 6H).

Example 136

N-(4-(2-(4-Amino-3-fluorophenyl)propyl)-6-(((R)-1-hydroxy-4-methylpentan-2-yl)amino)-1,3,5-triazin-2-yl)methanesulfonamide

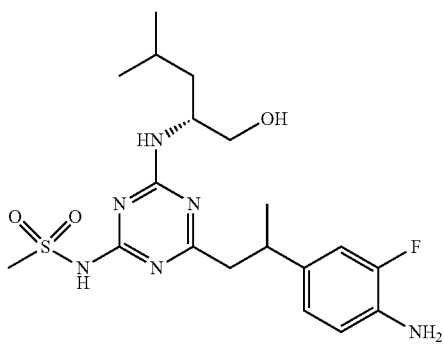 [SMILES: CC(C)C[C@H](CO)Nc1nc(CC(C)c2ccc(N)c(F)c2)nc(NS(C)(=O)=O)n1]

Prepared according to General Preparation Method A using 2-fluoro-4-(4,4,5,5-tetramethyl-1,3,2-dioxaborolan-2-yl)aniline as Intermediate B (59 mg, 250 µmol) and purified by preparative HPLC, PrepMethod H, (gradient 12-17%) to give the title compound (3.1 mg, 14%). HRMS (ESI) m/z [M+H]$^+$ calcd for $C_{19}H_{30}FN_6O_3S$: 441.2078, found: 441.2084; $^1$H NMR (600 MHz, DMSO-d$_6$) δ 7.3-7.74 (m, 1H), 6.81-6.9 (m, 1H), 6.62-6.77 (m, 2H), 4.77-4.94 (m, partially overlapping with the solvent), 3.95-4.16 (m, partially overlapping with the solvent), 3.36-3.39 (m, partially overlapping with the solvent), 3.00 (s, 3H), 1.52-1.61 (m, 1H), 1.29-1.44 (m, 2H), 1.12-1.18 (m, 3H), 0.81-0.92 (m, 6H).

Example 137

N-(4-(2-(3-Chloro-2-hydroxyphenyl)propyl)-6-(((R)-1-hydroxy-4-methylpentan-2-yl)amino)-1,3,5-triazin-2-yl)methanesulfonamide

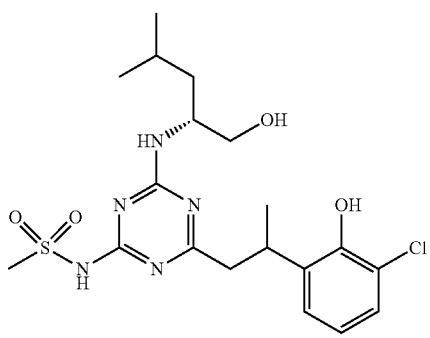 [SMILES: CC(C)C[C@H](CO)Nc1nc(CC(C)c2cccc(Cl)c2O)nc(NS(C)(=O)=O)n1]

Prepared according to General Preparation Method A using (3-chloro-2-hydroxyphenyl)boronic acid as Intermediate B (43 mg, 250 µmol) and purified by preparative HPLC, PrepMethod H, (gradient 12-17%) to give the title compound (5.8 mg, 25%). HRMS (ESI) m/z [M+H]$^+$ calcd for $C_{19}H_{29}ClN_5O_4S$: 458.1624, found: 458.1636; $^1$H NMR (600 MHz, DMSO-d$_6$) δ 7.58-8.04 (m, 1H), 7.1-7.23 (m, 2H), 6.77-6.87 (m, 1H), 4.44-4.83 (m, partially overlapping with the solvent), 3.99-4.15 (m, partially overlapping with the solvent), 3.68-3.77 (m, partially overlapping with the solvent), 3.01-3.1 (m, partially overlapping with the solvent), 2.66-2.82 (m, partially overlapping with the solvent), 1.51-1.62 (m, 1H), 1.27-1.46 (m, 2H), 1.17-1.23 (m, 3H), 0.8-0.89 (m, 6H).

Example 138

N-(4-(((R)-1-Hydroxy-4-methylpentan-2-yl)amino)-6-(2-(4-(2-morpholinoethyl)phenyl)propyl)-1,3,5-triazin-2-yl)methanesulfonamide

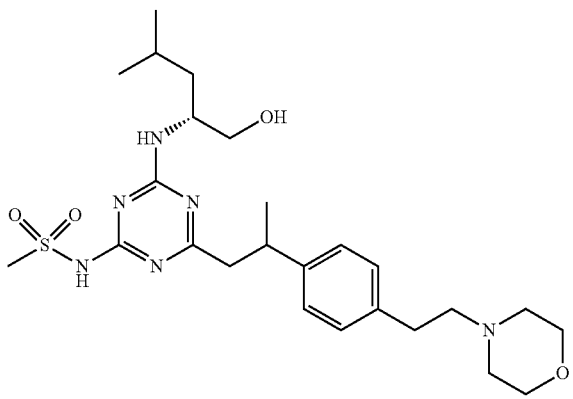 [SMILES: CC(C)C[C@H](CO)Nc1nc(CC(C)c2ccc(CCN3CCOCC3)cc2)nc(NS(C)(=O)=O)n1]

Prepared according to General Preparation Method A using 4-(4-(4,4,5,5-tetramethyl-1,3,2-dioxaborolan-2-yl)phenethyl)morpholine HCl salt as Intermediate B (88 mg, 250 µmol) and purified by preparative HPLC, PrepMethod K, (gradient 15-20%) to give the title compound (7.8 mg, 30%). HRMS (ESI) m/z [M+H]$^+$ calcd for $C_{25}H_{41}N_6O_4S$: 521.2904, found: 521.2902; $^1$H NMR (600 MHz, DMSO-d$_6$) δ 7.99-8.26 (m, 1H), 7.12-7.17 (m, 4H), 4.63-4.77 (m, 1H), 3.97-4.16 (m, 1H), 3.55-3.62 (m, partially overlapping with the solvent), 3.26-3.33 (m, partially overlapping with the solvent), 3.03-3.09 (m, 3H), 2.66-2.78 (m, partially overlapping with the solvent), 2.43-2.48 (m, partially overlapping with the solvent), 1.49-1.6 (m, 1H), 1.28-1.45 (m, 2H), 1.17-1.24 (m, 3H), 0.79-0.91 (m, 6H).

Example 139

N-(4-(2-(2-Hydroxy-3-methoxyphenyl)propyl)-6-(((R)-1-hydroxy-4-methylpentan-2-yl)amino)-1,3,5-triazin-2-yl)methanesulfonamide

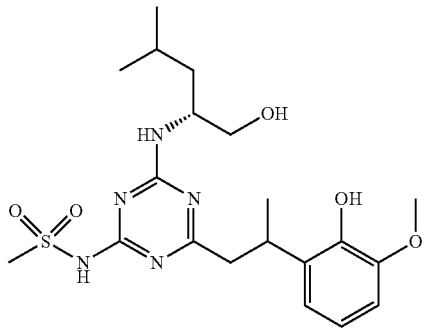

Prepared according to General Preparation Method A using (2-hydroxy-3-methoxyphenyl)boronic acid as Intermediate B (42 mg, 250 μmol) and purified by preparative HPLC, PrepMethod N, (gradient 2-94%) to give the title compound (10.9 mg, 48%). HRMS (ESI) m/z [M+H]$^+$ calcd for $C_{20}H_{32}N_5O_5S$: 454.2118, found: 454.2124; $^1$H NMR (600 MHz, DMSO-d$_6$) δ 8.16-8.59 (m, 1H), 6.69-6.84 (m, 3H), 4.63-4.73 (m, 1H), 4.01-4.19 (m, 1H), 3.77-3.81 (m, 3H), 3.64-3.74 (m, 1H), 3.36-3.43 (m, partially overlapping with the solvent), 3.01-3.08 (m, partially overlapping with the solvent), 2.73-2.87 (m, partially overlapping with the solvent), 1.52-1.62 (m, 1H), 1.37-1.49 (m, 1H), 1.22-1.36 (m, 1H), 1.12-1.2 (m, 3H), 0.8-0.91 (m, 6H).

Example 140

N-(4-(2-(3-Fluoro-4-isopropoxyphenyl)propyl)-6-(((R)-1-hydroxy-4-methylpentan-2-yl)amino)-1,3,5-triazin-2-yl)methanesulfonamide

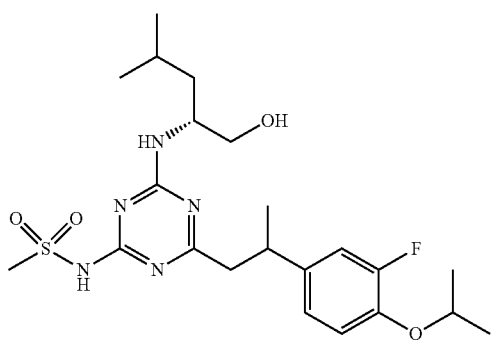 [SMILES: CC(C)C[C@H](CO)Nc1nc(CC(C)c2ccc(OC(C)C)c(F)c2)nc(NS(C)(=O)=O)n1]

Prepared according to General Preparation Method A using (3-fluoro-4-isopropoxyphenyl)boronic acid as Intermediate B (50 mg, 250 μmol) and purified by preparative HPLC, PrepMethod N, (gradient 4-94%) to give the title compound (2.5 mg, 10%). HRMS (ESI) m/z [M+H]$^+$ calcd for $C_{22}H_{35}FN_5O_4S$: 484.2388, found: 484.2396; $^1$H NMR (600 MHz, DMSO-d$_6$) δ 0.82-0.9 (m, 6H), 1.19-1.24 (m, 4H), 1.24-1.29 (7H, m), 1.31-1.48 (2H, m), 1.51-1.61 (1H, m), 3.01-3.13 (m, partially overlapping with the solvent), 3.35-3.42 (m, partially overlapping with the solvent), 4-4.15 (m, 1H), 4.51-4.59 (m, 1H), 4.62-4.74 (m, 1H), 6.93-6.99 (m, 1H), 7.01-7.13 (m, 2H), 7.86-8.39 (m, 1H).

Example 141

N-(4-(2-(4-Cyano-3-fluorophenyl)propyl)-6-(((R)-1-hydroxy-4-methylpentan-2-yl)amino)-1,3,5-triazin-2-yl)methanesulfonamide

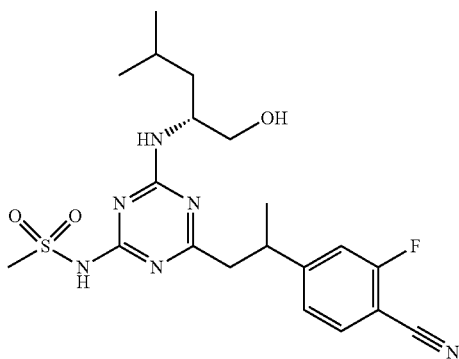 [SMILES: CC(C)C[C@H](CO)Nc1nc(CC(C)c2ccc(C#N)c(F)c2)nc(NS(C)(=O)=O)n1]

Prepared according to General Preparation Method A using (4-cyano-3-fluorophenyl)boronic acid as Intermediate B (25 mg, 150 μmol) and KOH (8.4 mg, 150 μmol), and purified by preparative HPLC, PrepMethod K, (gradient 15-20%) to give the title compound (2.3 mg, 10%). HRMS (ESI) m/z [M+H]$^+$ calcd for $C_{20}H_{28}FN_6O_3S$: 451.1922, found: 451.1922; $^1$H NMR (600 MHz, DMSO-d$_6$) δ 0.74-0.89 (m, 6H), 1.24-1.28 (m, 3H), 1.29-1.44 (m, 2H), 1.46-1.59 (m, 1H), 2.71-2.83 (m, partially overlapping with the solvent), 3.08-3.13 (m, 1H), 3.4-3.46 (m, partially overlapping with the solvent), 3.9-4.17 (m, 1H), 4.68 (s, 1H), 7.27-7.35 (m, 1H), 7.43-7.5 (m, 1H), 7.78-7.85 (m, 1H), 7.87-8.04 (m, 1H).

Example 142

N-(4-(2-(4-Fluoro-2-hydroxyphenyl)propyl)-6-(((R)-1-hydroxy-4-methylpentan-2-yl)amino)-1,3,5-triazin-2-yl)methanesulfonamide

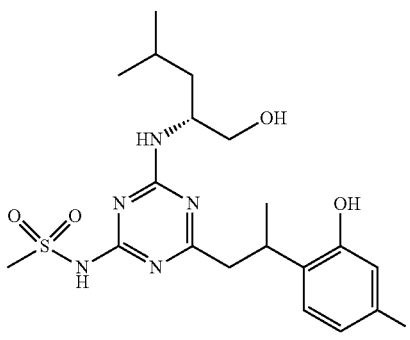

Prepared according to General Preparation Method A using (4-fluoro-2-hydroxyphenyl)boronic acid as Intermediate B (24 mg, 150 μmol) and KOH (8.4 mg, 150 μmol), and purified by preparative HPLC, PrepMethod K, (gradient 15-20%) to give the title compound (3.0 mg, 14%). HRMS (ESI) m/z [M+H]+ calcd for $C_{19}H_{29}FN_5O_4S$: 442.1918, found: 442.1920; $^1$H NMR (600 MHz, DMSO-$d_6$) δ 0.79-0.89 (m, 6H), 1.13-1.19 (m, 3H), 1.27-1.46 (m, 2H), 1.5-1.61 (m, 1H), 2.57-2.64 (m, partially overlapping with the solvent), 2.67-2.84 (m, partially overlapping with the solvent), 3.03-3.11 (m, 1H), 3.61 (dq, 1H), 3.96-4.2 (m, 2H), 4.6-4.77 (m, 1H), 6.49-6.6 (m, 2H), 7.06-7.15 (m, 1H), 7.94-8.28 (m, 1H).

Example 143

N-(4-((S*)-2-(2,3-Difluorophenyl)propyl)-6-(((R)-1-hydroxy-4-methylpentan-2-yl)amino)-1,3,5-triazin-2-yl)methanesulfonamide (Isomer 1)

Isomer 1

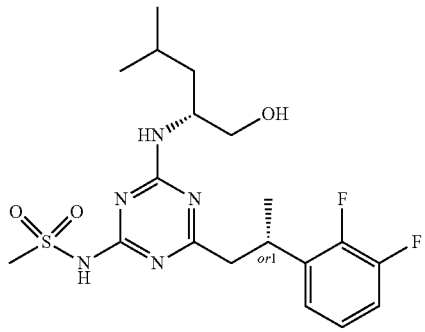

Example 144

N-(4-((R*)-2-(2,3-Difluorophenyl)propyl)-6-(((R)-1-hydroxy-4-methylpentan-2-yl)amino)-1,3,5-triazin-2-yl)methanesulfonamide (Isomer 2)

Isomer 2

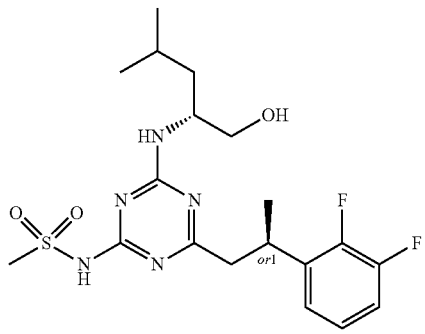

The diastereomers of N-(4-(2-(2,3-difluorophenyl)propyl)-6-(((R)-1-hydroxy-4-methylpentan-2-yl)amino)-1,3,5-triazin-2-yl)methanesulfonamide Intermediate 118 (50 mg, 0.11 mmol) were separated by preparative chiral HPLC on a Chiralpak OJ column (5 μm, 250×20 mm ID) using heptane/EtOH/TEA (80/20/0.1) as mobile phase, at a flow rate of 18 mL/min and detected at 254 nm, to give the first eluted compound N-(4-((S*)-2-(2,3-difluorophenyl)propyl)-6-(((R)-1-hydroxy-4-methylpentan-2-yl)amino)-1,3,5-triazin-2-yl)methanesulfonamide (Isomer 1) Example 143 that was purified by preparative HPLC, PrepMethod F, (gradient: 5-95%) to yield (14 mg, 29%); IRMS (ESI) m/z [M+H]+ calcd for $C_{19}H_{28}F_2N_5O_3S$: 444.1876, found: 444.1896; $^1$H NMR (600 MHz, DMSO-$d_6$) 0.75-0.88 (6H, m), 1.23-1.44 (5H, m), 1.46-1.59 (1H, m), 2.76 (1H, d), 2.82-2.90 (1H, m), 2.97-3.18 (3H, m), 3.26-3.32 (m, overlap with water signal), 3.60-3.73 (1H, m), 3.98-4.06 (1H, m), 4.62-4.74 (1H, m), 7.11-7.2 (2H, m), 7.20-7.30 (1H, m). The second eluted compound from the chiral separation, N-(4-((R*)-2-(2,3-difluorophenyl)propyl)-6-(((R)-1-hydroxy-4-methylpentan-2-yl)amino)-1,3,5-triazin-2-yl)methanesulfonamide (Isomer 2) Example 144 was purified by preparative HPLC, PrepMethod F, (gradient: 5-95%) to yield (22 mg, 43%); HRMS (ESI) m/z [M+H]+ calcd for $C_{19}H_{28}F_2N_5O_3S$: 444.1876, found: 444.1870; $^1$H NMR (600 MHz, DMSO-$d_6$) 0.80-0.88 (6H, m), 1.22-1.45 (5H, m), 1.47-1.60 (1H, m), 2.69-2.86 (2H, m), 2.97-3.18 (3H, m), 3.23-3.29 (m, partial overlap with water signal), 3.61-3.72 (1H, m), 3.98-4.08 (1H, m), 4.63-4.72 (1H, m), 7.11-7.19 (2H, m), 7.21-7.3 (1H, m).

Example 145

N-(4-((S*)-2-(2-Fluorophenyl)propyl)-6-(((R)-1-hydroxy-4-methylpentan-2-yl)amino)-1,3,5-triazin-2-yl)methanesulfonamide (Isomer 1)

Isomer 1

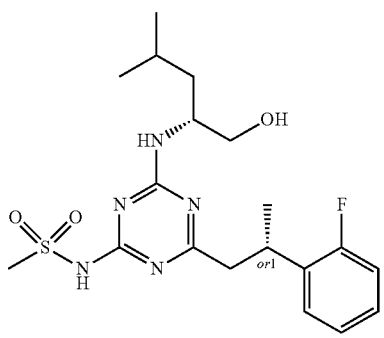

Example 146

N-(4-((R*)-2-(2-Fluorophenyl)propyl)-6-(((R)-1-hydroxy-4-methylpentan-2-yl)amino)-1,3,5-triazin-2-yl)methanesulfonamide (Isomer 2)

Isomer 2

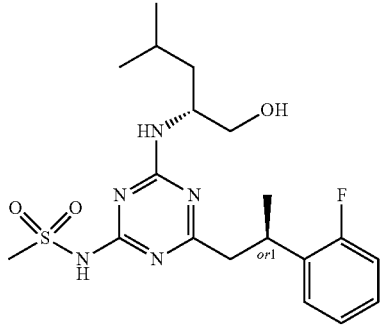

The diastereomers of N-(4-(2-(2-fluorophenyl)propyl)-6-(((R)-1-hydroxy-4-methylpentan-2-yl)amino)-1,3,5-triazin-2-yl)methanesulfonamide Intermediate 124 (3.83 g, 9.00 mmol) were separated by preparative chiral HPLC on a Chiralpak OJ column (5 µm, 250×30 mm ID) eluted with 20% MeOH/DEA (100/0.5) in $CO_2$, 120 bar at a flow rate of 130 mL/min and detected at 233 nm, to give the first eluted compound N-(4-((S*)-2-(2-fluorophenyl)propyl)-6-(((R)-1-hydroxy-4-methylpentan-2-yl)amino)-1,3,5-triazin-2-yl)methanesulfonamide (Isomer 1) Example 145 that was dissolved in DCM (60 mL), washed with 10% citric acid (2×15 mL) and brine (15 mL). The organic layer was dried over $Na_2SO_4$, filtered and evaporated. The residual oil was twice taken up in abs EtOH (30 mL) and concentrated. The final residue was dried in vacuo at 50° C. for 25 h to yield (0.72 g, 19%); HRMS (ESI) m/z [M+H]$^+$ calcd for $C_{19}H_{29}FN_5O_3S$: 426.1970, found: 426.1950; $^1$H NMR (600 MHz, CD30D) 0.87-0.97 (6H, m), 1.32-1.51 (5H, m), 1.58-1.69 (1H, m), 2.79-2.95 (2H, m), 3.13 (1.3H, s) 3.16 (1.7H, s), 3.45-3.59 (2H, m), 3.65-3.77 (1H, m), 4.17-4.26 (1H, m), 6.99-7.04 (1H, m), 7.08-7.14 (1H, m), 7.18-7.24 (1H, m), 7.38-7.33 (1H, m). The second eluted compound from the chiral separation, N-(4-((R*)-2-(2-fluorophenyl)propyl)-6-(((R)-1-hydroxy-4-methylpentan-2-yl)amino)-1,3,5-triazin-2-yl)methanesulfonamide (Isomer 2) Example 146 (1.8 g, 47%); $^1$H NMR (400 MHz, CDCl$_3$) 0.84-0.98 (6H, m), 1.30-1.49 (m, partial overlap with DEA), 1.56-1.77 (1H, m), 2.73-3.0 (m, partial overlap with DEA), 3.21 (3H, s), 3.51-3.61 (1H, m), 3.62-3.79 (2H, m), 4.09-4.22 (1H, m), 6.93-7.02 (1H, m), 7.03-7.10 (1H, m), 7.11-7.20 (1H, m), 7.22-7.29 (m, partial overlap with CDCl$_3$).

Example 147

N-(4-(((R)-1-Hydroxy-4-methylpentan-2-yl)amino)-6-((S*)-2-phenylpropyl)-1,3,5-triazin-2-yl)methanesulfonamide (Isomer 1)

Isomer 1

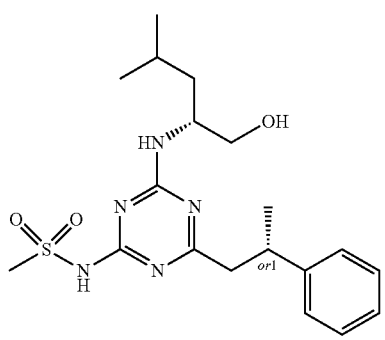

Example 148

N-(4-(((R)-1-Hydroxy-4-methylpentan-2-yl)amino)-6-((R*)-2-phenylpropyl)-1,3,5-triazin-2-yl)methanesulfonamide (Isomer 2)

Isomer 2

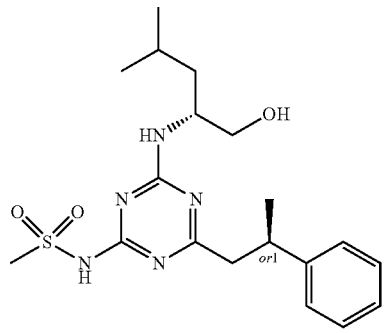

The diastereomers of N-(4-(((R)-1-hydroxy-4-methylpentan-2-yl)amino)-6-(2-phenylpropyl)-1,3,5-triazin-2-yl)methanesulfonamide Intermediate 130 (4.5 g, 11 mmol) were separated by preparative chiral HPLC on a CelluCoat column (5 µm, 250×30 mm ID) eluted with 20% IPA/DEA (100/0.5) in $CO_2$, 120 bar at a flow rate of 130 mL/min and detected at 230 nm, to give the first eluted compound N-(4-(((R)-1-hydroxy-4-methylpentan-2-yl)amino)-6-((S*)-2-phenylpropyl)-1,3,5-triazin-2-yl)methanesulfonamide (Isomer 1) Example 147 that was dissolved in DCM (60 mL) and washed with 1 M citric acid (2×10 mL) and water (10 mL). The organic layer was dried by passing through a phase separator and evaporated. The residue was co-evaporated with DCM and then abs EtOH, and dried in vacuo overnight to yield (1.9 g, 42%); MS (ESI m/z [M+H]$^+$ 408.4; $^1$H NMR (400 MHz, CD30D) 0.89-0.99 (6H, m), 1.27-1.55 (5H, m), 1.57-1.72 (1H, m), 2.71-2.90 (2H, m), 3.09-3.16 (3H, m), 3.31-3.38 (1H, m, partial overlap with water), 3.46-3.64 (2H, m), 4.17-4.31 (1H, m), 7.13-7.32 (5H, m). The second eluted compound from the chiral separation, N-(4-(((R)-1-hydroxy-4-methylpentan-2-yl)amino)-6-((R*)-2-phenylpropyl)-1,3,5-triazin-2-yl)methanesulfonamide (Isomer 2) Example 148 was treated in the same way as the first eluted isomer, to yield (1.9 g, 42%); HRMS (ESI) m/z [M+H]$^+$ calcd for $C_{19}H_{30}NSO_3S$: 408.2064, found: 408.2062; $^1$H NMR (600 MHz, CD$_3$OD) 0.90-0.97 (6H, m), 1.30-1.35 (3H, m), 1.36-1.53 (2H, m), 1.58-1.72 (1H, m), 2.73-2.87 (2H, m), 3.11-3.14 (3H, m), 3.35-3.44 (1H, m), 3.49-3.63 (2H, m), 4.21-4.31 (1H, m), 7.15-7.19 (1H, m), 7.22-7.29 (4H, m).

Example 149

N-(4-((S*)-2-(5-Chloropyridin-2-yl)propyl)-6-(((R)-1-hydroxy-4-methylpentan-2-yl)amino)-1,3,5-triazin-2-yl)methanesulfonamide (Isomer 1)

Isomer 1

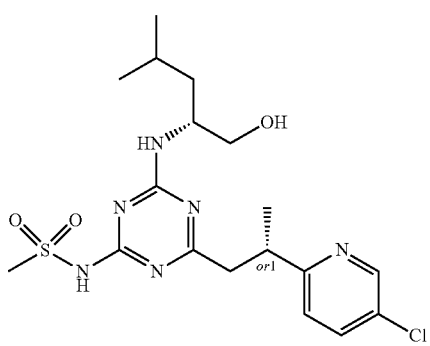

Example 150

N-(4-((R*)-2-(5-Chloropyridin-2-yl)propyl)-6-(((R)-1-hydroxy-4-methylpentan-2-yl)amino)-1,3,5-triazin-2-yl)methanesulfonamide (Isomer 2)

Isomer 2

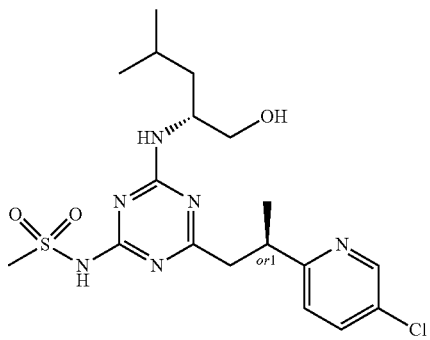

The diastereomers of N-(4-(2-(5-chloropyridin-2-yl)propyl)-6-(((R)-1-hydroxy-4-methylpentan-2-yl)amino)-1,3,5-triazin-2-yl)methanesulfonamide Intermediate 136 (27 mg, 0.06 mmol) were separated by preparative chiral HPLC on a Chiracel OJ column (5 µm, 250×30 mm) using 10% EtOH/DEA (100/0.5) in $CO_2$, 120 bar, at a flow rate of 78 mL/min and detected at 220 nm, to yield the first eluted compound N-(4-((S*)-2-(5-chloropyridin-2-yl)propyl)-6-(((R)-1-hydroxy-4-methylpentan-2-yl)amino)-1,3,5-triazin-2-yl)methanesulfonamide (Isomer 1) Example 149 (5.4 mg, 20%); HRMS (ESI) m/z [M+H]$^+$ calcd for $C_{18}H_{28}C_1N_6O_3S$: 443.1626, found: 443.1598; $^1$H NMR (500 MHz, $CD_3CN$) 0.80-0.93 (6H, m), 1.23-1.46 (5H, m), 1.51-1.67 (1H, m), 2.80-2.91 (m, partial overlap with DEA and water), 3.05 (3H, s), 3.38-3.57 (3H, m), 3.92-4.16 (1H, m), 7.20-7.27 (1H, m), 7.62-7.68 (1H, m), 8.45 (1H, br s), and the second eluted compound N-(4-((R*)-2-(5-chloropyridin-2-yl)propyl)-6-(((R)-1-hydroxy-4-methylpentan-2-yl)amino)-1,3,5-triazin-2-yl)methanesulfonamide (Isomer 2) Example 150 (4.5 mg, 17%); HRMS (ESI) m/z [M+H]$^+$ calcd for $C_{18}H_{28}C_1N_6O_3S$: 443.1626, found: 443.1614; $^1$H NMR (500 MHz, $CD_3CN$) 0.84-0.93 (6H, m), 1.24-1.48 (5H, m), 1.51-1.66 (1H, m), 2.86-2.95 (m, partial overlap with DEA and water), 3.04-3.13 (3H, m), 3.34-3.59 (3H, m), 4.02-4.15 (1H, m), 7.21-7.29 (1H, m), 7.62-7.69 (1H, m), 8.46 (1H, br s).

Example 151

N-(4-(((R)-1-Hydroxy-4-methylpentan-2-yl)amino)-6-(3,3,3-trifluoro-2-phenylpropyl)-1,3,5-triazin-2-yl)methanesulfonamide

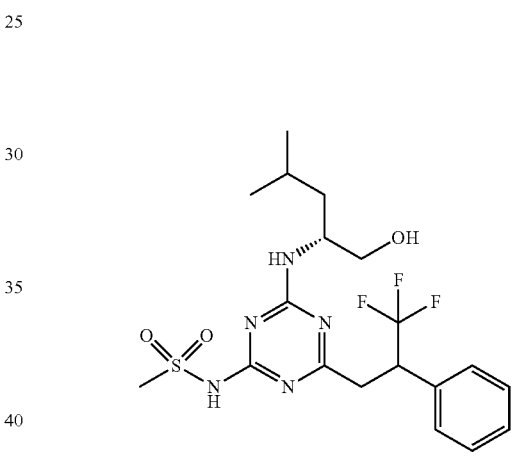

A mixture of (2R)-2-((4-chloro-6-(3,3,3-trifluoro-2-phenylpropyl)-1,3,5-triazin-2-yl)amino)-4-methylpentan-1-ol Intermediate 141 (242 mg, 0.60 mmol), $Pd_2(dba)_3$ (28 mg, 0.03 mmol), Xantphos (35 mg, 0.06 mmol) and $K_2CO_3$ (166 mg, 1.20 mmol) in THF (4 mL) was stirred at rt for 10 min under nitrogen atmosphere. A solution of methanesulfonamide (128 mg, 1.35 mmol) in THF (1 mL) was added and the reaction was heated at 55° C. overnight under nitrogen atmosphere. Water (5 mL) and DCM (30 mL) were added, the water layer was acidified with 1 M citric acid (4 mL) and extracted with DCM. The organic layers were concentrated and the residue was purified by preparative HPLC, Prep-Method M (gradient: 5-95%) to yield the title compound (118 mg, 43%); IRMS (ESI) m/z [M+H]$^+$ calcd for $C_{19}H_{27}F_3N_5O_3S$: 462.1780, found: 462.1770; $^1$H NMR (600 MHz, DMSO-$d_6$) 0.77-0.89 (6H, m), 1.26-1.43 (2H, m), 1.47-1.57 (1H, m), 3.01-3.33 (m, partial overlap with water), 3.92-4.12 (1H, m), 4.18-4.33 (1H, m), 4.2-4.74 (1H, m), 7.31-7.41 (5H, m).

Example 152

(R)—N-(4-((1-Hydroxy-4-methylpentan-2-yl) amino)-6-(2-methyl-2-phenylpropyl)-1,3,5-triazin-2-yl)methanesulfonamide

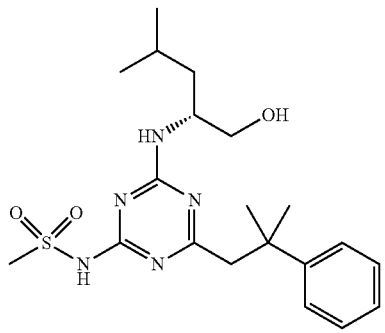 [SMILES: CC(C)C[C@H](CO)Nc1nc(CC(C)(C)c2ccccc2)nc(NS(C)(=O)=O)n1]

THF (4 mL) was added to a mixture of (R)-2-((4-chloro-6-(2-methyl-2-phenylpropyl)-1,3,5-triazin-2-yl)amino)-4-methylpentan-1-ol Intermediate 145 (0.201 g, 0.55 mmol), Pd$_2$dba$_3$ (0.025 g, 0.03 mmol), Xantphos (0.032 g, 0.06 mmol) and Cs$_2$CO$_3$ (0.361 g, 1.11 mmol) under an atmosphere of N$_2$(g) and the reaction mixture was stirred at rt for 10 min. Methanesulfonamide (0.105 g, 1.11 mmol) dissolved in THF (1 mL) was added and the reaction mixture was heated at 55° C. under an atmosphere of N$_2$(g) overnight. The reaction mixture was diluted with water (5 mL) and extracted with DCM (30 mL). The organic layer was concentrated and the crude residue was purified by preparative HPLC, PrepMethod M (gradient: 5-95%), to give the title compound (19 mg, 8%); IRMS (ESI) m/z [M+H]$^+$ calcd for C$_{20}$H$_{32}$N$_5$O$_3$S: 422.2220, found: 422.2226; $^1$H NMR (600 MHz, DMSO-d$_6$) δ 0.78-0.89 (6H, m) 1.26-1.44 (8H, m), 1.49-1.61 (1H, m), 2.68-2.84 (2H, m), 3.3 (3H, s, overlapping with the water peak), 3.23-3.31 (1H, m), 3.38 (1H, s), 3.86-4.07 (1H, m), 4.64-4.7 (1H, m), 7.18 (1H, dt), 7.30 (2H, dt), 7.40 (2H, ddd).

Example 153

(R)—N-(4-(3-(4-Chlorophenyl)-3,3-difluoropropyl)-6-((1-hydroxy-4-methylpentan-2-yl)amino)-1,3,5-triazin-2-yl)methanesulfonamide

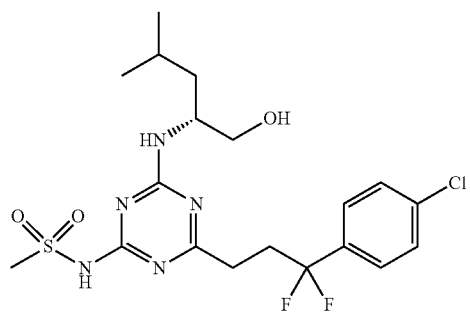 [SMILES: CC(C)C[C@H](CO)Nc1nc(CCC(F)(F)c2ccc(Cl)cc2)nc(NS(C)(=O)=O)n1]

A solution of 9-BBN in THF (0.5 M, 2.121 mL, 1.06 mmol) was added to 1-chloro-4-(1,1-difluoroallyl)benzene *Angew. Chem. Int. Ed.* 2021,60, 25746-25752 (100 mg, 0.53 mmol) under an atmosphere of N$_2$(g) and the reaction mixture was stirred at rt for 40 h. A degassed solution of K$_3$PO$_4$ (3 M, aq, 1.060 mL, 3.18 mmol) was added to the reaction mixture, followed by a degassed solution of (R)—N-(4-chloro-6-((1-hydroxy-4-methylpentan-2-yl)amino)-1,3,5-triazin-2-yl)methanesulfonamide Intermediate 1 (172 mg, 0.53 mmol) in THF (2 mL) and Pd(dppf)Cl$_2$·DCM (35 mg, 0.04 mmol). The reaction mixture was degassed and heated at 40° C. overnight. The reaction mixture was diluted with EtOAc, and the water layer was removed. The organic layer was washed with very dilute HCl, water and brine. The combined water phase was neutralized to pH5 and extracted once with EtOAc. The combined organic layer was dried over MgSO$_4$, treated with SiliaMetS Thiol, filtered, and concentrated in vacuo. The crude product was purified by preparative HPLC, PrepMethod A, (gradient: 15-65%), then by straight phase flash chromatography (eluted with increasing amounts of EtOAc in DCM) to give the title compound (15 mg, 6%) as a white solid; HRMS (ESI) m/z [M+H]$^+$ calcd for C$_{19}$H$_{27}$ClF$_2$N$_5$O$_3$S: 478.1486, found: 478.1458; $^1$H NMR (400 MHz, CDCl$_3$) δ 0.84-1.01 (6H, m) 1.3-1.56 (2H, m), 1.65 (1H, tq), 2.47-2.76 (2H, m), 2.74-2.93 (2H, m), 3.17-3.4 (3H, m), 3.58 (1H, dd), 3.69-3.86 (1H, m), 4.29 (1H, s), 7.31-7.63 (4H, m).

Example 154

(R)—N-(4-(3,3-Difluoro-3-(4-fluorophenyl)propyl)-6-((1-hydroxy-4-methylpentan-2-yl)amino)-1,3,5-triazin-2-yl)methanesulfonamide

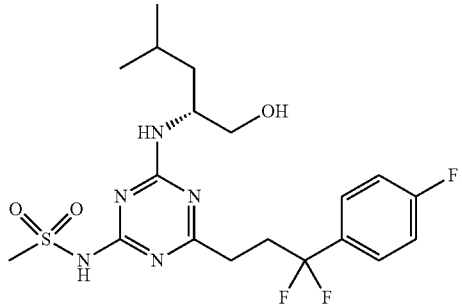 [SMILES: CC(C)C[C@H](CO)Nc1nc(CCC(F)(F)c2ccc(F)cc2)nc(NS(C)(=O)=O)n1]

A solution of 9-BBN in THF (0.5 M, 1853 μl, 0.93 mmol) was added to 1-(1,1-difluoroallyl)-4-fluorobenzene Intermediate 146 (96 mg, 0.56 mmol) under an atmosphere of N$_2$(g) and the reaction mixture was stirred at 75° C. for 1 h. A solution of degassed K$_3$PO$_4$ (3 M, aq, 618 μl, 1.85 mmol) was added to the reaction mixture. When the gas evolution had ceased (R)—N-(4-chloro-6-((1-hydroxy-4-methylpentan-2-yl)amino)-1,3,5-triazin-2-yl)methanesulfonamide Intermediate 1 (100 mg, 0.31 mmol) and Pd(dppf)Cl$_2$·DCM (17.6 mg, 0.02 mmol) were added and the reaction mixture was degassed and heated shortly at 50° C. K$_3$PO$_4$ (3 M, aq, 309 μl, 0.93 mmol) and PdCl$_2$(dppf) DCM (25.2 mg, 0.03 mmol) were added and the reaction mixture was stirred at 40° C. overnight. The reaction mixture was diluted with EtOAc and washed with dilute HCl and brine. The combined water layer was extracted with EtOAc, and the combined organic layer was dried over MgSO$_4$ and treated with SiliaMetS Thiol. The mixture was filtered and concentrated in vacuo and the residue was purified by preparative HPLC, PrepMethod A (gradient: 20-75%). The compound containing fractions were collected and evaporated, and the residue was dissolved in EtOAc and washed with water. The organic layer was concentrated, and the residue was purified by straight phase flash chromatography on silica (EtOAc) to give the title compound (52 mg, 37%) as a white solid; HRMS (ESI) m/z [M+H]+ calcd for $C_{19}H_{27}F_3N_5O_3S$: 462.1780, found: 462.1770; $^1$H NMR (400 MHz, CDCl$_3$) δ 0.88-0.97 (6H, m), 1.31-1.54 (2H, m), 1.57-1.73 (1H, m), 2.54-2.7 (2H, m), 2.81 (2H, dd), 3.35 (3H, s), 3.58 (1H, dd), 3.75 (1H, dd), 4.08-4.35 (m, partly overlapping with solvent), 7.04-7.14 (2H, m), 7.48 (2H, dt).

Example 155

N-(4-(2-(3-Fluoro-6-methylpyridin-2-yl)propyl)-6-(((R)-1-hydroxy-4-methylpentan-2-yl)amino)-1,3,5-triazin-2-yl)methanesulfonamide

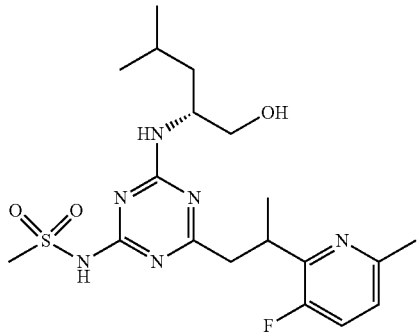

3-Fluoro-6-methyl-2-(prop-1-en-2-yl)pyridine Intermediate 147 (98 mg, 0.65 mmol) was added to a solution of 9-BBN dimer (120 mg, 0.50 mmol) in THF-d$_8$ (1.5 mL) under an atmosphere of N$_2$(g) and the reaction mixture was stirred at rt for 1 h. 9-BBN dimer (105 mg, 0.43 mmol) was added and the reaction mixture was stirred at rt for 30 min. Degassed K$_3$PO$_4$ (3M, aq, 0.867 mL, 2.60 mmol) was added followed by a solution of (R)—N-(4-((1-((tert-butyldimethylsilyl)oxy)-4-methylpentan-2-yl)amino)-6-chloro-1,3,5-triazin-2-yl)methanesulfonamide Intermediate 2 (190 mg, 0.43 mmol) and Pd(dppf)Cl$_2$·DCM (52.6 mg, 0.07 mmol). The reaction mixture was degassed and then stirred in an atmosphere of N$_2$(g) at 35° C. for 110 h. EtOAc and water were added to the reaction mixture and the phases were separated. The water layer was extracted once with EtOAc and the combined organic layer was washed with brine and concentrated. The residue was dissolved in EtOH (2 mL), and 12 M HCl (0.4 mL, 4.80 mmol) was added, and the mixture was stirred for 1 h and then concentrated in vacuo. The residue was purified by preparative HPLC, PrepMethod C (gradient: 15-60%) and then by preparative HPLC PrepMethod D (gradient: 0-50%) to give the title compound (1.7 mg, 1%); HRMS (ESI) m/z [M+H]+ calcd for $C_{19}H_{30}FN_6O_3S$: 441.2078, found: 441.2098; $^1$H NMR (500 MHz, CDCl$_3$) δ 0.88-0.98 (6H, m), 1.34-1.75 (m, partly overlapping with solvent), 2.55-2.64 (3H, m), 2.95-3.09 (2H, m), 3.15 (3H, d), 3.52-3.67 (1H, m), 3.76-3.86 (1H, m), 4.17-4.34 (1H, m), 6.99-7.09 (1H, m), 7.26 (m, partly overlapping with solvent).

Examples 156-158

The following Examples 156 to 158 were prepared as described in General Synthesis Scheme 1 and General Preparation Method A from Intermediate 4 and the appropriate boronic acid or boronic ester Intermediate B as described below. Intermediates B are commercially available if not otherwise stated.

Example 156

N-(4-(((R)-1-Hydroxy-4-methylpentan-2-yl)amino)-6-(2-(4-(morpholine-4-carbonyl)phenyl)propyl)-1,3,5-triazin-2-yl)methanesulfonamide

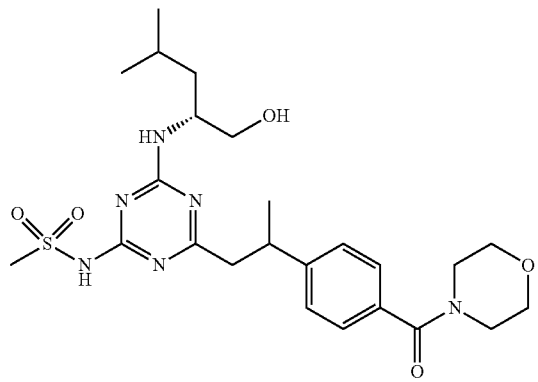 [SMILES: CC(C)C[C@H](CO)Nc1nc(CC(C)c2ccc(C(=O)N3CCOCC3)cc2)nc(NS(C)(=O)=O)n1]

Prepared according to General Preparation Method A using (4-(morpholine-4-carbonyl)phenyl)boronic acid as Intermediate B (35 mg, 150 µmol) and purified by preparative HPLC, PrepMethod N, (gradient 10-60%) to give the title compound (9.5 mg, 37%); MS (ESI) m/z [M+Na]+ 543.1; $^1$H NMR (600 MHz, DMSO-d$_6$) δ 0.82-0.93 (m, 6H), 1.23-1.29 (m, 3H), 1.31-1.49 (m, 2H), 1.52-1.62 (m, 1H), 2.7-2.81 (m, partially overlapping with the solvent), 3.01-3.12 (m, partially overlapping with the solvent), 3.36-3.42 (m, partially overlapping with the solvent), 3.49-3.69 (m, partially overlapping with the solvent), 3.99-4.17 (m, 1H), 4.62-4.75 (m, 1H), 7.28-7.39 (m, 4H), 8.28 (s, 1H), 12.45 (s, 1H).

Example 157

N-(4-(2-([1,1'-Biphenyl]-3-yl)propyl)-6-(((R)-1-hydroxy-4-methylpentan-2-yl)amino)-1,3,5-triazin-2-yl)methanesulfonamide

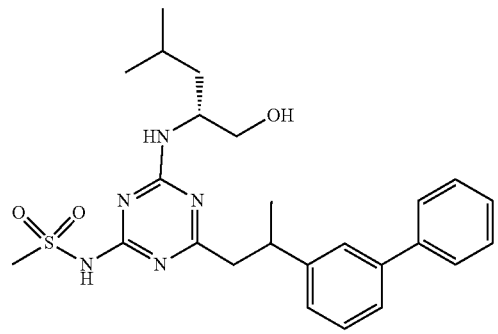 [SMILES: CC(C)C[C@H](CO)Nc1nc(CC(C)c2cccc(-c3ccccc3)c2)nc(NS(C)(=O)=O)n1]

Prepared according to General Preparation Method A using [1,1'-biphenyl]-3-ylboronic acid as Intermediate B (49 mg, 250 µmol) and purified by preparative HPLC, Prep-Method Q, (gradient 15-20%) to give the title compound (9.6 mg, 40%); HRMS (ESI) m/z [M+H]+ calcd for $C_{25}H_{34}N_5O_3S$: 484.2376, found: 484.2370; $^1$H NMR (600 MHz, DMSO-d$_6$) δ 0.77-0.89 (m, 6H), 1.27-1.46 (m, 5H), 1.49-1.6 (m, 1H), 2.71-2.89 (m, partially overlapping with the solvent), 3.01-3.1 (m, partially overlapping with the solvent), 3.39-3.48 (m, partially overlapping with the solvent), 3.98-4.17 (m, 1H), 4.62-4.78 (m, 1H), 7.22-7.29 (m, 1H), 7.34-7.42 (m, 2H), 7.43-7.54 (m, 4H), 7.6-7.69 (m, 2H), 8.20 (s, 1H), 12.41 (s, 1H).

Example 158

N-(4-(((R)-1-Hydroxy-4-methylpentan-2-yl)amino)-6-(2-(3-(1-hydroxycyclopropyl)phenyl)propyl)-1,3,5-triazin-2-yl)methanesulfonamide

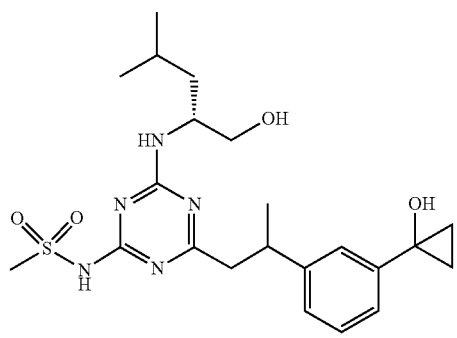 [SMILES: CC(C)C[C@H](CO)Nc1nc(CC(C)c2cccc(C3(O)CC3)c2)nc(NS(C)(=O)=O)n1]

Prepared according to General Preparation Method A using (3-(1-hydroxycyclopropyl)phenyl)boronic acid Intermediate 142 as Intermediate B (44 mg, 250 µmol) and purified by preparative HPLC, PrepMethod Q, (gradient 12-17%) to give the title compound (9.8 mg, 42%). HRMS (ESI) m/z [M+H]+ calcd for $C_{22}H_{34}N_5O_4S$: 464.2326, found: 464.2310; $^1$H NMR (600 MHz, DMSO-d$_6$) δ 0.8-0.9 (m, 6H), 1.05-1.12 (m, 3H), 1.25-1.45 (m, 5H), 1.48-1.61 (m, 1H), 2.7-2.83 (m, 2H), 3.0-3.1 (m, partially overlapping with the solvent), 3.28-3.46 (m, partially overlapping with the solvent), 3.98-4.11 (m, partially overlapping with the solvent), 7.41-7.48 (m, 1H), 7.49-7.55 (m, 1H), 7.77-7.83 (m, 2H), 8.09 (s, 1H).

Examples 159-167

Examples 159 to 167 were prepared as described in General Synthesis Scheme 2 and General Preparation Method B from Intermediate 4 and appropriate boronic acid or boronic ester Intermediate B as described below. Intermediates B are commercially available if not otherwise stated.

General Synthesis Scheme 2

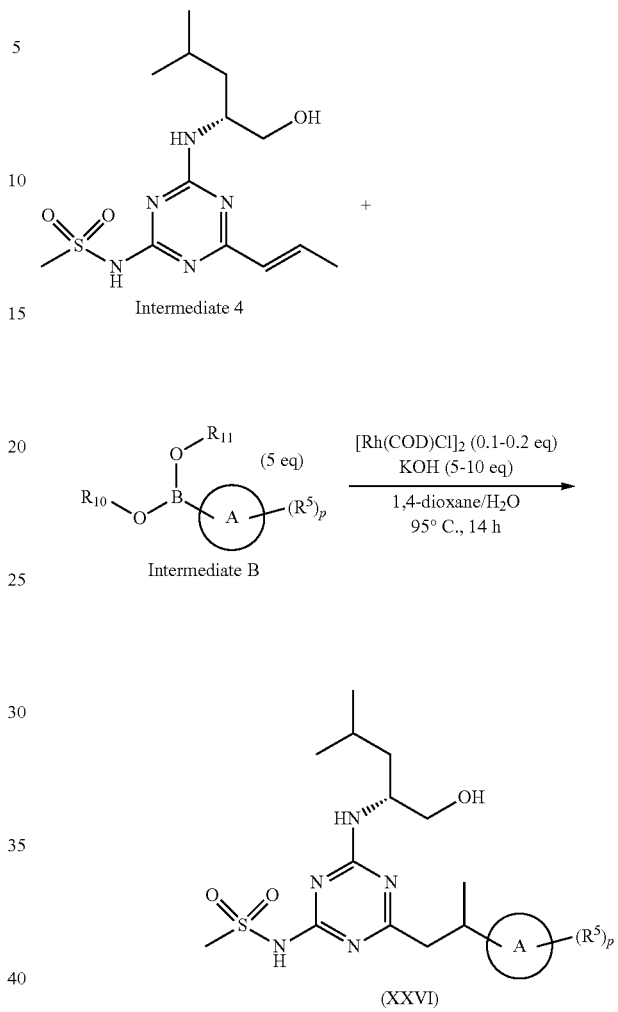

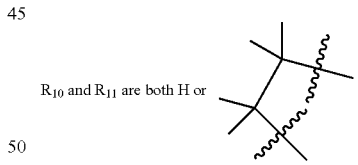

$R_{10}$ and $R_{11}$ are both H or

General Preparation Method B

A solution of [Rh(COD)Cl]$_2$ (0.1-0.2 eq) in 1,4-dioxane (0.02-0.04 M) was added to a solution of (R,E)-N-(4-((1-hydroxy-4-methylpentan-2-yl)amino)-6-(prop-1-en-1-yl)-1,3,5-triazin-2-yl)methanesulfonamide Intermediate 4 (100 mg, 0.3 mmol) and appropriate boronic acid/ester Intermediate B (10 eq) in 1,4-dioxane (~0.2 M) at 25° C. and under an atmosphere of N$_2$(g). KOH (7-10 eq) in water (1-2 M) was added and the reaction mixture was stirred at 95° C. for 14 h. The reaction mixture was filtered through a pad of celite and the celite was washed with DMSO. The filtrate was collected and concentrated to give the crude product in DMSO which was purified by preparative HPLC to give the title compound as a mixture of diastereoisomers.

Example 159

N-(4-(((R)-1-Hydroxy-4-methylpentan-2-yl)amino)-6-(2-(6-isopropoxypyridin-3-yl)propyl)-1,3,5-triazin-2-yl)methanesulfonamide

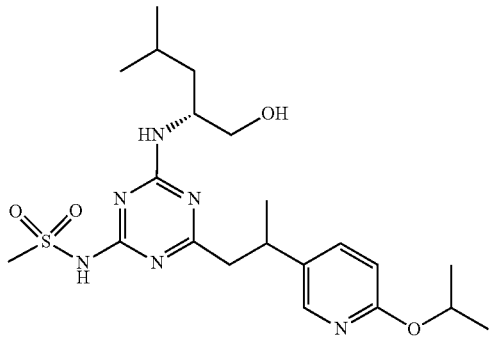 [SMILES: CC(C)C[C@H](CO)Nc1nc(CC(C)c2ccc(OC(C)C)nc2)nc(NS(C)(=O)=O)n1]

Prepared according to General Preparation Method B using (6-isopropoxypyridin-3-yl)boronic acid as Intermediate B (549 mg) and purified by preparative HPLC, PrepMethod O, (gradient: 36-43%) to give the title compound (20 mg, 14%); HRMS (ESI) m/z [M+H]$^+$ calcd for $C_{21}H_{35}N_6O_4S$: 467.2434, found: 467.2470; $^1$H NMR (500 MHz, DMSO-d$_6$) δ 0.8-0.9 (6H, m), 1.16-1.48 (12H, m), 1.48-1.62 (1H, m), 2.61-2.81 (2H, m), 3.25-3.41 (m, partly overlapping with solvent), 3.98-4.15 (1H, m), 5.13-5.25 (1H, m), 6.63-6.71 (1H, m), 7.55-7.62 (1H, m), 7.94-8.03 (1H, m).

Example 160

N-(4-(2-(3-Fluoro-2-methoxyphenyl)propyl)-6-(((R)-1-hydroxy-4-methylpentan-2-yl)amino)-1,3,5-triazin-2-yl)methanesulfonamide

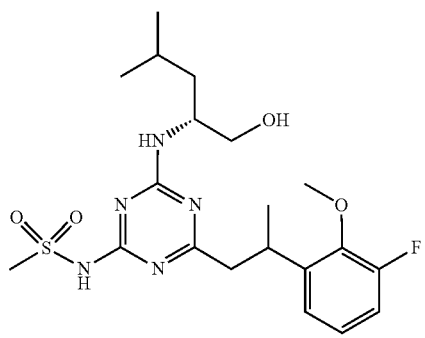 [SMILES: COc1c(F)cccc1C(C)Cc1nc(N[C@@H](CO)CC(C)C)nc(NS(C)(=O)=O)n1]

Prepared according to General Preparation Method B using (3-fluoro-2-methoxyphenyl)boronic acid as Intermediate B (516 mg) and purified by preparative HPLC, PrepMethod P, (gradient: 31-48%) to give the title compound (5 mg, 3%); HRMS (ESI) m/z [M+H]$^+$ calcd for $C_{20}H_{31}FN_5O_4S$: 456.2076, found: 456.2056; $^1$H NMR (500 MHz, DMSO-d$_6$) δ 0.79-0.89 (6H, m), 1.15-1.27 (3H, m), 1.27-1.47 (2H, m), 1.54 (1H, s), 2.68-2.81 (2H, m), 3.67-3.75 (1H, m), 3.81 (3H, td), 3.97-4.15 (2H, m), 7.09 (3H, td).

Example 161

N-(4-(2-(3-Cyano-4-fluorophenyl)propyl)-6-(((R)-1-hydroxy-4-methylpentan-2-yl)amino)-1,3,5-triazin-2-yl)methanesulfonamide

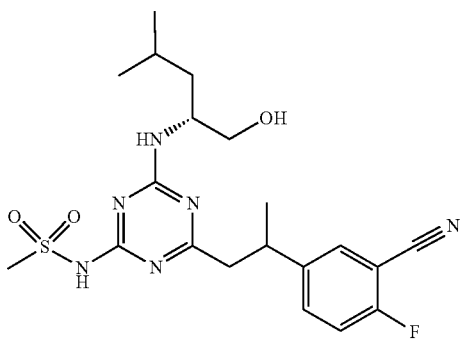 [SMILES: CC(C)C[C@H](CO)Nc1nc(CC(C)c2ccc(F)c(C#N)c2)nc(NS(C)(=O)=O)n1]

Prepared according to General Preparation Method B using (3-cyano-4-fluorophenyl)boronic acid as Intermediate B (501 mg) and purified by preparative HPLC, PrepMethod P, (gradient: 31-37%) to give the title compound (12 mg, 8%); HRMS (ESI) m/z [M+H]$^+$ calcd for $C_{20}H_{28}FN_6O_3S$: 451.1922, found: 451.1936; $^1$H NMR (500 MHz, DMSO-d$_6$) δ 0.76-0.89 (7H, m), 1.22-1.44 (5H, m), 1.46-1.59 (1H, m), 2.65-2.88 (2H, m), 3.23-3.4 (6H, m), 4.01 (1H, s), 7.38-7.48 (1H, m), 7.62-7.72 (1H, m), 7.8-7.87 (1H, m).

Example 162

N-(4-(2-(4-Fluoro-2-methoxyphenyl)propyl)-6-(((R)-1-hydroxy-4-methylpentan-2-yl)amino)-1,3,5-triazin-2-yl)methanesulfonamide

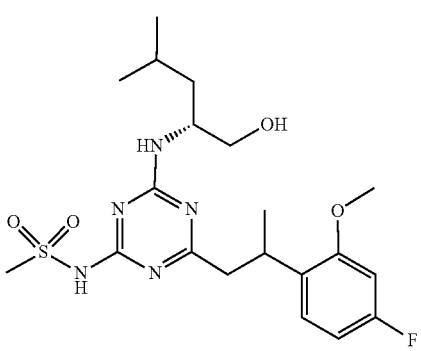 [SMILES: COc1cc(F)ccc1C(C)Cc1nc(N[C@@H](CO)CC(C)C)nc(NS(C)(=O)=O)n1]

Prepared according to General Preparation Method B using (4-fluoro-2-methoxyphenyl)boronic acid as Intermediate B (516 mg) and purified by preparative HPLC, PrepMethod P, (gradient: 33-48%) to give the title compound (7.2 mg, 5%); HRMS (ESI) m/z [M+H]$^+$ calcd for $C_{20}H_{31}FN_5O_4S$: 456.2076, found: 456.2066.

Example 163

N-(4-(((R)-1-Hydroxy-4-methylpentan-2-yl)amino)-6-(2-(2-oxoindolin-7-yl)propyl)-1,3,5-triazin-2-yl)methanesulfonamide

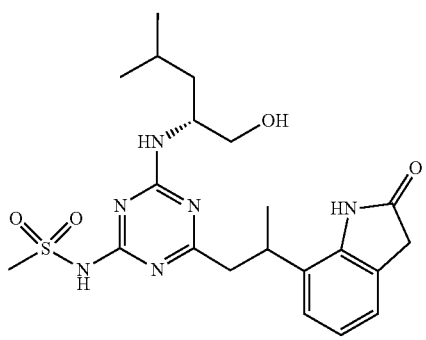 [SMILES: CC(C)C[C@H](CO)Nc1nc(CC(C)c2cccc3c2NC(=O)C3)nc(NS(C)(=O)=O)n1]

Prepared according to General Preparation Method B using 7-(4,4,5,5-tetramethyl-1,3,2-dioxaborolan-2-yl)indolin-2-one as Intermediate B (629 mg) and purified by preparative HPLC, PrepMethod M, (gradient: 23-35%) to give the title compound (48 mg, 34%). HRMS (ESI) m/z [M+H]$^+$ calcd for $C_{21}H_{31}N_6O_4S$: 463.2122, found: 463.2168.

Example 164 and 165

N-(4-((S*)-2-(4-Cyanophenyl)propyl)-6-(((R)-1-hydroxy-4-methylpentan-2-yl)amino)-1,3,5-triazin-2-yl)methanesulfonamide (Isomer 1) and N-(4-((R*)-2-(4-Cyanophenyl)propyl)-6-(((R)-1-hydroxy-4-methylpentan-2-yl)amino)-1,3,5-triazin-2-yl)methaneslfonamide (Isomer 2)

Isomer 1

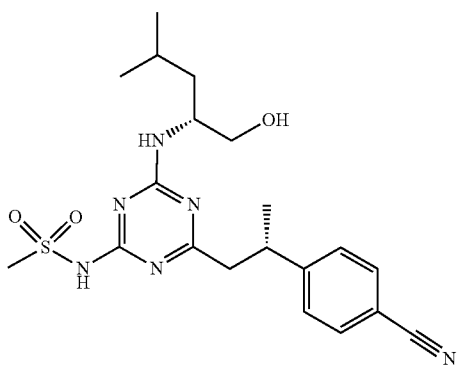

and

Isomer 2

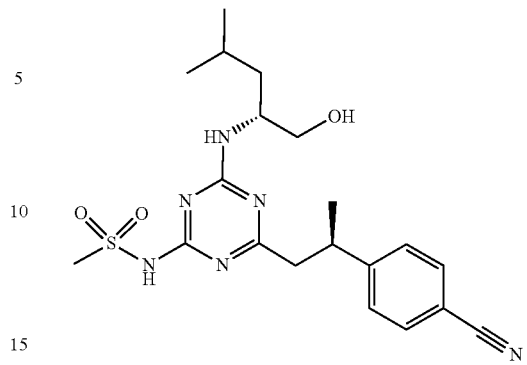

Prepared according to General Preparation Method B using 7-(4,4,5,5-tetramethyl-1,3,2-dioxaborolan-2-yl)indolin-2-one as Intermediate B (629 mg) and purified by preparative HPLC, PrepMethod P, (gradient: 29-35%) to give the diastereoisomeric mixture of the title compounds (90 mg, 34%). The stereoisomers were separated by chiral HPLC on a Chiralpak IH column (250×20, 5 μm), eluted with 30% EtOH in hexane (containing 0.5% 2M NH$_3$ in MeOH), at a flow rate of 20 mL/min, to give the first eluted compound N-(4-((S*)-2-(4-cyanophenyl)propyl)-6-(((R)16/09/2023-1-hydroxy-4-methylpentan-2-yl)amino)-1,3,5-triazin-2-yl)methanesulfonamide (Isomer 1) Example 164 (15 mg, 17%) as a white solid; HRMS (ESI) m/z [M+H]$^+$ calcd for $C_{20}H_{29}N_6O_3S$: 433.2016, found: 433.2004; $^1$H NMR (500 MHz, DMSO-d$_6$) δ 0.78-0.89 (6H, m), 1.23-1.43 (5H, m), 1.53 (1H, dq), 2.72 (1H, d), 2.82 (1H, qd), 3.07-3.46 (m, overlapping with solvent), 4.01 (1H, tq), 4.56-4.78 (1H, m), 7.47 (2H, dd), 7.76 (2H, t), 7.83-8.09 (1H, m);

And the second eluted compound N-(4-((R*)-2-(4-cyanophenyl)propyl)-6-(((R)-1-hydroxy-4-methylpentan-2-yl)amino)-1,3,5-triazin-2-yl)methanesulfonamide (Isomer 2) Example 165 (15 mg, 17%) as a white solid; HRMS (ESI) m/z [M+H]$^+$ calcd for $C_{20}H_{29}N_6O_3S$: 433.2016, found: 433.1986; $^1$H NMR (500 MHz, DMSO-d$_6$) δ 0.74-0.92 (6H, m), 1.2-1.45 (5H, m), 1.54 (1H, qd), 2.66-2.83 (2H, m), 3.0-3.47 (m, partly overlapping with solvent), 4.01 (1H, tt), 4.71 (1H, s), 7.47 (2H, t), 7.75 (2H, dd).

Example 166

N-(4-(((R)-1-Hydroxy-4-methylpentan-2-yl)amino)-6-(2-(6-methoxypyridin-2-yl)propyl)-1,3,5-triazin-2-yl)methanesulfonamide

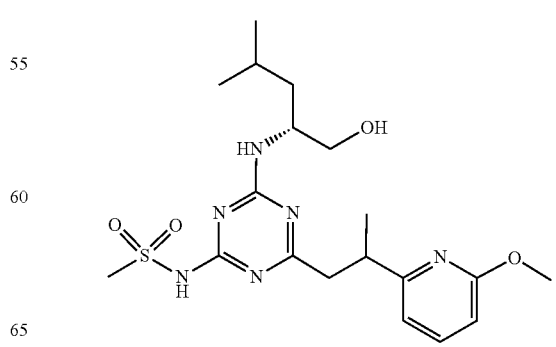

Prepared according to General Preparation Method B using (6-methoxypyridin-2-yl)boronic acid as Intermediate B (464 mg) and purified by preparative HPLC, PrepMethod P, (gradient: 25-42%) to give the title compound (20 mg, 15%); HRMS (ESI) m/z [M+H]$^+$ calcd for $C_{19}H_{31}N_6O_4S$: 439.2122, found: 439.2136.

Example 167

N-(4-(2-(6-Ethoxypyridin-3-yl)propyl)-6-(((R)-1-hydroxy-4-methylpentan-2-yl)amino)-1,3,5-triazin-2-yl)methanesulfonamide

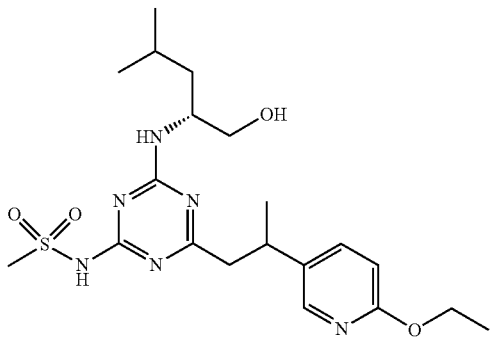 [SMILES: CCOc1ccc(C(C)Cc2nc(N[C@@H](CO)CC(C)C)nc(NS(C)(=O)=O)n2)cn1]

Prepared according to General Preparation Method B using (6-ethoxypyridin-3-yl)boronic acid as Intermediate B (507 mg) and purified by preparative HPLC, PrepMethod P, (gradient: 26-38%) to give the title compound (30 mg, 22%); IRMS (ESI) m/z [M+H]$^+$ calcd for $C_{20}H_{33}N_6O_4S$: 453.2278, found: 453.2310.

Example 168

N-(4-(2-([1,1'-Biphenyl]-4-yl)propyl)-6-(((R)-1-hydroxy-4-methylpentan-2-yl)amino)-1,3,5-triazin-2-yl)methanesulfonamide

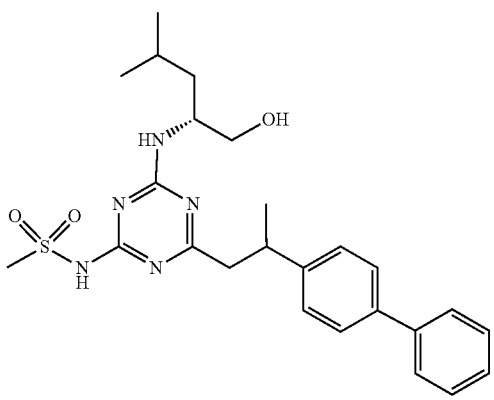 [SMILES: CC(C)C[C@H](CO)Nc1nc(CC(C)c2ccc(-c3ccccc3)cc2)nc(NS(C)(=O)=O)n1]

The title compound was prepared according to General Preparation Method B using [1,1'-biphenyl]-4-ylboronic acid as Intermediate B (601 mg) and purified by preparative HPLC, PrepMethod P, (gradient: 41-58%) to give the title compound (78 mg, 53%); IRMS (ESI) m/z [M+H]$^+$ calcd for $C_{25}H_{34}N_5O_3S$: 484.2376, found: 484.2412.

Example 169

N-(4-(2-(3-Chloro-4-cyanophenyl)propyl)-6-(((R)-1-hydroxy-4-methylpentan-2-yl)amino)-1,3,5-triazin-2-yl)methanesulfonamide

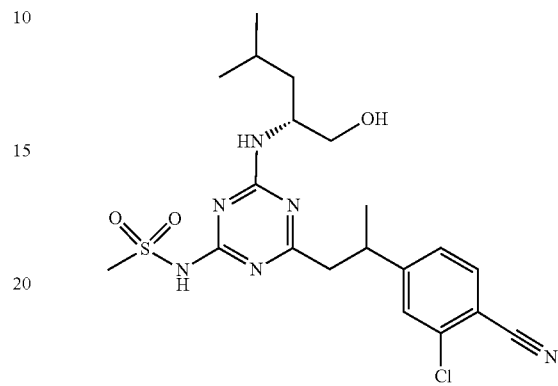

The title compound was prepared according to General Preparation Method A using (3-chloro-4-cyanophenyl)boronic acid as Intermediate B (45 mg, 250 µmol) and purified by preparative HPLC, PrepMethod E, (gradient 0-50%) to give the title compound (1.3 mg, 5%); HRMS (ESI) m/z [M+H]$^+$ calcd for $C_{20}H_{28}ClN_6O_3S$: 467.1626, found: 467.1640; $^1$H NMR (600 MHz, DMSO-d$_6$) δ 0.74-0.92 (m, 6H), 1.21-1.43 (m, 6H), 1.46-1.61 (m, 3H), 2.66-2.74 (m, partially overlapping with the solvent), 3.02-3.08 (m, partially overlapping with the solvent), 3.39-3.46 (m, partially overlapping with the solvent), 3.88-4.19 (m, partially overlapping with the solvent), 4.65 (d, 1H), 7.4-7.48 (m, 1H), 7.63-7.7 (m, 1H), 7.83-7.92 (m, 1H), 8.26 (s, 1H).

Example 170

N-(4-((S*)-2-(4-Chlorophenyl)propyl)-6-(((R)-1-hydroxy-4-methylpentan-2-yl)amino)-1,3,5-triazin-2-yl)methanesulfonamide (Isomer 1)

Isomer 1

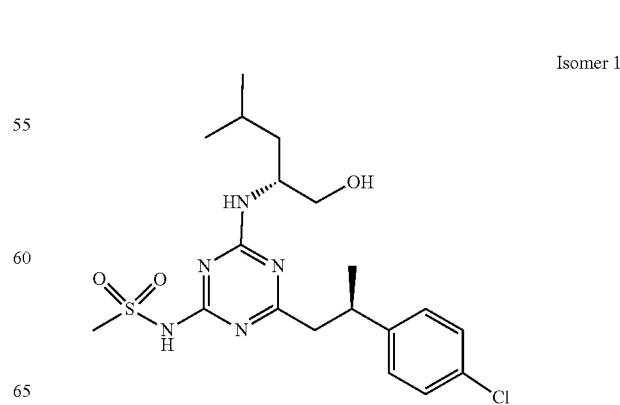

Example 171

N-(4-((R*)-2-(4-Chlorophenyl)propyl)-6-(((R)-1-hydroxy-4-methylpentan-2-yl)amino)-1,3,5-triazin-2-yl)methanesulfonamide, (Isomer 2)

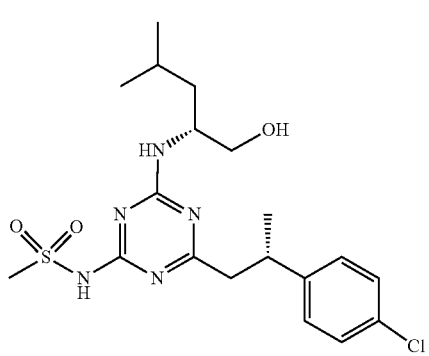

Isomer 2

The diastereomers of N-(4-(2-(4-chlorophenyl)propyl)-6-(((R)-1-hydroxy-4-methylpentan-2-yl)amino)-1,3,5-triazin-2-yl)methanesulfonamide Intermediate 149 (105 mg, 0.24 mmol) were separated by preparative chiral HPLC on a Chiralcel OJ column (250×30 mm, 5 μm), eluted with 25% EtOH/DEA (100/0.5) in $CO_2$, 120 bar at a flow rate of 80 mL/min and detected at 220 nm, to give the first eluting compound N-(4-((S*)-2-(4-chlorophenyl)propyl)-6-(((R)-1-hydroxy-4-methylpentan-2-yl)amino)-1,3,5-triazin-2-yl)methanesulfonamide (Isomer 1), Example 170 (46 mg, 44%); HRMS (ESI) m/z [M+H]+ calcd for $C_{19}H_{29}ClN_5O_3S$: 442.1674, found: 442.1678; and the second eluting compound, N-(4-((R*)-2-(4-chlorophenyl)propyl)-6-(((R)-1-hydroxy-4-methylpentan-2-yl)amino)-1,3,5-triazin-2-yl)methanesulfonamide (Isomer 2), Example 171 (47 mg, 44%); HRMS (ESI) m/z [M+H]+ calcd for $C_{19}H_{29}ClN_5O_3S$: 442.1674, found: 442.1680.

Pharmacological Activity

Materials

Adherent CHO-K1 cells stably expressing hCX3CR1 (ES-137-C) were purchased from PerkinElmer. The RPMI-8226 cell line (CCL-155) was purchased from A.T.C.C. The $CHO-K_1$ CX3CR1 β-arrestin cell line (93-0290$C_2$) was from DiscoveRx. hWB was collected from healthy volunteers. The work was performed in accordance with the Declaration of Helsinki (2013) of the World Medical Association and has been approved by the relevant ethical committee. AZD8797 (CAS911715-90-7) was synthesized as described previously (J. Med. Chem (2013), 56(8), 3177-3190; J, Labelled Comp. and Radiopharmaceuticals, (2012), 55(10), 387-392). [$^3$H]AZD8797 (50 Ci/mmol, 52.932 μM) was labelled in-house, $^{125}$I-CX3CL1 (2200 C/mmol) and [$^{35}$S]GTPγ S (guanosine 5'-[7-thio]triphosphate) (1250 Ci/mmol) were purchased from PerkinElmer, CX3CL1 (8.5 kDa, soluble chemokine domain, unless otherwise stated, was the ligand used) was from Peprotech and recombinant His-tagged full-length human CX3CL1 (365-FR-025/CF) was from R&D Systems. Pertussis toxin (PTX), polyethyleneimine (PEI), GTPδ S, GDP and gelatin type A were purchased from Sigma Aldrich. Vena8 Fluoro+ Biochips for cell adhesion assays were purchased from Cellix. 3,3'-dihexyloxacarbocyanine iodide (DiOC6) was from Molecular Probes and Hoechst 33342 was from Invitrogen. HEPES, Roswell Park Memorial Institute 1640 (RPMI 1640) medium, Ham's $F_{12}$ (Nutrient mixture F-12 Ham) medium, Dulbecco's modified eagle medium (DMEM), geneticin, phospate-buffered saline 200898-US-PSP 14 (PBS), Hanks' balanced salt solution (HBSS) and Opti-MEM were purchased from Gibco (Life Technologies).

Abbreviations and units used:
A.T.C.C. American Type Culture Collection; distributes reference microorganisms/cell lines for R&D
BSA Bovine serum albumin derived from cows and used as a protein concentration standard in lab and protein supplement in in vitro assays.
CHO-K1 an immortalized cell line isolated from the ovary of an adult, female Chinese hamster
Ci Curie=3.7 mmol-1×10$^{10}$ atoms that decay/second; Ci/mmol=amount radiolabeled mass in a sample
DiOC6 Dihexyloxacarbocyanine iodide
DMEM Dulbecco's modified eagle medium (cell medium)
FBS Fetal bovine serum
GDP Guanosine diphosphate
GTP Guanosine-5'-triphosphate
HBSS Hanks' balanced salt solution
HEPES (4-(2-hydroxyethyl)-1-piperazineethanesulfonic acid); zwitterionic sulfonic acid buffering agent
Hoechst 33342 a fluorescent stain for labeling DNA in fluorescence microscopy
kDa Kilodalton
Opti-MEM™ Reduced-Serum Medium; contains insulin, transferrin, hypoxanthine, thymidine, and trace elements
PBS Phosphate-buffered saline 200898-US-PSP 14
PEI Polyethyleneimine
PTX Pertussis toxin
RPMI 1640 Roswell Park Memorial Institute 1640 cell medium
WGA coated PVT Wheat germ agglutinin PEI-coated SPA beads for proximity-based radiometric scintillation assays

Example 172 hCX3CR1 [$^3$H]-AZD8797 Competitive Binding Assay (Filter)

CHO-hCX3CR1 membranes (9 μg per well) together with 2 nM [$^3$H]-AZD8797 and different concentrations of competitor compound were incubated in 25 mM HEPES (pH 7.4), 10 mM $MgCl_2$, 1 mM $CaCl_2$) and 0.5% BSA in a Corning polystyrene flat-bottom 96-well plate. The plate was incubated for 2 h at room temperature before free radioligand was separated from bound by vacuum filtration on to a Multiscreen HTS+HiFlow FB (Millipore) filter plate, using a Biomek FX (Beckman Coulter). The filter plate was washed in ice-cold 25 mM HEPES (pH 7.4), 5 mM $MgCl_2$, 1 mM $CaCl_2$) and 500 mM NaCl and dried at 50° C. for 1 h. Scintillation cocktail, Optiphase Supermix (PerkinElmer) was added to each well and the radioactivity was measured using a MicroBeta Trilux reader (PerkinElmer). The DMSO concentration was held constant at 1%. The results from this assay are shown below in Table 1.

Example 173 hCX3CR1 [$^{125}$I]-CX3CL1 Displacement Binding (SPA)

CHO-hCX3CR1 membranes (3 µg per well) together with 75 µM [$^{125}$I]-CX3CL1 (Perkin Elmer) and different concentrations of competitor compound were incubated together with 400 µg/well WGA coated PVT SPA beads (Perkin Elmer) in 50 mM HEPES (pH 7.4), 10 mM $MgCl_2$, 1 mM EDTA and 0.1% Gelatin in a Greiner polystyrene flat-bottom 384-well plate. The plate was incubated for 20 h at room temperature before the radioactivity was measured using a MicroBeta Trilux reader (PerkinElmer). The DMSO concentration was held constant at 1%. Results are shown below in Table 1.

Example 174

PathHunter β-Arrestin Recruitment Assay

β-Arrestin recruitment was measured using the PathHunter® eXpress enzyme fragment complementation assay (DiscoverX #93-0956E2). 3500 CHO-K1 CX3CR1 β-Arrestin cells/well in Opti-MEM were incubated together with different concentrations of CX3CL1 and antagonistic compound in a Greiner tissue culture treated flat-bottom 384-well plate. After 90 min of incubation at 37° C., the detection reagent supplied in the kit was added and incubation continued for 1 h at room temperature, before reading the luminescence with a Victor2 luminescence plate reader (PerkinElmer). The final DMSO concentration was held constant at 1%. The results from the assay are shown below in Table 1.

Example 175

[$^{35}$S]-GTPγS Binding Assay

CHO-hCX3CR1 membranes (5 µg per well) together with different concentrations of antagonistic compound were incubated in 50 mM HEPES (pH 7.4), 100 mM NaCl, 5 mM $MgCl_2$, 10 µM GDP and 0.01% gelatin in a MicroWell 96-well plate (Nunc). 0.56 µCi·ml-1 [$^{35}$S]-GTPγS and EC80 of CX3CL1 were then added. The plate was incubated at 30° C. for 1 h and subsequently unbound [$^{35}$S]-GTPγS was separated from bound by vacuum filtration to a Printed Filtermat B (PerkinElmer) using a Skatron Micro96 harvester and dried at 50° C. for 1 h. The filters were soaked with a melt-on scintillator sheet (MeltiLex, PerkinElmer), sealed using a MeltiLex heat sealer and measured in a MicroBeta Trilux reader (PerkinElmer). The different antagonistic compound concentrations were achieved by stepwise dilution in DMSO to achieve a final DMSO concentration of 1% in all wells after addition of assay buffer, regardless of compound concentration. The results from the assay are shown below in Table 1.

Example 176

Flow Adhesion Assays

Adhesion of cells to recombinant full-length human CX3CL1 was monitored under physiological flow using a Cellix VenaFlux microfluidics platform with connected fluorescent microscope and camera, and using Vena8 Fluoro+ Biochips (Cellix) pre-coated with anti-His monoclonal antibody (25 µg/mL; R&D Systems) and His-tagged full-length CX3CL1 (15 µg/mL; R&D Systems). The results from the assay are shown below in Table 1.

Example 177

CX3CR1-Dependent Cell Adhesion to Recombinant CX3CL1 in Human Whole Blood Under Flow Human whole blood from healthy volunteers was collected using heparin as anti-coagulant. To evaluate compound potency, $IC_{50}$ values were determined using an 8-step concentration response extending from 33.3 to 0.045 µM compound, including DMSO as vehicle control. Compound stocks or DMSO vehicle were added to 0.5 or 1.0 ml aliquots of blood such that the final concentration of DMSO was 0.1%, corresponding to a 1000-fold dilution of compound stock. Blood was pre-incubated with compound at room temperature for 60 minutes with gentle shaking. DiOC6 (Invitrogen, 5 µM) or Hoechst 33342 (Invitrogen, 300 PM) dye was subsequently added to fluorescently label cells and enable their detection during the flow adhesion assay. To monitor adhesion, blood was allowed to flow through the channels of a Vena8 Fluoro+ biochip at 2.25 dynes per $cm^2$ for 3-6 minutes prior to capturing images for quantification. Fluorescent cells adhering to the channels were counted and the mean and/or total count across five to six images in each channel were used for calculating concentration-response curves. Results are shown below in Table 1.

Example 178

Flow adhesion for human B-lymphocyte cell line RPMI-8226

Cells were cultured in RPMI 1640 medium with GlutaMAX and 20% FBS (HyClone, Perbio). Before each experiment, cells were centrifuged at 320 g and resuspended to 5×106 cells per ml in RPMI 1640 with 1% FBS. Cells were pre-incubated for 15 minutes at room temperature with CX3CR1 antagonist in an 8-step 3-fold dilution series starting at 3.3 µM. DMSO concentration was kept constant for all antagonist concentrations at 0.10. Cells were pumped through the channels of the Vena8 Fluoro+ biochip at 0.5 dynes per cm2 for 3 m prior to capturing microscope images for quantification. Cells adhering to channels were counted and the mean values across five images in each channel were used for calculating the concentration-response curves. Results are shown below in Table 1.

TABLE 1

| | | | Assay results | | |
|---|---|---|---|---|---|
| Example No | hCX3CR1 [$^3$H-AZD8797] competitive binding IC$_{50}$ (μM) | hCX3CR1 [$^{125}$I-CX3CL1] displacement binding SPA IC$_{50}$ (μM) | CX3CR1-dependent cell adhesion in human whole blood IC$_{50}$ (μM) | β-Arrestin recruitment EC$_{50}$ (μM) | hCX3CR1 B-cell adhesion IC$_{50}$ (μM) |
| 1 | | 1.97 | | | |
| 2 | 0.361 | 0.362 | | | |
| 3 | 0.124 | 0.448 | | | |
| 4 | 0.017 | 0.068 | 0.499 | | |
| 5 | 0.239 | 0.895 | | | |
| 6 | 0.096 | 0.948 | 0.109 | | |
| 7 | 0.055 | >10 | 2.46 | 0.400 | 0.128 |
| 8 | 1.35 | >20 | | | |
| 9 | 0.205 | >10 | | | |
| 10 | 0.922 | >20 | | | |
| 11 | >10 | >30 | | | |
| 12 | 0.176 | 1.86 | | | 0.255 |
| 13 | 0.614 | 4.25 | | | |
| 14 | >10 | | | | |
| 15 | 0.252 | 2.99 | | | |
| 16 | 4.93 | >30 | | | |
| 17 | 0.307 | 4.37 | | | |
| 18 | 0.758 | 16.7 | | | |
| 19 | 0.033 | | | | |
| 20 | 0.958 | | | | |
| 21 | 6.41 | | | | |
| 22 | 0.257 | | | | |
| 23 | 0.548 | | | | |
| 24 | 0.078 | | | | |
| 25 | 1.35 | 13.5 | | | |
| 26 | 0.044 | 0.682 | | | |
| 27 | 0.138 | | | | |
| 28 | 2.78 | | | | |
| 29 | 0.794 | | | | |
| 30 | 0.148 | | | | |
| 31 | 0.287 | | | | |
| 32 | 7.56 | | | | |
| 33 | 0.384 | | | | |
| 34 | 0.052 | | | | |
| 35 | 2.53 | | | | |
| 36 | 0.504 | | | | |
| 37 | 1.93 | | | | |
| 38 | 0.685 | | | | |
| 39 | >10 | | | | |
| 40 | 0.065 | | | | |
| 41 | >10 | | | | |
| 42 | 0.030 | | | | |
| 43 | 9.11 | | | | |
| 44 | 0.173 | | | | |
| 45 | 0.765 | | | | |
| 46 | 0.052 | | 1.40 | 0.100 | |
| 47 | 0.063 | | | | |
| 48 | 0.309 | | | | |
| 49 | 0.474 | | | | |
| 50 | 0.342 | | | | |
| 51 | 0.030 | | | | |
| 52 | 0.450 | 5.52 | | | |
| 53 | 0.528 | 11.0 | | | |
| 54 | 0.153 | | | | |
| 55 | 0.139 | | | | |
| 56 | 0.204 | | | | |
| 57 | 0.111 | | | | |
| 58 | 0.105 | | | | |
| 59 | 0.292 | | | | |
| 60 | 0.102 | | | | |
| 61 | 0.076 | | | | |
| 62 | 0.140 | | | | |
| 63 | 0.114 | | | | |
| 64 | 0.302 | | | | |
| 65 | 4.20 | | | | |
| 66 | 0.222 | | | | |
| 67 | 0.359 | 1.83 | | | |
| 68 | 0.336 | | | | |
| 69 | 0.830 | | | | |
| 70 | 0.298 | | | | |
| 71 | 0.331 | | | | |

TABLE 1-continued

| | Assay results | | | | |
|---|---|---|---|---|---|
| Example No | hCX3CR1 [³H-AZD8797] competitive binding IC$_{50}$ (μM) | hCX3CR1 [¹²⁵I-CX3CL1] displacement binding SPA IC$_{50}$ (μM) | CX3CR1-dependent cell adhesion in human whole blood IC$_{50}$ (μM) | β-Arrestin recruitment EC$_{50}$ (μM) | hCX3CR1 B-cell adhesion IC$_{50}$ (μM) |
| 72 | 0.340 | | | | |
| 73 | 0.633 | | | | |
| 74 | 0.925 | | | | |
| 75 | 2.70 | 5.18 | | | >3 |
| 76 | 0.048 | 0.886 | | | 0.158 |
| 77 | 3.25 | | | | |
| 78 | 0.022 | | | | |
| 79 | 0.198 | 2.47 | | | 0.054 |
| 80 | 2.21 | 4.90 | | | |
| 81 | 0.049 | 0.470 | 3.08 | | 0.014 |
| 82 | 0.128 | 0.566 | | | 0.011 |
| 83 | 0.156 | 0.424 | 1.29 | | |
| 84 | 0.173 | 0.348 | | | |
| 85 | 0.018 | | 0.691 | 0.050 | |
| 86 | 0.073 | | | | |
| 87 | 0.186 | | | | |
| 88 | 0.032 | | 0.115 | | |
| 89 | 0.250 | 0.987 | | | |
| 90 | 1.70 | | | | |
| 91 | 0.034 | | | | |
| 92 | 0.112 | | | | |
| 93 | 0.209 | | | | |
| 94 | 0.102 | | | | |
| 95 | 0.657 | | | | |
| 96 | 0.149 | | | | |
| 97 | 0.090 | | | | |
| 98 | 0.427 | | | | |
| 99 | 0.077 | | | | |
| 100 | 0.160 | | | | |
| 101 | 0.542 | | | | |
| 102 | 0.088 | | | | |
| 103 | 0.017 | | | | |
| 104 | 0.038 | | | | |
| 105 | 0.123 | | | | |
| 106 | 0.024 | | | | |
| 107 | 0.113 | | | | |
| 108 | 0.058 | | | | |
| 109 | 0.084 | | | | |
| 110 | 0.034 | | | | |
| 111 | 0.391 | | | | |
| 112 | 0.029 | | | | |
| 113 | 0.184 | | | | |
| 114 | 0.045 | | | | |
| 115 | 0.160 | | | | |
| 116 | 0.282 | | | | |
| 117 | 0.078 | | | | |
| 118 | 0.150 | | | | |
| 119 | 0.335 | | | | |
| 120 | 0.230 | | | | |
| 121 | 0.021 | | | | |
| 122 | 0.120 | | | | |
| 123 | 0.339 | | | | |
| 124 | 0.126 | | | | |
| 125 | 0.085 | | | | |
| 126 | 0.257 | | | | |
| 127 | 0.354 | | | | |
| 128 | 0.241 | | | | |
| 129 | 0.169 | | | | |
| 130 | 0.079 | | | | |
| 131 | 0.639 | | | | |
| 132 | 0.264 | | | | |
| 133 | 0.026 | | | | |
| 134 | 0.203 | | | | |
| 135 | 0.104 | | | | |
| 136 | 0.016 | | | | |
| 137 | 0.321 | | | | |
| 138 | 0.119 | | | | |
| 139 | 0.469 | | | | |
| 140 | 0.175 | | | | |
| 141 | 0.173 | | | | |
| 142 | 0.110 | | | | |

TABLE 1-continued

Assay results

| Example No | hCX3CR1 [³H-AZD8797] competitive binding IC$_{50}$ (μM) | hCX3CR1 [¹²⁵I-CX3CL1] displacement binding SPA IC$_{50}$ (μM) | CX3CR1-dependent cell adhesion in human whole blood IC$_{50}$ (μM) | β-Arrestin recruitment EC$_{50}$ (μM) | hCX3CR1 B-cell adhesion IC$_{50}$ (μM) |
|---|---|---|---|---|---|
| 143 | 0.156 | 0.430 | | | 0.522 |
| 144 | 0.013 | 0.104 | 0.150 | 0.043 | 0.006 |
| 145 | 0.129 | 0.637 | 0.543 | | 0.028 |
| 146 | 0.023 | 0.180 | 0.233 | | 0.011 |
| 147 | | >10 | | | |
| 148 | 0.037 | 0.484 | 0.326 | | 0.037 |
| 149 | | >30 | >30 | | |
| 150 | 0.185 | 1.53 | 1.60 | | |
| 151 | 0.493 | | | | |
| 152 | >8.010 | | | | |
| 153 | >10.000 | | | | |
| 155 | 1.554 | | | | |
| 156 | 1.960 | | | | |
| 157 | 4.346 | | | | |
| 158 | 2.705 | | | | |
| 159 | 0.264 | | | | |
| 160 | 0.350 | | | | |
| 161 | 1.253 | | | | |
| 162 | 1.316 | | | | |
| 163 | 5.226 | | | | |
| 164 | 1.496 | | | | |
| 165 | 0.283 | | | | |
| 166 | 0.726 | | | | |
| 167 | 0.310 | | | | |
| 169 | 0.815 | | | | |
| 171 | 0.771 | | | | |

All references cited herein, including patents, patent applications, papers, text books, and the like, and the references cited therein, to the extent that they are not already, are hereby incorporated herein by reference in their entirety for all purposes.

The invention claimed is:

1. A compound selected from N-(4-((R)-2-(2,3-Difluorophenyl)propyl)-6-(((R)-1-hydroxy-4-methylpentan-2-yl)amino)-1,3,5-triazin-2-yl)methanesulfonamide and N-(4-((S)-2-(2,3-Difluorophenyl)propyl)-6-(((R)-1-hydroxy-4-methylpentan-2-yl)amino)-1,3,5-triazin-2-yl)methanesulfonamide:

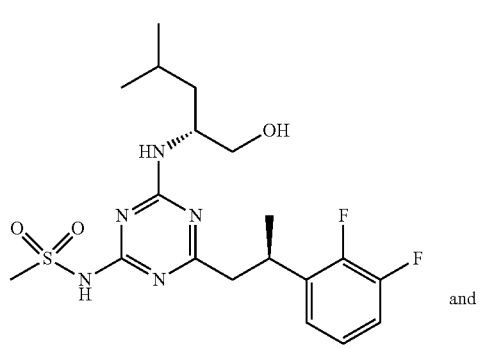

and

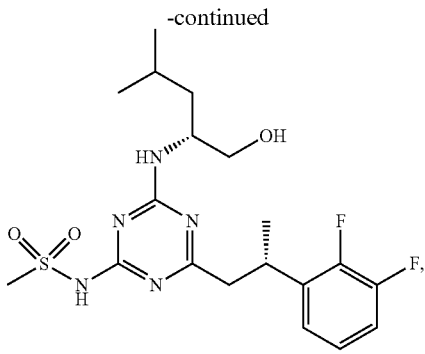

or a pharmaceutically acceptable salt thereof.

2. The compound of claim 1 which is N-(4-((R)-2-(2,3-Difluorophenyl)propyl)-6-(((R)-1-hydroxy-4-methylpentan-2-yl)amino)-1,3,5-triazin-2-yl)methanesulfonamide:

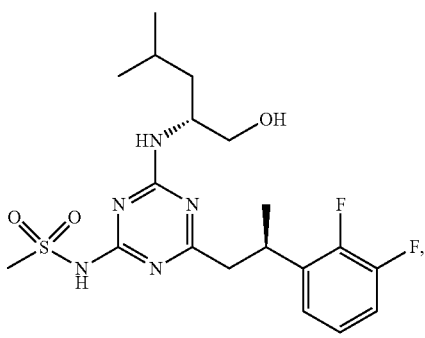 [SMILES: CC(C)C[C@H](CO)Nc1nc(C[C@@H](C)c2cccc(F)c2F)nc(NS(C)(=O)=O)n1]

or a pharmaceutically acceptable salt thereof.

3. The compound of claim 1 which is N-(4-((S)-2-(2,3-Difluorophenyl)propyl)-6-(((R)-1-hydroxy-4-methylpentan-2-yl)amino)-1,3,5-triazin-2-yl)methanesulfonamide:

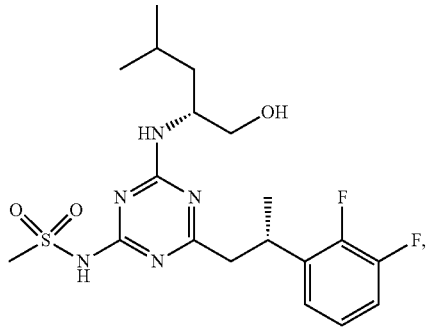 [SMILES: CC(C)C[C@H](CO)Nc1nc(C[C@H](C)c2cccc(F)c2F)nc(NS(C)(=O)=O)n1]

or a pharmaceutically acceptable salt thereof.

4. The compound of claim 2 which is N-(4-((R)-2-(2,3-Difluorophenyl)propyl)-6-(((R)-1-hydroxy-4-methylpentan-2-yl)amino)-1,3,5-triazin-2-yl)methanesulfonamide:

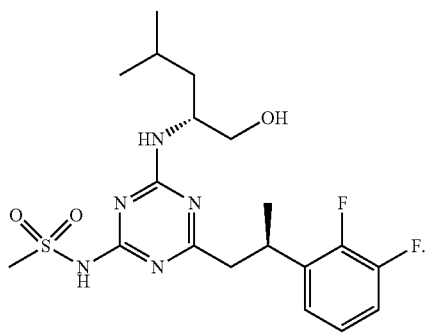 [SMILES: CC(C)C[C@H](CO)Nc1nc(C[C@@H](C)c2cccc(F)c2F)nc(NS(C)(=O)=O)n1]

5. The compound of claim 3 which is N-(4-((S)-2-(2,3-Difluorophenyl)propyl)-6-(((R)-1-hydroxy-4-methylpentan-2-yl)amino)-1,3,5-triazin-2-yl)methanesulfonamide:

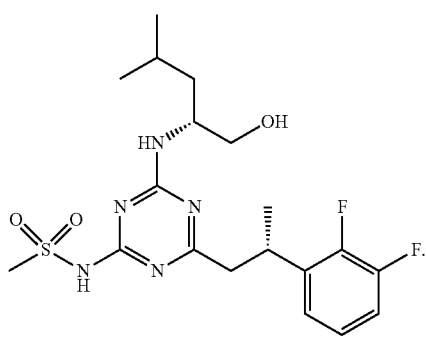 [SMILES: CC(C)C[C@H](CO)Nc1nc(C[C@H](C)c2cccc(F)c2F)nc(NS(C)(=O)=O)n1]

6. The pharmaceutically acceptable salt of claim 2, which is a pharmaceutically acceptable salt of N-(4-((R)-2-(2,3-Difluorophenyl)propyl)-6-(((R)-1-hydroxy-4-methylpentan-2-yl)amino)-1,3,5-triazin-2-yl)methanesulfonamide:

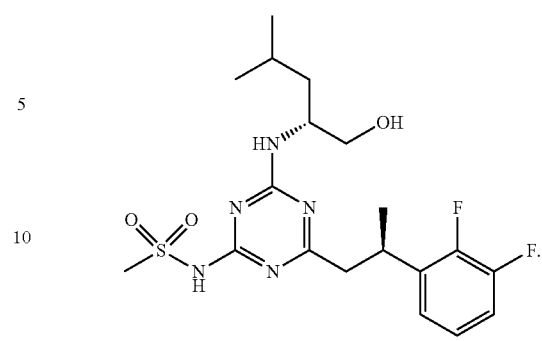

7. The pharmaceutically acceptable salt of claim 3, which is a pharmaceutically acceptable salt of N-(4-((S)-2-(2,3-Difluorophenyl)propyl)-6-(((R)-1-hydroxy-4-methylpentan-2-yl)amino)-1,3,5-triazin-2-yl)methanesulfonamide

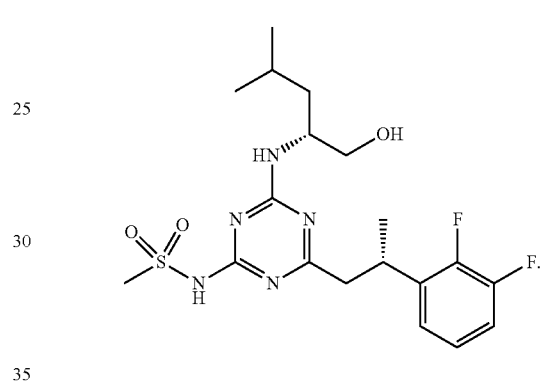

8. A pharmaceutical composition comprising the compound or pharmaceutically acceptable salt thereof according to claim 1.

9. A pharmaceutical composition comprising the compound or pharmaceutically acceptable salt thereof according to claim 2.

10. A pharmaceutical composition comprising the compound or pharmaceutically acceptable salt thereof according to claim 3.

11. A compound selected from N-(4-(((R)-1-Hydroxy-4-methylpentan-2-yl)amino)-6-((R)-2-(6-methoxypyridin-3yl)propyl)-1,3,5-triazin-2-yl)methanesulfonamide and N-(4-(((R)-1-Hydroxy-4-methylpentan-2-yl)amino)-6-((S)-2-(6-methoxypyridin-3yl)propyl)-1,3,5-triazin-2-yl)methanesulfonamide:

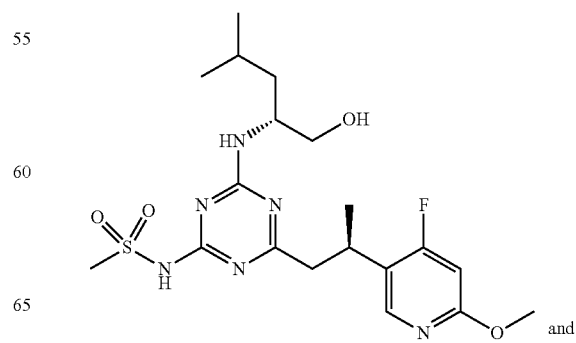

and

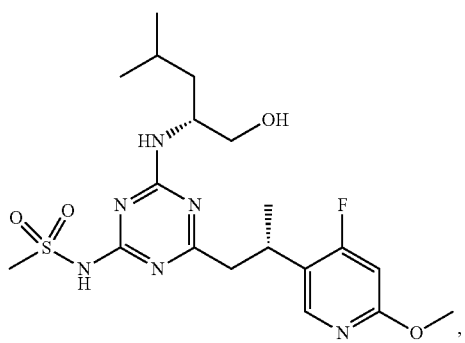

or a pharmaceutically acceptable salt thereof.

12. The compound of claim 11 which is N-(4-(((R)-1-Hydroxy-4-methylpentan-2-yl)amino)-6-((R)-2-(6-methoxypyridin-3yl)propyl)-1,3,5-triazin-2-yl)methanesulfonamide:

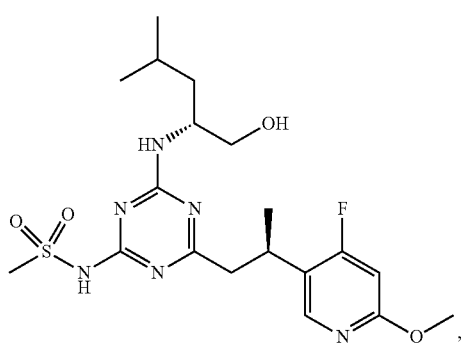

or a pharmaceutically acceptable salt thereof.

13. The compound of claim 11 which is N-(4-(((R)-1-Hydroxy-4-methylpentan-2-yl)amino)-6-((S)-2-(6-methoxypyridin-3yl)propyl)-1,3,5-triazin-2-yl)methanesulfonamide:

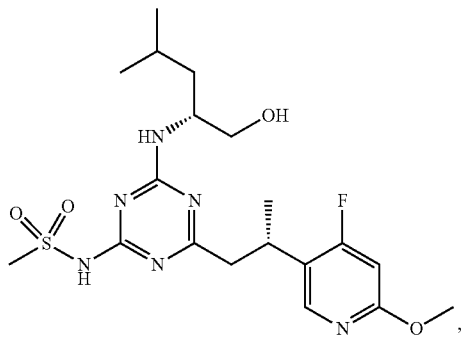

or a pharmaceutically acceptable salt thereof.

14. The compound of claim 12 which is N-(4-(((R)-1-Hydroxy-4-methylpentan-2-yl)amino)-6-((R)-2-(6-methoxypyridin-3yl)propyl)-1,3,5-triazin-2-yl)methanesulfonamide:

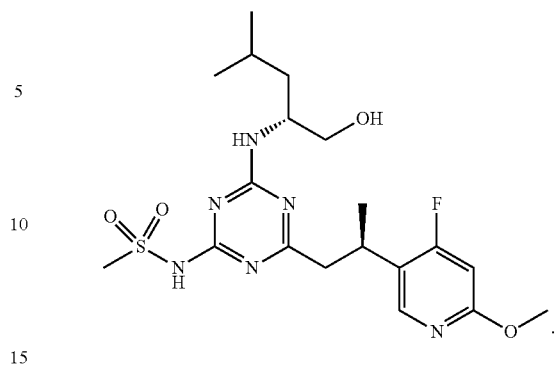

15. The compound of claim 13 which is N-(4-(((R)-1-Hydroxy-4-methylpentan-2-yl)amino)-6-((S)-2-(6-methoxypyridin-3yl)propyl)-1,3,5-triazin-2-yl)methanesulfonamide:

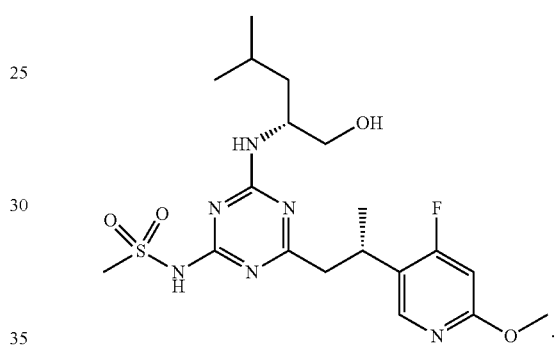

16. The pharmaceutically acceptable salt of claim 12, which is a pharmaceutically acceptable salt of N-(4-(((R)-1-Hydroxy-4-methylpentan-2-yl)amino)-6-((R)-2-(6-methoxypyridin-3yl)propyl)-1,3,5-triazin-2-yl)methanesulfonamide:

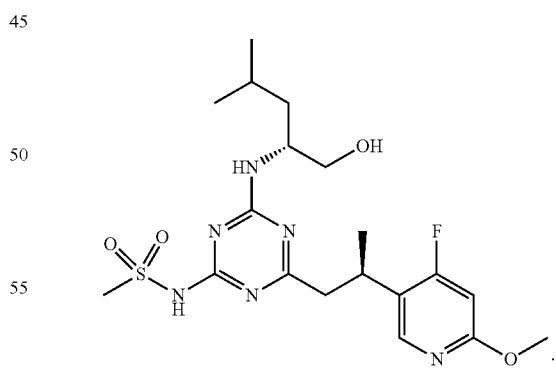

17. The pharmaceutically acceptable salt of claim 13, which is a pharmaceutically acceptable salt of N-(4-(((R)-1-Hydroxy-4-methylpentan-2-yl)amino)-6-((S)-2-(6-methoxypyridin-3yl)propyl)-1,3,5-triazin-2-yl)methanesulfonamide:

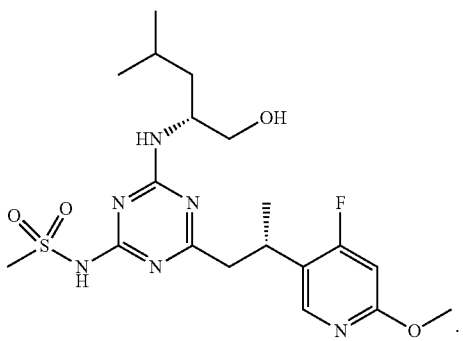

18. A pharmaceutical composition comprising the compound or pharmaceutically acceptable salt thereof according to claim 11.

19. A pharmaceutical composition comprising the compound or pharmaceutically acceptable salt thereof according to claim 12.

20. A pharmaceutical composition comprising the compound or pharmaceutically acceptable salt thereof according to claim 13.

21. A compound selected from N-(4-((R)-2-(5-Fluoro-6-methoxypyridin-3-yl)propyl)-6-(((R)-1-hydroxy-4-methylpentan-2-yl)amino)-1,3,5-triazin-2-yl)methanesulfonamide and N-(4-((S)-2-(5-Fluoro-6-methoxypyridin-3-yl)propyl)-6-(((R)-1-hydroxy-4-methylpentan-2-yl)amino)-1,3,5-triazin-2-yl)methanesulfonamide:

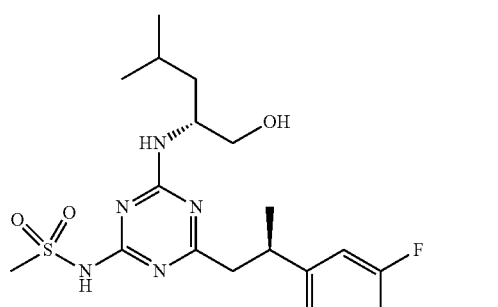

and

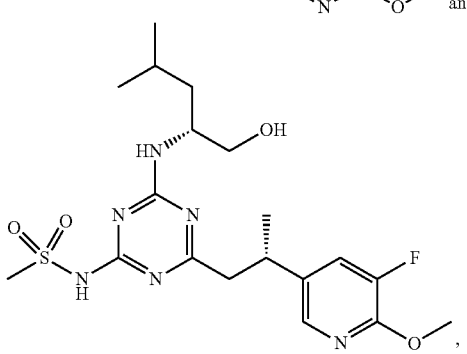

or a pharmaceutically acceptable salt thereof.

22. The compound of claim 21 which is N-(4-((R)-2-(5-Fluoro-6-methoxypyridin-3-yl)propyl)-6-(((R)-1-hydroxy-4-methylpentan-2-yl)amino)-1,3,5-triazin-2-yl)methanesulfonamide:

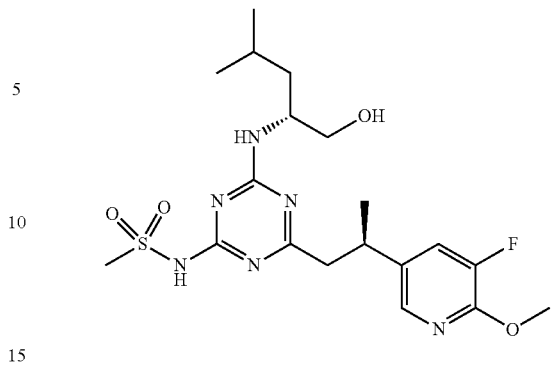

or a pharmaceutically acceptable salt thereof.

23. The compound of claim 21 which is N-(4-((S)-2-(5-Fluoro-6-methoxypyridin-3-yl)propyl)-6-(((R)-1-hydroxy-4-methylpentan-2-yl)amino)-1,3,5-triazin-2-yl)methanesulfonamide:

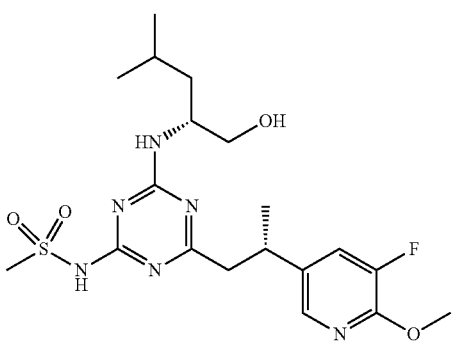

or a pharmaceutically acceptable salt thereof.

24. The compound of claim 22 which is N-(4-((R)-2-(5-Fluoro-6-methoxypyridin-3-yl)propyl)-6-(((R)-1-hydroxy-4-methylpentan-2-yl)amino)-1,3,5-triazin-2-yl)methanesulfonamide:

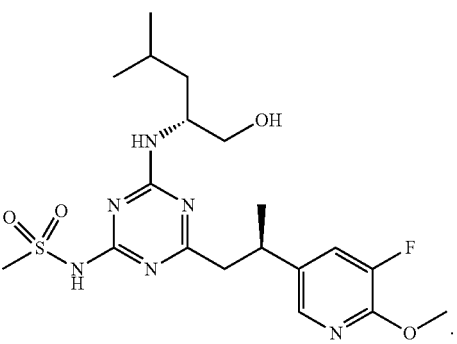

25. The compound of claim 23 which is N-(4-((S)-2-(5-Fluoro-6-methoxypyridin-3-yl)propyl)-6-(((R)-1-hydroxy-4-methylpentan-2-yl)amino)-1,3,5-triazin-2-yl)methanesulfonamide:

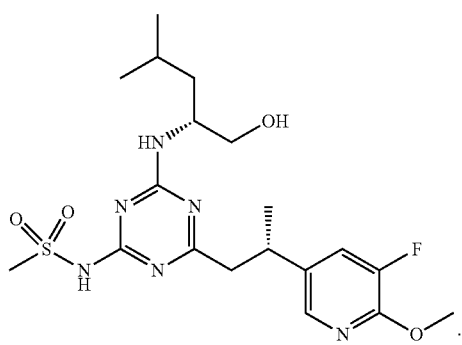

26. The pharmaceutically acceptable salt of claim 22, which is a pharmaceutically acceptable salt of N-(4-((R)-2-(5-Fluoro-6-methoxypyridin-3-yl)propyl)-6-(((R)-1-hydroxy-4-methylpentan-2-yl)amino)-1,3,5-triazin-2-yl)methanesulfonamide:

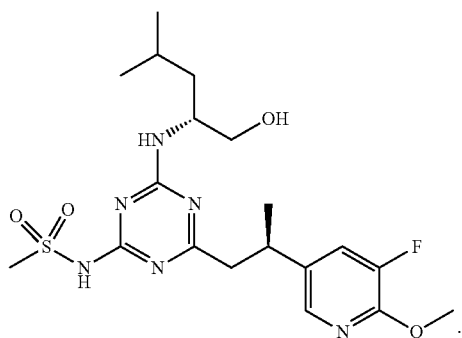

27. The pharmaceutically acceptable salt of claim 23, which is a pharmaceutically acceptable salt of N-(4-((S)-2-(5-Fluoro-6-methoxypyridin-3-yl)propyl)-6-(((R)-1-hydroxy-4-methylpentan-2-yl)amino)-1,3,5-triazin-2-yl)methanesulfonamide:

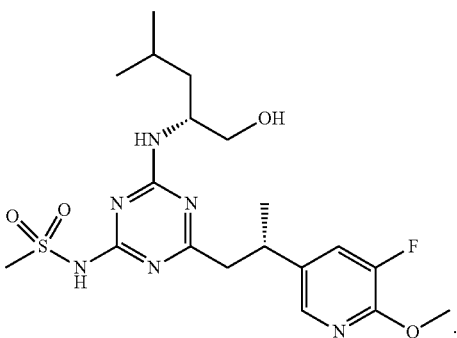

28. A pharmaceutical composition comprising the compound or pharmaceutically acceptable salt thereof according to claim 21.

29. A pharmaceutical composition comprising the compound or pharmaceutically acceptable salt thereof according to claim 22.

30. A pharmaceutical composition comprising the compound or pharmaceutically acceptable salt thereof according to claim 23.

* * * * *